US009102599B2

(12) United States Patent
Salvati et al.

(10) Patent No.: US 9,102,599 B2
(45) Date of Patent: *Aug. 11, 2015

(54) N-((3-BENZYL)-2,2-(BIS-PHENYL)-PROPAN-1-AMINE DERIVATIVES AS CETP INHIBITORS FOR THE TREATMENT OF ATHEROSCLEROSIS AND CARDIOVASCULAR DISEASES

(71) Applicant: Bristol-Myers Squibb Company, Princeton, NJ (US)

(72) Inventors: Mark E. Salvati, Pennington, NJ (US); James A. Johnson, Pennington, NJ (US); Ningning Xu, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 148 days.

This patent is subject to a terminal disclaimer.

(21) Appl. No.: 13/717,871

(22) Filed: Dec. 18, 2012

(65) Prior Publication Data

US 2013/0184279 A1 Jul. 18, 2013

Related U.S. Application Data

(62) Division of application No. 12/516,586, filed as application No. PCT/US2007/085733 on Nov. 28, 2007, now Pat. No. 8,404,896.

(60) Provisional application No. 60/868,112, filed on Dec. 1, 2006.

(51) Int. Cl.

| | |
|---|---|
| *C07C 211/00* | (2006.01) |
| *C07D 213/00* | (2006.01) |

(Continued)

(52) U.S. Cl.

CPC ............ *C07C 311/04* (2013.01); *C07C 211/03* (2013.01); *C07C 215/08* (2013.01);

(Continued)

(58) Field of Classification Search

None

See application file for complete search history.

(56) References Cited

U.S. PATENT DOCUMENTS

| | | | |
|---|---|---|---|
| 2,843,594 | A | 7/1958 | Leditschke et al. |
| 3,507,919 | A | 4/1970 | Blank et al. |

(Continued)

FOREIGN PATENT DOCUMENTS

| | | |
|---|---|---|
| DE | 2 143 744 | 3/1973 |
| EP | 1 219 294 | 7/2002 |

(Continued)

OTHER PUBLICATIONS

Shivmore et al. Int J. Cur. Res. Rev., May 2013, vol. 5 (9) p. 85-91.*

(Continued)

*Primary Examiner* — Clinton Brooks

(74) *Attorney, Agent, or Firm* — Mary K. VanAtten

(57) ABSTRACT

Compounds of formula Ia and Ib

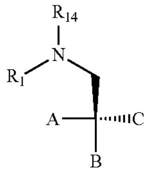

or

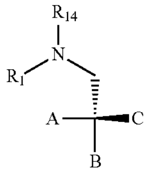

Ia Ib wherein A, B, C, $R_1$ and $R_{14}$ are described herein.

2 Claims, 1 Drawing Sheet

Single crystal X-ray structure of Enantiomer 1, Procedure 5.

(51) Int. Cl.

| | | |
|---|---|---|
| C07C 311/04 | (2006.01) | |
| C07C 215/08 | (2006.01) | |
| C07C 217/64 | (2006.01) | |
| C07C 217/84 | (2006.01) | |
| C07C 229/34 | (2006.01) | |
| C07C 233/18 | (2006.01) | |
| C07C 233/60 | (2006.01) | |
| C07C 235/08 | (2006.01) | |
| C07C 271/16 | (2006.01) | |
| C07C 271/48 | (2006.01) | |
| C07C 275/24 | (2006.01) | |
| C07C 275/26 | (2006.01) | |
| C07C 307/06 | (2006.01) | |
| C07C 311/10 | (2006.01) | |
| C07C 311/14 | (2006.01) | |
| C07C 311/17 | (2006.01) | |
| C07C 323/32 | (2006.01) | |
| C07D 209/14 | (2006.01) | |
| C07D 213/38 | (2006.01) | |
| C07D 213/61 | (2006.01) | |
| C07D 213/64 | (2006.01) | |
| C07D 231/12 | (2006.01) | |
| C07D 231/14 | (2006.01) | |
| C07D 231/16 | (2006.01) | |
| C07D 231/20 | (2006.01) | |
| C07D 239/42 | (2006.01) | |
| C07D 239/48 | (2006.01) | |
| C07D 261/08 | (2006.01) | |
| C07D 307/33 | (2006.01) | |
| C07D 309/04 | (2006.01) | |
| C07D 309/14 | (2006.01) | |
| C07D 317/46 | (2006.01) | |
| C07C 211/03 | (2006.01) | |
| C07C 233/22 | (2006.01) | |
| C07C 275/18 | (2006.01) | |
| C07D 307/20 | (2006.01) | |

(52) U.S. Cl.
CPC ............. *C07C217/64* (2013.01); *C07C 217/84* (2013.01); *C07C 229/34* (2013.01); *C07C 233/18* (2013.01); *C07C 233/22* (2013.01); *C07C 233/60* (2013.01); *C07C 235/08* (2013.01); *C07C 271/16* (2013.01); *C07C 271/48* (2013.01); *C07C 275/18* (2013.01); *C07C 275/24* (2013.01); *C07C 275/26* (2013.01); *C07C 307/06* (2013.01); *C07C 311/10* (2013.01); *C07C 311/14* (2013.01); *C07C 311/17* (2013.01); *C07C 323/32* (2013.01); *C07D 209/14* (2013.01); *C07D 213/38* (2013.01); *C07D 213/61* (2013.01); *C07D 213/64* (2013.01); *C07D 231/12* (2013.01); *C07D 231/14* (2013.01); *C07D 231/16* (2013.01); *C07D 231/20* (2013.01); *C07D 239/42* (2013.01); *C07D 239/48* (2013.01); *C07D 261/08* (2013.01); *C07D 307/20* (2013.01); *C07D 307/33* (2013.01); *C07D 309/04* (2013.01); *C07D 309/14* (2013.01); *C07D 317/46* (2013.01); *C07B 2200/07* (2013.01); *C07C 2101/02* (2013.01); *C07C 2101/04* (2013.01); *C07C 2101/08* (2013.01); *C07C 2101/14* (2013.01)

(56) References Cited

U.S. PATENT DOCUMENTS

| | | | |
|---|---|---|---|
| 4,118,494 | A | 10/1978 | Kunstmann et al. |
| 4,384,140 | A | 5/1983 | Bregnedal et al. |
| 4,623,662 | A | 11/1986 | De Vries |
| 4,650,900 | A | 3/1987 | Lassen et al. |
| 4,734,428 | A | 3/1988 | Aubard et al. |
| 6,710,089 | B2 | 3/2004 | Sikorski et al. |
| 7,790,770 | B2 | 9/2010 | Salvati et al. |

FOREIGN PATENT DOCUMENTS

| | | |
|---|---|---|
| EP | 1 393 728 | 3/2004 |
| EP | 1 500 652 | 1/2005 |
| JP | 11-71350 | 3/1999 |
| JP | 11-130757 | 5/1999 |
| WO | WO 97/24345 | 7/1997 |
| WO | WO 98/55124 | 12/1998 |
| WO | WO 02/24658 | 3/2002 |
| WO | WO 2005/003128 | 1/2005 |
| WO | WO 2005/037280 | 4/2005 |
| WO | WO 2005/061463 | 7/2005 |
| WO | WO 2005/085226 | 9/2005 |
| WO | WO 2005/100298 | 10/2005 |

OTHER PUBLICATIONS

Bigler, A.J. et al., "Novel Lipophilic Nitrosoureas", Serrou, B. et al., ed., Nitrosoureas in Cancer Treatment, INSERM Symposium No. 19, pp. 113-122, Elsevier/North Holland Biomedical Press, publ. (1981).
De Lucca, G.V. et al., "Discovery and Structure-Activity Relationship of N-(Ureidoalkyl)-Benzyl-Piperidines as Potent Small Molecule CC Chemokine Receptor-3 (CCR3) Antagonists", Journal of Medicinal Chemistry, vol. 45, No. 17, pp. 3794-3804 (2002).
DeVries, V.G. et al., "Potential Antiatherosclerotic Agents. 6. Hypocholesterolemic Trisubstituted Urea Analogues", Journal of Medicinal Chemistry, vol. 32, No. 10, pp. 2318-2325 (1989).
Ettmayer, P. et al., "Lessons Learned from Marketed and Investigational Prodrugs", Journal of Medicinal Chemistry, vol. 47, No. 10, pp. 2393-2404 (2004).
Hoefle, M.L. et al., "Synthesis and Antiarrhythmic Activity of cis-2,6-Dimethyl-α,α-diary1-1-piperidinebutanols", Journal of Medicinal Chemistry, vol. 34, No. 1, pp. 12-19 (1991).
Liu, W. et al., "Design, synthesis, and structure-activity relationship of podocarpic acid amides as liver X receptor agonists for potential treatment of atherosclerosis", Bioorganic & Medicinal Chemistry Letters, vol. 15, pp. 4574-4578 (2005).
Metzger, C. et al., "Reactions of O,O- and S,S-dialkyl N-alkyliminocarboxylates. I. Cycloaddition of dialkyl N-alkyliminodithiocarboxylates with ketenes", Chemische Berichte, vol. 101, No. 3, pp. 1120-1130 (1968).
Ng, H.P. et al., "Discovery of Novel Non-Peptide CCR1 Receptor Antagonists", Journal of Medicinal Chemistry, vol. 42, No. 22, pp. 4680-4694 (1999).
Perelman, M. et al., "2,2,3-Triarylpropionitriles and Related Compounds as Hypocholesterolemic Agents", Journal of Medicinal Chemistry, vol. 6, pp. 533-538 (1963).
Stella, V.J., "Prodrugs as therapeutics", Expert Opin. Ther. Patents, vol. 14, No. 3, pp. 277-280 (2004).
Testa, B., "Prodrug research: futile or fertile?", Biochemical Pharmacology, vol. 68, pp. 2097-2106 (2004).
Wolff, M.E., ed., Burger's Medicinal Chemistry and Drug Discovery, Fifth Edition, vol. 1: Principles and Practice, pp. 975-977, John Wiley & Sons, Inc., publ. (1994).
Database CAPLUS on STN, Abstract No. 1964:473059 (1964).
Database CAPLUS on STN, Abstract No. 1995:950892 (1995).

\* cited by examiner

Single crystal X-ray structure of Enantiomer 1, Procedure 5.
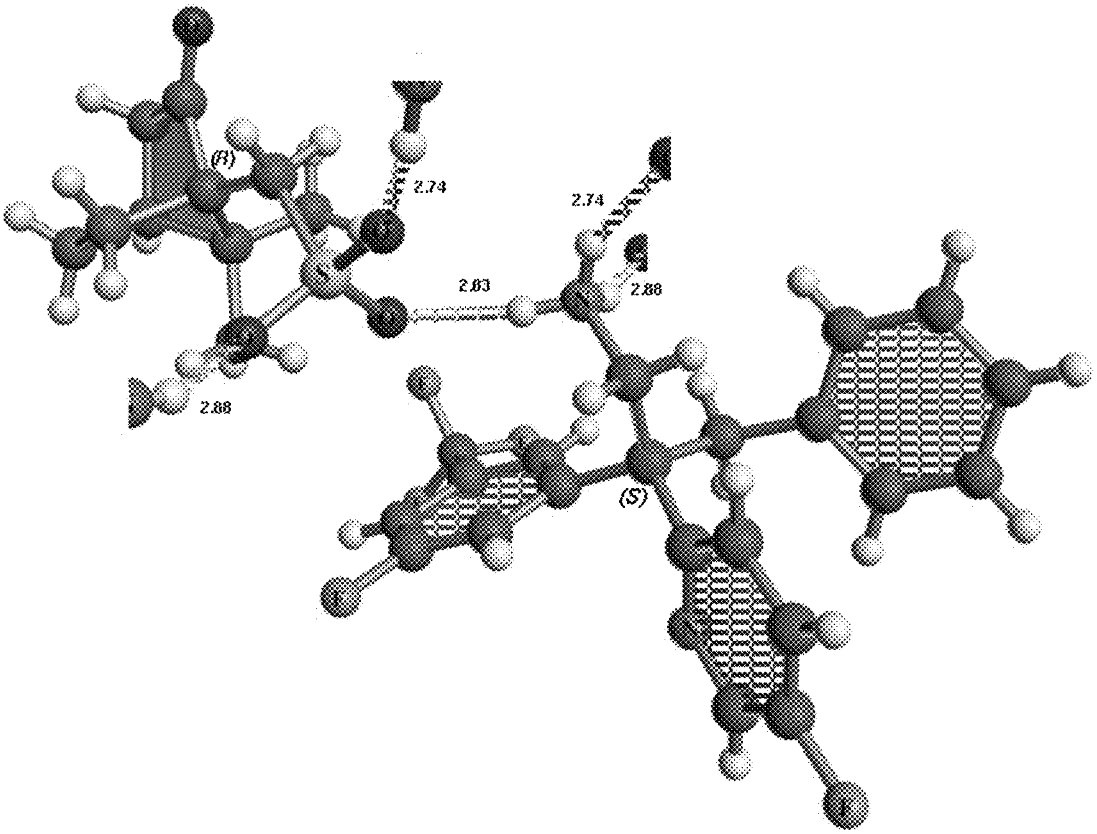

N-((3-BENZYL)-2,2-(BIS-PHENYL)-PROPAN-1-AMINE DERIVATIVES AS CETP INHIBITORS FOR THE TREATMENT OF ATHEROSCLEROSIS AND CARDIOVASCULAR DISEASES

RELATED APPLICATION

This application is a divisional of U.S. patent application Ser. No. 12/516,586, filed Sep. 25, 2009, now allowed, which claims benefit to International Application No. PCT/US2007/085733, filed Nov. 28, 2007, which claims benefit to U.S. provisional Application No. 60/868,112, filed Dec. 1, 2006, under 35 U.S.C. 119(e). The entire teachings of the referenced applications are herein incorporated by reference in their entirety.

FIELD OF THE INVENTION

This present invention provides for cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

FIELD OF THE INVENTION

This present invention provides for cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J. et al., "High-density Lipoprotein Cholesterol and Cardiovascular Disease", *Circulation,* 79:8-15 (1989)).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-C only modestly (about 10-12%). As a result, there is a significant unmet medical need for a well-tolerated agent which can significantly elevate plasma HDL levels, thereby reversing or slowing the progression of atherosclerosis.

Thus, although there are a variety of anti-atherosclerosis therapies, there is a continuing need and a continuing search in this field of art for alternative therapies.

SUMMARY OF THE INVENTION

In accordance with the present invention, heterocyclic compounds and related compounds are provided that have the general structures:

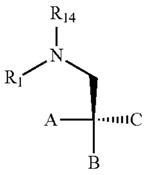

or

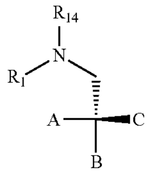

Ia

Ib wherein A, B, C, $R_1$ and $R_{14}$ are defined below.

By use of a respective effective amount of at least one compound described herein, provided are methods of treating, preventing or slowing the progression of a disease requiring cholesteryl ester transfer protein inhibition, or inhibiting the cholesteryl ester transfer protein.

Also provided are pharmaceutical compositions comprising a therapeutically effective amount of at least one compound described herein and a pharmaceutically acceptable vehicle or carrier thereof. Such compositions can further comprise one or more additional therapeutic agents.

DEFINITIONS

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups, such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term “alkenyl” refers to straight or branched chain hydrocarbon groups having 2 to 12 carbon atoms, or 2 to 4 carbon atoms, and at least one double carbon to carbon bond (either cis or trans), such as ethenyl. The term “substituted alkenyl” refers to alkenyl groups substituted with one or more groups, such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term “alkynyl” refers to straight or branched chain hydrocarbon groups having 2 to 12 carbon atoms, or 2 to 4 carbon atoms, and at least one triple carbon to carbon bond, such as ethynyl. The term “substituted alkynyl” refers to alkynyl groups substituted with one or more groups, such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term “aryl” refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term “substituted aryl” refers to aryl groups substituted with one or more groups, such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term “cycloalkyl” refers to mono-, bi- or tri homocyclic ring groups of 3 to 15 carbon atoms which are, respectively, fully saturated and partially unsaturated. The rings of multi-ring cycloalkyl groups may be either fused, bridged and/or joined through one or more spiro unions. The term “substituted cycloalkyl” refers to a cycloalkyl group substituted with one or more groups, such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms “halogen” and “halo” refer to fluorine, chlorine, bromine and iodine.

The terms “heterocycle”, “heterocyclic”, “heterocyclic group” or “heterocyclyl” refer to fully saturated or partially or completely unsaturated, including aromatic (“heteroaryl”) or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazolyl, triazolyl, morpholinyl, thiamorpholinyl, thiamorpholinyl sulfoxide, thiamorpholinyl sulfone, 1,3-dioxolane and tetrahydro-1,1-dioxothienyl,

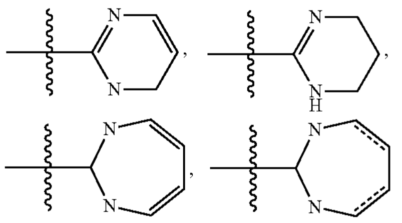

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

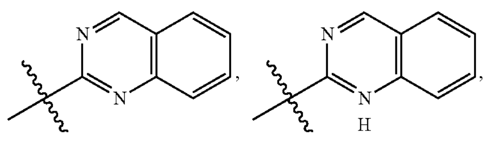

-continued

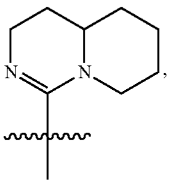
,
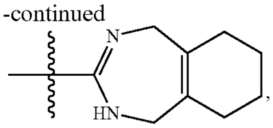
,
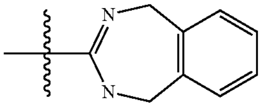

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclyl" refer to heterocycle, heterocyclic and heterocyclo groups substituted with one or more groups, such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

Throughout the specification, groups and substituents thereof may be chosen to provide stable moieties and compounds.

The compounds of formulas Ia and Ib form salts or solvates which are also within the scope of this invention. Reference to a compound of the formula Ia or Ib herein is understood to include reference to salts thereof, unless otherwise indicated. The term "salt(s)", as employed herein, denotes acidic and/or basic salts formed with inorganic and/or organic acids and bases. In addition, when a compound of formula Ia or Ib contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula Ia and Ib may be formed, for example, by reacting a compound of formula Ia or Ib with an amount of acid or base, such as an equivalent amount, in a medium such as one in which the salt precipitates or in an aqueous medium followed by lyophilization.

The compounds of formula Ia and Ib which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula Ia and Ib which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Any compound that can be converted in vivo to provide the bioactive agent (i.e., a compound of formula Ia or Ib) is a prodrug within the scope and spirit of the invention.

The term "prodrugs" as employed herein includes esters and carbonates formed by reacting one or more hydroxyls of compounds of formula Ia and Ib with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds., Ch. 5, pp. 113-191 (Harwood Academic Publishers, 1991); and d) *Hydrolysis in Drug and Prodrug Metabolism*, Bernard Testa and Joachim M. Mayer, (Wiley-VCH, 2003).

Said references are incorporated herein by reference.

In addition, compounds of the present invention are, subsequent to their preparation, preferably isolated and purified to obtain a composition containing an amount by weight equal to or greater than 99% formula Ia or Ib compound ("substantially pure" compound Ia or Ib), which may be used or formulated as described herein. Such "substantially pure" compounds of formula Ia and Ib are also contemplated herein as part of the present invention.

To the extent that compounds of the formula Ia and Ib, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

BRIEF DESCRIPTION OF THE DRAWINGS

FIG. 1. Single crystal X-ray structure of (1R)-(−)-10-camphorsulfonic acid salt of 2-(3-fluoro-5-(trifluoromethyl)phenyl)-2-(5-fluoropyridin-2-yl)-3-phenylpropan-1-amine (Enantiomer 1, Procedure 5).

DETAILED DESCRIPTION OF THE INVENTION

It will be understood that any given exemplary embodiment can be combined with one or more additional exemplary embodiments.

In accordance with the present invention, compounds of formula Ia and Ib are provided Ia

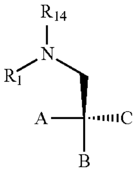

or

Ib

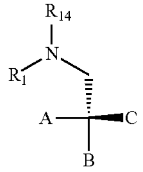

or stereoisomers or prodrugs or pharmaceutically acceptable salt forms thereof, wherein:

A is:

(a) phenyl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) ═O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s;

(b) heteroaryl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) ═O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or (c) heterocyclyl, other than heteroaryl, which may be optionally substituted with one or more substituents selected from the group consisting of: 1) halo, 2) ($C_1$-$C_6$)-alkyl, which may be optionally substituted with one or more $R_{40}$'s, 3) —$OR^{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) ═O, $R_{40}$'$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$;

B is:

(a) phenyl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$; or (b) heteroaryl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo $(C_1-C_6)$alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is:

(a) alkyl, which may be optionally substituted with one or more substituents selected from the group consisting of: 1) halo, 2) $(C_1-C_6)$-alkyl, which may be optionally substituted with one or more $R_{40}$'s, 3) —$OR_{46}$, 4) $(C_1-C_6)$-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo$(C_1-C_6)$alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

(b) alkenyl, which may be optionally substituted with one or more substituents selected from the group consisting of: 1) halo, 2) $(C_1-C_6)$-alkyl, which may be optionally substituted with one or more $R_{40}$'s, 3) —$OR_{46}$, 4) $(C_1-C_6)$-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, and 14) halo$(C_1-C_6)$alkyl;

(c) cycloalkyl, which may be optionally substituted with one or more substituents selected from the group consisting of: 1) halo, 2) $(C_1-C_6)$-alkyl, which may be optionally substituted with one or more $R_{40}$'s, 3) —$OR_{46}$, 4) $(C_1-C_6)$-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo$(C_1-C_6)$alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$; or (d) heterocyclo, which may be optionally substituted with one or more substituents selected from the group consisting of: 1) halo, 2) $(C_1-C_6)$-alkyl, which may be optionally substituted with one or more $R_{40}$'s, 3) —$OR_{46}$, 4) $(C_1-C_6)$-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo$(C_1-C_6)$alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NR_2R_3$, —$C(O)OR_4$, —$SO_2R_5$, —$SO_2NR_2R_3$, —$R_7$ or —$CR_8R_8R_8$;

$R_2$ is H, alkyl, alkenyl or cycloalkyl, wherein the alkyl, alkenyl or cycloalkyl may be optionally substituted with one or more $R_{25}$'s;

$R_3$ is alkyl, alkenyl, aryl, cycloalkyl, heteroaryl, or heterocyclyl, other than heteroaryl, all of which may be optionally substituted with one or more $R_{26}$'s;

or $R_2$ and $R_3$ are taken together to form a 3- to 9-membered ring, which may optionally contain 1-4 heteroatoms selected from N, O, and S;

$R_4$ is alkyl, alkenyl, aryl, cycloalkyl, heteroaryl, or heterocyclyl, other than heteroaryl, all of which may be optionally substituted with one or more $R_{26}$'s;

$R_5$ is alkyl, alkenyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently H, alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, alkylthio, cyano, nitro, —$NR_{29}R_{30}$, aryl, heteroaryl, heterocyclyl, haloalkyl, haloalkyloxy, —$COR_{46}$, ═O, —$S(O)_pR_{46}$, —$SO_2NHR_{46}$, —$COOR_{46}$, —$NHC(CN)NHR_{46}$, —$CONR_{46}R_{46}$, —$OCOR_{46}$, —$OS(O)_pR_{46}$, —$OSO_2NHR_{46}$, —$OCOOR_{46}$ or —$OCONR_{46}R_{46}$, wherein the alkyl, aryl, heteroaryl or heterocyclyl may be optionally substituted with one or more $R_{40}$'s;

$R_{25}$ is halo, —OH, alkyl, alkyloxy, alkylthio, cyano, nitro, —$NR_{29}R_{30}$, aryl, heteroaryl, heterocyclyl, haloalkyl, haloalkyloxy, —$COR_{46}$, ═O, —$CO_2R_{46}$, —$CONR_{46}R_{46}$, alkenyl, arylalkyloxy, alkynyl, —$S(O)_pR_{46}$, —$SO_2NHR_{46}$, —$NHC(CN)NHR_{46}$, —$OCOR_{46}$, —$OS(O)_pR_{46}$, —$OSO_2NHR_{46}$, —$OCOOR_{46}$, —$OCONR_{46}R_{46}$ or cycloalkyl, wherein the alkyl, aryl, heteroaryl, heterocyclyl or cycloalkyl may be optionally substituted with one or more $R_{40}$'s;

$R_{26}$ is halo, —OH, alkyl, alkyloxy, alkylthio, cyano, nitro, ═O, —$NR_{29}R_{30}$, aryl, heteroaryl, heterocyclyl, haloalkyl, haloalkyloxy, —$CONR_{46}R_{46}$, alkenyl, arylalkyloxy, alkynyl, —$COR_{46}$, —$S(O)_pR_{46}$, —$SO_2NHR_{46}$, —$COOR_{46}$, —$NHC(CN)NHR_{46}$, —$OCOR_{46}$, —$OS(O)_pR_{46}$, —$OSO_2NHR_{46}$, —$OCOOR_{46}$, —$OCONR_{46}R_{46}$ or cycloalkyl, wherein the alkyl, aryl, heteroaryl, heterocyclyl or cycloalkyl may be optionally substituted with one or more $R_{40}$'s;

$R_{28}$ is halo, —OH, alkyl, alkyloxy, alkylthio, cyano, nitro, —$NR_{29}R_{30}$, aryl, heteroaryl, heterocyclyl, haloalkyl, haloalkyloxy, alkenyl, arylalkyloxy, arylalkynyl, —$CONR_{46}R_{46}$, ═O, alkynyl, —$COR_{46}$, —$S(O)_pR_{46}$, —$SO_2NHR_{46}$, —$COOR_{46}$, or —$NHC(CN)NHR_{46}$, —$OCOR_{46}$, —$OS(O)_pR_{46}$, —$OSO_2NHR_{46}$, —$OCOOR_{46}$ or —$OCONR_{46}R_{46}$, wherein the alkyl, aryl, heteroaryl, or heterocyclyl may be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, —$CONR_{46}R^{46}$, alkynyl, —$COR_{46}$, —$S(O)_pR_{46}$, —$SO_2NHR_{46}$, —$COOR_{46}$, or —$C(CN)NHR_{46}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, nitro, —$NR_{49}R_{50}$, aryl, heteroaryl, heterocyclyl, haloalkyl, haloalkyloxy, alkenyl, arylalkyloxy, ═O, alkynyl, —$COR_{46}$, —$S(O)_pR_{46}$, —$SO_2NHR_{46}$, —$COOR_{46}$, —NHC(CN)

$NHR_{46}$, cycloalkyl or —$CONR_{46}R_{46}$, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{46}R_{46}$, alkenyl, arylalkyloxy, =O, alkynyl, cycloalkyl, cycloalkylalkyl, —$COR_{46}$, —$S(O)_pR_{46}$, —$SO_2NHR_{46}$, —$COOR_{46}$, or —NHC(CN)$NHR_{46}$;

$R_{46}$, at each occurrence, is independently hydrogen, alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{47}$'s;

$R_{47}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In one embodiment, compounds of the present invention are provided wherein A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{16}$, 16) =O, 17) —$S(O)_pR_{46}$, 18) —$SO_2NHR_{16}$, 19) —$COOR_{46}$, 20) —NHC(CN)$NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s;

(b) heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN)$NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or (c) heterocyclyl, other than heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo ($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN) $NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$.

In one embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN)$NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s;

(b) heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17)

—S(O)$_p$R$_{46}$, 18) —SO$_2$NHR$_{46}$, 19) —COOR$_{46}$, 20) —NHC(CN)NHR$_{46}$, 21) —CONR$_{46}$R$_{46}$, 22) (C$_2$-C$_6$)-alkynyl, which may be optionally substituted with one or more R$_{40}$'s, 23) (C$_2$-C$_6$)-alkenyl, which may be optionally substituted with one or more R$_{40}$'s, 24) —OCOR$_{46}$, 25) —OCOOR$_{46}$, or 26) —OCONR$_{46}$R$_{46}$; or (c) heterocyclyl, other than heteroaryl, which is substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more R$_{40}$'s, 9) arylalkyl, which may be optionally substituted with one or more R$_{40}$'s, 10) heteroaryl, which may be optionally substituted with one or more R$_{40}$'s, 11) heteroarylalkyl, which may be optionally substituted with one or more R$_{40}$'s, 12) heterocyclyl, which may be optionally substituted with one or more R$_{40}$'s, 13) heterocyclylalkyl, which may be optionally substituted with one or more R$_{40}$'s, 14) halo(C$_1$-C$_6$)alkyl, 15) —COR$_{46}$, 16) =O, 17) —S(O)$_p$R$_{46}$, 18) —SO$_2$NHR$_{46}$, 19) —COOR$_{46}$, 20) —NHC(CN)NHR$_{46}$, 21) —CONR$_{46}$R$_{46}$, 22) (C$_2$-C$_6$)-alkynyl, which may be optionally substituted with one or more R$_{40}$'s, 23) (C$_2$-C$_6$)-alkenyl, which may be optionally substituted with one or more R$_{40}$'s, 24) —OCOR$_{46}$, 25) —OCOOR$_{46}$, or 26) —OCONR$_{46}$R$_{46}$; and B is:

(a) phenyl, which is substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more R$_{40}$'s, 9) arylalkyl, which may be optionally substituted with one or more R$_{40}$'s, 10) heteroaryl, which may be optionally substituted with one or more R$_{40}$'s, 11) heteroarylalkyl, which may be optionally substituted with one or more R$_{40}$'s, 12) heterocyclyl, which may be optionally substituted with one or more R$_{40}$'s, 13) heterocyclylalkyl, which may be optionally substituted with one or more R$_{40}$'s, 14) halo(C$_1$-C$_6$)alkyl, 15) —COR$_{46}$, 16) —S(O)$_p$R$_{46}$, 17) —SO$_2$NHR$_{46}$, 18) —COOR$_{46}$, 19) —NHC(CN)NHR$_{46}$, and 20) —CONR$_{46}$R$_{46}$; or (b) heteroaryl, which is substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more R$_{40}$'s, 9) arylalkyl, which may be optionally substituted with one or more R$_{40}$'s, 10) heteroaryl, which may be optionally substituted with one or more R$_{40}$'s, 11) heteroarylalkyl, which may be optionally substituted with one or more R$_{40}$'s, 12) heterocyclyl, which may be optionally substituted with one or more R$_{40}$'s, 13) heterocyclylalkyl, which may be optionally substituted with one or more R$_{40}$'s, 14) halo(C$_1$-C$_6$)alkyl, 15) —COR$_{46}$, 16) —S(O)$_p$R$_{46}$, 17) —SO$_2$NHR$_{46}$, 18) —COOR$_{46}$, 19) —NHC(CN)NHR$_{46}$, and 20) —CONR$_{46}$R$_{46}$.

In one embodiment, compounds of the present invention are provided wherein:

A is:

(a) phenyl, which is substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more R$_{40}$'s, 9) arylalkyl, which may be optionally substituted with one or more R$_{40}$'s, 10) heteroaryl, which may be optionally substituted with one or more R$_{40}$'s, 11) heteroarylalkyl, which may be optionally substituted with one or more R$_{40}$'s, 12) heterocyclyl, which may be optionally substituted with one or more R$_{40}$'s, 13) heterocyclylalkyl, which may be optionally substituted with one or more R$_{40}$'s, 14) halo(C$_1$-C$_6$)alkyl, 15) —COR$_{46}$, 16) =O, 17) —S(O)$_p$R$_{46}$, 18) —SO$_2$NHR$_{46}$, 19) —COOR$_{46}$, 20) —NHC(CN)NHR$_{46}$, 21) —CONR$_{46}$R$_{46}$, 22) (C$_2$-C$_6$)-alkynyl, which may be optionally substituted with one or more R$_{40}$'s, 23) (C$_2$-C$_6$)-alkenyl, which may be optionally substituted with one or more R$_{40}$'s, 24) —OCOR$_{46}$, 25) —OCOOR$_{46}$, or 26) —OCONR$_{46}$R$_{46}$; or any two adjacent substituents may join together to form a 4- to 8-membered ring, which optionally may contain 1-4 heteroatoms selected from N, O, and S and be optionally substituted with one or more R$_{40}$'s;

(b) heteroaryl, which is substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more R$_{40}$'s, 9) arylalkyl, which may be optionally substituted with one or more R$_{40}$'s, 10) heteroaryl, which may be optionally substituted with one or more R$_{40}$'s, 11) heteroarylalkyl, which may be optionally substituted with one or more R$_{40}$'s, 12) heterocyclyl, which may be optionally substituted with one or more R$_{40}$'s, 13) heterocyclylalkyl, which may be optionally substituted with one or more R$_{40}$'s, 14) halo(C$_1$-C$_6$)alkyl, 15) —COR$_{46}$, 16) =O, 17) —S(O)$_p$R$_{46}$, 18) —SO$_2$NHR$_{46}$, 19) —COOR$_{46}$, 20) —NHC(CN)NHR$_{46}$, 21) —CONR$_{46}$R$_{46}$, 22) (C$_2$-C$_6$)-alkynyl, which may be optionally substituted with one or more R$_{40}$'s, 23) (C$_2$-C$_6$)-alkenyl, which may be optionally substituted with one or more R$_{40}$'s, 24) —OCOR$_{46}$, 25) —OCOOR$_{46}$, or 26) —OCONR$_{46}$R$_{46}$; or (c) heterocyclyl, other than heteroaryl, which is optionally substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more R$_{40}$'s, 9) arylalkyl, which may be optionally substituted with one or more R$_{40}$'s, 10) heteroaryl, which may be optionally substituted with one or more R$_{40}$'s, 11) heteroarylalkyl, which may be optionally substituted with one or more R$_{40}$'s, 12) heterocyclyl, which may be optionally substituted with one or more R$_{40}$'s, 13) heterocyclylalkyl, which may be optionally substituted with one or more R$_{40}$'s, 14) halo(C$_1$-C$_6$)alkyl, 15) —COR$_{46}$, 16) =O, 17) —S(O)$_p$R$_{46}$, 18) —SO$_2$NHR$_{46}$, 19) —COOR$_{46}$, 20) —NHC(CN)NHR$_{46}$, 21) —CONR$_{46}$R$_{46}$, 22) (C$_2$-C$_6$)-alkynyl, which may be optionally substituted with one or more R$_{40}$'s, 23) (C$_2$-C$_6$)-alkenyl, which may be optionally substituted with one or more R$_{40}$'s, 24) —OCOR$_{46}$, 25) —OCOOR$_{46}$, or 26) —OCONR$_{46}$R$_{46}$;

B is:

(a) phenyl, which is substituted with one or more substituents selected from the group consisting of: 1) halo, 2) (C$_1$-C$_6$)-alkyl, which may be optionally substituted with one or more R$_{40}$'s, 3) —OR$_{46}$, 4) (C$_1$-C$_6$)-alkylthio, 5) cyano, 6) nitro, 7) —NR$_{29}$R$_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$; or (b) heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is:

(a) alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$) alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

(b) alkenyl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, and 14) halo($C_1$-$C_6$)alkyl;

(c) cycloalkyl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$; or (d) heterocyclo, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NR_2R_3$, —$C(O)OR_4$, —$R_7$ or —$CH_2R_8$;

$R_2$ is H, alkyl, alkenyl or cycloalkyl, wherein the alkyl, alkenyl or cycloalkyl may be optionally substituted with one or more $R_{25}$'s;

$R_3$ is alkyl, aryl, cycloalkyl, heteroaryl, or heterocyclyl, other than heteroaryl, all of which may be optionally substituted with one or more $R_{26}$'s;

$R_4$ is alkyl, aryl, cycloalkyl or alkenyl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, alkylthio, cyano, nitro, —$NR_{29}R_{30}$, aryl, heteroaryl, heterocyclyl, haloalkyl, haloalkyloxy, —$COR_{46}$, =O, —$S(O)_pR_{46}$, —$SO_2NHR_{46}$, —$COOR_{46}$, —$NHC(CN)NHR_{46}$, —$CONR_{46}R_{46}$, —$OCOR_{46}$, —$OS(O)_pR_{46}$, —$OSO_2NHR_{46}$, —$OCOOR_{46}$ or —$OCONR_{46}R_{46}$, wherein the alkyl, aryl, heteroaryl or heterocyclyl may be optionally substituted with one or more $R_{40}$'s;

$R_{25}$ is halo, —OH, alkyl, alkyloxy, alkylthio, cyano, nitro, —$NR_{29}R_{30}$, aryl, heteroaryl, heterocyclyl, haloalkyl, haloalkyloxy, —$COR_{46}$, —$CO_2R_{46}$, —$CONR_{46}R_{46}$, alkenyl, alkynyl, —$S(O)_pR_{46}$, —$SO_2NHR_{46}$, —$NHC(CN)NHR_{46}$, —$OCOR_{46}$, —$OS(O)_pR_{46}$, —$OSO_2NHR_{46}$, —$OCOOR_{46}$, or —$OCONR_{46}R_{46}$, wherein the alkyl, aryl, heteroaryl or heterocyclyl may be optionally substituted with one or more $R_{40}$'s;

$R_{26}$ is halo, —OH, alkyl, alkyloxy, alkylthio, cyano, nitro, =O, —$NR_{29}R_{30}$, aryl, heteroaryl, heterocyclyl, haloalkyl, haloalkyloxy, —$CONR_{46}R_{46}$, alkenyl, arylalkyloxy, alkynyl, —$COR_{46}$, —$COOR_{46}$, —$OCOR_{46}$, —$OCOOR_{46}$, or —$OCONR_{46}R_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, nitro, —$NR_{29}R_{30}$, aryl, heteroaryl, heterocyclyl, haloalkyl, haloalkyloxy, alkenyl, arylalkyloxy, arylalkynyl, —$CONR_{46}R_{46}$, =O, alkynyl, —$COR_{46}$, —$COOR_{46}$, —$OCOR_{46}$, —$OCOOR_{46}$ or —$OCONR_{46}R_{46}$, wherein the alkyl, aryl, heteroaryl, or heterocyclyl may be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, —$CONR_{46}R_{46}$, alkynyl, —$COR_{46}$ or —$COOR_{46}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, nitro, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$, cycloalkyl or —$CONR_{46}R_{46}$, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{46}R_{46}$, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{47}$'s;

$R_{47}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 3;

s is 0 to 2; and p is 1 or 2.

In yet another embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s; or (b) heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$;

B is:

(a) phenyl, which is substituted with one or more substituents selected from the group consisting of: 1) halo, 2) ($C_1$-$C_6$)-alkyl, which may be optionally substituted with one or more $R_{40}$'s; 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s; 9) arylalkyl, which may be optionally substituted with one or more $R_{40}$'s; 10) heteroaryl, which may be optionally substituted with one or more $R_{40}$'s; 11) heteroarylalkyl, which may be optionally substituted with one or more $R_{40}$'s; 12) heterocyclyl, which may be optionally substituted with one or more $R_{40}$'s; 13) heterocyclylalkyl, which may be optionally substituted with one or more $R_{40}$'s; 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$; or (b) heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is:

(a) alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$) alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

(b) alkenyl, which may be optionally substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, and 14) halo($C_1$-$C_6$)alkyl;

$R_1$ is —C(O)$R_3$, —C(O)$NR_2R_3$, —$R_7$ or —$CH_2R_8$;

$R_2$ is H, alkyl or cycloalkyl, wherein the alkyl or cycloalkyl may be optionally substituted with one or more $R_{25}$'s;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, alkylthio, cyano, nitro, —$NR_{29}R_{30}$, aryl, heteroaryl, heterocyclyl, haloalkyl, haloalkyloxy, —$COR_{46}$, =O, —$S(O)_pR_{46}$, —$SO_2NHR_{46}$, —$COOR_{46}$, —NHC(CN)$NHR_{46}$, —$CONR_{46}R_{46}$, —$OCOR_{46}$, —$OS(O)_pR_{46}$, —$OSO_2NHR_{46}$, —$OCOOR_{46}$ or —$OCONR_{46}R_{46}$, wherein the alkyl, aryl, heteroaryl or heterocyclyl may be optionally substituted with one or more $R_{40}$'s;

$R_{25}$ is halo, —OH, alkyl, alkyloxy, alkylthio, cyano, nitro, —$NR_{29}R_{30}$, aryl, heteroaryl, heterocyclyl, haloalkyl, haloalkyloxy, —$COR_{46}$, —$CO_2R_{46}$, —$CONR_{46}R_{46}$, alkenyl, alkynyl, —$OCOR_{46}$, —$OCOOR_{46}$ or —$OCONR_{46}R_{46}$, wherein the alkyl, aryl, heteroaryl or heterocyclyl may be optionally substituted with one or more $R_{40}$'s;

$R_{26}$ is halo, —OH, alkyl, alkyloxy, alkylthio, cyano, nitro, =O, —$NR_{29}R_{30}$, aryl, heteroaryl, heterocyclyl, haloalkyl, haloalkyloxy, —$CONR_{46}R_{46}$, alkenyl, arylalkyloxy, alkynyl, —$COR_{46}$, —$COOR_{46}$, —$OCOR_{46}$, —$OCOOR_{46}$, or —$OCONR_{46}R_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, nitro, —$NR_{29}R_{30}$, aryl, heteroaryl, heterocyclyl, haloalkyl, haloalkyloxy, alkenyl, arylalkyloxy, —$CONR_{46}R_{46}$, =O, alkynyl, —$COR_{46}$, —$COOR_{46}$, —$OCOR_{46}$, —$OCOOR_{46}$ or —$OCONR_{46}R_{46}$, wherein the alkyl, aryl, heteroaryl, or heterocyclyl may be optionally substituted with one or more $R_{40}$'s, $R_{29}$ and $R_{30}$ are independently hydrogen, —$[(C=O)O_r]_s$aryl, —$[(C=O)O_r]_s$alkenyl, —$[(C=O)O_r]_s$alkyl, heterocyclyl, alkynyl, —$COR_{46}$ or —$COOR_{46}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, nitro, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$, cycloalkyl or —$CONR_{46}R_{46}$, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{46}R_{46}$, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{47}$'s;

$R_{47}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, alkynyl, cycloalkyl, cycloalkylalkyl, —$COR_{46}$ or —$COOR_{46}$;

$R_{49}$ and $R_{50}$, at each occurrence, are independently hydrogen, alkyl, aryl, cycloalkyl, heteroaryl or heterocyclyl, other than heteroaryl;

r is 0 to 2;

s is 0 to 1; and p is 1 or 2.

In still yet another embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN)$NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{16}$; or any two adjacent substituents may join together to form a 4- to 8-membered ring, which optionally may contain 1-4 heteroatoms selected from N, O, and S and be optionally substituted with one or more Ro's; or (b) a nitrogen or oxygen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo ($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN) $NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$;

B is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$; or (b) a nitrogen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NR_2R_3$, —$R_7$ or —$CH_2R_8$;

$R_2$ is H or alkyl, wherein the alkyl may be optionally substituted with one or more $R_{25}$'s;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, alkylthio, cyano, —$NR_{29}R_{30}$, aryl, heteroaryl, heterocyclyl, haloalkyl, haloalkyloxy, —$COR_{46}$, =O, —$COOR_{46}$, —$OCOR_{46}$ or —$OCOOR_{46}$, wherein the alkyl, aryl, heteroaryl or heterocyclyl may be optionally substituted with one or more $R_{40}$'s;

$R_{25}$ is halo, —OH, alkyl, alkyloxy, alkylthio, cyano, —$NR_{29}R_{30}$, aryl, heteroaryl, heterocyclyl, haloalkyl, haloalkyloxy, —$COR_{46}$, —$CO_2R_{46}$, —$CONR_{46}R_{46}$, alkenyl, alkynyl, —$OCOR_{46}$, —$OCOOR_{46}$ or —$OCONR_{46}R_{46}$, wherein the alkyl, aryl, heteroaryl or heterocyclyl may be optionally substituted with one or more $R_{40}$'s;

$R_{26}$ is halo, —OH, alkyl, alkyloxy, alkylthio, cyano, =O, —$NR_{29}R_{30}$, aryl, heteroaryl, heterocyclyl, haloalkyl, haloalkyloxy, —$CONR_{46}R_{46}$, alkenyl, arylalkyloxy, alkynyl, —$COR_{46}$, —$COOR_{46}$, —$OCOR_{46}$, —$OCOOR_{46}$, or —$OCONR_{46}R_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, —$NR_{29}R_{30}$, aryl, heteroaryl, heterocyclyl, haloalkyl, haloalkyloxy, alkenyl, arylalkyloxy, —$CONR_{46}R_{46}$, =O, alkynyl, —$COR_{46}$, —$COOR_{46}$, —$OCOR_{46}$, —$OCOOR_{46}$ or —$OCONR_{46}R_{46}$, wherein the alkyl, aryl, heteroaryl, or heterocyclyl may be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, alkynyl, or —$COR_{46}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$, cycloalkyl or —$CONR_{46}R_{46}$, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, —$CONR_{46}R_{46}$, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{47}$'s;

$R_{47}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 2;

s is 0 to 1; and p is 1 or 2.

In one embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s; or (b) a 5- to 10-membered nitrogen or oxygen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{16}$;

B is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$; or (b) a 6- to 10-membered nitrogen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NHR_3$, —$R_7$ or —$CH_2R_8$;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, alkylthio, cyano, —$NR_{29}R_{30}$, aryl, heteroaryl, heterocyclyl, haloalkyl, haloalkyloxy, —$COR_{46}$, =O, —$COOR_{46}$, —$OCOR_{46}$ or —$OCOOR_{46}$, wherein the alkyl, aryl, heteroaryl or heterocyclyl may be optionally substituted with one or more $R_{40}$'s;

$R_{26}$ is halo, —OH, alkyl, alkyloxy, alkylthio, cyano, =O, —$NR_{29}R_{30}$, aryl, heteroaryl, heterocyclyl, haloalkyl, haloalkyloxy, —$CONR_{46}R_{46}$, alkenyl, arylalkyloxy, alkynyl, —$COR_{46}$, —$COOR_{46}$, —$OCOR_{46}$, —$OCOOR_{46}$, or —$OCONR_{46}R_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, —$NR_{29}R_{30}$, aryl, heteroaryl, heterocyclyl, haloalkyl, haloalkyloxy, alkenyl, arylalkyloxy, —$CONR_{46}R_{46}$, =O, alkynyl, —$COR_{46}$, —$COOR_{46}$, —$OCOR_{46}$, —$OCOOR_{46}$ or —$OCONR_{46}R_{46}$, wherein the alkyl, aryl, heteroaryl, or heterocyclyl may be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl or alkynyl, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$, cycloalkyl or —$CONR_{46}R_{46}$, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, —$CONR_{46}R_{46}$, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{47}$'s;

$R_{47}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl, cycloalkyl or heteroaryl;

r is 0 to 2;

s is 0 to 1; and p is 1 or 2.

In another embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s; or (b) a 5- to 10-membered nitrogen or oxygen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo ($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{16}$;

B is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$; or (b) a 6- to 10-membered nitrogen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NHR_3$, —$R_7$ or —$CH_2R_8$;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, cyano, —$NR_{29}R_{30}$, aryl, heteroaryl, heterocyclyl, haloalkyl, haloalkyloxy, —$COR_{46}$, =O, —$COOR_{46}$, or —$OCOR_{46}$, wherein the alkyl, aryl, heteroaryl or heterocyclyl may be optionally substituted with one or more $R_{40}$'s;

$R_{26}$ is halo, —OH, alkyl, alkyloxy, alkylthio, cyano, =O, —$NR_{29}R_{30}$, aryl, heteroaryl, heterocyclyl, haloalkyl, haloalkyloxy, alkenyl, arylalkyloxy, alkynyl, —$COR_{46}$, —$COOR_{46}$, —$OCOR_{46}$, or —$OCOOR_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, —$NR_{29}R_{30}$, aryl, heteroaryl, heterocyclyl, haloalkyl, haloalkyloxy, alkenyl, arylalkyloxy, =O, alkynyl, —$COR_{46}$, —$COOR_{46}$, —$OCOR_{46}$ or —$OCOOR_{46}$, wherein the alkyl, aryl, heteroaryl, or heterocyclyl may be optionally substituted with one or more $R_{40}$'s;

$R_{29}$ and $R_{30}$ are independently hydrogen, —[(C=O)$O_r$]$_s$aryl, —[(C=O)$O_r$]$_s$alkenyl, —[(C=O)$O_r$]$_s$alkyl or heterocyclyl, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$ or cycloalkyl, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl, cycloalkyl or heteroaryl, wherein the alkyl, aryl, cycloalkyl or heteroaryl may be optionally substituted with one or more $R_{47}$'s;

$R_{47}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl or heteroaryl;

r is 0 to 2;

s is 0 to 1; and p is 1 or 2.

In yet another embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN)$NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or any two adjacent substituents may join together to form a 4- to 8-membered ring, which optionally may contain 1-4 heteroatoms selected from N, O, and S and be optionally substituted with one or more $R_{40}$'s; or (b) a 6-membered nitrogen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —NHC(CN)$NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{16}$;

B is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —NHC(CN)$NHR_{46}$, and 20) —$CONR_{46}R_{46}$; or (b) a 6-membered nitrogen containing heteroaryl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —NHC(CN)$NHR_{46}$, and 20) —$CONR_{46}R_{46}$;

C is alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13)

—$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NHR_3$, —$R_7$ or —$CH_2R_8$;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, cyano, —$NR_{29}R_{30}$, heteroaryl, heterocyclyl, haloalkyl, haloalkyloxy, —$COR_{46}$, =O or —$COOR_{46}$, wherein the alkyl, heteroaryl or heterocyclyl may be optionally substituted with one or more $R_{40}$'s;

$R_{26}$ is halo, —OH, alkyl, alkyloxy, alkylthio, cyano, aryl, heteroaryl, heterocyclyl, haloalkyl, haloalkyloxy, alkenyl, arylalkyloxy, alkynyl, —$COR_{46}$ or —$COOR_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, aryl, heteroaryl, heterocyclyl, haloalkyl, haloalkyloxy, alkenyl, arylalkyloxy, alkynyl, —$COR_{46}$ or —$COOR_{46}$, wherein the alkyl, aryl, heteroaryl, or heterocyclyl may be optionally substituted with one or more $R_{40}$'s;

$R_{29}$ and $R_{30}$ are independently hydrogen, —$[(C=O)O_r]_s$aryl, —$[(C=O)O_r]_s$alkyl or heterocyclyl, wherein the aryl, alkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$ or cycloalkyl, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl or heteroaryl, wherein the alkyl, aryl or heteroaryl may be optionally substituted with one or more $R_{47}$'s;

$R_{47}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, cycloalkylalkyl, —$COR_{49}$ or —$COOR_{49}$;

$R_{49}$ and $R_{50}$, at each occurrence, are independently hydrogen, alkyl or aryl;

r is 0 to 2;

s is 0 to 1; and p is 1 or 2.

In still yet another embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$; or (b) pyridyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) =O, 17) —$S(O)_pR_{46}$, 18) —$SO_2NHR_{46}$, 19) —$COOR_{46}$, 20) —$NHC(CN)NHR_{46}$, 21) —$CONR_{46}R_{46}$, 22) ($C_2$-$C_6$)-alkynyl, which may be optionally substituted with one or more $R_{40}$'s, 23) ($C_2$-$C_6$)-alkenyl, which may be optionally substituted with one or more $R_{40}$'s, 24) —$OCOR_{46}$, 25) —$OCOOR_{46}$, or 26) —$OCONR_{46}R_{46}$;

B is phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) arylalkyl, which may be optionally substituted with one or more $R_{40}$'s, 10) heteroaryl, which may be optionally substituted with one or more $R_{40}$'s, 11) heteroarylalkyl, which may be optionally substituted with one or more $R_{40}$'s, 12) heterocyclyl, which may be optionally substituted with one or more $R_{40}$'s, 13) heterocyclylalkyl, which may be optionally substituted with one or more $R_{40}$'s, 14) halo($C_1$-$C_6$)alkyl, 15) —$COR_{46}$, 16) —$S(O)_pR_{46}$, 17) —$SO_2NHR_{46}$, 18) —$COOR_{46}$, 19) —$NHC(CN)NHR_{46}$, and 20) —$CONR_{46}R_{46}$;

C is alkyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) —$NR_{29}R_{30}$, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) —$COR_{46}$, 13) —$CONR_{46}R_{46}$, 14) —$S(O)_pR_{46}$, 15) —$SO_2NHR_{46}$, 16) —$COOR_{46}$, and 17) —$NHC(CN)NHR_{46}$;

$R_1$ is —$C(O)R_3$, —$C(O)NHR_3$, —$R_7$ or —$CH_2R_8$;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, cyano, —$NR_{29}R_{30}$, heteroaryl, heterocyclyl, haloalkyl, haloalkyloxy, —$COR_{46}$ or —$COOR_{46}$, wherein the alkyl, heteroaryl or heterocyclyl may be optionally substituted with one or more $R_{40}$'s;

$R_{26}$ is halo, —OH, alkyl, alkyloxy, alkylthio, cyano, aryl, heteroaryl, heterocyclyl, haloalkyl, haloalkyloxy, alkenyl, arylalkyloxy, alkynyl, —$COR_{46}$ or —$COOR_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, aryl, heteroaryl, heterocyclyl, haloalkyl, haloalkyloxy, alkenyl, arylalkyloxy, alkynyl, —$COR_{46}$ or —$COOR_{46}$, wherein the alkyl, aryl, heteroaryl, or heterocyclyl may be optionally substituted with one or more $R_{40}$'s;

$R_{29}$ and $R_{30}$ are independently hydrogen, —$[(C{=}O)O_r]_s$aryl or —$[(C{=}O)O_r]_s$alkyl, wherein the aryl or alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{40}$ is halo, —$OR_{46}$, alkyl, alkyloxy, alkylthio, cyano, —$NR_{49}R_{50}$, aryl, heteroaryl, heterocyclyl, haloalkyl, haloalkyloxy, alkenyl, arylalkyloxy, alkynyl, —$COR_{46}$, —$COOR_{46}$ or cycloalkyl, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, cycloalkylalkyl, —$COR_{46}$ or —$COOR_{46}$;

$R_{46}$, at each occurrence, is independently hydrogen, alkyl, aryl or heteroaryl, wherein the alkyl, aryl or heteroaryl may be optionally substituted with one or more $R_{47}$'s;

$R_{47}$ is halo, —OH, alkyl, alkyloxy, alkylthio, cyano, —$NR_{49}R_{50}$, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, cycloalkylalkyl, —$COR_{49}$ or —$COOR_{49}$;

$R_{49}$ and $R_{50}$, at each occurrence, are independently hydrogen or alkyl;

r is 0 to 2;

s is 0 to 1; and p is 1 or 2.

In one embodiment, compounds of the present invention are provided wherein:

A is:

(a) phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) aryl, which may be optionally substituted with one or more $R_{40}$'s, 8) arylalkyl, which may be optionally substituted with one or more $R_{40}$'s, 9) heteroaryl, which may be optionally substituted with one or more $R_{40}$'s, 10) heteroarylalkyl, which may be optionally substituted with one or more $R_{40}$'s, 11) heterocyclyl, which may be optionally substituted with one or more $R_{40}$'s, 12) heterocyclylalkyl, which may be optionally substituted with one or more $R_{40}$'s, 13) halo($C_1$-$C_6$)alkyl, 14) —$COR_{46}$, 15) =O, 16) —$SO_2NHR_{46}$, 17) —$COOR_{46}$, 18) —$NHC(CN)NHR_{46}$, 19) —$CONR_{46}R_{46}$, 20) ($C_2$-$C_6$)-alkynyl, which may be optionally substituted with one or more $R_{40}$'s, 21) ($C_2$-$C_6$)-alkenyl, which may be optionally substituted with one or more $R_{40}$'s, 22) —$OCOR_{46}$, 23) —$OCOOR_{46}$, or 24) —$OCONR_{46}R_{46}$; or (b) pyridyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) aryl, which may be optionally substituted with one or more $R_{40}$'s, 8) arylalkyl, which may be optionally substituted with one or more $R_{40}$'s, 9) heteroaryl, which may be optionally substituted with one or more $R_{40}$'s, 10) heteroarylalkyl, which may be optionally substituted with one or more $R_{40}$'s, 11) heterocyclyl, which may be optionally substituted with one or more $R_{40}$'s, 12) heterocyclylalkyl, which may be optionally substituted with one or more $R_{40}$'s, 13) halo($C_1$-$C_6$)alkyl, 14) —$COR_{46}$, 15) =O, 16) —$SO_2NHR_{46}$, 17) —$COOR_{46}$, 18) —$NHC(CN)NHR_{46}$, 19) —$CONR_{46}R_{46}$, 20) ($C_2$-$C_6$)-alkynyl, which may be optionally substituted with one or more $R_{40}$'s, 21) ($C_2$-$C_6$)-alkenyl, which may be optionally substituted with one or more $R_{40}$'s, 22) —$OCOR_{46}$, 23) —$OCOOR_{46}$, or 24) —$OCONR_{46}R_{46}$;

B is phenyl, which is substituted with one or more substituents selected from the group consisting of: 1) halo, 2) ($C_1$-$C_6$)-alkyl, which may be optionally substituted with one or more $R_{40}$'s, 3) —$OR_{46}$, 4) ($C_1$-$C_6$)-alkylthio, 5) cyano, 6) nitro, 7) aryl, which may be optionally substituted with one or more $R_{40}$'s, 8) arylalkyl, which may be optionally substituted with one or more $R_{40}$'s, 9) heteroaryl, which may be optionally substituted with one or more $R_{40}$'s, 10) heteroarylalkyl, which may be optionally substituted with one or more $R_{40}$'s, 11) heterocyclyl, which may be optionally substituted with one or more $R_{40}$'s, 12) heterocyclylalkyl, which may be optionally substituted with one or more $R_{40}$'s, 13) halo($C_1$-$C_6$)alkyl, 14) —$COR_{46}$, 15) —$SO_2NHR_{46}$, 16) —$COOR_{46}$, 17) —$NHC(CN)NHR_{46}$, and 18) —$CONR_{46}R_{46}$;

C is methylphenyl, which may be optionally substituted with one or more $R_{40}$'s;

$R_1$ is —$C(O)R_3$, —$C(O)NHR_3$, —$R_7$ or —$CH_2R_8$;

$R_3$ is alkyl, aryl, cycloalkyl, heteroaryl, or heterocyclyl, other than heteroaryl, all of which may be optionally substituted with one or more $R_{26}$'s;

$R_7$ is independently aryl, cycloalkyl, heteroaryl or heterocyclyl, other than heteroaryl, wherein the aryl, cycloalkyl, heteroaryl or heterocyclyl may be optionally substituted with one or more $R_{26}$'s;

$R_8$ is independently alkyl, aryl, cycloalkyl, heteroaryl, or heterocyclyl, other than heteroaryl, wherein the alkyl, aryl, cycloalkyl, heteroaryl or heterocyclyl may be optionally substituted with one or more $R_{28}$'s;

$R_{14}$ is hydrogen or alkyl, wherein the alkyl may be optionally substituted with one or more $R_{24a}$'s;

$R_{24a}$, at each occurrence, is halo, alkyl, —$OR_{46}$, cyano, heteroaryl, heterocyclyl, haloalkyl, haloalkyloxy, —$COR_{46}$ or —$COOR_{46}$, wherein the alkyl, heteroaryl or heterocyclyl may be optionally substituted with one or more $R_{40}$'s;

$R_{26}$ is halo, —OH, alkyl, alkyloxy, alkylthio, cyano, aryl, heteroaryl, heterocyclyl, haloalkyl, haloalkyloxy, alkenyl, arylalkyloxy, alkynyl, —$COR_{46}$ or —$COOR_{46}$, wherein the alkyl, aryl, heteroaryl or heterocyclyl may be optionally substituted with one or more $R_{40}$'s;

$R_{28}$ is halo, —OH, alkyl, alkyloxy, alkylthio, cyano, aryl, heteroaryl, heterocyclyl, haloalkyl, haloalkyloxy, alkenyl, arylalkyloxy, alkynyl, —$COR_{46}$ or —$COOR_{46}$, wherein the alkyl, aryl, heteroaryl, or heterocyclyl may be optionally substituted with one or more $R_{40}$'s;

$R_{40}$ is halo, —$OR_{46}$, alkyl, alkyloxy, alkylthio, cyano, aryl, heteroaryl, heterocyclyl, haloalkyl, haloalkyloxy, alkenyl, arylalkyloxy, alkynyl, —$COR_{46}$, —$COOR_{46}$ or cycloalkyl, wherein the alkyl, aryl, heteroaryl, heterocyclyl or cycloalkyl may be optionally substituted with one or more $R_{41}$'s;

$R_{41}$ is halo, —OH, alkyl, alkyloxy, alkylthio, cyano, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl, or cycloalkylalkyl;

$R_{46}$, at each occurrence, is independently hydrogen, alkyl, aryl or heteroaryl, wherein the alkyl, aryl or heteroaryl may be optionally substituted with one or more $R_{47}$'s; and $R_{47}$ is halo, —OH, alkyl, alkyloxy, alkylthio, cyano, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl or cycloalkylalkyl.

In yet another embodiment, compounds of the present invention are provided wherein:

A is:

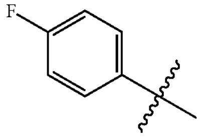
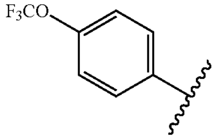
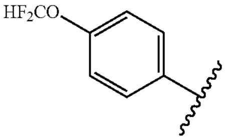
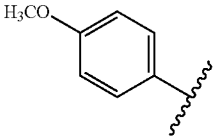
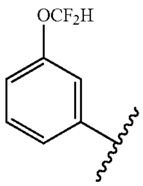
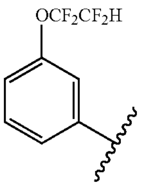
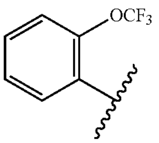
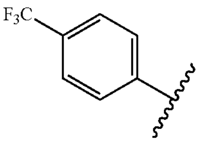
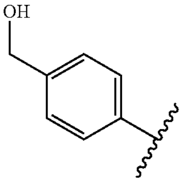

-continued

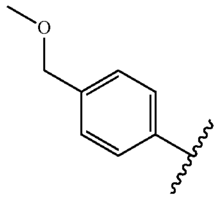
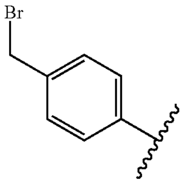
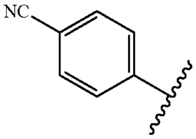
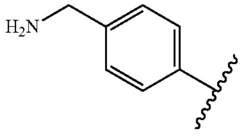
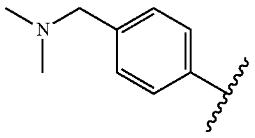
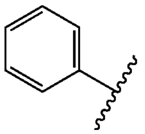
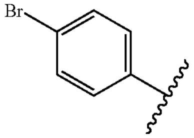
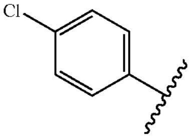
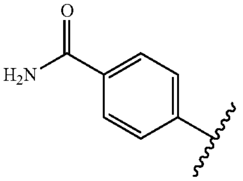
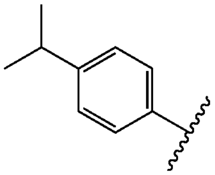
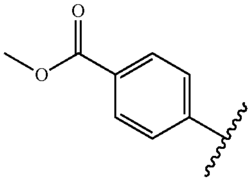
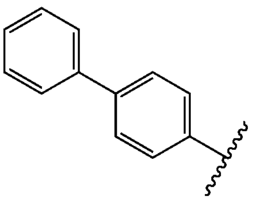
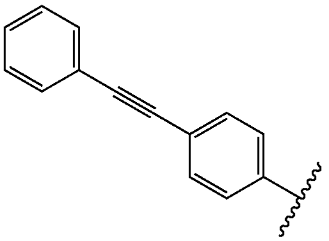
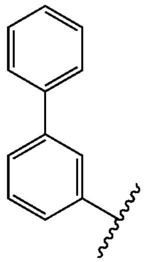
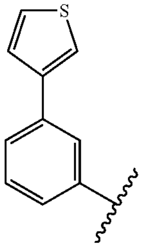
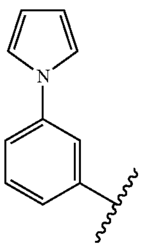
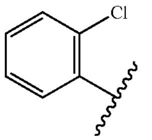
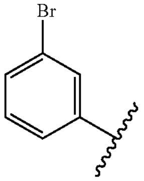
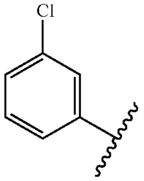
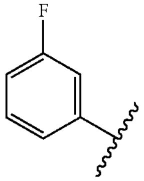

-continued
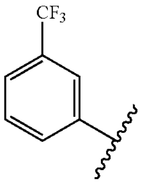
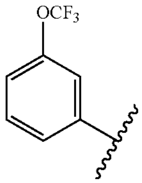
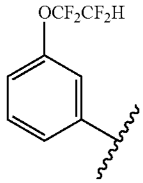
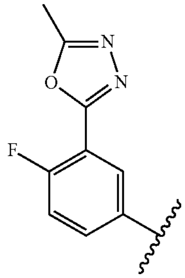
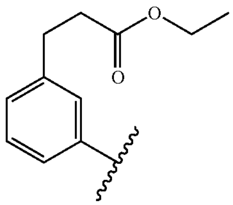
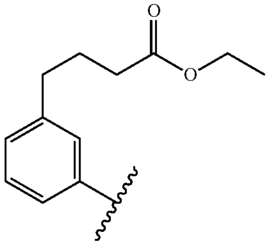
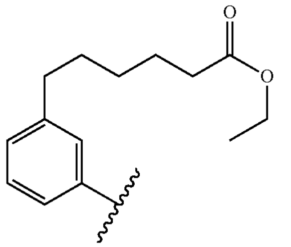
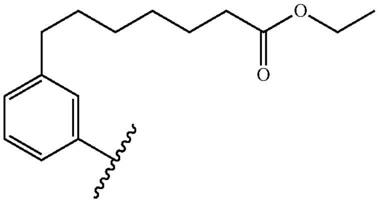
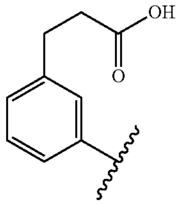
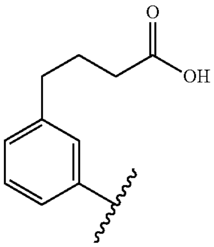
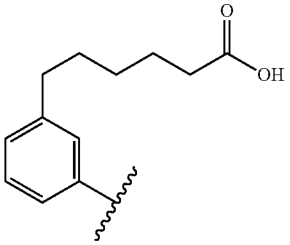
-continued
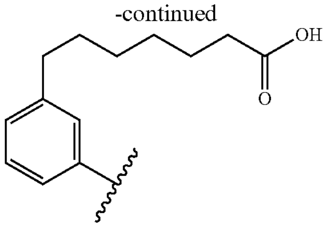
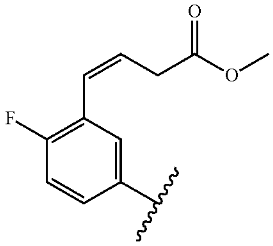
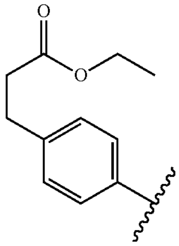
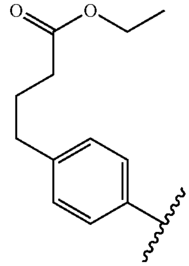
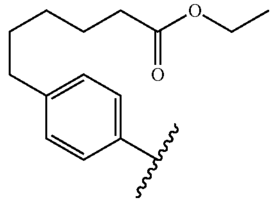
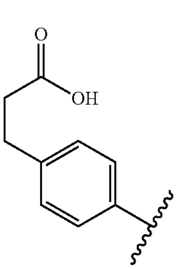
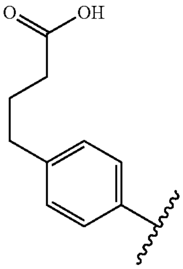
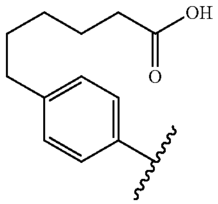
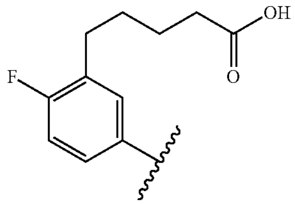
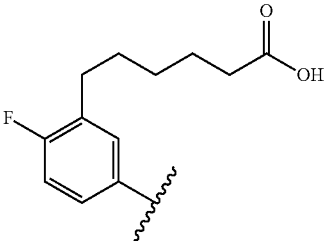
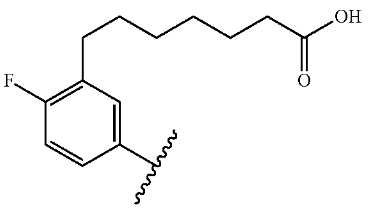

-continued
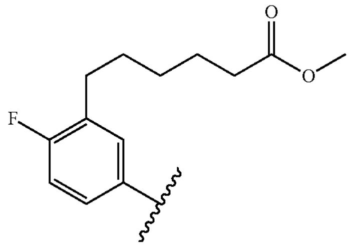
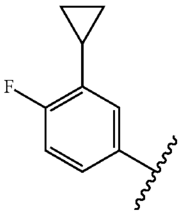
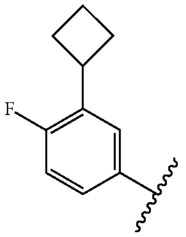
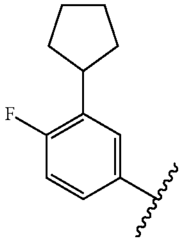
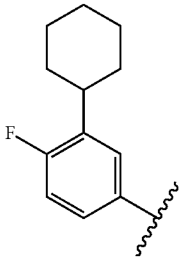
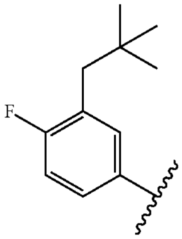
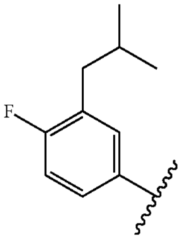
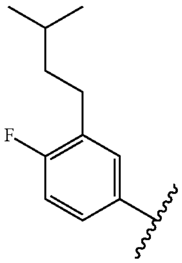
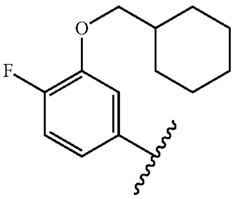
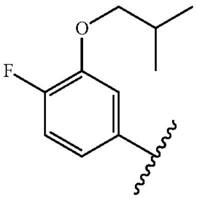
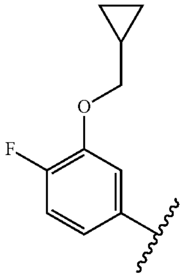
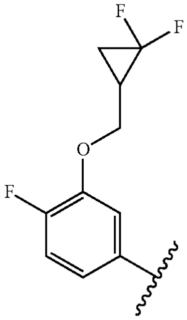
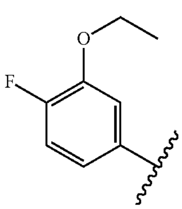
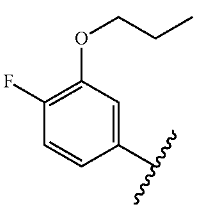
-continued
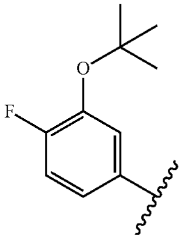
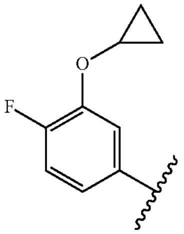
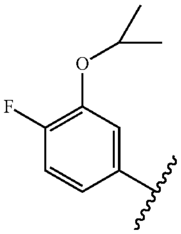
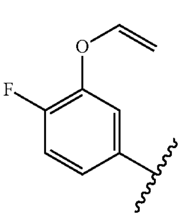
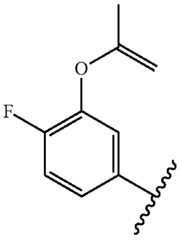
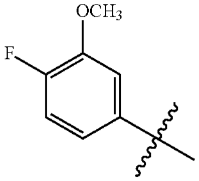
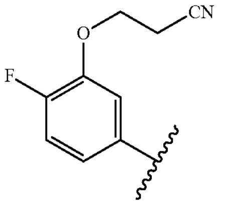
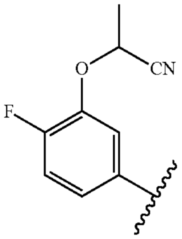
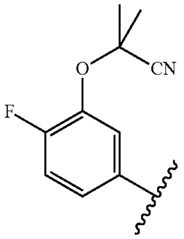
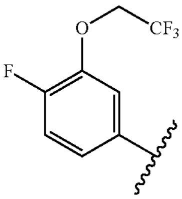
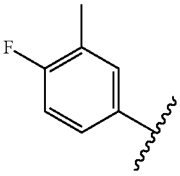
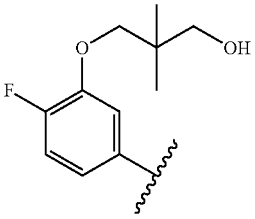
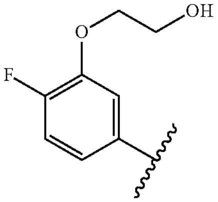
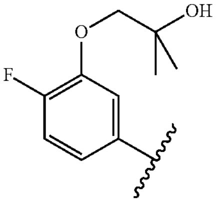
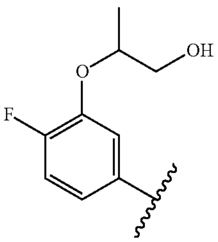
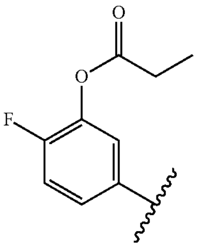

-continued
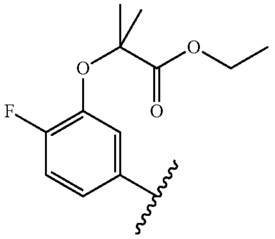
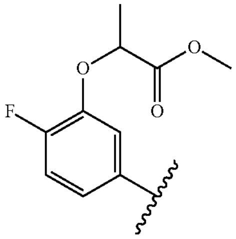
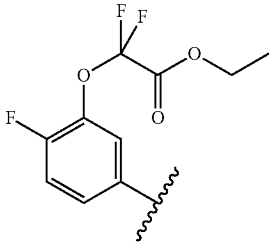
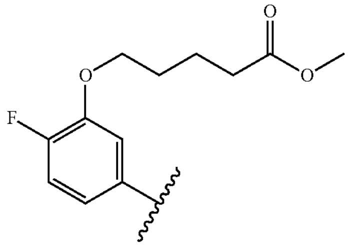
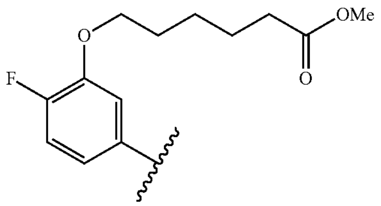
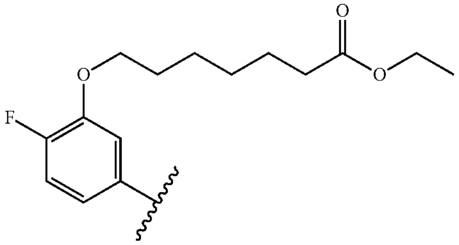
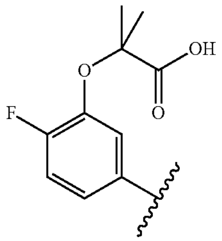
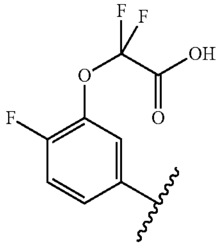
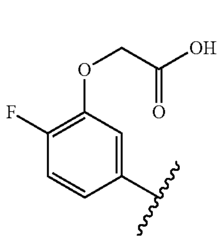
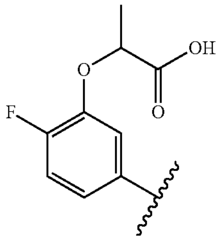
-continued
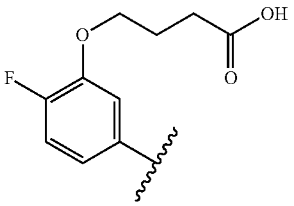
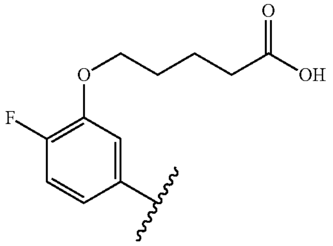
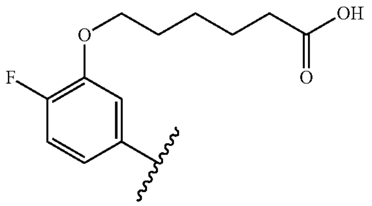
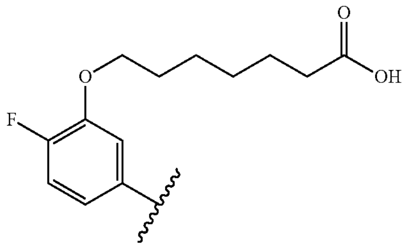
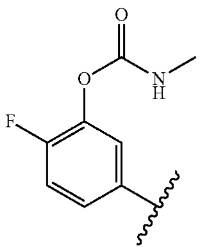
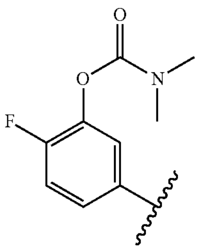
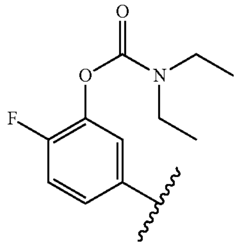
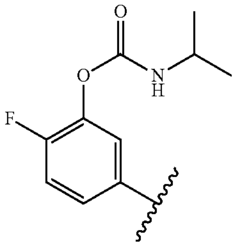
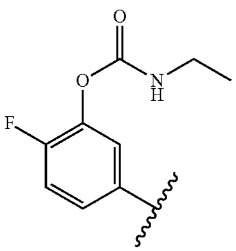
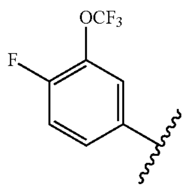

-continued
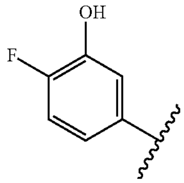
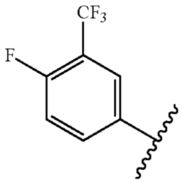
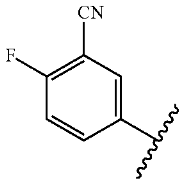
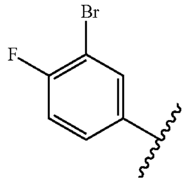
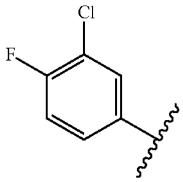
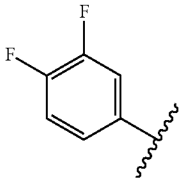
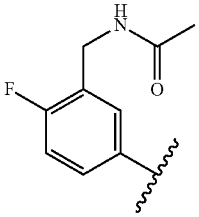
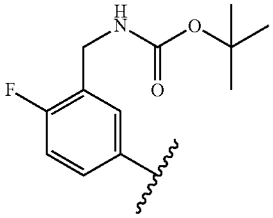
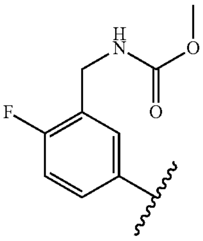
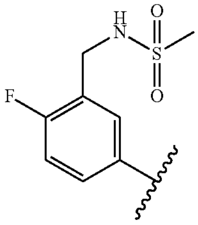
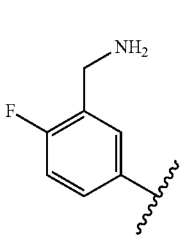
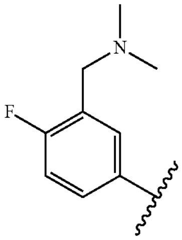
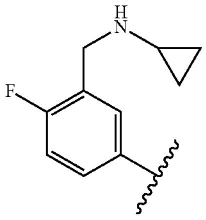
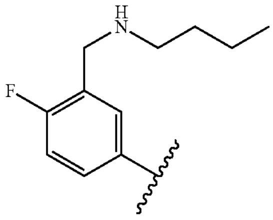
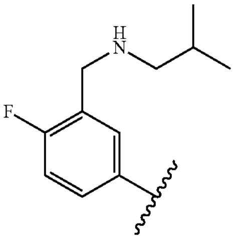
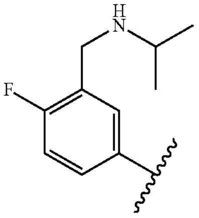
-continued
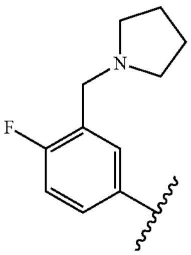
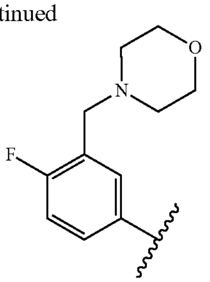
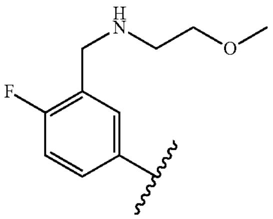
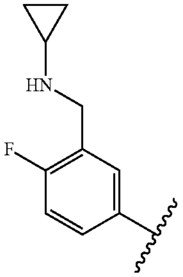
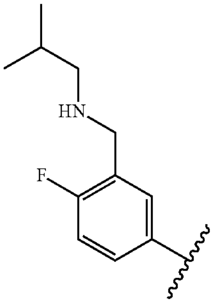
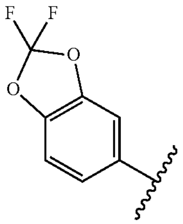
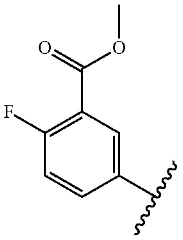
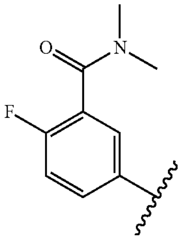
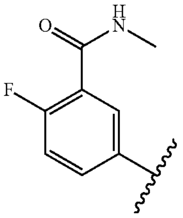
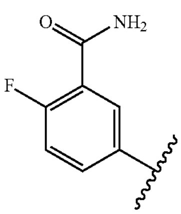
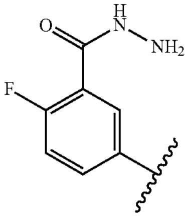
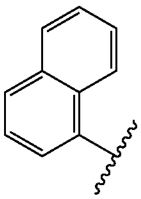
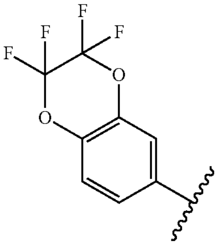
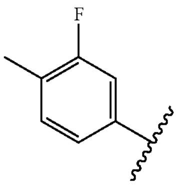
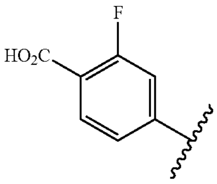
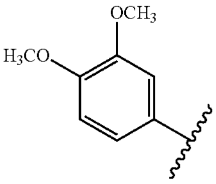

-continued
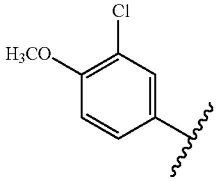
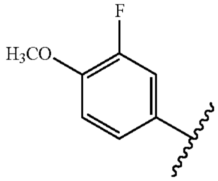
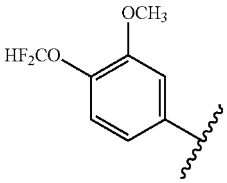
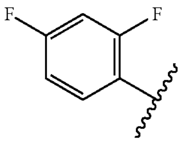
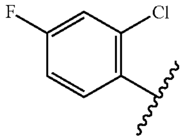
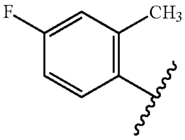
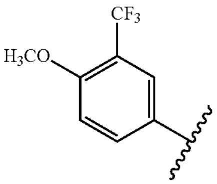
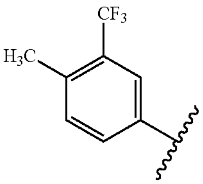
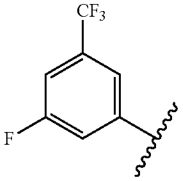
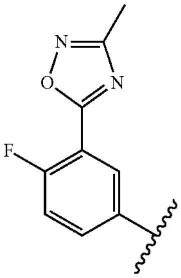
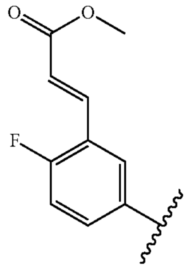
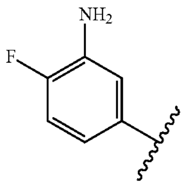
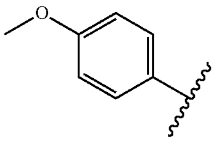
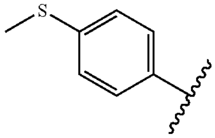
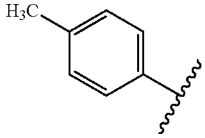
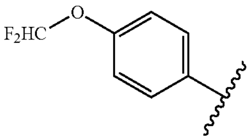
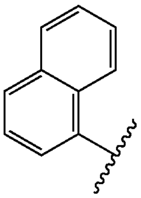
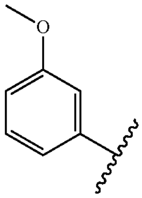
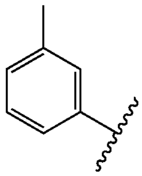
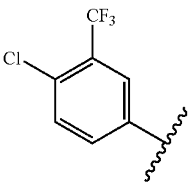
-continued
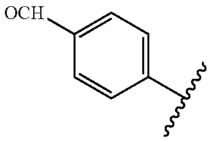
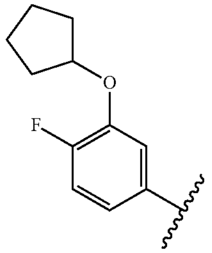
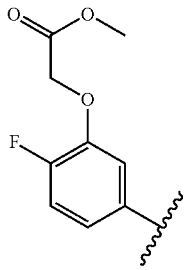
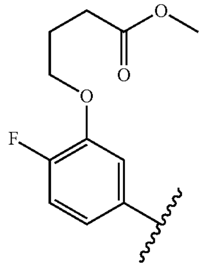
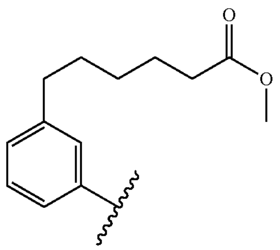
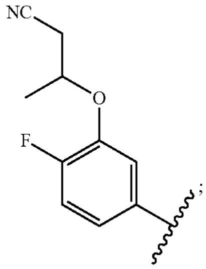
;
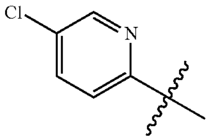
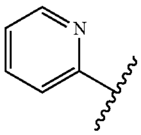
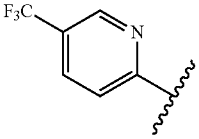
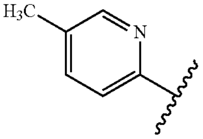
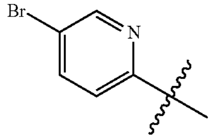
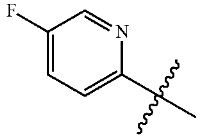
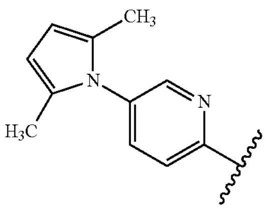
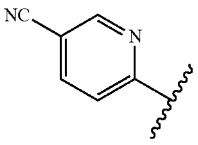
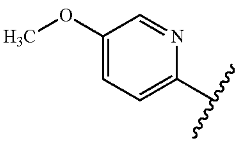
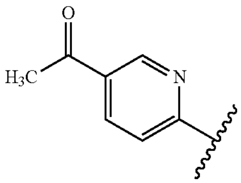
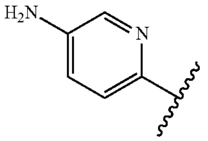

-continued
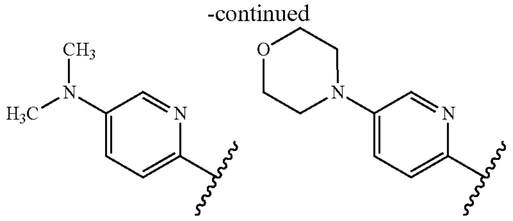
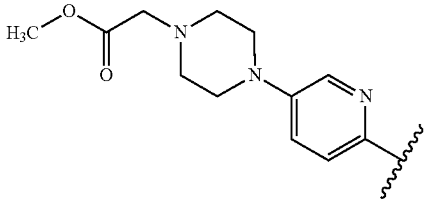
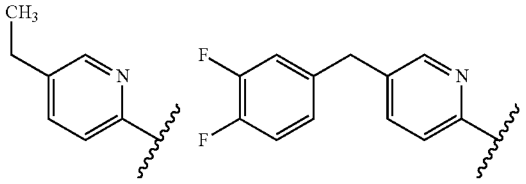
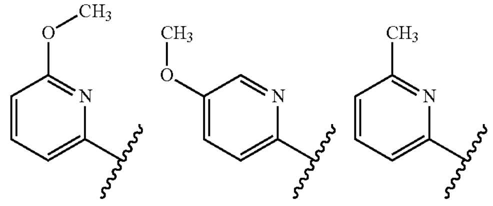
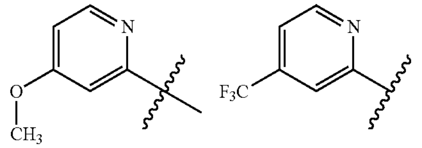
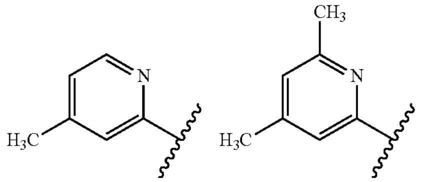
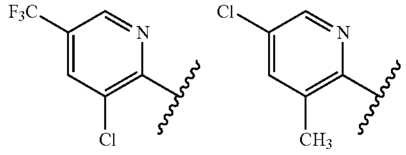
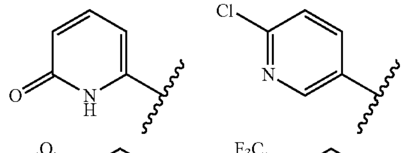
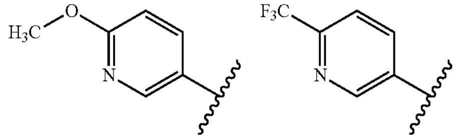
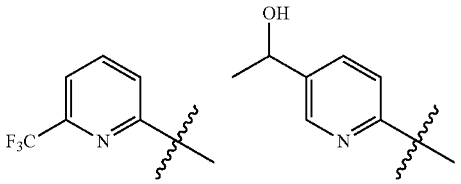
-continued
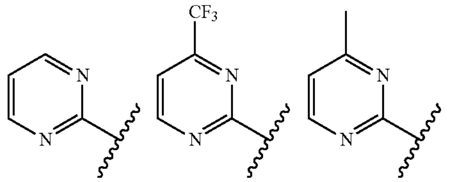
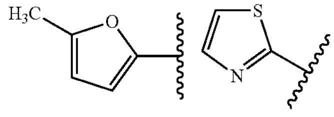
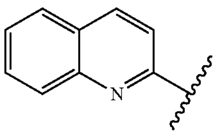
or
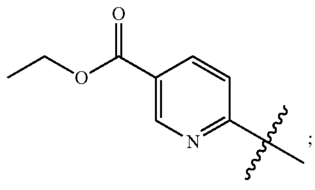
;
B is:
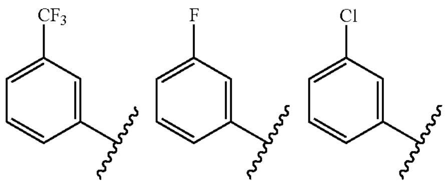
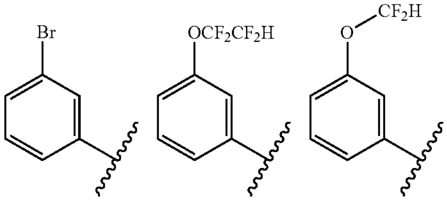
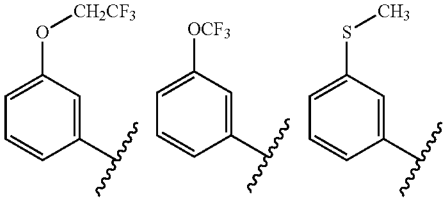
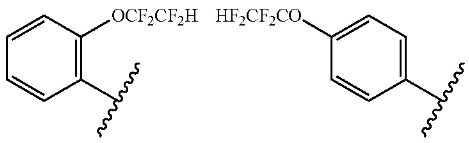
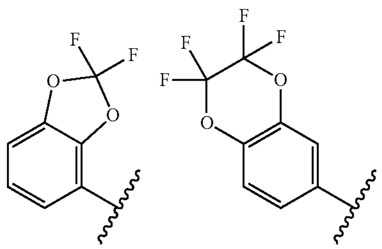

-continued
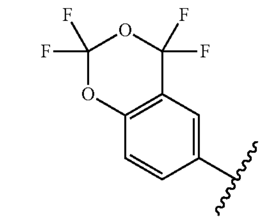
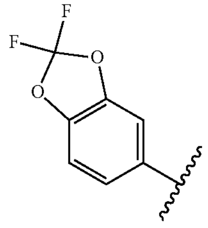
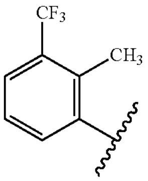
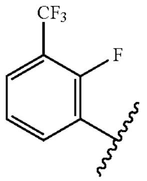
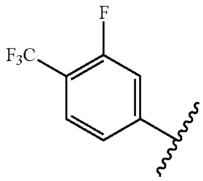
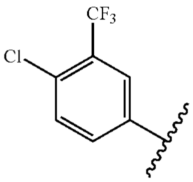
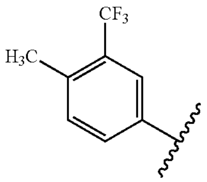
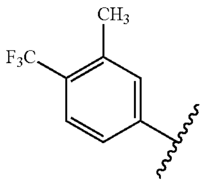
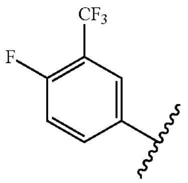
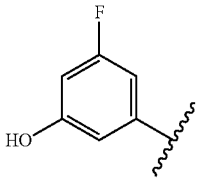
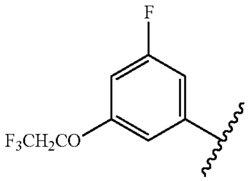
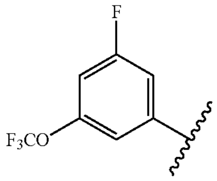
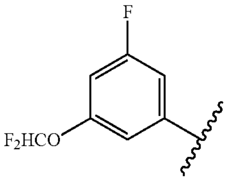
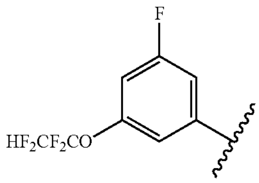
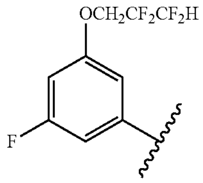
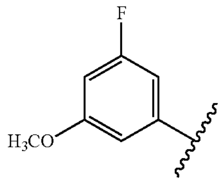
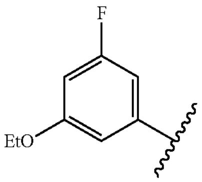
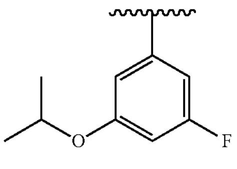
-continued
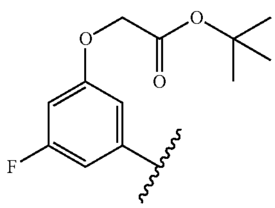
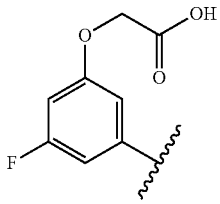
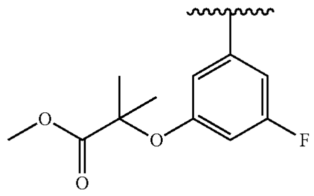
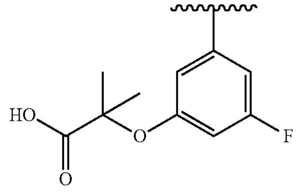
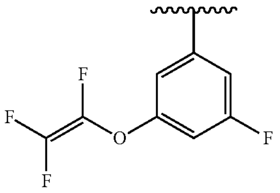
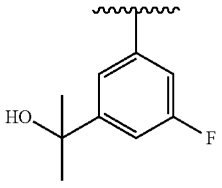
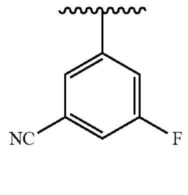
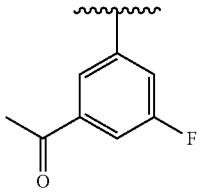
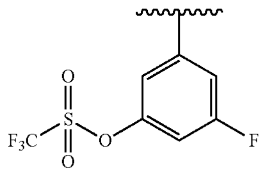
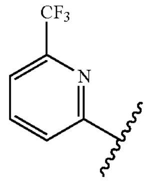
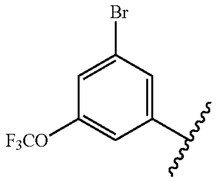
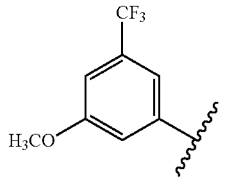
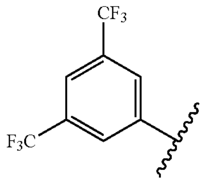
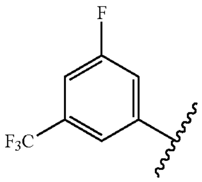
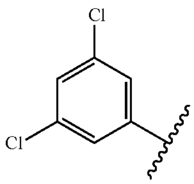
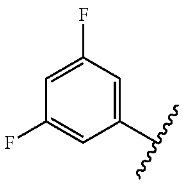
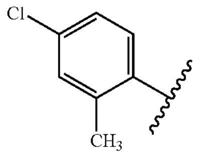
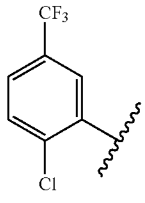
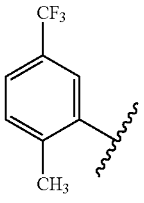

-continued
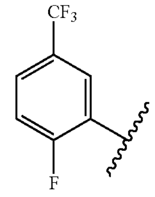
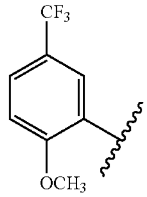
or
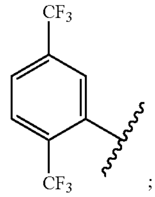
;
C is:
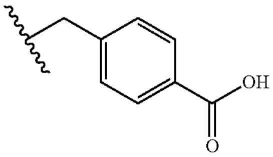
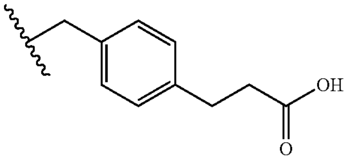
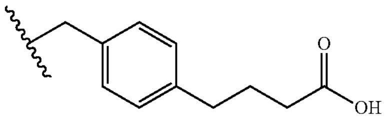
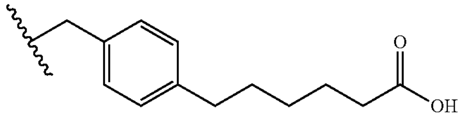
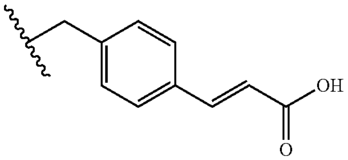
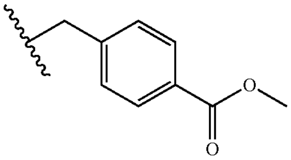
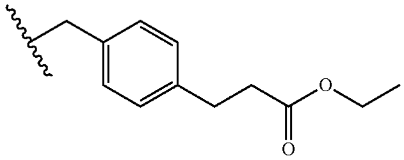
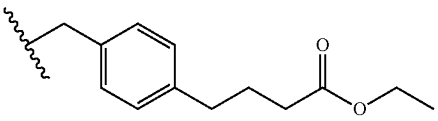
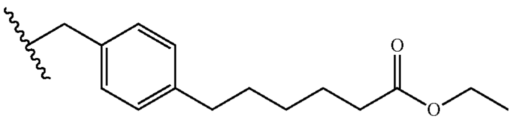
-continued
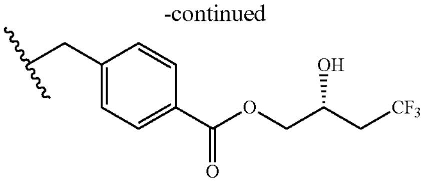
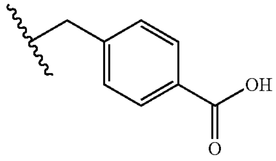
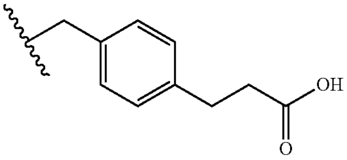
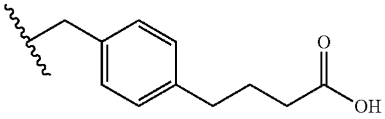
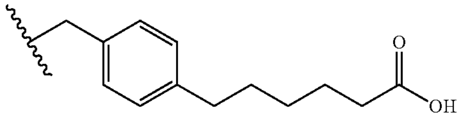
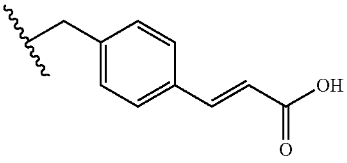
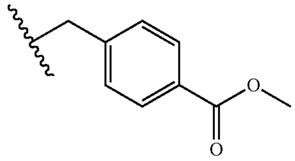
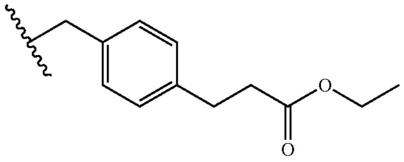
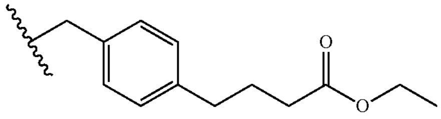
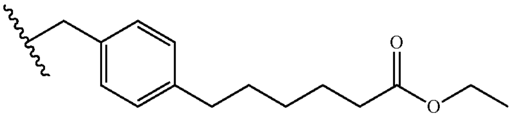
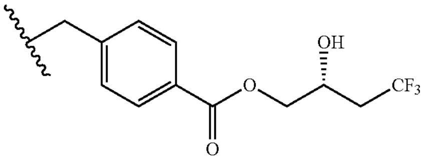
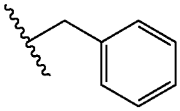
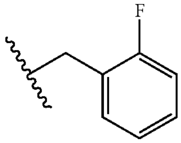
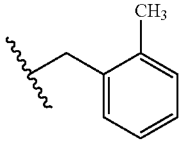

-continued
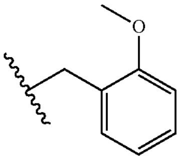
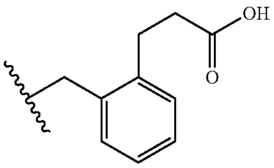
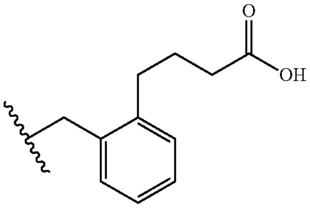
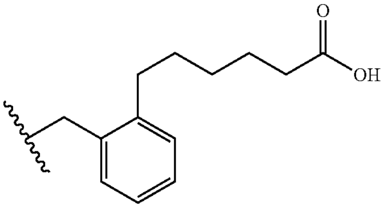
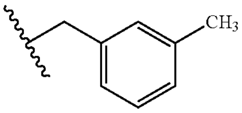
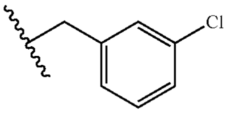
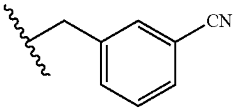
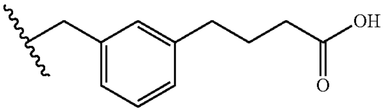
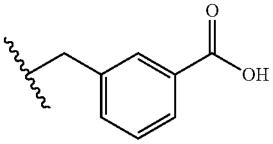
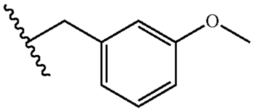
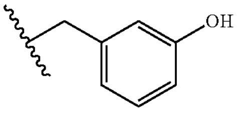
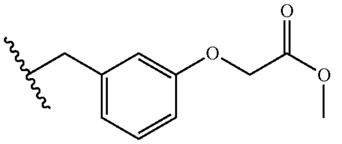
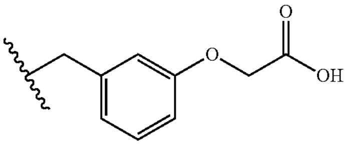
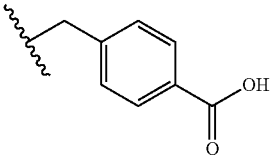
-continued
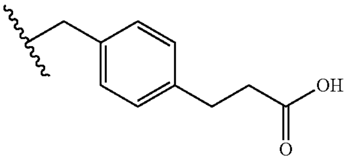
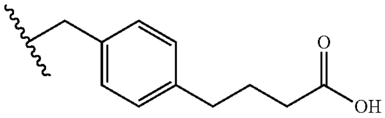
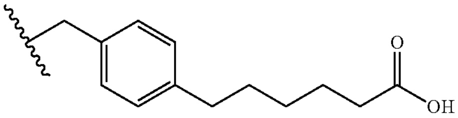
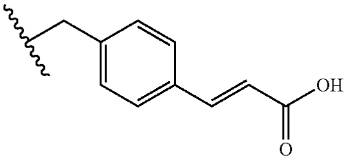
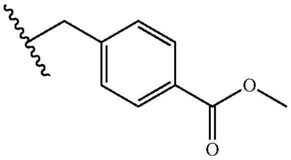
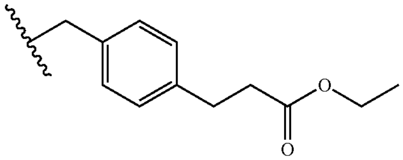
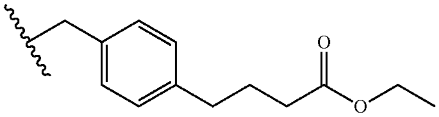
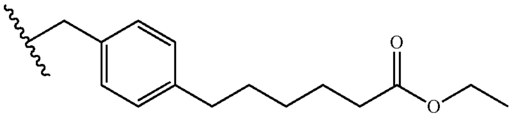
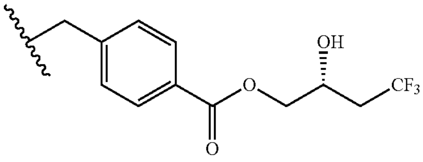
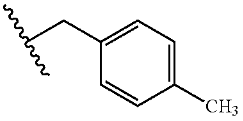
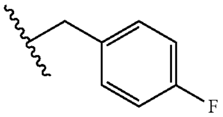
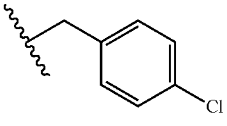
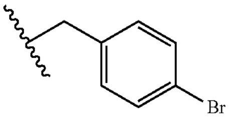
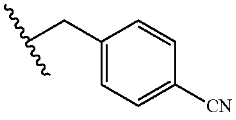
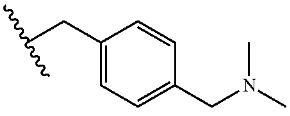

-continued
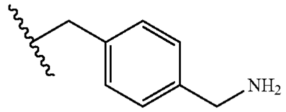
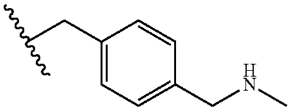
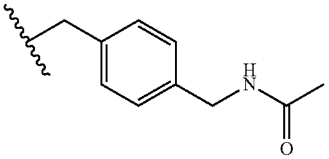
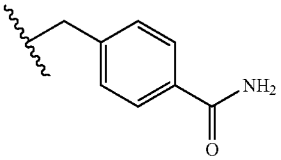
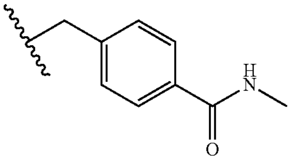
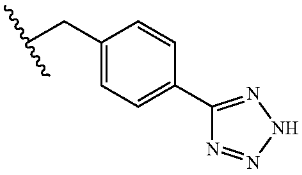
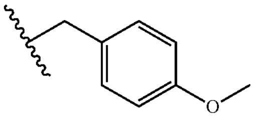
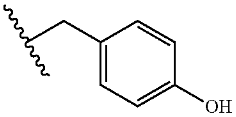
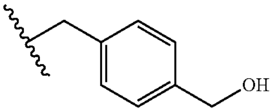
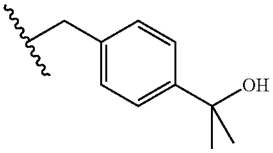
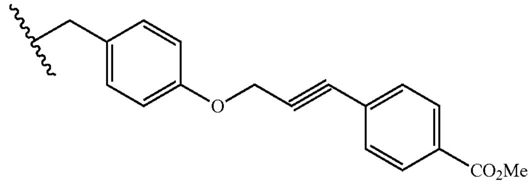
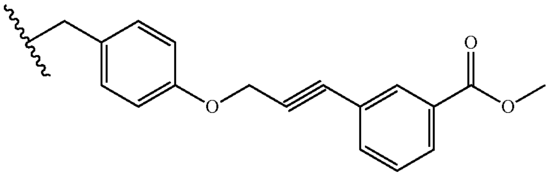
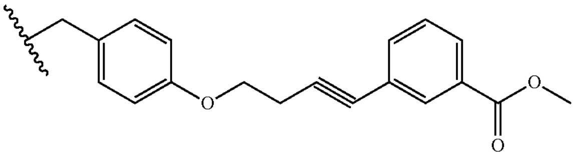
-continued
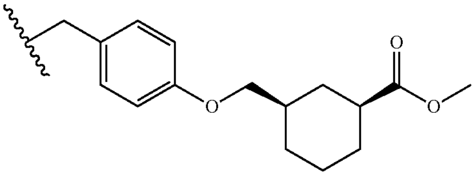
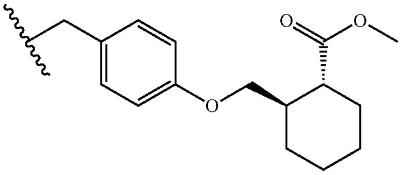
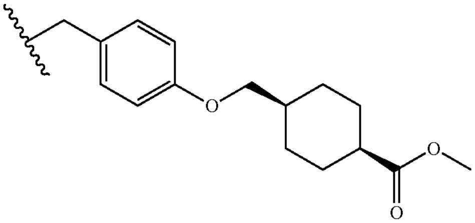
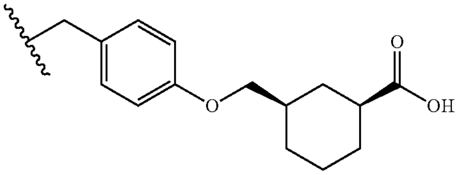
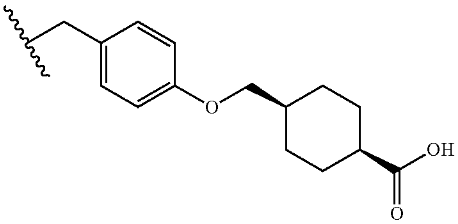
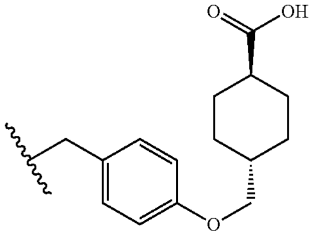
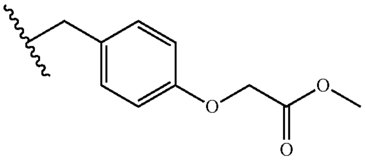
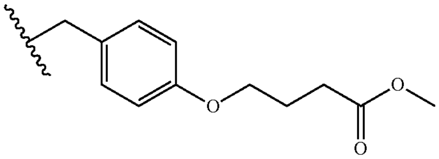
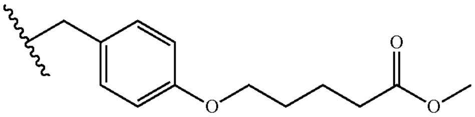

-continued
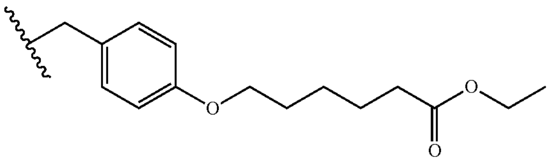
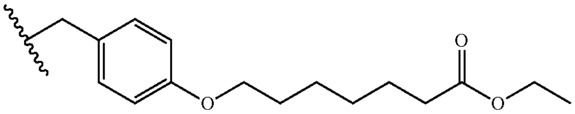
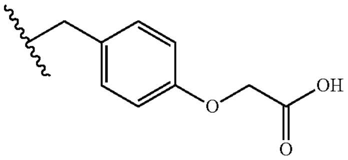
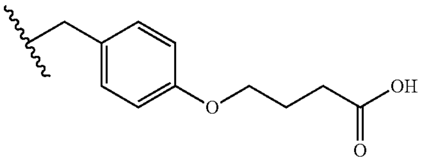
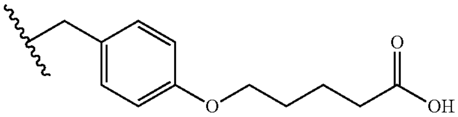
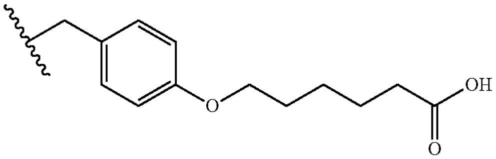
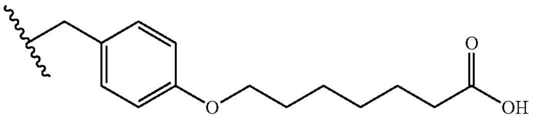
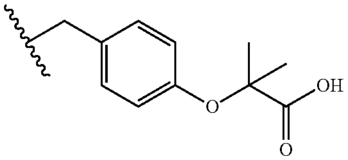
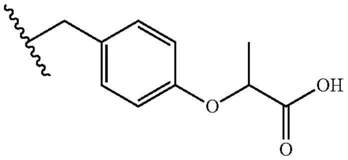
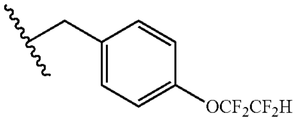
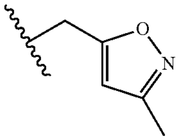
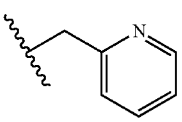
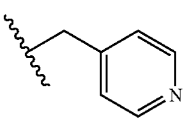
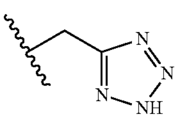
-continued
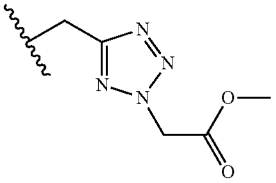
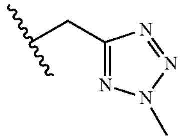
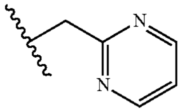
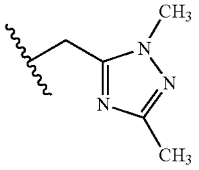
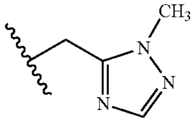
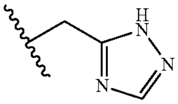
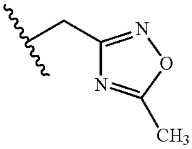
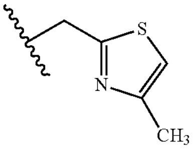
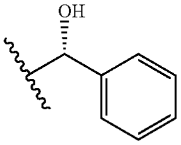
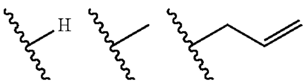
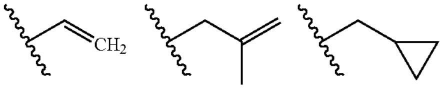
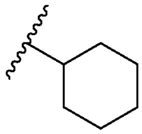
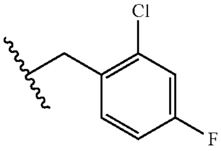
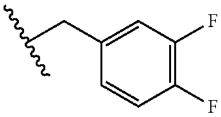
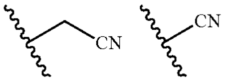
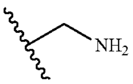
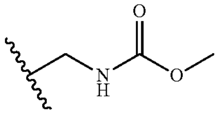
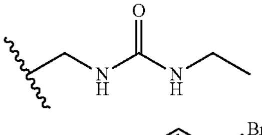
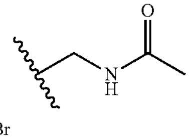
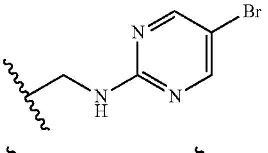
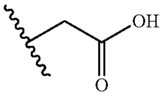
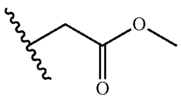
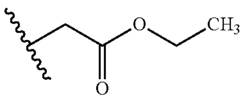
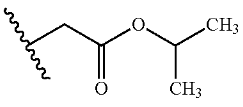
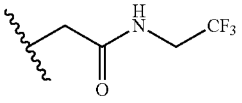

-continued
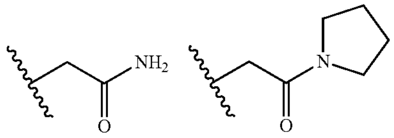
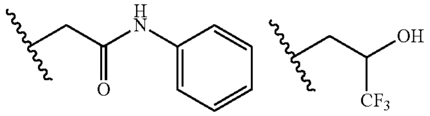
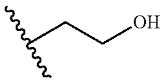
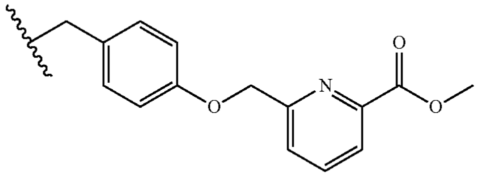
or
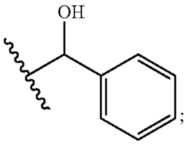
;
R₁ is:
(a) —C(O)$R_3$, wherein $R_3$ is:
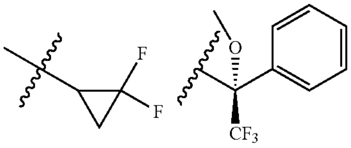
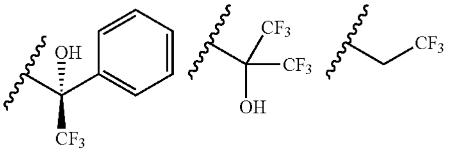
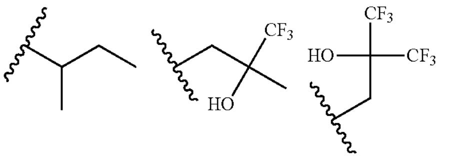
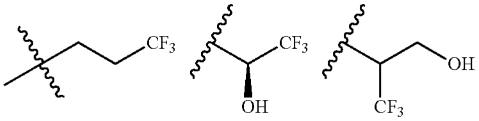
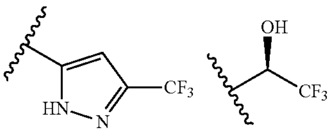
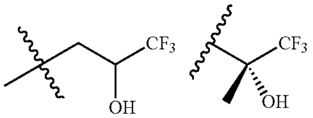
-continued
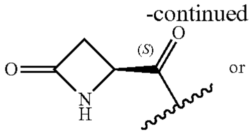
or
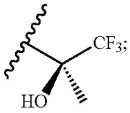
(b) —C(O)$NHR_3$, wherein $R_3$ is:
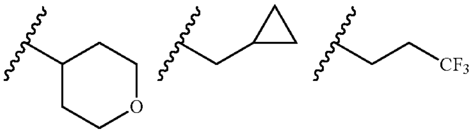
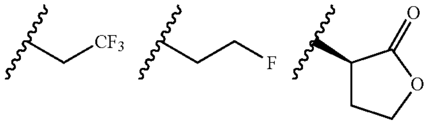
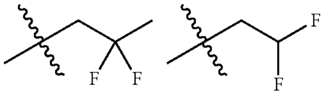
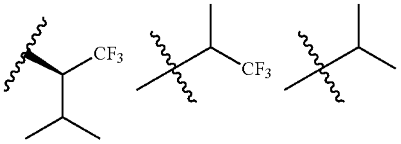
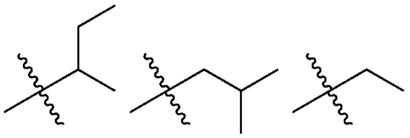
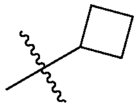
or
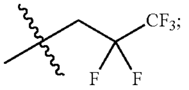
(c) —C(O)$OR_4$, wherein $R_4$ is:
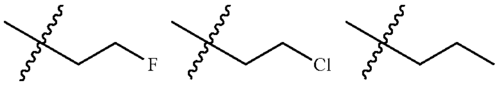
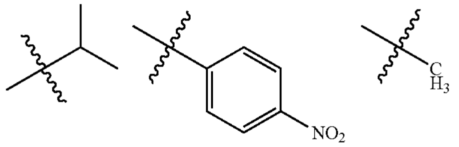
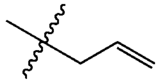
or
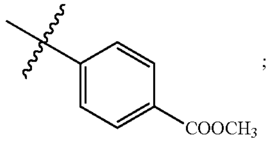
;
(d) —$CH_2R_8$, wherein $R_8$ is:
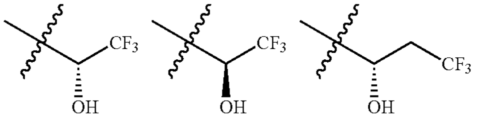

-continued
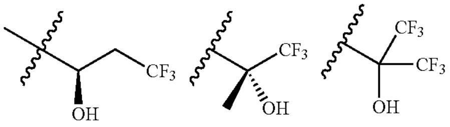
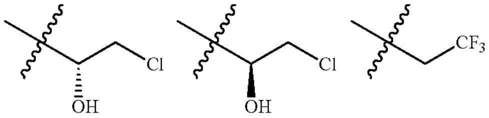
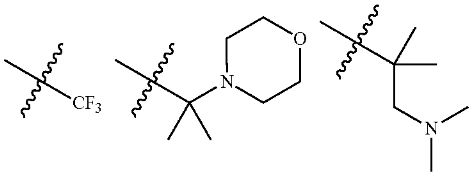
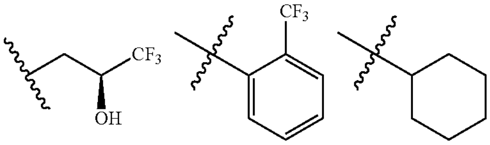
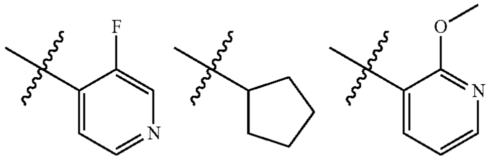
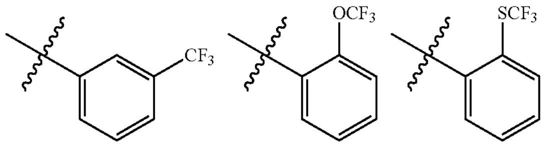
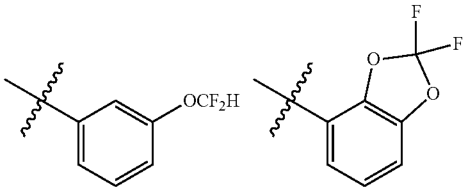
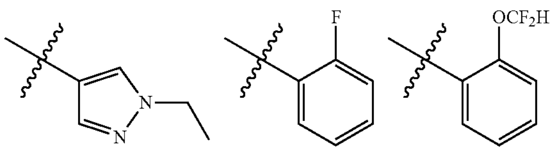
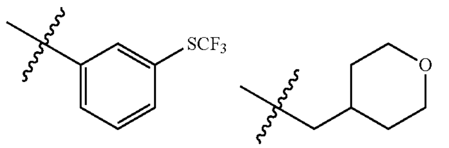
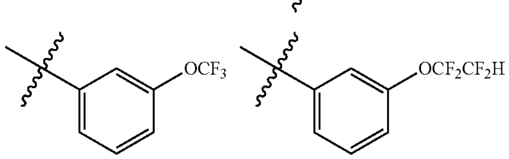
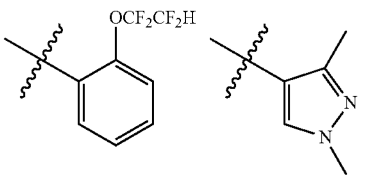
-continued
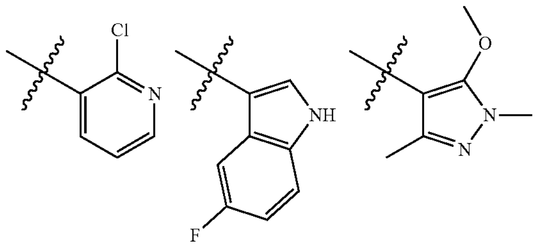
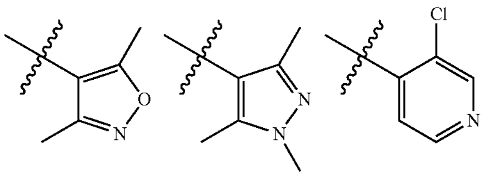
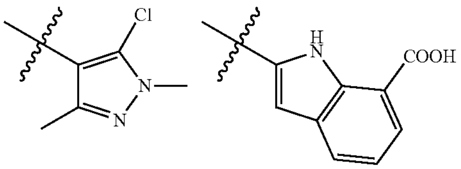
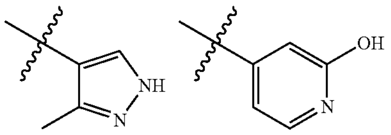
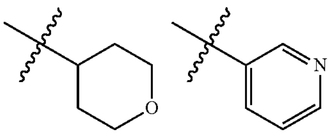
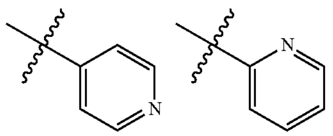
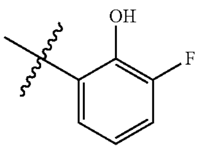
or
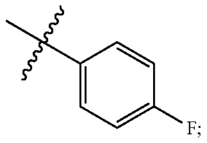
(e) —$SO_2R_5$, wherein $R_5$ is:
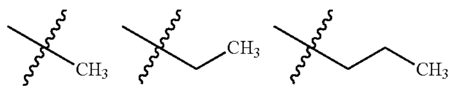
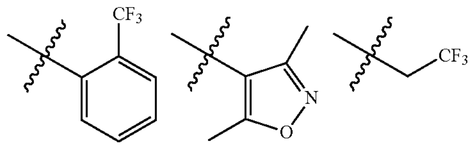
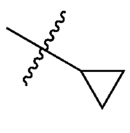
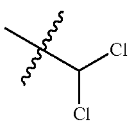
or
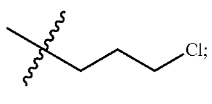

(f) —$SO_2NR_2R_3$, wherein $NR_2R_3$ is
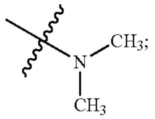 [SMILES: *N(C)C]
(g) —$R_7$, wherein $R_7$ is:
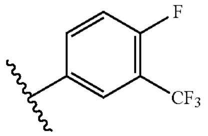 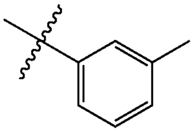
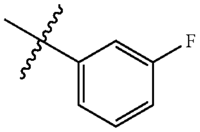 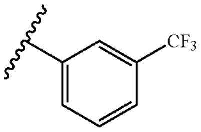
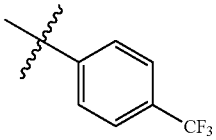 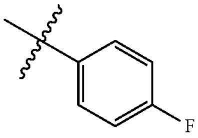
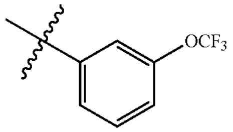 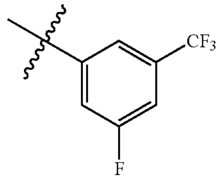
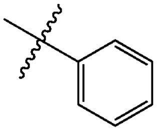 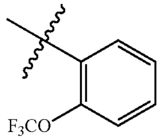
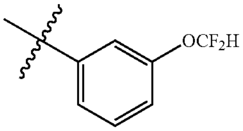 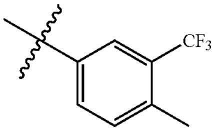
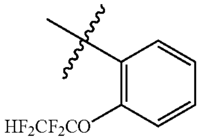 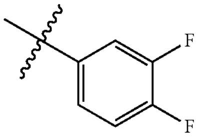
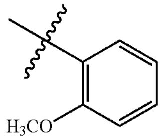 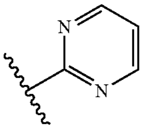 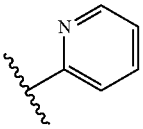
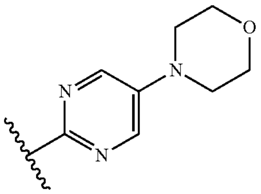
-continued
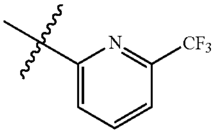 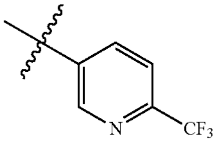
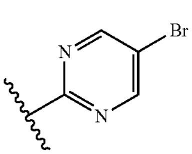 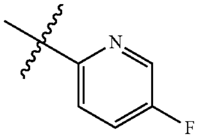 or
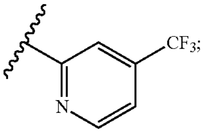
and
$R_{14}$ is H or
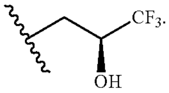 [SMILES: *C[C@H](O)C(F)(F)F]
In yet another embodiment, compounds of the present invention are provided wherein:
A is:
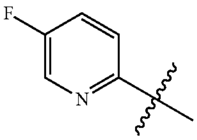 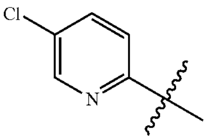
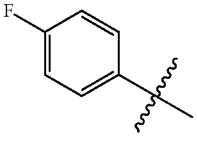 or 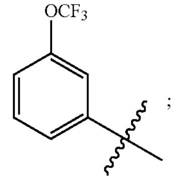 ;
B is:
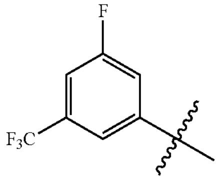 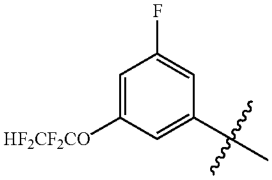 or
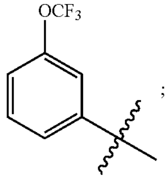 ;

C is:
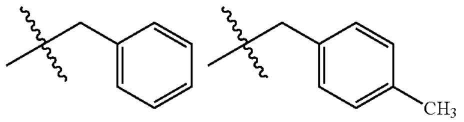
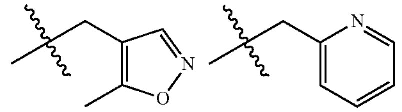
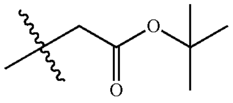
or
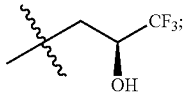
$R_1$ is:
(a) —$C(O)R_3$, wherein $R_3$ is:
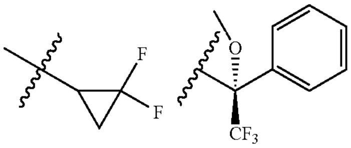
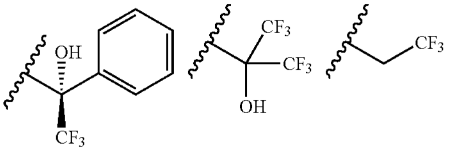
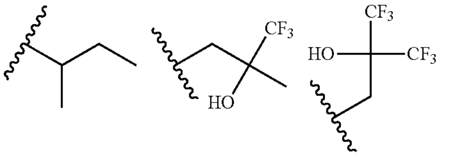
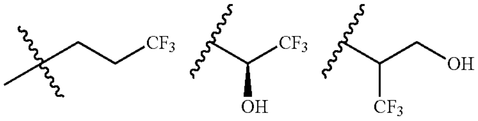
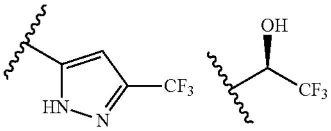
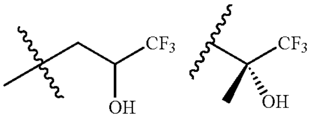
or
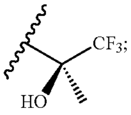
(b) —$C(O)NHR_3$, wherein $R_3$ is:
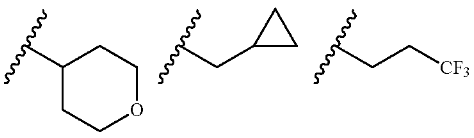
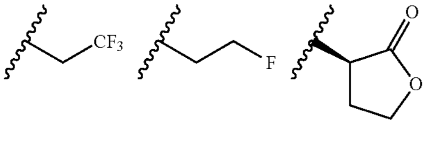
-continued
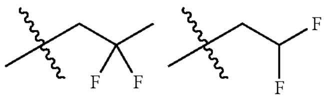
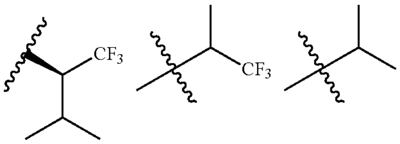
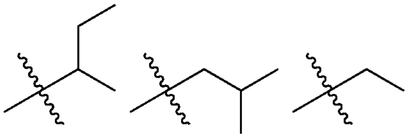
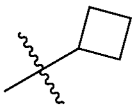
or
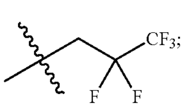
(c) —$C(O)OR_4$, wherein $R_4$ is:
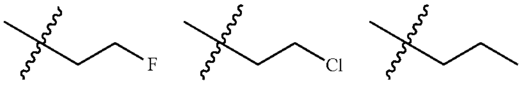
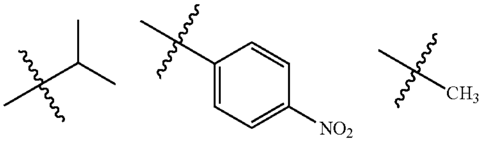
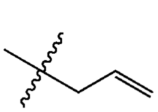
or
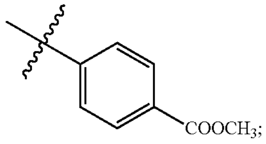
(d) —$CH_2R_8$, wherein $R_8$ is:
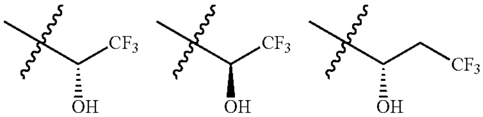
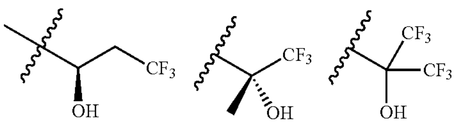
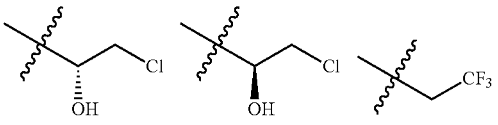
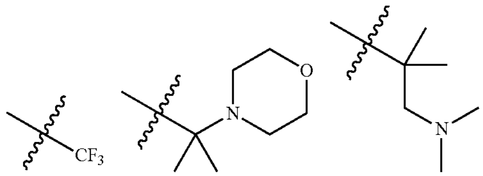

-continued
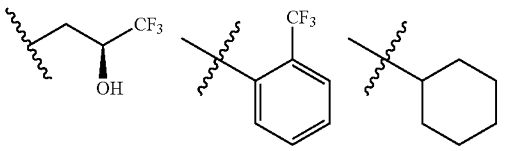
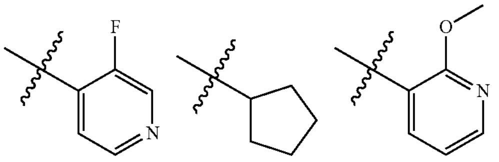
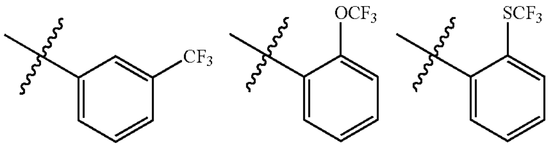
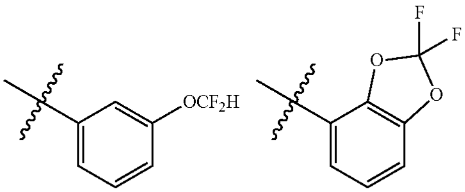
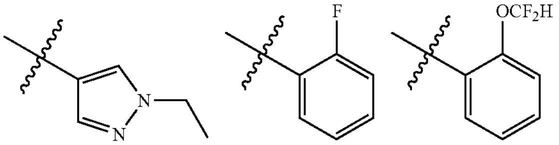
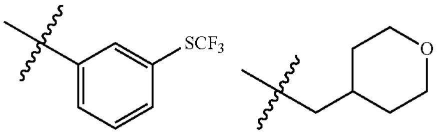
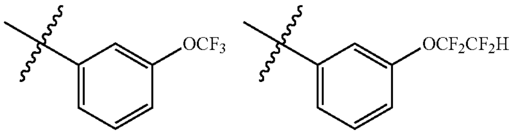
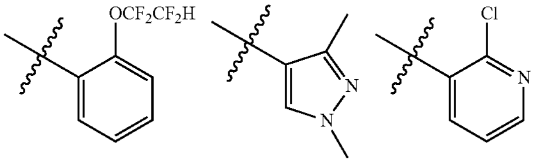
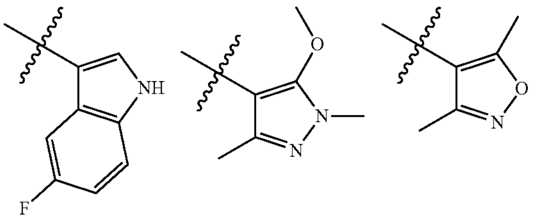
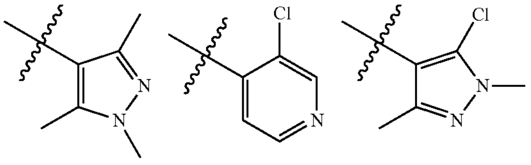
-continued
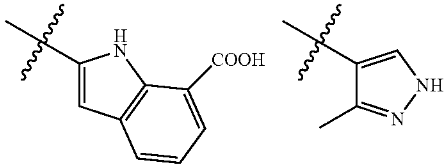
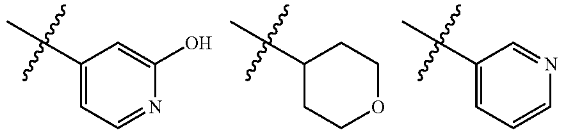
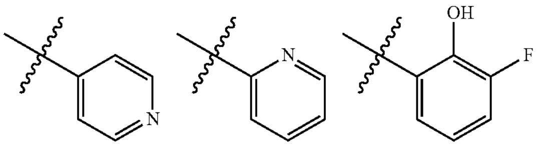
or
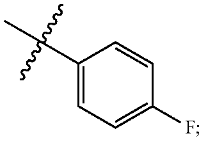
(e) —$SO_2R_5$, wherein $R_5$ is:
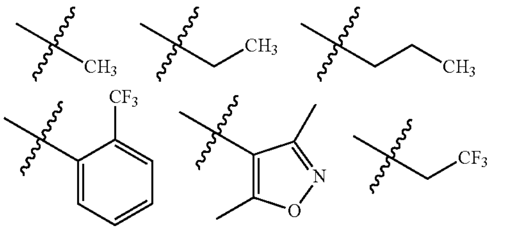
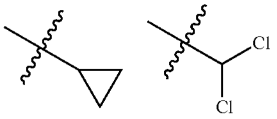
or
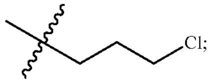
(f) —$SO_2NR_2R_3$, wherein $NR_2R_3$ is
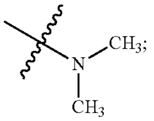 [SMILES: *N(C)C]
(g) —$R_2$, wherein $R_7$ is:
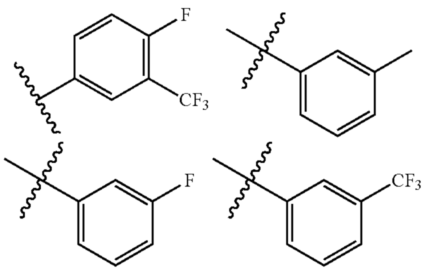

-continued

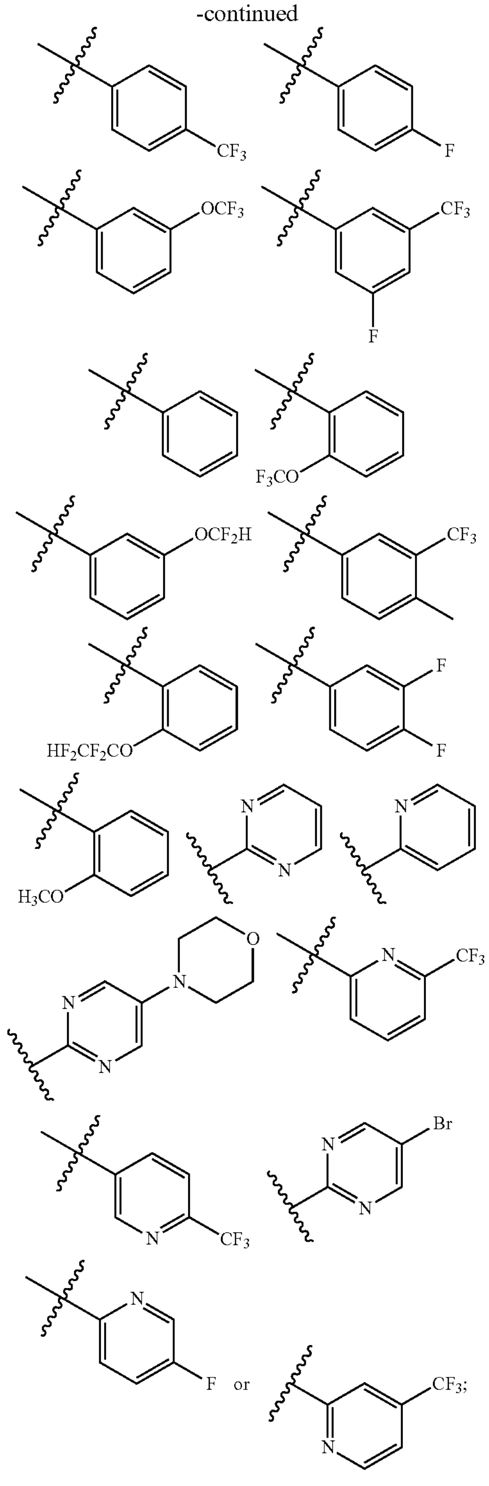

or and $R_{14}$ is H or

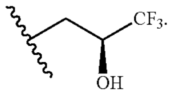 [SMILES: *C[C@H](O)C(F)(F)F]

In another embodiment, compounds of the present invention are selected from the compounds exemplified in the examples.

In yet another embodiment, pharmaceutical compositions comprised of compounds of the present invention alone or in combination with a pharmaceutically acceptable carrier and/or at least one additional therapeutic agent.

In still yet another embodiment, methods of inhibiting the cholesteryl ester transfer protein comprising administering to a mammal in need of treatment a compound and/or pharmaceutical composition of the present invention are provided.

In one embodiment, methods for treating, preventing or slowing the progression of Alzheimer's, atherosclerosis, venous thrombosis, coronary artery disease, coronary heart disease, coronary vascular disease, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being either male or female) by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia treating, preventing or slowing amount of a compound and/or pharmaceutical composition of the present invention are provided.

In another embodiment, methods for treating, preventing or slowing the progression of atherosclerosis in a mammal by administering to a mammal in need of such treatment an atherosclerotic treating, preventing or slowing amount of a compound and/or pharmaceutical composition of the present invention are provided.

In another embodiment, methods for treating, preventing or slowing the progression of peripheral vascular disease in a mammal by administering to a mammal in need of such treatment a peripheral vascular disease treating, preventing or slowing amount of a compound and/or pharmaceutical composition of the present invention are provided.

In yet another embodiment, methods for treating, preventing or slowing the progression of dyslipidemia in a mammal by administering to a mammal in need of such treatment a dyslipidemia treating, preventing or slowing amount of a compound and/or pharmaceutical composition of the present invention are provided.

In still yet another embodiment, methods for treating, preventing or slowing the progression of hyperbetalipoproteinemia in a mammal by administering to a mammal in need of such treatment a hyperbetalipoproteinemia treating, preventing or slowing amount of a compound and/or pharmaceutical composition of the present invention are provided.

In one embodiment, methods for treating, preventing or slowing the progression of hypoalphalipoproteinemia in a mammal by administering to a mammal in need of such treatment a hypoalphalipoproteinemia treating, preventing or slowing amount of a compound and/or pharmaceutical composition of the present invention are provided.

In another embodiment, methods for treating, preventing or slowing the progression of hypercholesterolemia in a mammal by administering to a mammal in need of such treatment a hypercholesterolemia treating, preventing or slowing amount of a compound and/or pharmaceutical composition of the present invention are provided.

In yet another embodiment, methods for treating, preventing or slowing the progression of hypertriglyceridemia in a mammal by administering to a mammal in need of such treatment a hypertriglyceridemia treating, preventing or slowing amount of a compound and/or pharmaceutical composition of the present invention are provided.

In still yet another embodiment, methods for treating, preventing or slowing the progression of familial-hypercholesterolemia in a mammal by administering to a mammal in need of such treatment a familial-hypercholesterolemia treating, preventing or slowing amount of a compound and/or pharmaceutical composition of the present invention are provided.

In one embodiment, methods for treating, preventing or slowing the progression of cardiovascular disorders in a mammal by administering to a mammal in need of such treatment a cardiovascular disorder treating, preventing or slowing amount of a compound and/or pharmaceutical composition of the present invention are provided.

In another embodiment, methods for treating, preventing or slowing the progression of angina in a mammal by administering to a mammal in need of such treatment an angina treating, preventing or slowing amount of a compound and/or pharmaceutical composition of the present invention are provided.

In yet another embodiment, methods for treating, preventing or slowing the progression of ischemia in a mammal by administering to a mammal in need of such treatment an ischemic disease treating, preventing or slowing amount of a compound and/or pharmaceutical composition of the present invention are provided.

In still yet another embodiment, methods for treating, preventing or slowing the progression of cardiac ischemia in a mammal by administering to a mammal in need of such treatment a cardiac ischemic treating, preventing or slowing amount of a compound and/or pharmaceutical composition of the present invention are provided.

In one embodiment, methods for treating, preventing or slowing the progression of stroke in a mammal by administering to a mammal in need of such treatment a stroke treating, preventing or slowing amount of a compound and/or pharmaceutical composition of the present invention are provided.

In one embodiment, methods for treating, preventing or slowing the progression of a myocardial infarction in a mammal by administering to a mammal in need of such treatment a myocardial infarction treating, preventing or slowing amount of a compound and/or pharmaceutical composition of the present invention are provided.

In another embodiment, methods for treating, preventing or slowing the progression of reperfusion injury in a mammal by administering to a mammal in need of such treatment a reperfusion injury treating, preventing or slowing amount of a compound and/or pharmaceutical composition of the present invention are provided.

In another embodiment, methods for treating, preventing or slowing the progression of angioplastic restenosis in a mammal by administering to a mammal in need of such treatment an angioplastic restenosis treating, preventing or slowing amount of a compound and/or pharmaceutical composition of the present invention are provided.

In yet another embodiment, methods for treating, preventing or slowing the progression of hypertension in a mammal by administering to a mammal in need of such treatment a hypertension treating, preventing or slowing amount of a compound and/or pharmaceutical composition of the present invention are provided.

In yet another embodiment, methods for treating, preventing or slowing the progression of the ascular complications of diabetes in a mammal by administering to a mammal in need of such treatment a vascular complications of diabetes treating, preventing or slowing amount of a compound and/or pharmaceutical composition of the present invention are provided.

In still yet another embodiment, methods for treating, preventing or slowing the progression of obesity in a mammal by administering to a mammal in need of such treatment an obesity treating, preventing or slowing amount of a compound and/or pharmaceutical composition of the present invention are provided.

In one embodiment, methods for treating, preventing or slowing the progression of endotoxemia in a mammal by administering to a mammal in need of such treatment an endotoxemia treating, preventing or slowing amount of a compound and/or pharmaceutical composition of the present invention are provided.

In another embodiment, methods for treating, preventing or slowing the progression of a disease requiring cholesteryl ester transfer protein inhibitor therapy comprising administering, concurrently or sequentially, to a mammal in need of treatment, prevention or slowing a therapeutically effective amount of a compound of the present invention and at least one additional therapeutic agent.

In yet another embodiment, methods of inhibiting remnant lipoprotein production comprising administering to a mammal a compound and/or pharmaceutical composition of the present invention are provided.

In still yet another embodiment, methods of raising HDL cholesterol in a mammal comprising administering to a mammal in need of treatment a compound and/or pharmaceutical composition of the present invention are provided.

SYNTHESIS

Generally, compounds of the present invention may be prepared by methods such as those illustrated in the following Schemes Ito XIII. Exemplary compounds of the present invention were prepared by the methods illustrated in the examples set forth below. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques.

SCHEME I

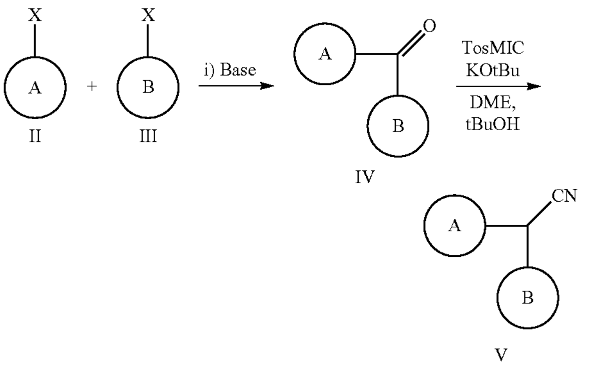

II III IV V

As illustrated in Scheme I, a substituted reagent of Formula II, wherein the composition of A is as described under Formula Ia and Ib, with the requirement that at least one of the substituents (X) attached to the reagent of Formula II is a nitrile group or a halogen group, such as bromine, can be combined with a reagent of Formula III, wherein the composition of B is as described under Formula Ia and Ib, with the requirement that at least one of the substituents (X) attached to the reagent of Formula III is a halide group, such as bromine, or a nitrile group, followed by treatment with a base, such as nBuLi, to yield an intermediate of Formula IV. Alternatively, a substituted reagent of Formula II, wherein the composition of A is as described under Formula Ia and Ib, with the requirement that at least one of the substituents (X) attached to the reagent of Formula II is an aldehyde group or a halogen group, such as bromine, can be combined with a reagent of Formula III, wherein the composition of B is as described under Formula Ia and Ib, with the requirement that at least one of the substituents (X) attached to the reagent of Formula III is a halide group, such as bromine, or an aldehyde group, followed by treatment with a base, such as nBuLi, followed by treatment with an oxidizing agent such as, $MnO_2$ or Jones' Reagent, to yield an intermediate of Formula IV. Alternatively, a substituted reagent of Formula II, wherein the composition of A is as described under Formula Ia and Ib, with the requirement that at least one of the substituents (X) attached to the reagent of Formula II is an alkyl ester group, such as a methyl or an ethyl ester or a halide group, such as bromine, can be combined with a reagent of Formula III, wherein the composition of B is as described under Formula Ia and Ib, with the requirement that at least one of the substituents (X) attached to the reagent of Formula III is a halide group, such as bromine, or an alkyl ester group, such as a methyl or an ethyl ester followed by treatment with a base, such as nBuLi, to yield an intermediate of Formula IV. Alternatively, a substituted reagent of Formula II, wherein the composition of A is as described under Formula Ia and Ib, with the requirement that at least one of the substituents (X) attached to the reagent of Formula II is a N-methoxy-N-methylacetamide group or a halide group, such as bromine, can be combined with a reagent of Formula III, wherein the composition of B is as described under Formula Ia and Ib, with the requirement that at least one of the substituents (X) attached to the reagent of Formula III is a halide group, such as bromine, or a N-methoxy-N-methylacetamide group followed by treatment with a base, such as nBuLi, to yield an intermediate of Formula IV. The intermediates of Formula IV, derived as described in Scheme I or derived by other approaches known to one skilled in the art, can be treated with a reagent, such as tosylmethyl isocyanide (TosMIC), in the presence of a base, such as potassium tertbutoxide (KOtBu), in a mixed solvent system such as, 1,2-dimethoxyethane (DME) and tert-butyl alcohol (tBuOH), to yield an intermediate of Formula V. An intermediate of Formula V is a critical intermediate on route to compounds of Formula Ia and Ib.

SCHEME II

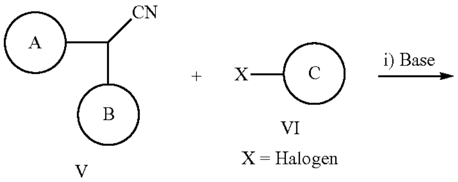

V

VI

X = Halogen

-continued

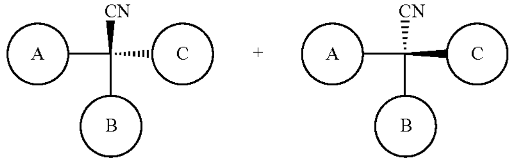

VIIa VIIb

As illustrated in Scheme II, a reagent of Formula V, can be combined with a reagent of Formula VI, wherein the composition of C found in the reagent of Formula VI is as described under Formula Ia and Ib, with the requirement that at least one of the substituents attached to the reagent of Formula VI is a halide group, such as bromine, followed by treatment with a base, such as nBuLi, to yield an intermediate of Formula VIIa and VIIb. An intermediate of Formula VII is a critical intermediate on route to compounds of Formula Ia and Ib. The formation of an intermediate of Formula VIIa or VIIb from an intermediate of Formula V, as described above, can also be performed in the presence of a chiral catalyst such as, but not limited to, N-benzylcinchoninium chloride or N-benzylcinchonidinium chloride, to enrich the formation of the intermediate of Formula VIIa over the intermediate of Formula VIIb or to enrich the formation of the intermediate of Formula VIIb over the intermediate of Formula VIIa as needed to make compounds of Formula Ia and Ib.

SCHEME III

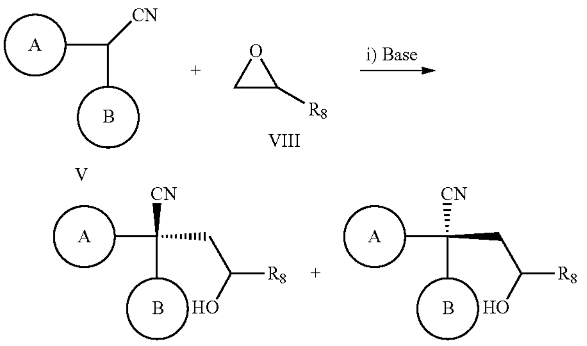

V

VIII

IXa

IXb

As illustrated in Scheme III, a reagent of Formula V, can be combined with an oxirane reagent of Formula VIII, ($CH_2OCHR_8$), wherein the composition of the reagent of Formula VIII supplies functionality that falls within the composition of C as is described for Formula Ia and Ib, followed by treatment with a base, such as nBuLi, to yield an intermediate of Formula IXa and IXb. An intermediate of Formula IXa and IXb, which is embodied by an intermediate of Formula VIIa and VIIb, is a critical intermediate on route to compounds of Formula Ia and Ib.

SCHEME IV

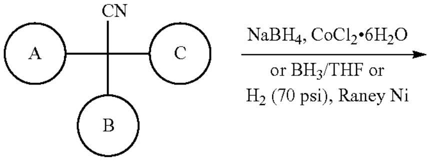

VIIa/b

-continued

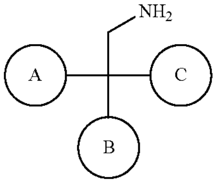

Xa/b

As illustrated in Scheme IV, the intermediate of Formula VIIa/b, or the intermediate of Formula IXa/b which is embodied by the intermediate of Formula VIIa/b, can be treated with a variety of reducing conditions known to one skilled in the art, such as, but not limited to, sodium borohydride and cobalt (II) chloride hexahydrate, or borane tetrahydrofuran complex or hydrogen gas over Raney nickel catalyst, to yield an advanced intermediate of Formula Xa/b. An advanced intermediate of Formula Xa/b is a critical intermediate on route to compounds of Formula Ia and Ib.

SCHEME V

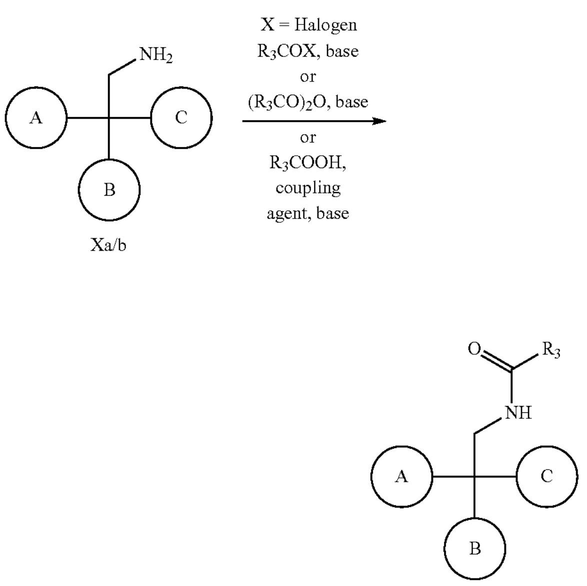

Xa/b

XIa/b

As illustrated in Scheme V, an advanced intermediate of Formula Xa/b can be treated with an acylating agent, such as an acid halide of Formula $R_3COX$, where X is a halide, or an anhydride of Formula $(R_3CO)_2O$, with or without the presence of a base, such as triethylamine, pyridine or N-ethyl-N-isopropylpropan-2-amine, to generate an amide derivative of Formula XIa/b, where $R_3$ is derived from the afore mentioned reactive acylating agent and is as described for Formula Ia and Ib. Alternatively, one can utilize a carboxylate intermediate of Formula $R_3COOH$, where $R_3$ is as described for Formula Ia and Ib, along with a coupling agent, such as EDCI, DCC or other agents known to one skilled in the art for facilitating amide bond formation, along with a base, such as triethylamine, pyridine or N-ethyl-N-isopropylpropan-2-amine, to generate an amide derivative of Formula XIa/b, which is a compound of Formula Ia and Ib, where $R_3$ is as described for Formula Ia and Ib.

SCHEME VI

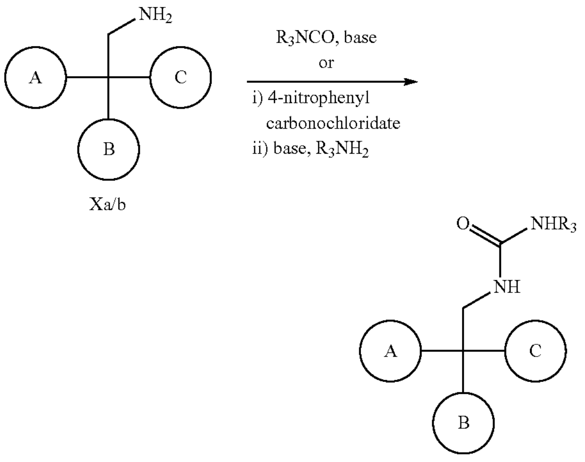

Xa/b

XIIa/b

As illustrated in Scheme VI, an advanced intermediate of Formula Xa/b can be treated with an isocyanate of Formula $R_3NCO$, with or without the presence of a base, such as triethylamine, pyridine or N-ethyl-N-isopropylpropan-2-amine, to generate an urea derivative of Formula XIIa/b, where $R_3$ is derived from the afore mentioned isocyanate reagent and is as described for Formula Ia and Ib. Alternatively, one can react an advanced intermediate of Formula Xa/b with an agent such as 4-nitrophenyl carbonochloridate or prop-1-en-2-yl carbonochloridate, to create a reactive carbamate intermediate which can then be reacted with a amine or amine salt intermediate of Formula $R_3NH_2$, with or without the presence of a base, such as triethylamine, pyridine or N-ethyl-N-isopropylpropan-2-amine, to generate an urea derivative of Formula XIIa/b, which is a compound of Formula Ia and Ib, where $R_3$ is as described for Formula Ia and Ib.

SCHEME VII

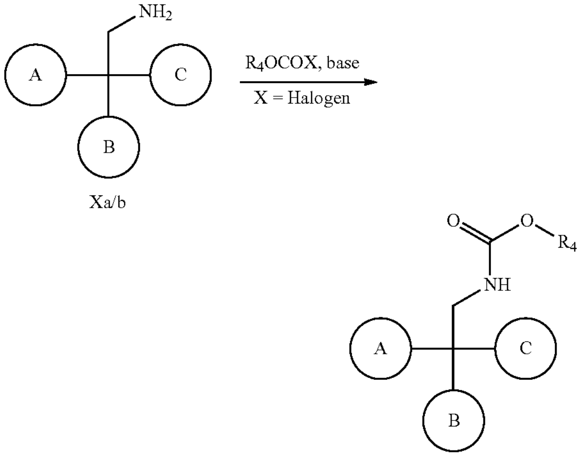

Xa/b

XIIIa/b

As illustrated in Scheme VII, an advanced intermediate of Formula Xa/b can be treated with a carbonochloridate of Formula $R_4OCOCl$, in the presence of a base, such as potassium carbonate, to generate a carbamate derivative of Formula XIIIa/b, which is a compound of Formula Ia and Ib, where $R_4$ is derived from the afore mentioned carbonochloridate reagents and is as described for Formula Ia and Ib.

SCHEME VIII

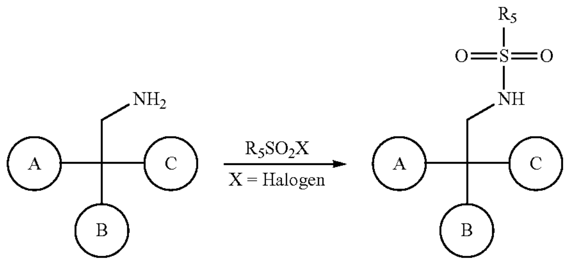

Xa/b

XIVa/b

As illustrated in Scheme VIII, an advanced intermediate of Formula Xa/b can be treated with a sulfonyl chloride of Formula $R_5SO_2Cl$, in the presence of a base, such as triethylamine, pyridine or N-ethyl-N-isopropylpropan-2-amine, to generate a sulfonamide derivative of Formula XIVa/b, which is a compound of Formula Ia and Ib, where $R_5$ is derived from the afore mentioned sulfonyl chloride reagents and is as described for Formula Ia and Ib.

SCHEME IX

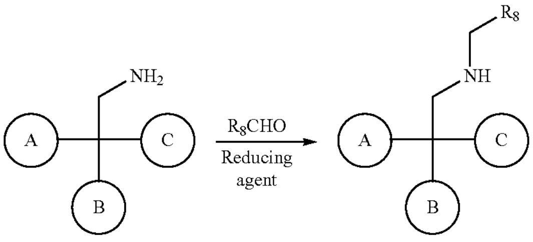

Xa/b

XVa/b

As illustrated in Scheme IX, an advanced intermediate of Formula Xa/b can be treated with an aldehyde of Formula $R_8CHO$, with or without a catalytic amount of an acid, such as acetic acid, followed by treatment with a reducing agent, such as sodium triacetoxyborohydride, to generate an alkyl amine derivative of Formula XVa/b, which is a compound of Formula Ia and Ib, where $R_8$ is derived from the afore mentioned aldehyde reagents and is as described for Formula Ia and Ib.

SCHEME X

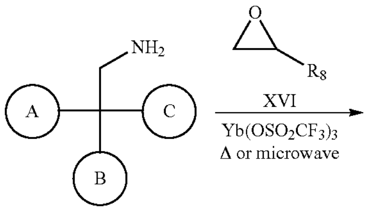

Xa/b

-continued

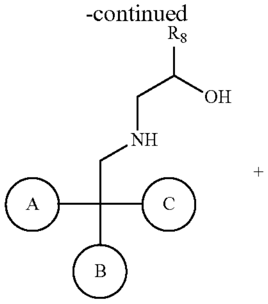

XVIIa/b

+

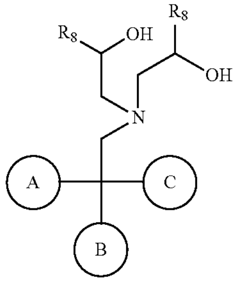

XVIIIa/b

As illustrated in Scheme X, an advanced intermediate of Formula Xa/b can be treated with an oxirane reagent of Formula XVI, ($CH_2OCHR_8$), in the presence of a catalyst, such as ytterbium trifluoromethylsulfonate ($Yb(OSO_2CF_3)_3$), with standard heating or via irradiation in a microwave, to generate the mono or bi-alkyl hydroxy amine derivatives of Formula XVIIa/b and XVIIIa/b, which are compounds of Formula Ia and Ib, where $R_8$ is derived from the afore mentioned oxirane reagents and is as described for Formula Ia and Ib. The composition of the ratio of the compounds of Formula XVIIa/b and XVIIIa/b can be altered as desired by one skilled in the art by modification of several reaction conditions, such as, but not limited to, the amount of oxirane reagent used, the solvent employed, the temperature utilized or the time of the reaction.

SCHEME XI

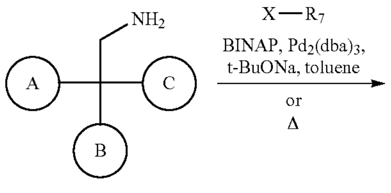

Xa/b

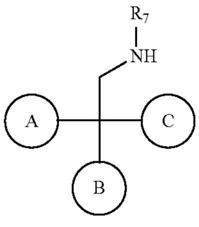

XIXa/b

As illustrated in Scheme XI, an advanced intermediate of Formula Xa/b can be treated with an arylhalide, heterocyclohalide or heteroarylhalide reagent, of Formula $R_7$—X, where X is a halide, such as bromine or iodine, and $R_7$ is as defined by Formula Ia and Ib, in the presence of a variety of coupling reagents known to one skilled in the art, such as but not limited to, 2,2'-bis(diphenylphosphino)-1,1'-binaphthyl (BINAP) combined with tris-(dibenzylideneacetone) dipalladium(0) ($Pd_2(dba)_3$), along with a base, such as sodium tert-butoxide (t-BuONa), in a solvent such a toluene, to yield alkyl amine derivative of Formula XIXa/b, which is a compound of Formula Ia and Ib, where $R_7$ is derived from the afore mentioned arylhalide, heterocyclohalide or heteroarylhalide reagent of Formula $R_7$—X and is defined as described for Formula Ia and Ib. Alternatively, an advanced intermediate of Formula Xa/b can be treated with an cycloalkylhalide or heterocyclohalide reagent, of Formula $R_7$—X, where X is a halide, such as bromine or iodine, and $R_7$ is as defined by Formula Ia and Ib, along with heating, to yield alkyl amine derivative of Formula XIXa/b, which is a compound of Formula Ia and Ib, where $R_7$ is derived from the afore mentioned cycloalkylhalide or heterocyclohalide reagent of Formula $R_7$—X and is as described for Formula Ia and Ib.

SCHEME XII

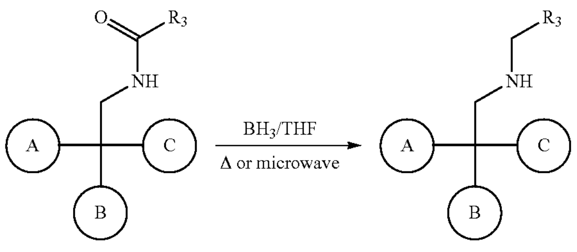

XIa/b XXa/b

As illustrated in Scheme XII, an amide derivative of Formula XIa/b, which is a compound of Formula Ia and Ib, where $R_3$ is as described for Formula I, can be treated by a reducing agent, such as borane tetrahydrofuran complex, along with standard heating or microwave irradiation, to yield an alkyl amine compound of Formula XXa/b, which is a compound of Formula Ia and Ib, where $R_3$ is as described for Formula Ia and Ib.

SCHEME XIII

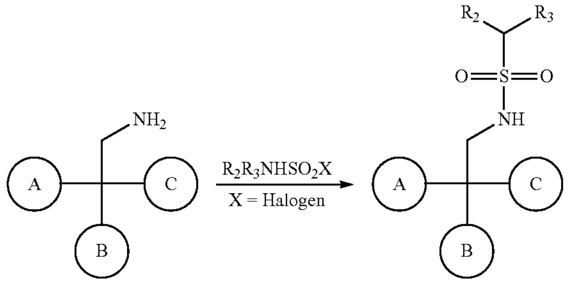

Xa/b XXIa/b

As illustrated in Scheme XIII, an advanced intermediate of Formula Xa/b can be treated with a sulfonyl chloride of Formula $R_2R_3NHSO_2Cl$, in the presence of a base, such as triethylamine, pyridine or N-ethyl-N-isopropylpropan-2-amine, to generate a sulfonamide derivative of Formula XXIa/b, which is a compound of Formula Ia and Ib, where $R_2$ and $R_3$ are derived from the afore mentioned sulfamoyl chloride reagents and is as described for Formula Ia and Ib.

The included schemes give an overview of several general processes for the synthesis of compounds of Formula Ia and Ib. Additional compounds of Formula Ia and Ib can readily be made by one of ordinary skill in the art by further modification of functional groups at positions A, B, C, $R_1$ or $R_{14}$ of compounds of Formula Ia and Ib made by the processes illustrated in the included schemes.

The following examples further illustrate the present invention, but of course, should not be construed as in any way limiting its scope.

The following abbreviations are used herein:

ee=enantiomeric excess
DMF=dimethylformamide
EtOAc=ethyl acetate
LDA=lithium diisopropylamide
DIEA=N,N-diisopropylethylamine
Me=methyl
RT=retention time
TFA=trifluoroacetic acid
THF=tetrahydrofuran
TLC=thin layer chromatography
TMS=trimethylsilyl
t-Bu=tert-butyl
MeI=methyl iodide
$(BOC)_2O$=di-tert-butyl dicarbonate
TEA=triethylamine
n-BuLi=n-butyllithium
rt=room temperature
LC=liquid chromatography
Ph=phenyl
EtOH=ethanol
DCE=dichloroethane
DMSO=dimethylsulfoxide
MS=molecular sieves
MS (ES)=Electro-Spray Mass Spectrometry
sat.=saturated
AcOH=acetic acid
MeOH=methanol
$Et_2O$=diethyl ether
Ac=acetyl
h=hours
Et=ethyl
EDCI=water soluble dicarbonyl diimide, 1-(3-dimethylaminopropyl)-3-ethylcarbodiimide hydrochloride
HOAT=1-hydroxy-7-azabenzotriazole
HOBT=1-hydroxy-benzotriazole
TBAF=tetrabutylammonium fluoride
DMA=dimethylacetamide
DME=1,2-dimethoxyethane
HRMS=high resolution mass spectrometry
TBME=MTBE=methyl tert-butyl ether (i.e., 2-methoxy-2-methyl-propane)
PyBroP=bromo-tris-pyrrolidino-phosphonium hexafluorophosphate
DEA=diethylamine
IPA=isopropylamine
TMSCl=trimethylsilylchloride
MS=mass spectrum
NMR=nuclear magnetic resonance
TMSI=trimethylsilyliodide
PPA=polyphosphoric acid LDA=lithium diisopropylamine UV=ultraviolet DCM=dichloromethane DMAC=N,N-dimethylacetamide DAST=diethylaminosulfurtrifluoride HPLC=high performance liquid chromatography TosMIC=tosylmethyl isocyanide BINAP=2,2'-bis(diphenylphosphino)-1,1'-binaphthyl $Pd_2(dba)_3$=tris-(dibenzylideneacetone) dipalladium(0)

Ar=argon

AcCN=acetonitrile t-BuOK=potassium tertiary butoxide t-BuOH=tertiary butanol

BnBr=benzyl bromide t-BuONa=sodium tertiary butoxide

TBAB=tetrabutylammonium bromide

Examples 1 to 134 were prepared in the manner described in Procedures 1 to 36. The structure, the compound name, retention time, molecular mass, and the procedures employed, are set forth in Tables 1 to Table 8. The absolute configuration of exemplified chiral examples was assigned by X-ray crystallography of the corresponding (1R)-(−)-10-camphorsulfonic acid salts of enantiomerically pure intermediate amines. Enantiomerically pure intermediate amines were obtained by separation of the racemic mixtures using the normal phase preparative chiral chromatography.

The chromatography techniques used to determine the compound retention times of Table 1 to 8 are as follows: (1) LCMS=Phenomenex Luna C18 column, 4.6×50 mm eluting with 10-90% MeOH/$H_2O$ over 4 minutes containing 0.1% TFA; 4 mL/min, monitoring at 220 nm; (2) LCMS=Phenomenex Luna C18 column, 4.6×30 mm eluting with 10-90% MeOH/$H_2O$ over 2 minutes containing 0.1% TFA; 5 mL/min, monitoring at 220 nm; (3) LCMS=Waters Sunfire C18 column, 4.6×50 mm×5 μm eluting with 10-90% MeOH/$H_2O$ over 4 minutes containing 0.1% TFA; 4 mL/min, monitoring at 220 nm; (4) LC=YMC S5 ODS column 4 6×50 mm eluting with 10-90% MeOH/$H_2O$ over 4 minutes containing 0.2% phosphoric acid, 4 mL/min, monitoring at 220 nm. The molecular mass of the compounds listed in Tables 1 to 8 were determined by MS (ES) by the formula m/z.

EXAMPLE 1

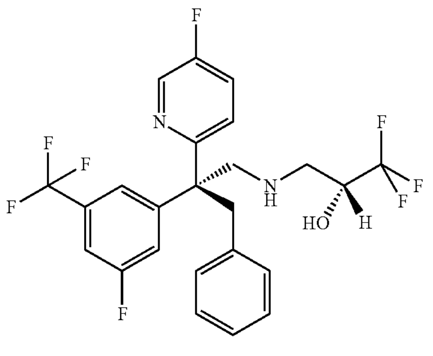 [SMILES: O[C@H](CNC[C@](Cc1ccccc1)(c1cc(F)cc(C(F)(F)F)c1)c1ccc(F)cn1)C(F)(F)F]

(R)-1,1,1-trifluoro-3-((S)-2-(3-fluoro-5-(trifluoromethyl)phenyl)-2-(5-fluoropyridin-2-yl)-3-phenylpropylamino)propan-2-ol Procedure 1

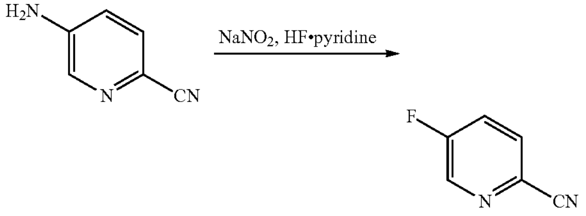

To a 100 mL round bottom flask charged with 5-aminopicolinonitrile (285 mg, 2.44 mmol) at 0° C. was added HF.pyridine (5 mL) under $N_2$. A pale brown solution was formed. In 4 aliquots, $NaNO_2$ (250 mg, 3.62 mmol) was added with stirring. The solution turned green and a brown gas was liberated. After 20 min at 0° C., the solution was allowed to reach rt and stirred for an additional 20 min. A reflux condenser was attached and the reaction mixture was heated at 65° C. for 20 min then allowed to cool to rt. The orange slurry was quenched by the addition of crushed ice and the aqueous layer was extracted with DCM (3×10 mL). The combined organic portions were dried over $Na_2SO_4$, decanted and concentrated under reduced pressure to yield 5-fluoropicolinonitrile (152 mg, 52% yield) as a pale orange powder. LCMS: RT=0.63 min [M+H] 122.9 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=0.99 min (Phenomenex Luna C18 column, 4.6×50 mm eluting with 10-90% MeOH/$H_2O$ over 4 minutes containing 0.2% PPA; 4 mL/min, monitoring at 220 nm, Purity 96%); NMR: 400 MHz $^1H(CDCl_3)$ ppm 8.52 (d, J=2.64 Hz, 1H), 7.70 (dd, J=4.4 and J=8.36 Hz, 1H), 7.50 (m, 1H).

Procedure 2

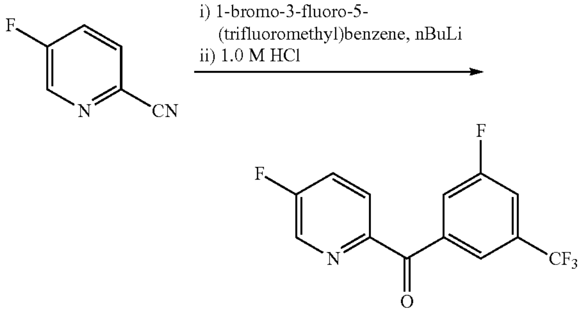

An ether solution (2 mL) of 1-bromo-3-fluoro-5-(trifluoromethyl)benzene (0.200 g, 0.826 mmol) was stirred in an oven-dried round bottom flask at −78° C. under Ar. To this solution, n-BuLi (2.0 M in cyclohexane, 0.41 mL, 0.82 mmol, 1.0 eq) was added dropwise. The resulting solution was stirred at −78° C. for 30 min. 5-Fluoropicolinonitrile (0.101 g, 0.828 mmol, 1.0 eq), prepared as described in Procedure 1, was added as a solid via addition funnel The resulting red solution was stirred at −78° C. for 1 h. The reaction mixture was quenched with HCl (10 mL, 1.0 M) and extracted with EtOAc (3×10 mL). The combined organic portions were dried over $Na_2SO_4$, decanted and the volume was reduced to 5 mL under reduced pressure. The resulting oil was loaded directly onto a silica gel ISCO cartridge (40 g). Gradient elution from 0-70% EtOAc in hexane over 20 min yielded (3-fluoro-5-(trifluoromethyl)phenyl)(5-fluoropyridin-2-yl) methanone as a pale brown oil at a retention time of 7 min (0.117 g, 49% yield). LCMS: RT=1.91 min [M+H] 288.2 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.69 min (Phenomenex Luna C18 column, 4.6×50 mm eluting with 10-90% MeOH/$H_2O$ over 4 minutes containing 0.2% PPA; 4 mL/min, monitoring at 220 nm, purity 97%); NMR: 400 MHz $^1H(CDCl_3)$ ppm 8.50 (d, J=2.4 Hz, 1 H), 8.19 (dd, J=4.0 and J=8.0 Hz, 1 H), 8.15 (s, 1 H), 8.00 (d, J=8.0 Hz, 1 H), 7.57 (ddd, J=3.08, J=2.4 and J=8.0 Hz).

Procedure 3

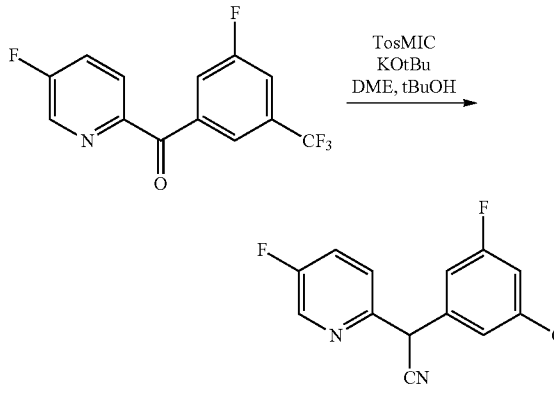

To a solution of (3-fluoro-5-(trifluoromethyl)phenyl)(5-fluoropyridin-2-yl)methanone (2.43 g, 8.5 mmol), prepared as described in Procedure 2, in DME (60 mL), was added TosMIC (2.23 g, 11.4 mmol). The reaction mixture was cooled in an ice bath. A solution of potassium tert butoxide (1.0 M potassium ten butoxide in tert butanol, 22.8 mmol) in tert butanol/DME (22 mL t-BuOH, 20 mL DME) was added via a funnel at a slow stream. Upon completion of addition, the ice bath was removed and the reaction mixture was stirred at rt overnight. The reaction mixture was quenched with water (approx 50 mL). The aqueous phase was extracted with $CH_2Cl_2$ (3×50 mL) and the combined organic portions were washed with sat. NaCl, dried over anhydrous $Na_2SO_4$, filtered and concentrated under reduced pressure to yield a yellow oil. The yellow oil was dissolved in $CH_2Cl_2$ and loaded directly onto a silica gel ISCO cartridge (120 g) with elution at 40 mL/min gradient 0 to 15% EtOAc in hexane over 30 min (RT=23-29 min) 2-(3-Fluoro-5-(trifluoromethyl)phenyl)-2-(5-fluoropyridin-2-yl)acetonitrile (1.8 g, 72% yield) was isolated as a yellow oil. LCMS: RT=1.73 min [M+H] 298.99 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.98 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H(CDCl_3)$ ppm 5.35 (s, 1 H), 7.31 (d, J=7.91 Hz, 1 H), 7.38 (d, J=8.79 Hz, 1 H), 7.46-7.47 (m, 2H), 7.50 (s, 1 H), 8.46 (s, 1 H).

Procedure 4

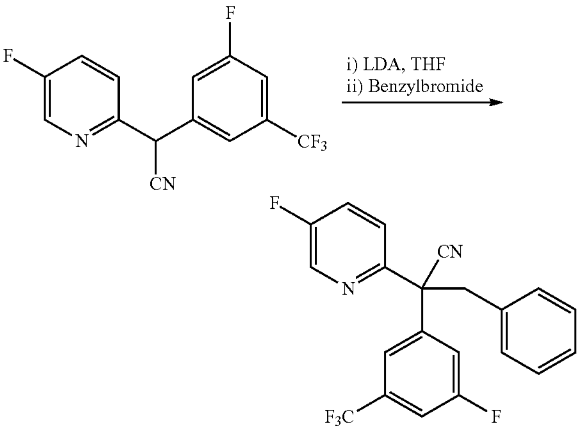

To a solution of LDA (2.0 M in THF, 3.7 mL) in THF (20 mL) at −78° C. under argon was added dropwise a solution of 2-(3-fluoro-5-(trifluoromethyl)phenyl)-2-(5-fluoropyridin-2-yl)acetonitrile (1.7 g, 5.7 mmol), prepared as described in Procedure 3, in THF (4 mL). The resulting solution was stirred at −78° C. for 1 h. Benzylbromide (0.88 mL, 7.4 mmol) was added to the reaction mixture and allowed to warm to room temperature. The reaction mixture was stirred at rt for 1 h, concentrated under reduced pressure and diluted with EtOAc (approx 100 mL). The resulting solution was washed with water (30 mL) and sat. NaCl (30 mL), dried over anhydrous $Na_2SO_4$, filtered and concentrated under reduced pressure to yield a yellow oil. The yellow oil was dissolved in $CH_2Cl_2$ and loaded directly onto a silica gel ISCO cartridge (40 g) with elution at 35 mL/min gradient 0 to 30% EtOAc in hexane over 35 min (RT=27-32 min). 2-(3-Fluoro-5-(trifluoromethyl)phenyl)-2-(5-fluoropyridin-2-yl)-3-phenylpropanenitrile (1.6 g, 72% yield) was isolated as a pale yellow oil. LCMS: RT=2.17 min [M+H] 389.0 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.24 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H$ $(CDCl_3)$ ppm 3.59 (d, J=13.18 Hz, 1 H), 3.90 (d, J=13.62 Hz, 1 H), 6.89 (d, J=6.59 Hz, 2 H), 7.09-7.15 (m, 3 H), 7.20 (d, J=7.91 Hz, 1 H), 7.32 (td, J=8.35, 3.08 Hz, 1H), 7.37 (d, J=9.23 Hz, 1 H), 7.45-7.48 (m, 1 H), 7.49 (s, 1 H), 8.50 (d, J=2.64 Hz, 1H).

Procedure 5

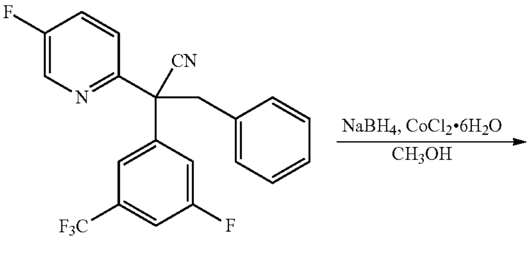

-continued

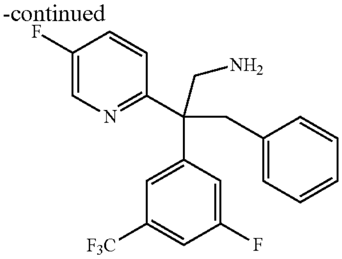

To a solution of 2-(3-fluoro-5-(trifluoromethyl)phenyl)-2-(5-fluoropyridin-2-yl)-3-phenylpropanenitrile (1.6 g, 4.12 mmol), prepared as described in Procedure 4, in $CH_3OH$ (40 mL) was added $CoCl_2.6H_2O$ (1.07 g, 8.25 mmol). The resulting solution turned purple in color. $NaBH_4$ (1.57 g, 41.2 mmol) was then added in portions over 10 min. The resulting black solution was stirred at rt for 1 h. After this time, the reaction mixture was concentrated under reduced pressure, quenched with 6N HCl (4 mL), and diluted with sat. ammonium chloride (40 mL). The aqueous phase was extracted with $CH_2Cl_2$ (4×50 mL). The combined organic portions were washed successively with sat. $NaHCO_3$ (50 mL) and sat. NaCl (50 mL), then dried over anhydrous $Na_2SO_4$, filtered and concentrated under reduced pressure to yield a yellow oil. The yellow oil was dissolved in $CH_2Cl_2$ and loaded directly onto a silica gel ISCO cartridge (40 g) with elution at 35 mL/min gradient 0 to 5% $CH_3OH$ in $CH_2Cl_2$ over 22 min (RT=17-19 min) 2-(3-Fluoro-5-(trifluoromethyl)phenyl)-2-(5-fluoropyridin-2-yl)-3-phenylpropan-1-amine (1.0 g, 60% yield) was isolated as a pale yellow oil. LCMS: RT=1.68 min [M+H] 393.04 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.31 min (Phenomenex Luna C18 column, 4.6×50 mm eluting with 10-90% $MeOH/H_2O$ over 4 minutes containing 0.2% PPA; 4 mL/min, monitoring at 220 nm); NMR: 400 MHz $^1H$ ($CDCl_3$) ppm 3.29-3.37 (m, 2 H), 3.59 (t, J=13.2 Hz, 2 H), 6.62 (d, J=7.0 Hz, 2 H), 6.97 (d, J=10.1 Hz, 1 H), 7.06-7.14 (m, 5 H), 7.20 (d, J=8.35 Hz, 1H), 7.34 (td, J=8.57, 3.08 Hz, 1 H), 8.45 (d, J=3.08 Hz, 1 H). The racemate (1.0 g) was dissolved in $CH_3OH$ and resolved by chiral prep HPLC (Chiralpak AD 20μ column, 5×50 cm isocratic elution with 100% $EtOH/CH_3OH$(50/50)/0.1% DEA, 50 mL/min, monitoring at 254 nm). Enantiomer 1 (470 mg) was isolated as a yellow oil: analytical chiral HPLC (Diacel Chiralpak AD 10μ column, 4.6×250 mm isocratic elution with 100% EtOH/$CH_3OH$(50/50)/0.1% DEA, 1 mL/min, monitoring at 254 nm), RT=3.70 min. Enantiomer 2 (470 mg) was isolated as a yellow oil: analytical chiral HPLC (Diacel Chiralpak AD 10μ column, 4.6×250 mm isocratic elution with 100% EtOH/$CH_3OH$(50/50)/0.1% DEA, 1 mL/min, monitoring at 254 nm), RT=4.05 min.

The (1R)-(−)-10-camphorsulfonic acid salt of 2-(3-fluoro-5-(trifluoromethyl)phenyl)-2-(5-fluoropyridin-2-yl)-3-phenylpropan-1-amine (Enantiomer 1) was crystallized from absolute ethanol and the crystal structure was determined by single beam X-ray defraction studies. The absolute stereochemistry of the quaternary center of Enantiomer 1 was shown to be S configuration, and the stereochemistry of the quaternary center of Enantiomer 2 was designated to be R configuration.

Procedure 6

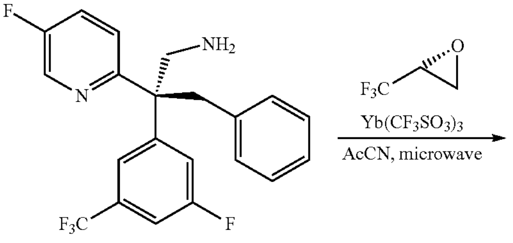

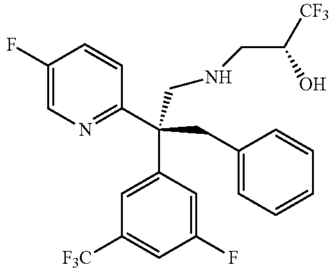

(R)-2-(trifluoromethyl)oxirane was prepared as described by Ramachandran, P. V. et al., *J. Org. Chem.,* 7:1307 (1995). and the % ee was determined as described in Schaus, S. E. et al., *J. Am. Chem. Soc.,* 1:41-46 (2002).

(S)-2-(3-fluoro-5-(trifluoromethyl)phenyl)-2-(5-fluoropyridin-2-yl)-3-phenylpropan-1-amine (40 mg, 0.1 mmol), prepared as described in Procedure 5, was dissolved in anhydrous acetonitrile (0.5 mL) in a microwave vial. (R)-2-(trifluoromethyl)oxirane (0.1 g, 0.9 mmol) was added to the solution, followed by $Yb(CF_3SO_3)_3$ (0.04 g, 0.06 mmol). The reaction mixture was sealed in a vial and heated to 130° C. for 20 min under microwave irradiation. The crude product was purified by preparative HPLC (YMC Sunfire 5μ column, 30×100 mm eluting with 10-90% $MeOH/H_2O$ over 10 minutes containing 0.1% TFA; 40 mL/min, monitoring at 220 nm) to provide Example 1 as a colorless oil (25 mg, 48% yield). LCMS: RT=1.65 min [M+H] 505.03 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.3 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H(CDCl_3)$ ppm 3.00 (t, J=11.21 Hz, 1 H), 3.28 (dd, J=11.86, 3.08 Hz, 1 H), 3.50-3.58 (m, 3 H), 3.71-3.77 (m, 1 H), 4.37 (d, J=6.15 Hz, 1 H), 6.71 (d, J=7.03 Hz, 2 H), 6.85 (d, J=9.67 Hz, 1 H), 7.16-7.21 (m, 3 H),

| T | a (Å) | b (Å) | C (Å) | α° | β° | γ° | V (Å$^3$) | Z' | Vm | sg | dcalc | mp (° C.) | R | Flack |
|---|---|---|---|---|---|---|---|---|---|---|---|---|---|---|
| −50 | 14.7285 (3) | 7.1445 (1) | 14.7969 (3) | 90 | 111.599 (1) | 90 | 1447.71 (5) | 1 | 724 | $P2_1$ | 1.433 | 185-240 | .04 | 0.00 (2) |

7.22-7.29 (m, 4 H), 7.53 (dd, J=8.79, 3.95 Hz, 1 H), 7.65-7.70 (m, 1H), 8.40 (d, J=3.08 Hz, 1 H).

EXAMPLE 2

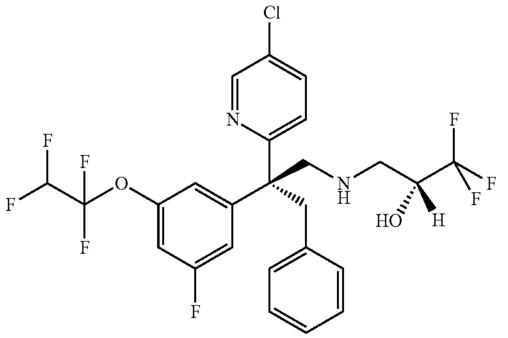 [SMILES: O[C@H](CNC[C@@](Cc1ccccc1)(c1cc(F)cc(OC(F)(F)C(F)F)c1)c1ccc(Cl)cn1)C(F)(F)F]

(R)-3-OR)-2-(5-chloropyridin-2-yl)-2-(3-fluoro-5-(1,1,2,2-tetrafluoroethoxy)phenyl)-3-phenylpropylamino)-1,1,1-trifluoropropan-2-ol Procedure 7

Step 1

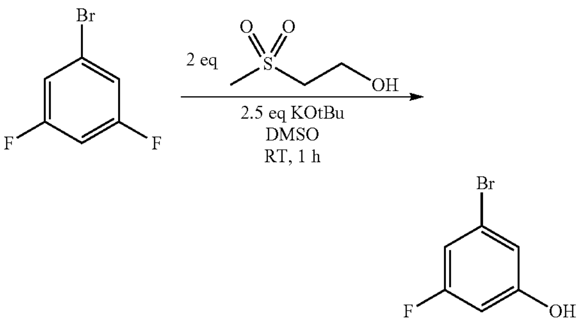

A solution of 1-bromo-3,5-difluorobenzene (20.0 g, 104 mmol) was cooled in an ice water bath and 2-(methylsulfonyl)ethanol (26.0 g, 207 mmol) in DMSO (100 mL) was added. KOtBu (29.0 g, 260 mmol) was added to the reaction mixture in portions. The reaction mixture turned dark. After the addition was complete, the ice water bath was removed and the reaction mixture was stirred at rt for 1 h. At the conclusion of this period, the solution was brought to pH 1 by addition of 1 N HCl, and the reaction mixture was extracted with ether (3×200 mL). The combined organic portions were washed with aqueous 1N NaOH (2×200 mL). The combined NaOH layers were acidified to pH 1 and extracted with ether (3×200 mL). The combined organic layers were dried over anhydrous $Na_2SO_4$ and filtered. The filtrate solvent volume was concentrated under reduced pressure, but care was taken not to concentrate to complete dryness due to volatility of 3-bromo-5-fluorophenol. The mixture was used directly in the next step without further purification. NMR: 400 MHz $^1H(CDCl_3)$ ppm 6.81 (dt, J=8.35 Hz and 1.98 Hz, 1 H), 6.78 (m, 1 H), 6.50 (dt, J=9.67 Hz and 2.20 Hz, 1 H).

Step 2

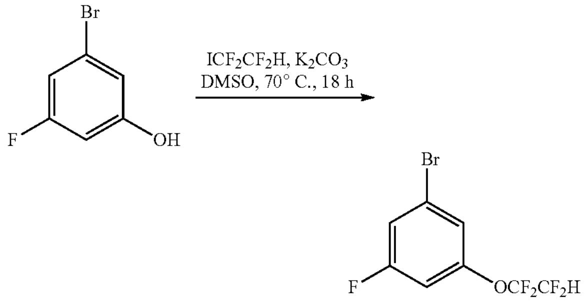

To a solution of 3-bromo-5-fluorophenol (104 mmol crude), prepared as described in Step 1, Procedure 7, and iodo-1,1,2,2,-tetrafluoroethane (28.4 g, 125 mmol) in DMSO (80 mL) was added $K_2CO_3$ (57.0 g, 420 mmol). The reaction mixture was sealed in a thick walled glass pressure round bottom flask and heated at 70° C. for 18 h. The reaction mixture was cooled to rt, diluted with water (500 mL) and extracted with ether (3×200 mL). The combined ether layers were washed with 1N NaOH (2×200 mL), water (2×200 mL) and sat. NaCl (200 mL). The combined organic layers were dried over $Na_2SO_4$, filtered and concentrated under reduced pressure to yield a residue. The residue was dissolved in ether (150 mL) and filtered through a plug of activated basic alumina The filtrate was concentrated under reduced pressure to give 1-bromo-3-fluoro-5-(1,1,2,2-tetrafluoroethoxy)benzene as a pale yellow oil (27.2 g, 88% for two steps) which was used without further purification. LCMS: RT=1.91 min, [M+H] No Ionizable peak (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.76 min (Phenomenex Luna C18 column, 4.6×50 mm eluting with 10-90% $MeOH/H_2O$ over 4 minutes containing 0.2% PPA; 4 mL/min, monitoring at 220 nm, Purity 100%); NMR: 400 MHz $^1H(CDCl_3)$ ppm 7.19 (m, 2 H), 6.92 (d, J=8.35 Hz, 1 H), 5.88 (tt; J=52.95 Hz and J=2.64 Hz, 1 H).

Step 3

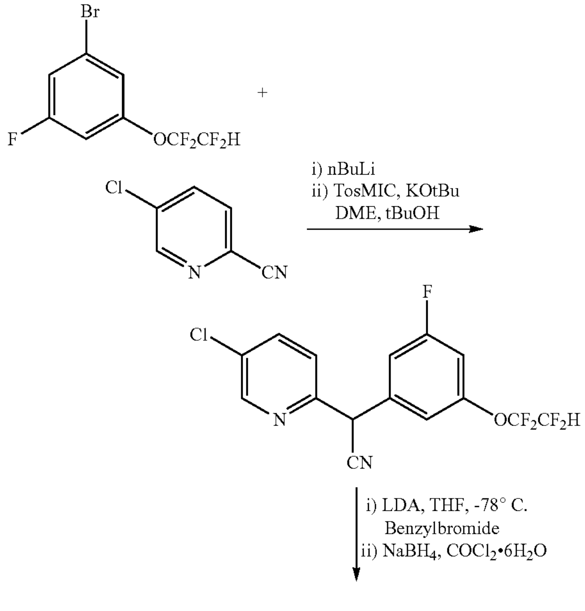

-continued

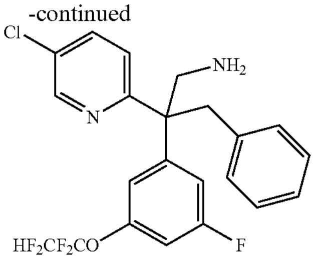

Following Procedures 2, 3, 4 and 5, 2-(5-chloropyridin-2-yl)-2-(3-fluoro-5-(1,1,2,2-tetrafluoroethoxy)phenyl)-3-phenylpropan-1-amine was prepared (550 mg, 22% yield for 4 steps). LCMS: RT=1.74 min [M+H] 457.04 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.47 min (Phenomenex Luna C18 column, 4.6×50 mm eluting with 10-90% $MeOH/H_2O$ over 4 minutes containing 0.2% PPA; 4 mL/min, monitoring at 220 nm); NMR: 400 MHz $^1H(CDCl_3)$ ppm 3.24-3.34 (m, 2 H), 3.46-3.54 (m, 1 H), 3.56-3.63 (m, 1 H), 4.12 (q, J=7.03 Hz, 2 H), 5.86 (tt, J=52.95 Hz and J=2.64 Hz, 1 H), 6.65 (d, J=6.59 Hz, 2H), 6.71 (s, 1 H), 6.74 (d, J=9.67 Hz, 1 H), 6.87 (d, J=8.79 Hz, 1 H), 7.01-7.15 (m, 4H), 7.56-7.62 (m, 1 H), 8.54 (d, J=2.20 Hz, 1 H). The racemate (550 mg) was dissolved in $CH_3OH$ and resolved by chiral prep HPLC (Chiralpak AD 20μ column, 5×50 cm isocratic elution with 100% $EtOH/CH_3OH$(50/50)/0.1% DEA, 50 mL/min, monitoring at 254 nm). Enantiomer 1 (160 mg) was isolated as a yellow oil: analytical chiral HPLC (Diacel Chiralpak AD 10μ column, 4.6×250 mm isocratic elution with 100% EtOH/ $CH_3OH$ (50/50)/0.1% DEA, 1 mL/min, monitoring at 254 nm), RT=3.89 min. Enantiomer 2 (160 mg) was isolated as a yellow oil: analytical chiral HPLC (Diacel Chiralpak AD 10μ column, 4.6×250 mm isocratic elution with 100% EtOH/ $CH_3OH$(50/50)/0.1% DEA, 1 mL/min, monitoring at 254 nm), RT=4.33 min. By analogy with Procedure 5, the 1st eluted enantiomer (Enantiomer 1) was assigned S configuration and the 2nd eluted enantiomer (Enantiomer 2) was assigned R configuration.

Step 4

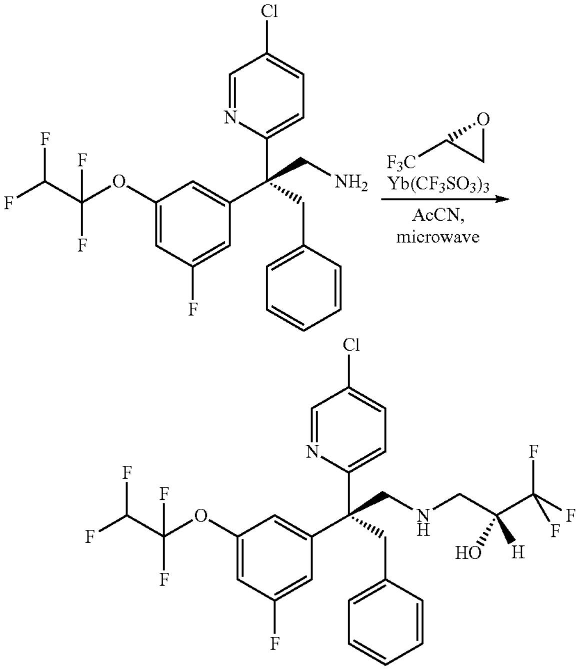

Following Procedure 6, Example 2 was prepared (6 mg, 20% yield). LCMS: RT=1.74 min [M+H] 567.0 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.49 min (Phenomenex Luna C18 column, 4.6×50 mm eluting with 10-90% MeOH/ $H_2O$ over 4 minutes containing 0.2% PPA; 4 mL/min, monitoring at 220 nm); NMR: 400 MHz $^1H$, $(CDCl_3)$ ppm 2.78-2.89 (m, 2 H), 3.18-3.26 (m, 2 H), 3.43-3.49 (m, 1 H), 3.58-3.63 (m, 1 H), 3.87-3.94 (m, 1 H), 5.87 (tt, J=52.95 Hz and J=2.64 Hz, 1 H), 6.60 (d, J=6.59 Hz, 2 H), 6.73 (s, 1 H), 6.76 (d, J=10.11 Hz, 1 H), 6.90 (d, J=8.79 Hz, 1 H), 7.04-7.16 (m, 4H), 7.62 (dd, J=8.35, 2.64 Hz, 1 H), 8.51 (d, J=2.64 Hz, 1 H).

EXAMPLE 3

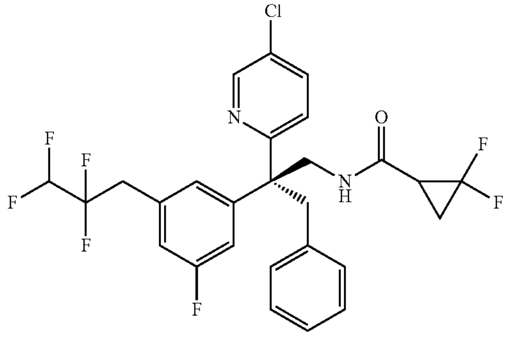 [SMILES: O=C(NC[C@@](Cc1ccccc1)(c1cc(F)cc(CC(F)(F)C(F)F)c1)c1ccc(Cl)cn1)C1CC1(F)F]

N—((R)-2-(5-chloropyridin-2-yl)-2-(3-fluoro-5-(2,2,3,3-tetrafluoropropyl)phenyl)-3-phenylpropyl)-2,2-difluorocyclopropanecarboxamide Procedure 8

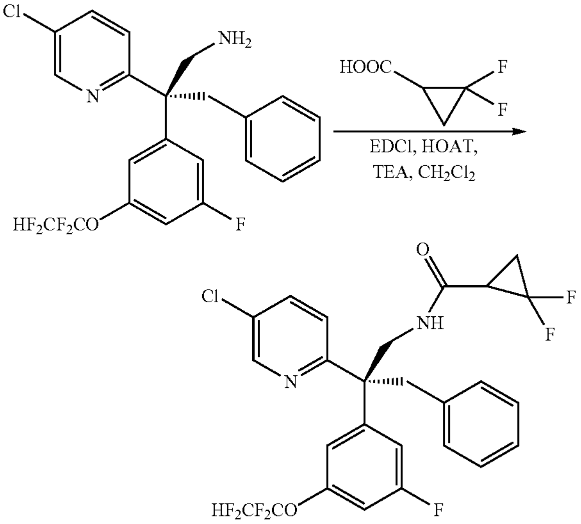

(R)-2-(5-chloropyridin-2-yl)-2-(3-fluoro-5-(2,2,3,3-tetrafluoropropyl)phenyl)-3-phenylpropan-1-amine (30 mg, 0.07 mmol), prepared as described in procedure 7, was dissolved in anhydrous $CH_2Cl_2$ (2 mL), then 2,2-difluorocyclopropanecarboxylic acid (10 mg, 0.08 mmol, racemate), EDCI (15 mg, 0.08 mmol) and HOAT (11 mg, 0.08 mmol) were added to the solution followed by TEA (0.027 mL, 0.2 mmol). The reaction mixture was stirred at rt for 2 hr to yield crude product. The crude product was purified by a silica gel ISCO cartridge (12 g) with elution at 25 mL/min gradient 0 to 30% EtOAc in hexane over 16 min (RT=12-14 min) to yield Example 3 as a white solid (35 mg, 94% yield, 1:1 RS:RR diastereomer mixture). LCMS: RT=2.11 min [M+H] 561.1 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.16 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H(CDCl_3)$ ppm 1.45-1.55 (m, 1 H), 1.82-1.91 (m, 1 H), 1.97-2.06 (m, 1 H), 3.30-3.38 (m, 1 H), 3.48 (dd, J=13.40, 2.86 Hz, 1 H), 3.73 (ddd, J=13.84, 5.05, 4.83 Hz, 1 H), 3.97-4.08 (m, 1 H), 5.79 (tt, J=52.95 Hz and J=2.64 Hz, 1 H), 6.36 (d, J=5.71 Hz, 1 H), 6.58-6.66 (m, 4H), 6.82 (d, J=8.79 Hz, 1 H), 7.01-7.10 (m, 4 H), 7.60 (dd, J=8.79, 2.64 Hz, 1 H), 8.44-8.47 (m, 1 H).

EXAMPLE 4

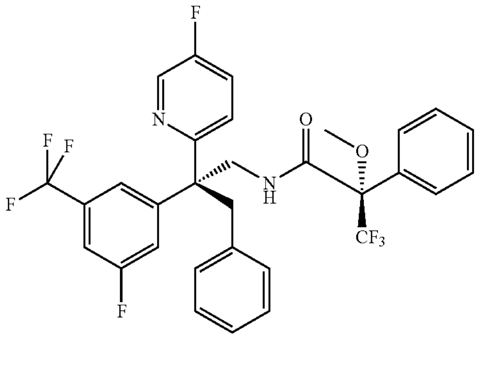

(S)-3,3,3-trifluoro-N—((S)-2-(3-fluoro-5-(trifluoromethyl)phenyl)-2-(5-fluoropyridin-2-yl)-3-phenylpropyl)-2-methoxy-2-phenylpropanamide

Procedure 9

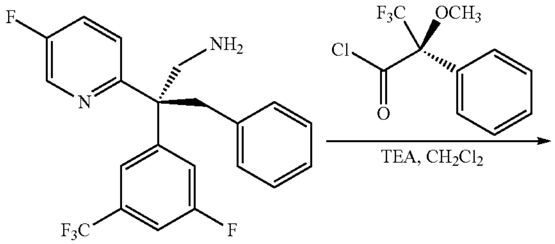

-continued

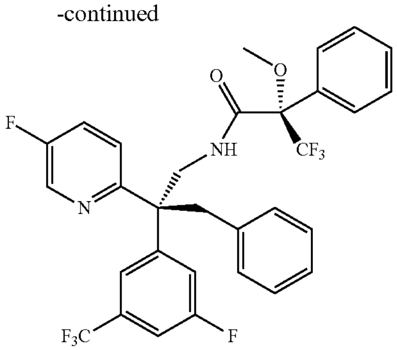

(S)-2-(3-fluoro-5-(trifluoromethyl)phenyl)-2-(5-fluoropyridin-2-yl)-3-phenylpropan-1-amine (39 mg, 0.1 mmol), prepared as described in Procedure 5, was dissolved in anhydrous $CH_2Cl_2$ (2 mL), then (R)-3,3,3-trifluoro-2-methoxy-2-phenylpropanoyl chloride (30 mg, 0.12 mmol) and TEA (0.04 mL, 0.3 mmol) were added to the solution. The reaction mixture was stirred at rt for 2 h to yield crude product. The crude product was purified by a silica gel ISCO cartridge (12 g) with elution at 25 mL/min gradient 0 to 20% EtOAc in hexane over 15 min (RT=8.5-10.5 min) to yield Example 4 as a clear oil (35 mg, 57% yield). LCMS: RT=2.20 min [M+H] 608.94 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 3.20 (s, 3 H), 3.39-3.44 (m, 1 H), 3.54-3.58 (m, 1 H), 3.83 (dd, J=13.62, 4.83 Hz, 1 H), 4.15 (dd, J=13.62, 7.03 Hz, 1 H), 6.60 (d, J=7.03 Hz, 2 H), 6.93 (d, J=10.11 Hz, 1 H), 7.06-7.18 (m, 5 H), 7.24 (d, J=7.91 Hz, 1 H), 7.32-7.41 (m, 7 H), 8.38 (d, J=3.08 Hz, 1 H).

EXAMPLE 5

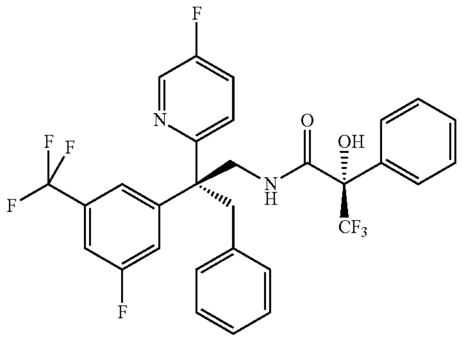

(S)-3,3,3-trifluoro-N—((R)-2-(3-fluoro-5-(trifluoromethyl)phenyl)-2-(5-fluoropyridin-2-yl)-3-phenylpropyl)-2-hydroxy-2-phenylpropanamide

Procedure 10

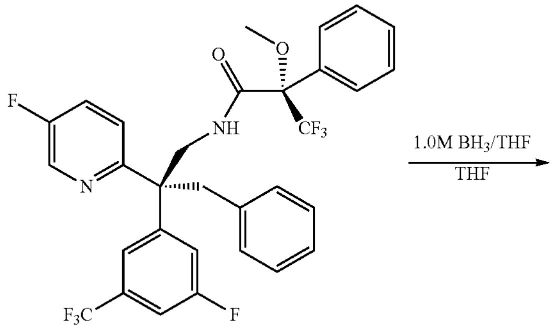

-continued

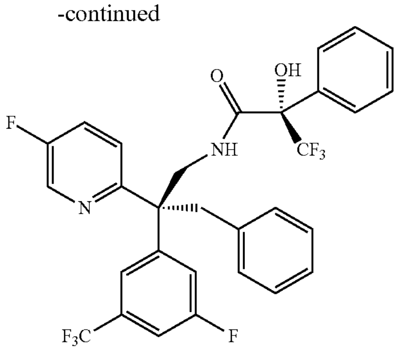

(S)-3,3,3-trifluoro-N—((R)-2-(3-fluoro-5-(trifluoromethyl)phenyl)-2-(5-fluoropyridin-2-yl)-3-phenylpropyl)-2-methoxy-2-phenylpropanamide (15 mg, 0.025 mmol), prepared as described in procedure 8, was dissolved in anhydrous THF (2 mL), followed by the addition of 1.0 M $BH_3$ solution in THF (0.15 mL, 0.15 mmol). The reaction was heated at 70° C. overnight, then cooled to rt, quenched with water and extracted with EtOAc (3×10 mL). The combined organic portions were washed with sat. NaCl, dried over $Na_2SO_4$, filtered and concentrated under reduced pressure to yield crude product. The crude product was purified by preparative HPLC (YMC Sunfire 5μ column, 30×100 mm eluting with 10-90% MeOH/$H_2O$ over 10 minutes containing 0.1% TFA, 40 mL/min, monitoring at 220 nm) to yield Example 5 as a white solid (6 mg, 40% yield). LCMS: RT=2.13 min [M+H] 595.2 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.22 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H(CDCl_3)$ ppm 3.24-3.29 (m, 1 H), 3.35-3.43 (m, 1 H), 3.62 (dd, J=13.62, 3.52 Hz, 1 H), 4.04-4.12 (m, 1 H), 6.48 (d, J=7.03 Hz, 2 H), 6.75 (d, J=10.11 Hz, 1 H), 6.97-7.15 (m, 6 H), 7.23-7.28 (m, 1 H), 7.30-7.42 (m, 4 H), 7.44 (m, 2 H), 8.18 (d, J=3.08 Hz, 1 H).

TABLE 1

| Ex. No. | Structure | Name | Retention Time Min./ Molecular Mass | Prepared in the manner described in: |
|---|---|---|---|---|
| 6 | 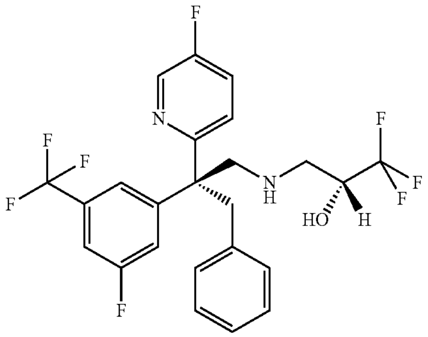 [SMILES: O[C@H](CNC[C@@](Cc1ccccc1)(c1cc(F)cc(C(F)(F)F)c1)c1ccc(F)cn1)C(F)(F)F] | (R)-1,1,1-trifluoro-3-((R)-2-(3-fluoro-5-(trifluoromethyl)phenyl)-2-(5-fluoropyridin-2-yl)-3-phenylpropylamino)propan-2-ol | 3.391 LC (4) 505.03 [M + H]$^+$ | Procedure 1, 2, 3, 4, 5, 6 |
| 7 | 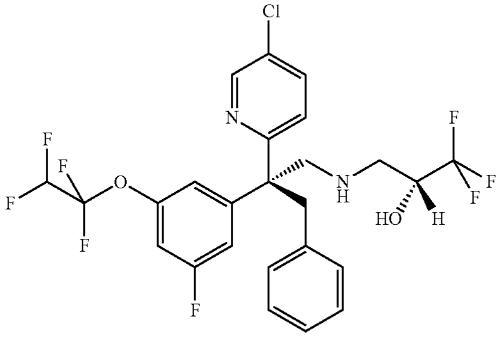 [SMILES: O[C@H](CNC[C@](Cc1ccccc1)(c1cc(F)cc(OC(F)(F)C(F)F)c1)c1ccc(Cl)cn1)C(F)(F)F] | (R)-3-((S)-2-(5-chloropyridin-2-yl)-2-(3-fluoro-5-(1,1,2,2-tetrafluoroethoxy)phenyl)-3-phenylpropylamino)-1,1,1-trifluoropropan-2-ol | 1.738 LC (2) 568.96 [M + H]$^+$ | Procedure 2, 3, 4, 5, 6, 7 |

TABLE 1-continued

| Ex. No. | Structure | Name | Retention Time Min./ Molecular Mass | Prepared in the manner described in: |
|---|---|---|---|---|
| 8 | 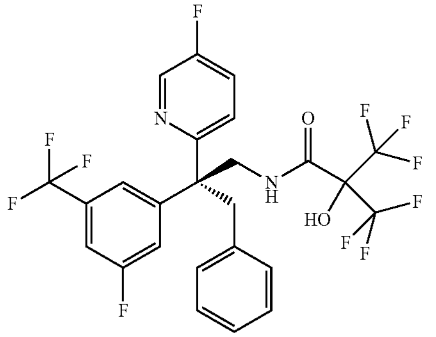 [SMILES: O=C(NC[C@@](Cc1ccccc1)(c1cc(F)cc(C(F)(F)F)c1)c1ccc(F)cn1)C(O)(C(F)(F)F)C(F)(F)F] | (R)-3,3,3-trifluoro-N-(2-(3-fluoro-5-(trifluoromethyl)phenyl)-2-(5-fluoropyridin-2-yl)-3-phenylpropyl)-2-hydroxy-2-(trifluoromethyl)propanamide | 4.145 LC (4) 587.1 [M + H]$^+$ | Procedure 1, 2, 3, 4, 5, 8 |

EXAMPLE 9

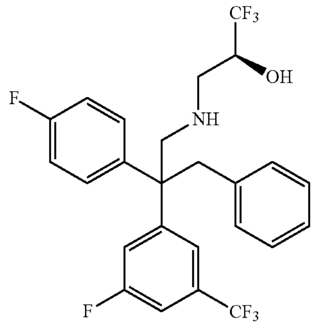 [SMILES: O[C@@H](CNCC(Cc1ccccc1)(c1ccc(F)cc1)c1cc(F)cc(C(F)(F)F)c1)C(F)(F)F]

(2S)-1,1,1-trifluoro-3-(2-(3-fluoro-5-(trifluoromethyl)phenyl)-2-(4-fluorophenyl)-3-phenylpropylamino)propan-2-ol Procedure 11

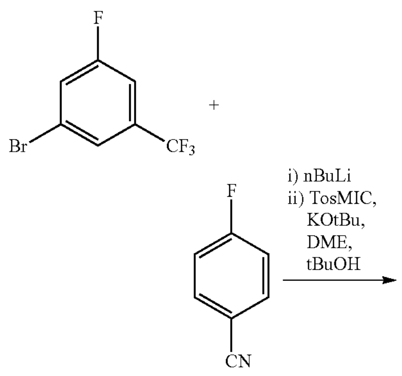

-continued

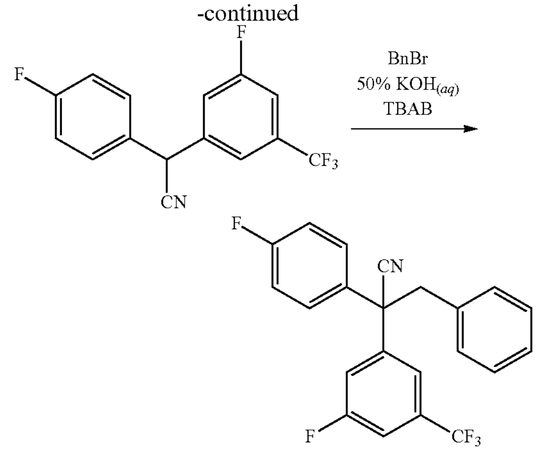

Step 1

Following Procedures 2 and 3, 2-(3-fluoro-5-(trifluoromethyl)phenyl)-2-(4-fluorophenyl)acetonitrile was prepared as a clear colorless oil (2.2 g, 61% yield). LCMS: RT=1.93 min [M-CN] 271.2 (2 min Phenomenex Luna C18 column, 4.6×30 mm eluting with 10-90% MeOH/$H_2O$ over 4 minutes containing 0.1% TFA; 5 mL/min, monitoring at 220 nm); NMR: 400 MHz $^1H(CDCl_3)$ ppm 5.18 (s, 1 H), 7.09-7.16 (m, J=8.57 Hz, 2 H), 7.22-7.28 (m, 1 H), 7.30-7.36 (m, 3 H), 7.41 (s, 2 H).

Step 2

To a solution of 2-(3-fluoro-5-(trifluoromethyl)phenyl)-2-(4-fluorophenyl)acetonitrile (200 mg, 0.67 mmol) in toluene (7 mL) was added tetrabutylammonium bromide (65 mg, 0.20 mmol) and benzyl bromide (0.095 mL, 0.80 mmol) followed by an aqueous solution of 50% KOH (2.2 mL). The reaction mixture was vigorously stirred for 5 min, then poured into $H_2O$ (20 mL) and extracted with diethyl ether (2×20 mL). The combined organic portions were dried over anhydrous $MgSO_4$, filtered and concentrated under reduced pressure to yield a residue. The residue was crystallized from methanol to give 2-(3-fluoro-5-(trifluoromethyl)phenyl)-2-(4-fluorophenyl)-3-phenylpropanenitrile (153 mg, 59% yield) as a white solid. LCMS: RT=2.11 min [M+H] 388.3 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H$ ($CDCl_3$) ppm 3.59 (d, J=12.75 Hz, 1 H), 3.65 (d, J=13.18 Hz, 1 H), 6.87 (d, J=7.03 Hz, 2 H), 7.08 (t, J=8.35 Hz, 2 H), 7.18-7.32 (m, 8 H).

Procedure 12

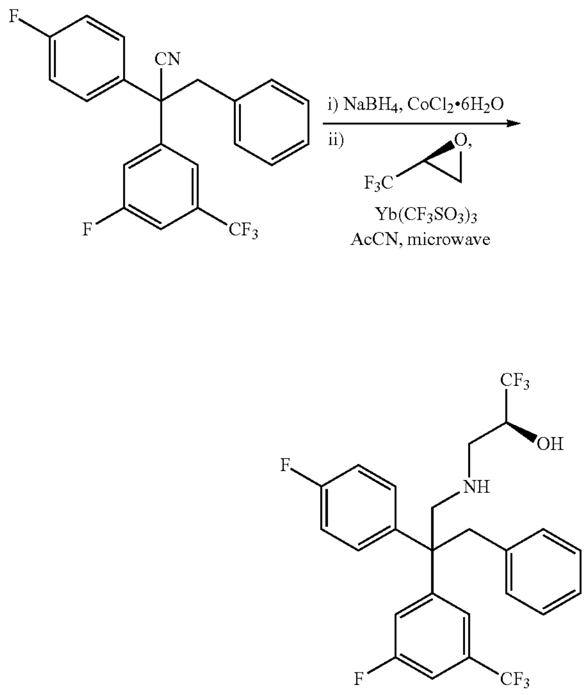

Step 1

Following Procedure 5, 2-(3-fluoro-5-(trifluoromethyl)phenyl)-2-(4-fluorophenyl)-3-phenylpropan-1-amine was prepared as a clear colorless glass (22 mg, 43% yield). LCMS: RT=1.80 min [M+H] 392.3 (2 min Phenomenex Luna C18 column, 4.6x30 mm eluting with 10-90% $MeOH/H_2O$ over 2 minutes containing 0.1% TFA; 5 mL/min, monitoring at 220 nm); NMR: 400 MHz $^1H(CDCl_3)$ ppm 3.21 (s, 2 H), 3.41 (d, J=12.31 Hz, 1 H), 3.47 (d, J=12.74 Hz, 1 H), 6.59 (d, J=7.91 Hz, 2H), 6.93-7.22 (m, 10 H).

Step 2

(S)-2-(trifluoromethyl)oxirane was prepared as described in Ramachandran, P. V. et al., *J. Org. Chem.,* 7:1307 (1995) and % ee was determined as described in Schaus, S. E. et al., *J. Am. Chem. Soc.,* 1:41-46 2002.

Step 3

Following Procedure 6, Example 9 was prepared as a clear colorless glass (75% yield, 1:1 mixture of diastereomers). LCMS: RT=1.85 min [M+H] 504.3 (2 min Phenomenex Luna C18 column, 4.6x30 mm eluting with 10-90% $MeOH/H_2O$ over 2 minutes containing 0.1% TFA; 5 mL/min, monitoring at 220 nm); NMR: 400 MHz $^1H(CDCl_3)$ ppm 2.78-2.94 (m, 2 H), 3.05-3.16 (m, 2 H), 3.32 (d, J=12.31, 0. 5H, benzylic proton of diastereomer 1), 3.47 (s, 1H, benzylic protons of diastereomer 2), 3.62 (d, J=12.75 Hz, 0.5 H, benzylic proton of diastereomer 1), 3.87-4.02 (m, 1 H), 6.50-6.57 (m, 2 H), 6.86-7.25 (m, 10 H).

Example 10

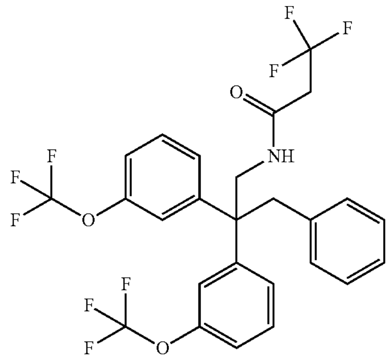 [SMILES: O=C(CC(F)(F)F)NCC(Cc1ccccc1)(c1cccc(OC(F)(F)F)c1)c1cccc(OC(F)(F)F)c1]

3,3,3-trifluoro-N-(3-phenyl-2,2-bis(3-(trifluoromethoxy)phenyl)propyl)propanamide Procedure 13

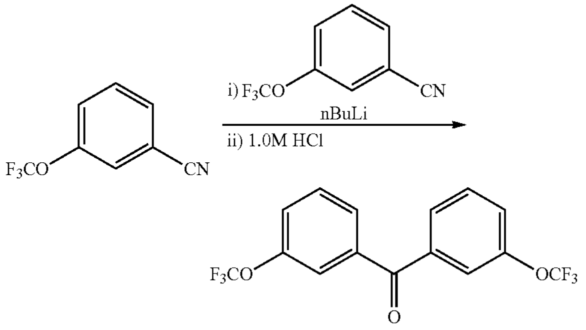

To a solution of 1-bromo-3-(trifluoromethoxy)benzene (1.52 g, 6.3 mmol) in diethyl ether (50 mL) at −78° C. was added dropwise a solution of 1.6 M n-BuLi in hexane (4.2 mL, 6.6 mmol) and the reaction mixture was stirred at −78° C. for 30 min. A solution of 3-(trifluoromethoxy)benzonitrile (1.23 g, 6.6 mmol) in diethyl ether (5 mL) was added dropwise and the reaction mixture was stirred at −78° C. for 1.5 h. 3N HCl (40 mL) was added and the reaction was allowed to warm to rt followed by stirring at rt for 1.5 h. The reaction mixture was diluted with $H_2O$ (40 mL) and extracted with EtOAc (3x75 mL). The combined organic extracts were dried over $Na_2SO_4$, filtered and concentrated under reduced pressure to yield a residue. The residue was purified by a silica gel ISCO cartridge with elution at gradient 10% EtOAc/hexane to give bis(3-(trifluoromethoxy)phenyl)methanone (1.99 g, 90% yield) as a white solid. LCMS: RT=2.10 min [M+H] 351.3 (2 min Phenomenex Luna C18 column, 4.6x30 mm eluting with 10-90% $MeOH/H_2O$ over 2 minutes containing 0.1% TFA; 5 mL/min, monitoring at 220 nm); NMR: 400

MHz $^1H(CDCl_3)$ ppm 7.46 (d, J=8.35 Hz 1 H), 7.54 (t, J=7.91 Hz, 1 H), 7.64 (s, 1 H), 7.70 (d, J=7.91 Hz, 1 H).

Procedure 14

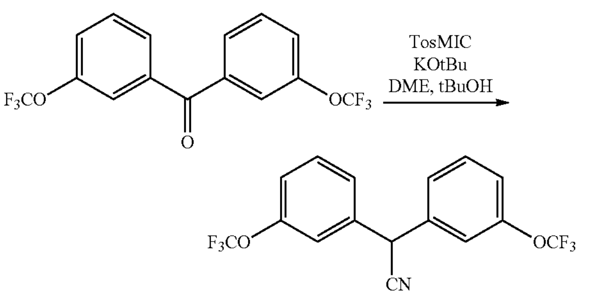

To a solution of bis(3-(trifluoromethoxy)phenyl)methanone (9.94 g, 28.4 mmol), prepared as described in Procedure 13, in DME (200 mL) was added TosMIC (7.49 g, 38.3 mmol). The reaction mixture was cooled in an ice-bath and a 1.0 M solution of t-BuOK in t-BuOH (77 mL, 77 mmol) in DME (77 mL) was added via cannula as a slow stream. Upon completion of addition, the ice-bath was removed and the reaction mixture was stirred at rt for 16 h. After this time, additional TosMIC (3.75 g, 19.2 mmol) was added at rt and the reaction mixture was stirred for an additional hour. At the conclusion of this period, the reaction was poured into $H_2O$ (150 mL) and extracted with hexane (3×200 mL). The organic portions were combined and dried over $Na_2SO_4$, filtered and concentrated under reduced pressure to yield a residue. The residue was purified on a silica gel ISCO cartridge with elution at 0 to 15% EtOAc/hexane to give 2,2-bis(3-(trifluoromethoxy)phenyl)acetonitrile (6.7 g, 67% yield) as a clear yellow oil. LCMS: RT=3.90 min [M−H] 360.2 (2 min Phenomenex Luna C18 column, 4.6×50 mm eluting with 10-90% MeOH/$H_2O$ over 4 minutes containing 0.1% $NH_4OAc$; 4 mL/min, monitoring at 220 nm); NMR: 400 MHz $^1H(CDCl_3)$ ppm 5.18 (s, 1 H), 7.18 (s, 2 H), 7.24 (d, J=9.67 Hz, 2 H), 7.30 (d, J=7.91 Hz, 2 H), 7.46 (t, J=7.91 Hz, 2 H).

Procedure 15

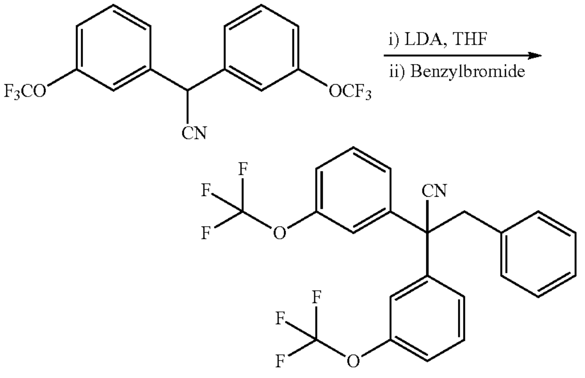

To a solution of diisopropyl amine (2.48 mL, 17.5 mmol) in THF (60 mL) at −78° C. was added dropwise n-BuLi (1.6 M in hexane, 11.5 mL, 18.3 mmol) and the reaction mixture was stirred for 5 min. A solution of (2,2-bis(3-(trifluoromethoxy) phenyl)acetonitrile (5.51 g, 15.3 mmol), prepared as described in Procedure 14, in THF (5 mL) was added dropwise to the reaction mixture and stirred for 1h. Benzyl bromide (2.17 mL, 18.3 mmol) was added dropwise, then the cooling bath was removed and the reaction mixture was stirred at rt for 45 min. The reaction mixture was poured into $H_2O$ (75 mL) and extracted with diethyl ether (2×75 mL). The combined organic portions were dried over $Na_2SO_4$, filtered and concentrated under reduced pressure to yield a residue. The residue was purified on a silica gel ISCO cartridge with elution at 5 to 15% $Et_2O$/hexane to give 3-phenyl-2,2-bis(3-(trifluoromethoxy)phenyl)propanenitrile (6.75 g, 98% yield) as a clear yellow oil. LCMS: RT=2.18 min [M-CN] 425.1 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 3.63 (s, 2 H), 6.87 (d, J=7.03 Hz, 2 H), 7.15-7.26 (m, 9 H), 7.40 (t, J=8.13 Hz, 2 H).

Procedure 16

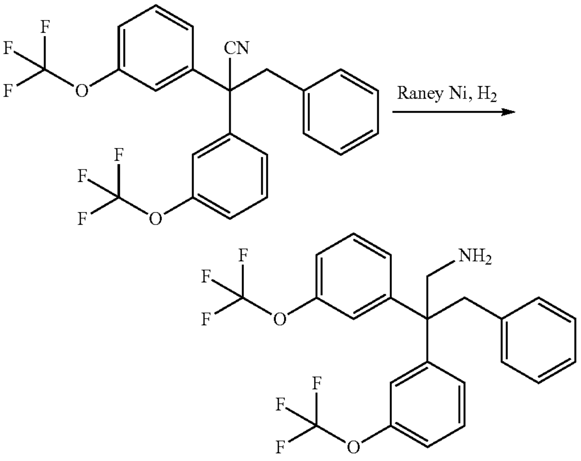

To a solution of 3-phenyl-2,2-bis(3-(trifluoromethoxy) phenyl)-propanenitrile (2.20 g, 4.88 mmol), prepared as described in Procedure 15, in EtOH (45 mL) was added an aqueous slurry of Raney 2800 nickel (4 mL). The reaction mixture was stirred under an atmosphere of hydrogen (70 psi) for 42 h. The reaction mixture was filtered through celite and concentrated under reduced pressure to give 3-phenyl-2,2-bis (3-(trifluoromethoxy)phenyl)propan-1-amine (2.04 g, 92% yield) as a clear, colorless oil. LCMS: RT=1.87 min [M+H] 456.2 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H$ $(CDCl_3)$ ppm 3.21 (s, 2 H), 3.45 (s, 2 H), 6.59 (d, J=7.03 Hz, 2 H), 6.92 (s, 2 H), 7.01-7.15 (m, 7 H), 7.31 (t, J=8.13 Hz, 2 H).

Procedure 17

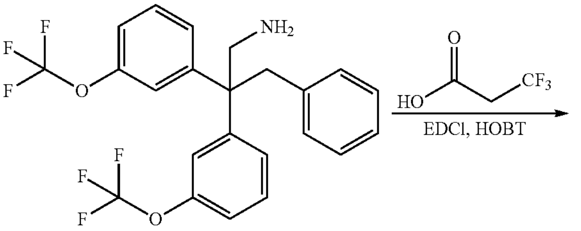

-continued

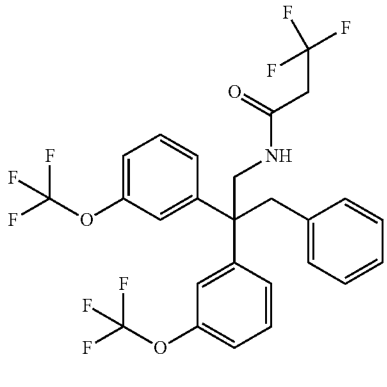

3-Phenyl-2,2-bis(3-(trifluoromethoxy)phenyl)propan-1-amine (23 mg, 0.05 mmol), prepared as described in Procedure 16, was dissolved in anhydrous DMF, then N,N-diisopropylethylamine (0.043 mL, 0.25 mmol), EDCI (12 mg, 0.06 mmol) and HOBT (8.5 mg, 0.06 mmol) followed by 3,3,3-trifluoropropanoic acid (8.1 mg, 0.06 mmol) were added to the solution. The reaction mixture was heated to 60° C. and stirred overnight. At the conclusion of this period, the reaction mixture was concentrated under reduced pressure and the resulting oil was dissolved in DMF and purified by preparative HPLC (Waters SunFire C18 OBD column, 19×100 mm×5 μm eluting with 10-90% $MeOH/H_2O$ over 10 minutes containing 0.1% TFA; 20 mL/min, monitoring at 220 nm) to provide Example 10 (17 mg, 60% yield). LCMS: [M+H] 566.17 (4 min Waters Sunfire C18 column, 4.6×50 mm×5 μm eluting with 10-90% $MeOH/H_2O$ over 4 minutes containing 0.1% TFA; 4 mL/min, monitoring at 220 nm); HPLC: RT=4.24 min (4 min Waters Sunfire C18 column, 4.6×50 mm×5 μm eluting with 10-90% $MeOH/H_2O$ over 4 minutes containing 0.1% TFA; 4 mL/min, monitoring at 220 nm.

TABLE 2

| Ex. No. | Structure | Name | Retention Time Min./ Molecular Mass | Prepared in the manner described in: |
|---|---|---|---|---|
| 11 | 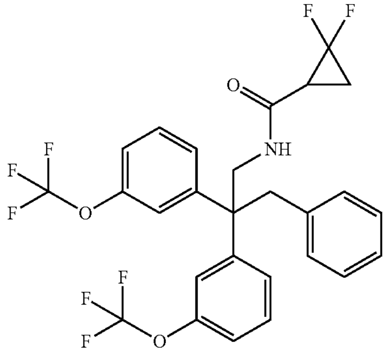 [SMILES: O=C(NCC(Cc1ccccc1)(c1cccc(OC(F)(F)F)c1)c1cccc(OC(F)(F)F)c1)C1CC1(F)F] | 2,2-difluoro-N-(3-phenyl-2,2-bis(3-(trifluoromethoxy)phenyl) propyl)cyclopropanecarboxamide | 4.24 LC (3) 560.19 $[M + H]^+$ | Procedure 13, 14, 15, 16, 17 |
| 12 | 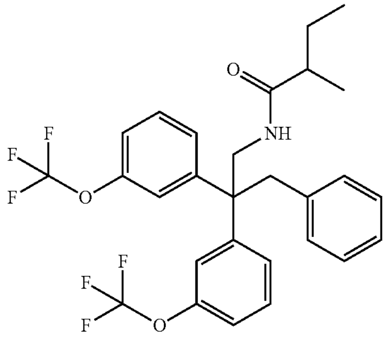 [SMILES: CCC(C)C(=O)NCC(Cc1ccccc1)(c1cccc(OC(F)(F)F)c1)c1cccc(OC(F)(F)F)c1] | 2-methyl-N-(3-phenyl-2,2-bis(3-(trifluoromethoxy)phenyl)propyl) butanamide | 4.28 LC (3) 540.2 $[M + H]^+$ | Procedure 13, 14, 15, 16, 17 |
| 13 | 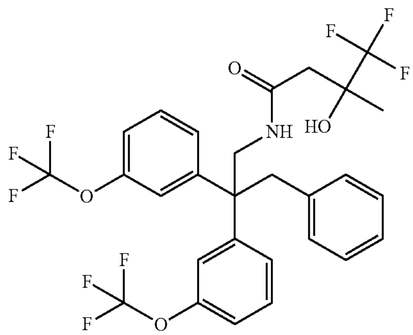 [SMILES: CC(O)(CC(=O)NCC(Cc1ccccc1)(c1cccc(OC(F)(F)F)c1)c1cccc(OC(F)(F)F)c1)C(F)(F)F] | 4,4,4-trifluoro-3-hydroxy-3-methyl-N-(3-phenyl-2,2-bis(3-(trifluoromethoxy)phenyl)propyl) butanamide | 4.21 LC (3) 610.2 $[M + H]^+$ | Procedure 13, 14, 15, 16, 17 |

TABLE 2-continued

| Ex. No. | Structure | Name | Retention Time Min./ Molecular Mass | Prepared in the manner described in: |
|---|---|---|---|---|
| 14 | 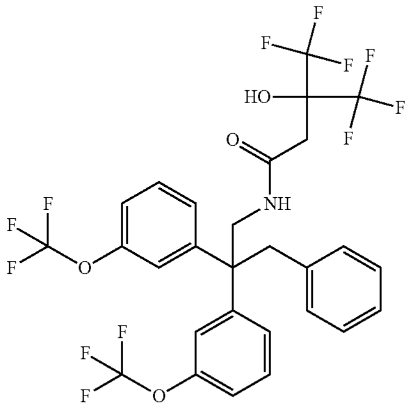 [SMILES: O=C(CC(O)(C(F)(F)F)C(F)(F)F)NCC(Cc1ccccc1)(c1cccc(OC(F)(F)F)c1)c1cccc(OC(F)(F)F)c1] | 4,4,4-trifluoro-3-hydroxy-N-(3-phenyl-2,2-bis(3-(trifluoromethoxy)phenyl)propyl)-3-(trifluoromethyl)butanamide | 4.32 LC (3) 664.2 $[M + H]^+$ | Procedure 13, 14, 15, 16, 17 |
| 15 | 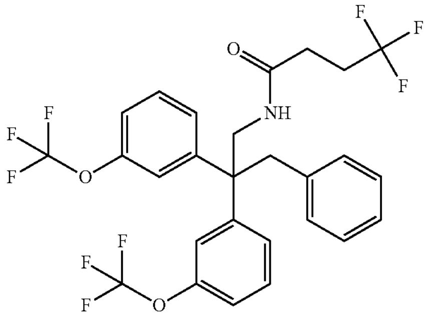 [SMILES: O=C(CCC(F)(F)F)NCC(Cc1ccccc1)(c1cccc(OC(F)(F)F)c1)c1cccc(OC(F)(F)F)c1] | 4,4,4-trifluoro-N-(3-phenyl-2,2-bis(3-(trifluoromethoxy)phenyl) propyl)butanamide | 4.23 LC (3) 580.22 $[M + H]^+$ | Procedure 13, 14, 15, 16, 17 |
| 16 | 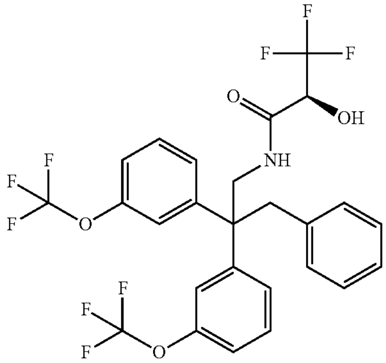 [SMILES: O=C(NCC(Cc1ccccc1)(c1cccc(OC(F)(F)F)c1)c1cccc(OC(F)(F)F)c1)[C@H](O)C(F)(F)F] | (S)-3,3,3-trifluoro-2-hydroxy-N-(3-phenyl-2,2-bis(3-(trifluoromethoxy)phenyl)propyl) propanamide | 4.17 LC (3) 582.15 $[M + H]^+$ | Procedure 13, 14, 15, 16, 17 |
| 17 | 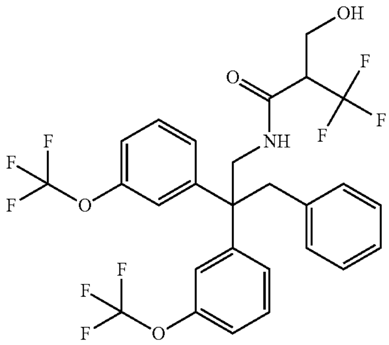 [SMILES: O=C(NCC(Cc1ccccc1)(c1cccc(OC(F)(F)F)c1)c1cccc(OC(F)(F)F)c1)C(CO)C(F)(F)F] | 3,3,3-trifluoro-2-(hydroxymethyl)-N-(3-phenyl-2,2-bis(3-(trifluoromethoxy)phenyl)propyl) propanamide | 4.15 LC (3) 596.16 $[M + H]^+$ | Procedure 13, 14, 15, 16, 17 |

TABLE 2-continued

| Ex. No. | Structure | Name | Retention Time Min./ Molecular Mass | Prepared in the manner described in: |
|---|---|---|---|---|
| 18 | 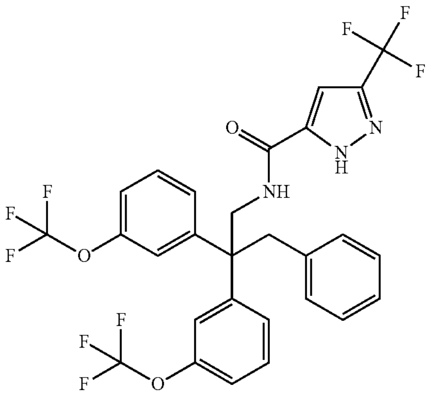 [SMILES: O=C(NCC(Cc1ccccc1)(c1cccc(OC(F)(F)F)c1)c1cccc(OC(F)(F)F)c1)c1cc(C(F)(F)F)n[nH]1] | N-(3-phenyl-2,2-bis(3-(trifluoromethoxy)phenyl)propyl)-3-(trifluoromethyl)-1H-pyrazole-5-carboxamide | 4.27 LC (3) 618.17 [M + H]+ | Procedure 13, 14, 15, 16, 17 |
| 19 | 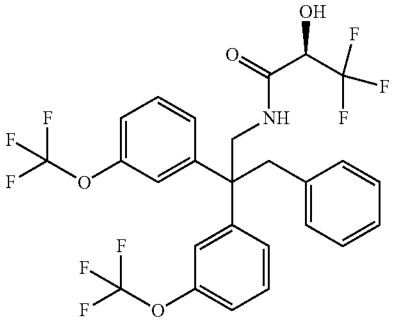 [SMILES: O=C(NCC(Cc1ccccc1)(c1cccc(OC(F)(F)F)c1)c1cccc(OC(F)(F)F)c1)[C@@H](O)C(F)(F)F] | (R)-3,3,3-trifluoro-2-hydroxy-N-(3-phenyl-2,2-bis(3-(trifluoromethoxy)phenyl)propyl) propanamide | 4.17 LC (3) 582.15 [M + H]+ | Procedure 13, 14, 15, 16, 17 |
| 20 | 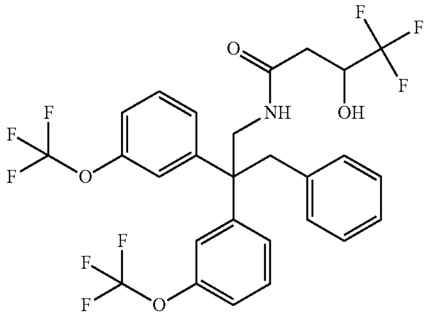 [SMILES: O=C(CC(O)C(F)(F)F)NCC(Cc1ccccc1)(c1cccc(OC(F)(F)F)c1)c1cccc(OC(F)(F)F)c1] | 4,4,4-trifluoro-3-hydroxy-N-(3-phenyl-2,2-bis(3-(trifluoromethoxy)phenyl)propyl) butanamide | 4.16 LC (3) 596.16 [M + H]+ | Procedure 13, 14, 15, 16, 17 |
| 21 | 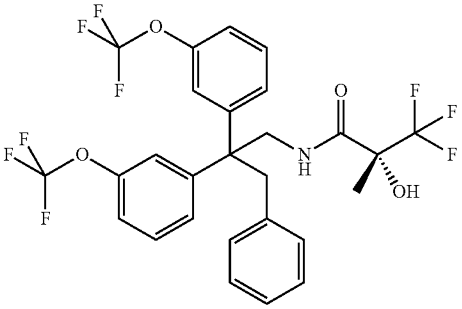 [SMILES: C[C@@](O)(C(=O)NCC(Cc1ccccc1)(c1cccc(OC(F)(F)F)c1)c1cccc(OC(F)(F)F)c1)C(F)(F)F] | (R)-3,3,3-trifluoro-2-hydroxy-2-methyl-N-(3-phenyl-2,2-bis(3-(trifluoromethoxy)phenyl)propyl) propanamide | 4.351 LC (4) 596.09 [M + H]+ | Procedure 13, 14, 15, 16, 17 |

TABLE 2-continued

| Ex. No. | Structure | Name | Retention Time Min./ Molecular Mass | Prepared in the manner described in: |
|---|---|---|---|---|
| 22 | 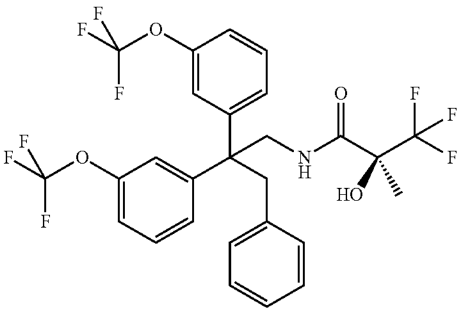 [SMILES: C[C@](O)(C(=O)NCC(Cc1ccccc1)(c1cccc(OC(F)(F)F)c1)c1cccc(OC(F)(F)F)c1)C(F)(F)F] | (S)-3,3,3-trifluoro-2-hydroxy-2-methyl-N-(3-phenyl-2,2-bis(3-(trifluoromethoxy)phenyl)propyl) propanamide | 4.351 LC (4) 596.09 $[M + H]^+$ | Procedure 13, 14, 15, 16, 17 |
| 23 | 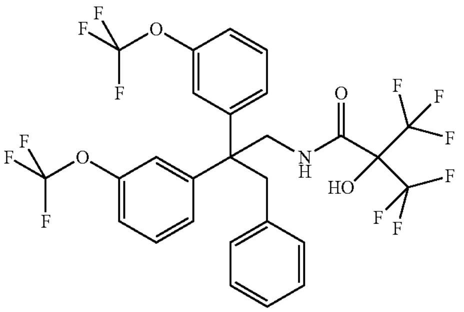 [SMILES: O=C(NCC(Cc1ccccc1)(c1cccc(OC(F)(F)F)c1)c1cccc(OC(F)(F)F)c1)C(O)(C(F)(F)F)C(F)(F)F] | 3,3,3-trifluoro-2-hydroxy-N-(3-phenyl-2,2-bis(3-(trifluoromethoxy)phenyl)propyl)-2-(trifluoromethyl)propanamide | 4.398 LC (4) 650.1 $[M + H]^+$ | Procedure 13, 14, 15, 16, 17 |

EXAMPLE 24

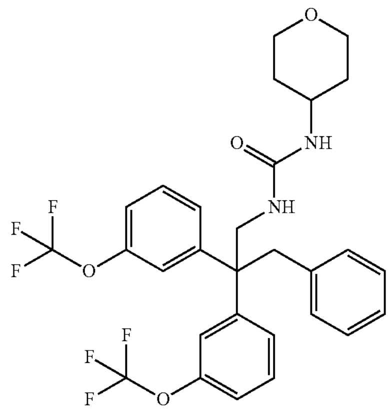 [SMILES: O=C(NCC(Cc1ccccc1)(c1cccc(OC(F)(F)F)c1)c1cccc(OC(F)(F)F)c1)NC1CCOCC1]

1-(3-phenyl-2,2-bis(3-(trifluoromethoxy)phenyl) propyl)-3-(tetrahydro-2H-pyran-4-yl)urea Procedure 18

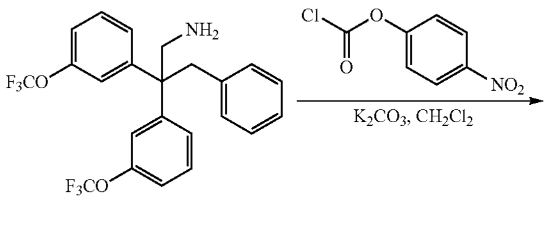

-continued

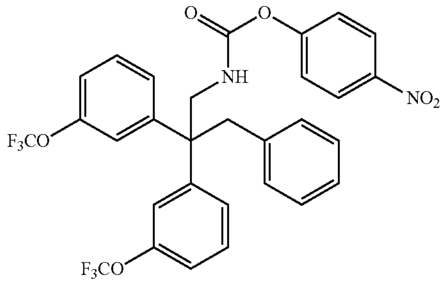

To a solution of 3-phenyl-2,2-bis(3-(trifluoromethoxy) phenyl)propan-1-amine (1.37 g, 3.00 mmol), prepared as described in Example 10 (Procedure 13, 14, 15, and 16), in $CH_2Cl_2$ (35 mL) was added $K_2CO_3$ (2.1 g, 15 mmol) followed by 4-nitrophenyl carbonochloridate (806 mg, 4.0 mmol) and the reaction mixture was stirred at rt for 5 h. The reaction mixture was diluted with $CH_2Cl_2$ (25 mL) and washed with 1N $Na_2CO_3$ (6×50 mL), then dried over $Na_2SO_4$, filtered and concentrated under reduced pressure to yield a residue. The residue was purified on a silica gel ISCO cartridge with elution at 0 to 40% EtOAc/hexane to yield [3-phenyl-2,2-bis-(3- trifluoromethoxy-phenyl)-propyl]-carbamic acid 4-nitro-phenyl ester (1.50 g, 81% yield) as a clear, colorless oil. LCMS: RT=2.30 min [M+H] 620.94 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 3.42 (s, 2 H), 3.92 (d, J=6.15 Hz, 2 H), 4.72 (t, J=5.71 Hz, 1 H), 6.60 (d, J=7.03 Hz, 2 H), 7.05-7.26 (m, 9 H), 7.37 (t, J=8.13 Hz, 2 H), 8.23 (d, J=9.23 Hz, 2 H).

Procedure 19

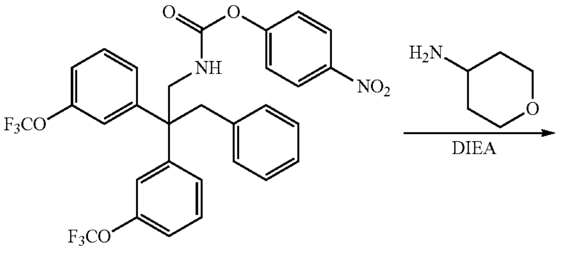

-continued

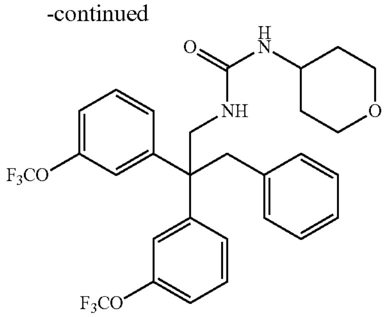

3-Phenyl-2,2-bis-(3-trifluoromethoxy-phenyl)-propyl]-carbamic acid 4-nitro-phenyl ester (31 mg, 0.05 mmol), prepared as described in procedure 18, was dissolved in anhydrous DCE, then N,N-diisopropylethylamine (0.022 mL, 0.13 mmol) and tetrahydro-2H-pyran-4-amine (10 mg, 0.1 mmol) were added to the solution. The reaction mixture was stirred at rt overnight. The reaction mixture was concentrated under reduced pressure, dissolved in DMF and purified by preparative HPLC (Waters SunFire C18 OBD column, 19×100 mm×5 μm eluting with 10-90% MeOH/$H_2O$ over 10 minutes containing 0.1% TFA; 20 mL/min, monitoring at 220 nm) to provide Example 24 (16 mg, 56% yield). LCMS: [M+H] 583.22 (4 min Waters Sunfire C18 column, 4.6×50 mm×5 μm eluting with 10-90% MeOH/$H_2O$ over 4 minutes containing 0.1% TFA; 4 mL/min, monitoring at 220 nm); HPLC: RT=4.22 min (4 min Waters Sunfire C18 column, 4.6×50 mm×5 μm eluting with 10-90% MeOH/$H_2O$ over 4 minutes containing 0.1% TFA; 4 mL/min, monitoring at 220 nm.

TABLE 3

| Ex. No. | Structure | Name | Retention Time Min./ Molecular Mass | Prepared in the manner described in: |
|---|---|---|---|---|
| 25 | 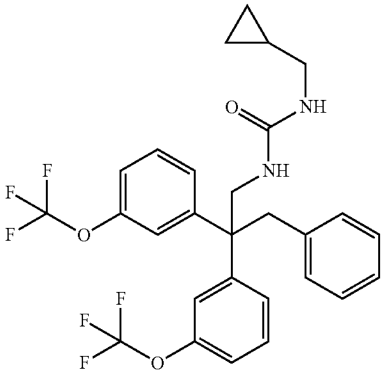 [SMILES: O=C(NCC1CC1)NCC(Cc1ccccc1)(c1cccc(OC(F)(F)F)c1)c1cccc(OC(F)(F)F)c1] | 1-(cyclopropylmethyl)-3 -(3-phenyl-2,2-bis(3-(trifluoromethoxy)phenyl) propyl)urea | 4.22 LC (3) 583.22 $[M + H]^+$ | Procedure 18, 19 |

TABLE 3-continued

| Ex. No. | Structure | Name | Retention Time Min./ Molecular Mass | Prepared in the manner described in: |
|---|---|---|---|---|
| 26 | 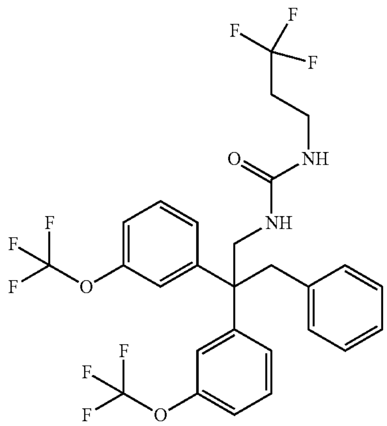 [SMILES: O=C(NCCC(F)(F)F)NCC(Cc1ccccc1)(c1cccc(OC(F)(F)F)c1)c1cccc(OC(F)(F)F)c1] | 1-(3-phenyl-2,2-bis(3-(trifluoromethoxy)phenyl)propyl)-3-(3,3,3-trifluoropropyl)urea | 4.29 LC (3) 595.17 $[M + H]^+$ | Procedure 18, 19 |
| 27 | 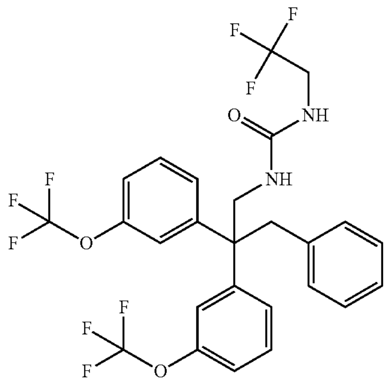 [SMILES: O=C(NCC(F)(F)F)NCC(Cc1ccccc1)(c1cccc(OC(F)(F)F)c1)c1cccc(OC(F)(F)F)c1] | 1-(3-phenyl-2,2-bis(3-(trifluoromethoxy)phenyl)propyl)-3-(2,2,2-trifluoroethyl)urea | 4.25 LC (3) 581.15 $[M + H]^+$ | Procedure 18, 19 |
| 28 | 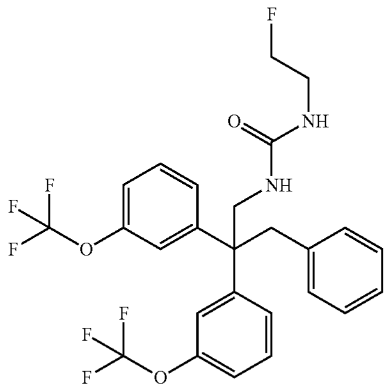 [SMILES: O=C(NCCF)NCC(Cc1ccccc1)(c1cccc(OC(F)(F)F)c1)c1cccc(OC(F)(F)F)c1] | 1-(2-fluoroethyl)-3-(3-phenyl-2,2-bis(3-(trifluoromethoxy)phenyl) propyl)urea | 4.19 LC (3) 545.2 $[M + H]^+$ | Procedure 18, 19 |

TABLE 3-continued

| Ex. No. | Structure | Name | Retention Time Min./ Molecular Mass | Prepared in the manner described in: |
|---|---|---|---|---|
| 29 | 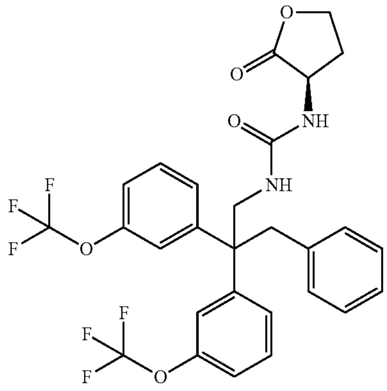 [SMILES: O=C(NCC(Cc1ccccc1)(c1cccc(OC(F)(F)F)c1)c1cccc(OC(F)(F)F)c1)N[C@@H]1CCOC1=O] | (R)-1-(2-oxo-tetrahydrofuran-3-yl)-3-(3-phenyl-2,2-bis(3-(trifluoromethoxy)phenyl)propyl) urea | 4.11 LC (3) 583.2 $[M + H]^+$ | Procedure 18, 19 |
| 30 | 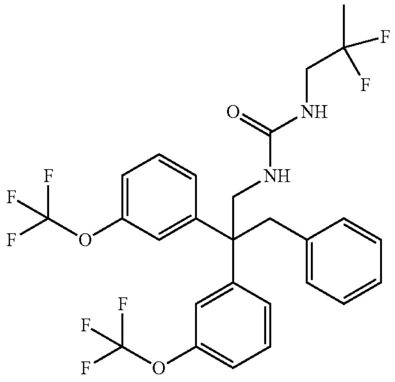 [SMILES: CC(F)(F)CNC(=O)NCC(Cc1ccccc1)(c1cccc(OC(F)(F)F)c1)c1cccc(OC(F)(F)F)c1] | 1-(2,2-difluoropropyl)-3-(3-phenyl-2,2-bis(3-(trifluoromethoxy)phenyl) propyl)urea | 4.26 LC (3) 577.22 $[M + H]^+$ | Procedure 18, 19 |
| 31 | 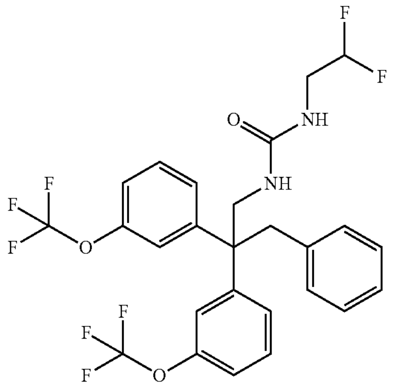 [SMILES: O=C(NCC(F)F)NCC(Cc1ccccc1)(c1cccc(OC(F)(F)F)c1)c1cccc(OC(F)(F)F)c1] | 1-(2,2-difluoroethyl)-3-(3-phenyl-2,2-bis(3-(trifluoromethoxy)phenyl) propyl)urea | 4.21 LC (3) 563.2 $[M + H]^+$ | Procedure 18, 19 |

TABLE 3-continued

| Ex. No. | Structure | Name | Retention Time Min./ Molecular Mass | Prepared in the manner described in: |
|---|---|---|---|---|
| 32 | 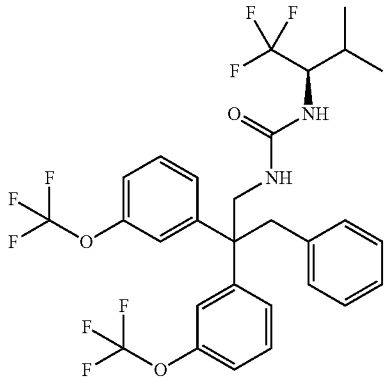 [SMILES: CC(C)[C@@H](NC(=O)NCC(Cc1ccccc1)(c1cccc(OC(F)(F)F)c1)c1cccc(OC(F)(F)F)c1)C(F)(F)F] | (R)-1-(3-phenyl-2,2-bis(3-(trifluoromethoxy)phenyl)propyl)-3-(1,1,1-trifluoro-3-methylbutan-2-yl)urea | 4.38 LC (3) 623.24 $[M + H]^+$ | Procedure 18, 19 |
| 33 | 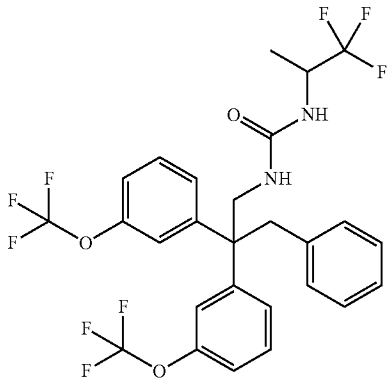 [SMILES: CC(NC(=O)NCC(Cc1ccccc1)(c1cccc(OC(F)(F)F)c1)c1cccc(OC(F)(F)F)c1)C(F)(F)F] | 1-(3-phenyl-2,2-bis(3-(trifluoromethoxy)phenyl)propyl)-3-(1,1,1-trifluoropropan-2-yl)urea | 4.28 LC (3) 595.22 $[M + H]^+$ | Procedure 18, 19 |
| 34 | 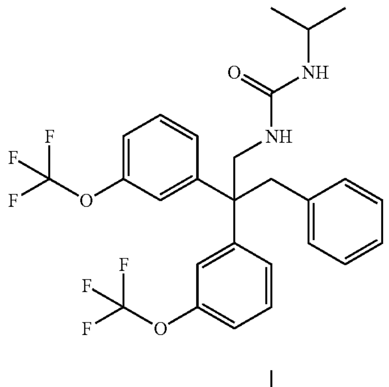 | 1-isopropyl-3-(3-phenyl-2,2-bis(3-(trifluoromethoxy)phenyl)propyl) urea | 4.27 LC (3) 541.2 $[M + H]^+$ | Procedure 18, 19 |
| 35 | 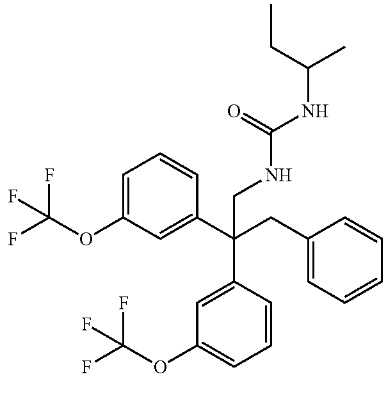 [SMILES: CCC(C)NC(=O)NCC(Cc1ccccc1)(c1cccc(OC(F)(F)F)c1)c1cccc(OC(F)(F)F)c1] | 1-sec-butyl-3-(3-phenyl-2,2-bis(3-(trifluoromethoxy)phenyl)propyl) urea | 4.32 LC (3) 555.21 $[M + H]^+$ | Procedure 18, 19 |

TABLE 3-continued

| Ex. No. | Structure | Name | Retention Time Min./ Molecular Mass | Prepared in the manner described in: |
|---|---|---|---|---|
| 36 | 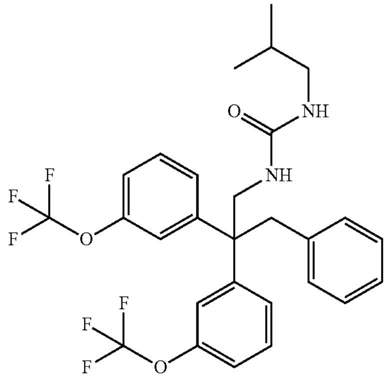 [SMILES: CC(C)CNC(=O)NCC(Cc1ccccc1)(c1cccc(OC(F)(F)F)c1)c1cccc(OC(F)(F)F)c1] | 1-isobutyl-3-(3-phenyl-2,2-bis(3-(trifluoromethoxy)phenyl)propyl) urea | 4.34 LC (3) 555.25 $[M + H]^+$ | Procedure 18, 19 |
| 37 | 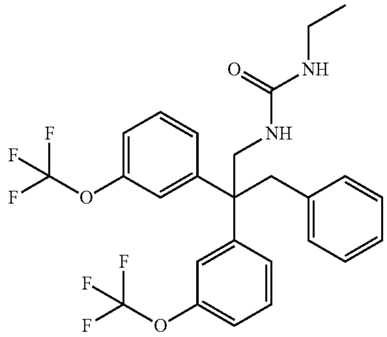 [SMILES: CCNC(=O)NCC(Cc1ccccc1)(c1cccc(OC(F)(F)F)c1)c1cccc(OC(F)(F)F)c1] | 1-ethyl-3-(3-phenyl-2,2-bis(3-(trifluoromethoxy)phenyl)propyl) urea | 4.25 LC (3) 527.2 $[M + H]^+$ | Procedure 18, 19 |
| 38 | 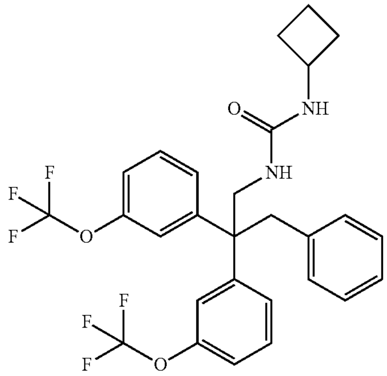 [SMILES: O=C(NCC(Cc1ccccc1)(c1cccc(OC(F)(F)F)c1)c1cccc(OC(F)(F)F)c1)NC1CCC1] | 1-cyclobutyl-3-(3-phenyl-2,2-bis(3-(trifluoromethoxy)phenyl)propyl) urea | 4.31 LC (3) 553.21 $[M + H]^+$ | Procedure 18, 19 |
| 39 | 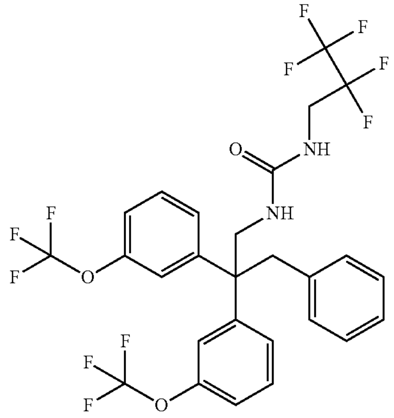 [SMILES: O=C(NCC(Cc1ccccc1)(c1cccc(OC(F)(F)F)c1)c1cccc(OC(F)(F)F)c1)NCC(F)(F)C(F)(F)F] | 1-(2,2,3,3,3-pentafluoropropyl)-3-(3-phenyl-2,2-bis(3-(trifluoromethoxy)phenyl)propyl) urea | 4.33 LC (3) 631.15 $[M + H]^+$ | Procedure 18, 19 |

EXAMPLE 40

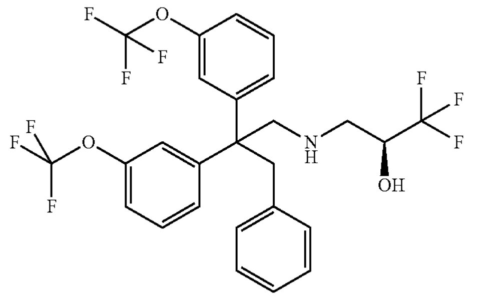 [SMILES: O[C@@H](CNCC(Cc1ccccc1)(c1cccc(OC(F)(F)F)c1)c1cccc(OC(F)(F)F)c1)C(F)(F)F]

(S)-1,1,1-trifluoro-3-(3-phenyl-2,2-bis(3-(trifluoromethoxy)phenyl)propylamino)propan-2-ol Procedure 20

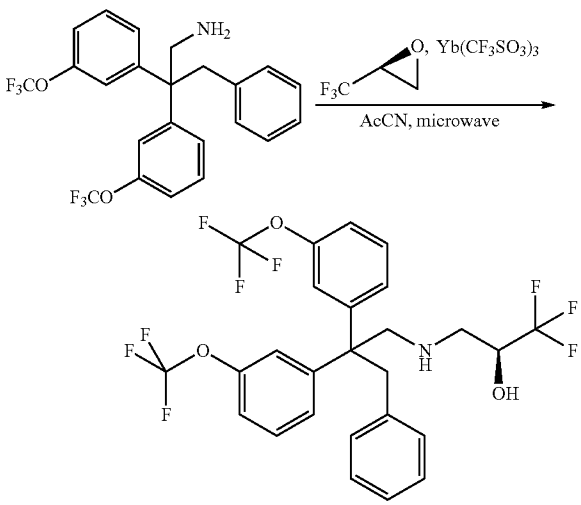

3-Phenyl-2,2-bis(3-(trifluoromethoxy)phenyl)propan-1-amine (60 mg, 0.1 mmol), prepared as described in Example 10 (Procedure 13, 14, 15, and 16), was dissolved in anhydrous acetonitrile (1 mL) in a microwave vial. (S)-2-(trifluoromethyl)oxirane (0.78 g, 7 mmol, 70% ee, purchased from TCI America) was added to the solution followed by $Yb(CF_3SO_3)_3$ (60 mg, 0.1 mmol). The sealed vial was heated to 130° C. for 10 minutes under microwave irradiation. The reaction mixture was concentrated and the crude product was dissolved in $CH_2Cl_2$ and purified by a silica gel ISCO cartridge (12 g) with elution at 25 mL/min gradient 0% to 15% EtOAc in hexane over 20 min (RT=11-13.5 min) to provide Example 40 as a clear oil (40 mg, 53% yield, 70% ee). LCMS: RT=1.88 min [M+H] 568.35 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.91 min (Phenomenex Luna C18 column, 4.6×50 mm eluting with 10-90% $MeOH/H_2O$ over 4 minutes containing 0.2% PPA; 4 mL/min, monitoring at 220 nm); NMR: 400 MHz $^1H(CDCl_3)$ ppm 2.76-2.82 (m, 1 H), 2.84-2.89 (m, 1 H), 3.05-3.13 (m, 2 H), 3.36 (d, J=12.74 Hz, 1 H), 3.53 (d, J=12.74 Hz, 1 H), 3.90-3.95 (m, 1H), 6.52 (d, J=7.03 Hz, 2 H), 6.84 (s, 1 H), 6.94-6.98 (m, 2 H), 7.03-7.14 (m, 6 H), 7.31 (ddd, J=12.19, 8.02, 7.91 Hz, 2 H).

EXAMPLE 41

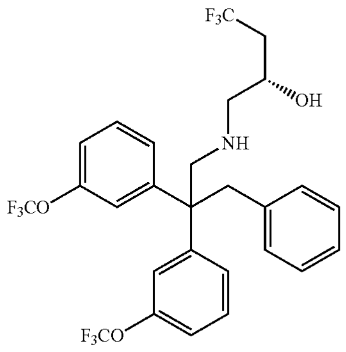 [SMILES: O[C@H](CNCC(Cc1ccccc1)(c1cccc(OC(F)(F)F)c1)c1cccc(OC(F)(F)F)c1)CC(F)(F)F]

(S)-4,4,4-trifluoro-1-(3-phenyl-2,2-bis(3-(trifluoromethoxy)phenyl)propylamino)butan-2-ol

EXAMPLE 42

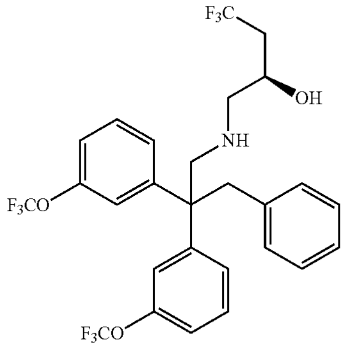 [SMILES: O[C@@H](CNCC(Cc1ccccc1)(c1cccc(OC(F)(F)F)c1)c1cccc(OC(F)(F)F)c1)CC(F)(F)F]

(R)-4,4,4-trifluoro-1-(3-phenyl-2,2-bis(3-(trifluoromethoxy)phenyl)propylamino)butan-2-ol Procedure 21

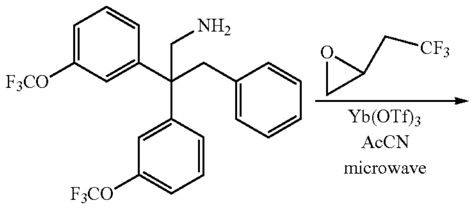

-continued

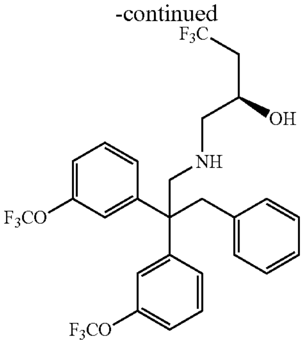

+

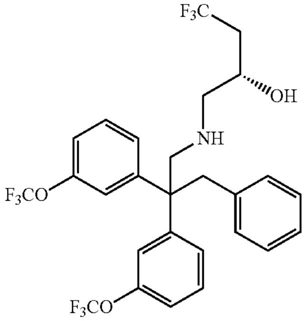

3-Phenyl-2,2-bis(3-(trifluoromethoxy)phenyl)propan-1-amine (40 mg, 0.09 mmol), prepared as described in Example 10 (Procedure 13, 14, 15, and 16), was dissolved in anhydrous acetonitrile (0.5 mL) in a microwave vial. 2-(2,2,2-Trifluoroethyl)oxirane (0.51 g, 4 mmol) was added to the solution followed by $Yb(CF_3SO_3)_3$ (0.04 g, 0.06 mmol). The sealed vial was heated to 130° C. for 12 min under microwave irradiation. The reaction mixture was concentrated under reduced pressure and the crude product was purified by preparative HPLC (YMC Sunfire 5μ column, 30×100 mm eluting with 10-90% $MeOH/H_2O$ over 10 minutes containing 0.1% TFA; 40 mL/min, monitoring at 220 nm) to give a racemic mixture of R/S-4,4,4-trifluoro-1-(3-phenyl-2,2-bis(3-(trifluoromethoxy)phenyl)propylamino)-butan-2-ol as a white solid (50 mg, 95% yield). LCMS: RT=1.93 min [M+H] 581.96 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=3.686 min (Phenomenex Luna C18 column, 4.6×50 mm eluting with 10-90% $MeOH/H_2O$ over 4 minutes containing 0.2% PPA; 4 mL/min, monitoring at 220 nm). The racemic mixture (50 mg) was dissolved in $CH_3OH$ and resolved by chiral prep HPLC (Chiralpak AD 20μ column, 5×50 cm isocratic elution with 5% isopropanol/heptane, 50 mL/min, monitoring at 254 nm) to provide Example 41 (18 mg) as a colorless oil: analytical chiral HPLC (Diacel Chiralpak AD 10μ column, 4.6×250 mm isocratic elution with 5% isopropanol/heptane, 1 mL/min, monitoring at 254 nm), RT=5.03 min; NMR: 400 MHz $^1H(CDCl_3)$ ppm 2.14 (ddd, J=15.27, 11.10, 4.39 Hz, 1 H), 2.29 (ddd, J=14.94, 10.99, 7.47 Hz, 1 H), 2.48 (dd, J=12.08, 9.01 Hz, 1 H), 2.73 (dd, J=11.86, 3.08 Hz, 1 H), 3.02-3.08 (m, 1 H), 3.13-3.20 (m, 1 H), 3.39-3.45 (m, 1 H), 3.47-3.52 (m, 1 H), 3.91 (ddd, J=8.02, 4.17, 4.06 Hz, 1H), 6.53 (d, J=7.03 Hz, 2 H), 6.89 (d, J=10.11 Hz, 2 H), 6.98-7.08 (m, 4 H), 7.11 (d, J=7.47 Hz, 3 H), 7.31 (td, J=8.13, 3.52 Hz, 2 H); and Example 42 (22 mg) as a colorless oil: analytical chiral HPLC (Diacel Chiralpak AD 10μ column, 4.6×250 mm isocratic elution with 5% isopropanol/heptane, 1 mL/min, monitoring at 254 nm), RT=5.46 min; NMR: 400 MHz $^1H(CDCl_3)$ ppm 2.05-2.16 (m, 1 H), 2.33 (ddd, J=15.16, 10.77, 6.59 Hz, 1 H), 2.63 (t, J=11.42 Hz, 1 H), 2.95 (dd, J=12.08, 2.86 Hz, 1 H), 3.33 (d, J=11.86 Hz, 1 H), 3.49-3.55 (m, 1 H), 3.57-3.65 (m, 2 H), 4.19 (d, J=6.59 Hz, 1 H), 6.56 (d, J=7.03 Hz, 2 H), 6.83 (s, 1 H), 6.90 (s, 1 H), 6.96 (d, J=7.91 Hz, 1 H), 7.09 (t, J=7.25 Hz, 3 H), 7.14-7.22 (m, 3 H), 7.32-7.42 (m, 2 H).

EXAMPLE 43

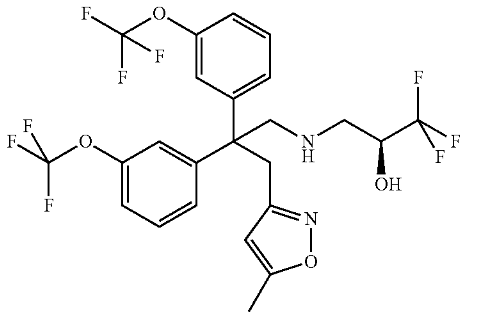 [SMILES: Cc1cc(CC(CNC[C@H](O)C(F)(F)F)(c2cccc(OC(F)(F)F)c2)c2cccc(OC(F)(F)F)c2)no1]

(S)-1,1,1-trifluoro-3-(3-(5-methylisoxazol-3-yl)-2,2-bis(3-(trifluoromethoxy)phenyl)propylamino)propan-2-ol

Procedure 22

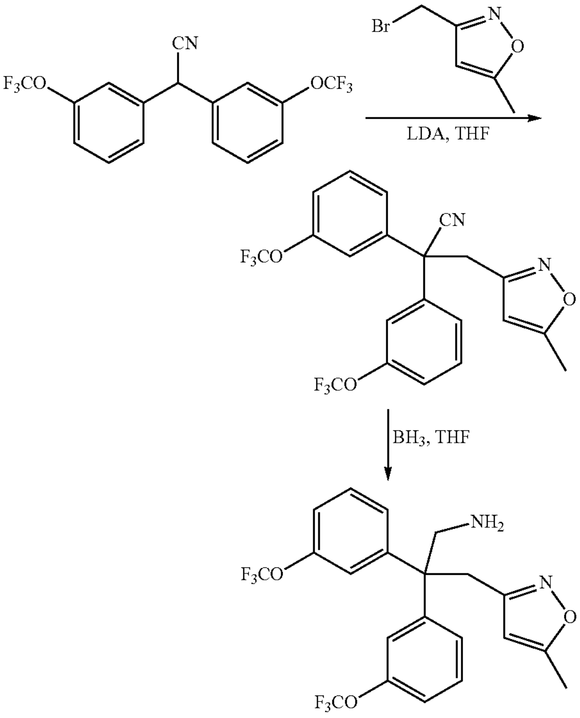

Step 1

3-(5-Methylisoxazol-3-yl)-2,2-bis(3-(trifluoromethoxy)phenyl)-propanenitrile (476 mg, 94% yield) was prepared as described in Example 10 (Procedure 13 and 14). LCMS: RT=2.05 min [M+H] 456.97 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=4.113 min (Phenomenex Luna C18 column, 4.6×50 mm eluting with 10-90% MeOH/$H_2O$ over 4 minutes containing 0.2% PPA; 4 mL/min, monitoring at 220 nm). To a solution of 3-(5-methylisoxazol-3-yl)-2,2-bis(3-(trifluoromethoxy)phenyl)propanenitrile (0.172 g, 3.77 mmol) in THF was added $BH_3$ (1.0 M in THF, 1.5 ml, 9.05 mmol) and the reaction was heated at 70° C. for 2 h. The reaction mixture was quenched with 1N HCl and the pH was adjusted to pH>10 by addition of 4N NaOH. The aqueous portion was extracted with EtOAc (3×30 mL). The combined organic portions were washed with water, sat. NaCl, dried over anhydrous $Na_2SO_4$, filtered and concentrated under reduced pressure to yield 3-(5-methylisoxazol-3-yl)-2,2-bis(3-(trifluoromethoxy)phenyl)propan-1-amine as a clear oil (112 mg, 65% yield) which was used without further purification. LCMS: RT=1.78 min [M+H] 461.1 (2 min Phenomenex Luna C18 column, 4.6×30 mm eluting with 10-90% MeOH/$H_2O$ over 2 minutes containing 0.1% TFA; 5 mL/min, monitoring at 220 nm.

Step 2

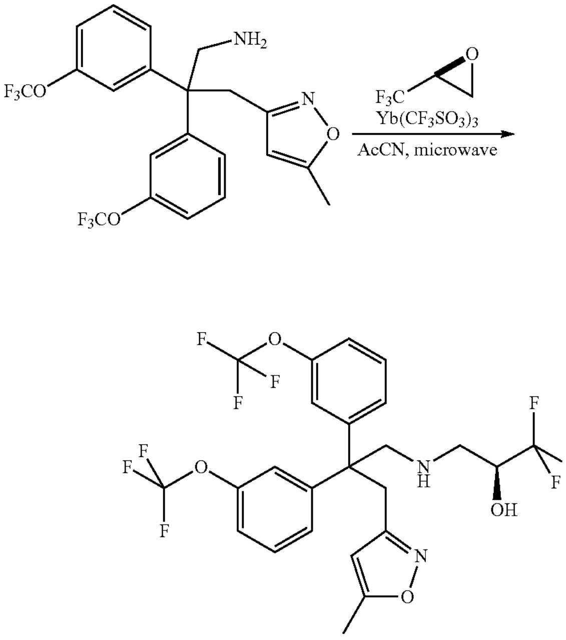

3-(5-Methylisoxazol-3-yl)-2,2-bis(3-(trifluoromethoxy)phenyl)propan-1-amine, prepared as described above, was converted to Example 43 (10 mg, 15% yield) as described in Procedure 6. LCMS: RT=1.82 min [M+H] 573.2 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.65 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H(CDCl_3)$ ppm 2.19 (s, 3 H), 2.82-2.87 (m, 2 H), 3.11-3.19 (m, 2H), 3.47 (d, J=12.74 Hz, 1 H), 3.68 (d, J=12.74 Hz, 1 H), 3.93-4.01 (m, 1 H), 4.57 (s, 1 H), 6.95 (d, J=15.82 Hz, 2 H), 7.06 (dd, J=14.94, 7.91 Hz, 2 H), 7.14 (d, J=8.35 Hz, 2 H), 7.34 (td, J=8.13, 2.64 Hz, 2 H).

EXAMPLE 44

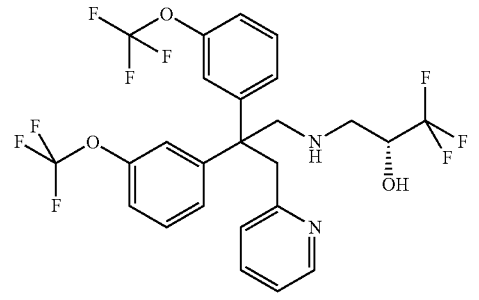 [SMILES: O[C@H](CNCC(Cc1ccccn1)(c1cccc(OC(F)(F)F)c1)c1cccc(OC(F)(F)F)c1)C(F)(F)F]

(R)-1,1,1-trifluoro-3-(3-(pyridin-2-yl)-2,2-bis(3-(trifluoromethoxy)phenyl)propylamino)propan-2-ol Procedure 23

Step 1

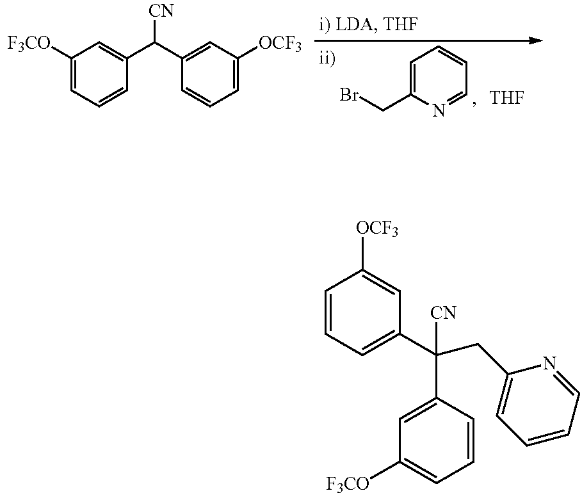

2,2-Bis(3-(trifluoromethoxy)phenyl)acetonitrile (100 mg, 0.3 mmol), prepared as described in Example 10 (Procedure 13 and 14), was converted to crude 3-(pyridin-2-yl)-2,2-bis(3-(trifluoromethoxy)phenyl)propanenitrile as described in Procedure 15. The crude 3-(pyridin-2-yl)-2,2-bis(3-(trifluoromethoxy)phenyl)-propanenitrile was purified by a silica gel ISCO cartridge with elution at gradient 0 to 100% EtOAc in hexane to yield a clear colorless oil (87 mg, 69% yield). LCMS: RT=1.92 min [M+H] 452.96 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 3.85 (s, 2 H), 7.07 (d, J=7.91 Hz, 1 H), 7.13 (dd, J=6.59, 4.83 Hz, 1 H), 7.20 (d, J=7.03 Hz, 2 H), 7.23 (s, 2H), 7.30 (d, J=7.03 Hz, 2 H), 7.40 (t, J=8.13 Hz, 2 H), 7.54 (td, J=7.69, 1.76 Hz, 1 H), 8.44 (d, J=4.83 Hz, 1 H).

Step 2

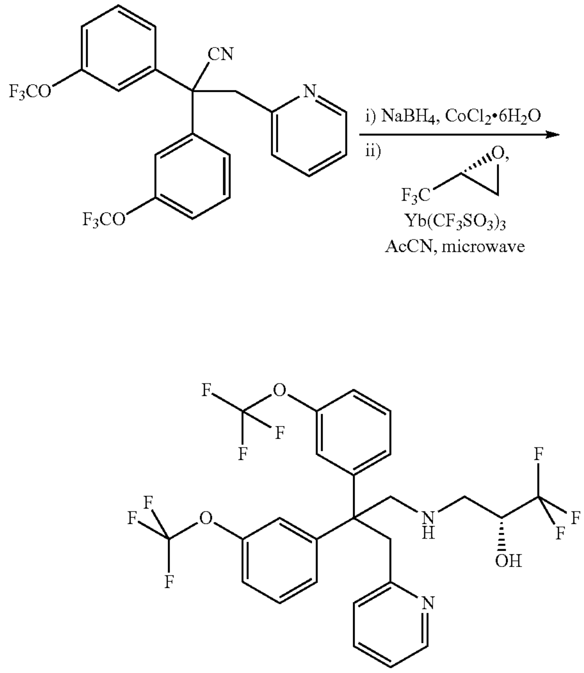

Purified 3-(pyridin-2-yl)-2,2-bis(3-(trifluoromethoxy)phenyl)propanenitrile (100 mg, 0.2 mmol) was converted to crude 3-(pyridin-2-yl)-2,2-bis(3-(trifluoromethoxy)phenyl)propan-1-amine as described in Procedure 5. 3-(Pyridin-2-yl)-2,2-bis(3-(trifluoromethoxy)phenyl)propan-1-amine was purified by a silica gel ISCO cartridge (12 g) with elution at 25 mL/min gradient 0 to 5% $MeOH/CH_2Cl_2$ to yield a clear oil (50 mg, 63% yield). LCMS: RT=1.71 min [M+H] 457.13 (2 min Phenomenex Luna C18 column, 4.6x30 mm eluting with 10-90% $MeOH/H_2O$ over 2 minutes containing 0.1% TFA; 5 mL/min, monitoring at 220 nm). The purified 3-(pyridin-2-yl)-2,2-bis(3-(trifluoromethoxy)phenyl)propan-1-amine was subsequently converted to Example 44 as described in Procedure 6. The reaction mixture was first purified by preparative HPLC YMC Sunfire 5μ column, 30×100 mm eluting with 10-90% $MeOH/H_2O$ over 10 minutes containing 0.1% TFA; 40 mL/min, monitoring at 220 nm, then further purified using a silica gel ISCO cartridge (12 g) with elution at 25 mL/min gradient 0 to 5% MeOH in $CH_2Cl_2$ over 16 min to provide Example 44 as a colorless oil (7 mg, 16% yield). LCMS: RT=1.77 min [M+H] 568.94 (2 min Phenomenex Luna C18 column, 4.6x30 mm eluting with 10-90% $MeOH/H_2O$ over 2 minutes containing 0.1% TFA; 5 mL/min, monitoring at 220 nm); NMR: 400 MHz $^1H(CDCl_3)$ ppm 2.79-2.90 (m, 2 H), 3.07-3.12 (m, 1 H), 3.15-3.21 (m, 1 H), 3.59 (d, J=11.86 Hz, 1 H), 3.78 (d, J=11.86 Hz, 1H), 3.99-4.07 (m, 1 H), 5.99 (d, J=7.91 Hz, 1 H), 6.77 (s, 1 H), 6.85 (s, 1 H), 6.91 (d, J=7.91 Hz, 1 H), 6.98 (d, J=7.91 Hz, 1 H), 7.04 (d, J=6.15 Hz, 3 H), 7.18-7.28 (m, 3H), 8.42 (d, J=3.95 Hz, 1 H).

EXAMPLE 45

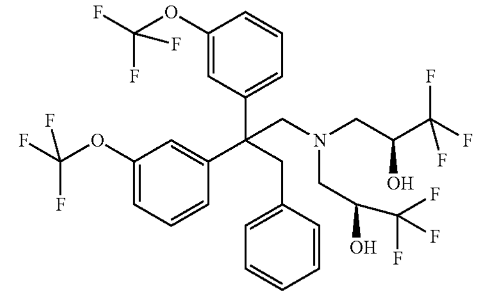 [SMILES: O[C@@H](CN(C[C@H](O)C(F)(F)F)CC(Cc1ccccc1)(c1cccc(OC(F)(F)F)c1)c1cccc(OC(F)(F)F)c1)C(F)(F)F]

(2S,2'S)-3,3'-(3-phenyl-2,2-bis(3-(trifluoromethoxy)phenyl)propylazanediyl)bis(1,1,1-trifluoropropan-2-ol)

Procedure 24

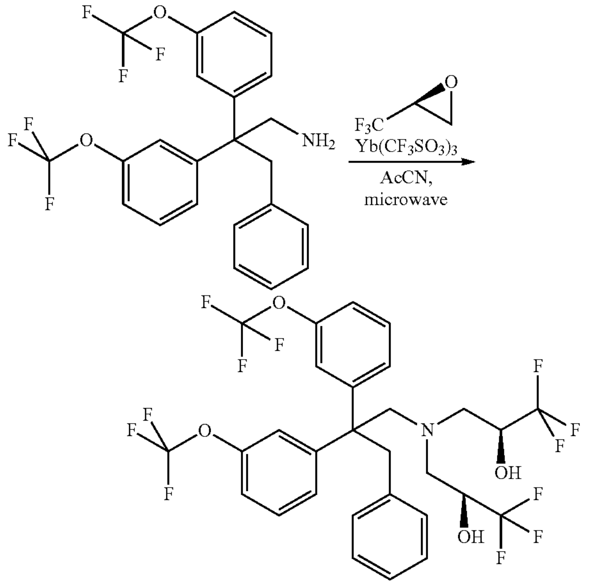

3-Phenyl-2,2-bis(3-(trifluoromethoxy)phenyl)propan-1-amine (40 mg, 0.09 mmol), prepared as described in Example 10 (Procedure 13, 14, 15, and 16), was dissolved in anhydrous acetonitrile (0.5 mL) in a microwave vial. (S)-2-(trifluoromethyl)oxirane (0.78 g, 7 mmol, 70% ee, purchased from TCI America) was added to the solution followed by $Yb(CF_3SO_3)_3$ (50 mg, 0.08 mmol). The sealed vial was heated to 135° C. for 30 min under microwave irradiation. The reaction mixture was purified by preparative HPLC (YMC Sunfire 5μ column, 30×100 mm eluting with 10-90% $MeOH/H_2O$ over 10 minutes containing 0.1% TFA; 40 mL/min, monitoring at 220 nm) to provide Example 45 as a colorless oil (15 mg, 25% yield, diastereomer mixture). LCMS: RT=2.29 min [M+H] 680.2 (2 min Phenomenex Luna C18 column, 4.6x30 mm eluting with 10-90% $MeOH/H_2O$ over 2 minutes containing 0.1% TFA; 5 mL/min, monitoring at 220 nm); HPLC: RT=4.516 min (Phenomenex Luna C18 column, 4.6x50 mm eluting with 10-90% $MeOH/H_2O$ over 4 minutes containing 0.2% PPA; 4 mL/min, monitoring at 220 nm); NMR: 400 MHz $^1H(CDCl_3)$ ppm 2.64-2.80 (m, 5 H), 3.34-3.40 (m, 1 H), 3.49-3.60 (m, 4 H), 3.63-3.68 (m, 1 H), 6.59 (d, J=7.03 Hz, 2 H), 6.90 (s, 1 H), 7.02-7.20 (m, 8 H), 7.33 (dq, J=8.13, 7.98 Hz, 2 H).

EXAMPLE 46

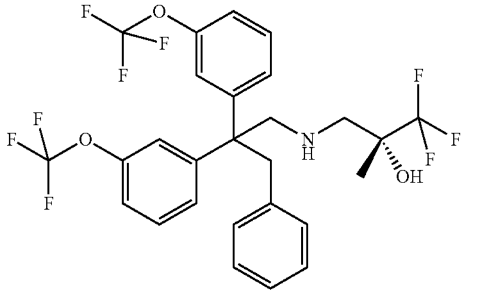 [SMILES: C[C@@](O)(CNCC(Cc1ccccc1)(c1cccc(OC(F)(F)F)c1)c1cccc(OC(F)(F)F)c1)C(F)(F)F]

((R)-1,1,1-trifluoro-2-methyl-3-(3-phenyl-2,2-bis(3-(trifluoromethoxy)phenyl)propylamino)propan-2-ol Procedure 25

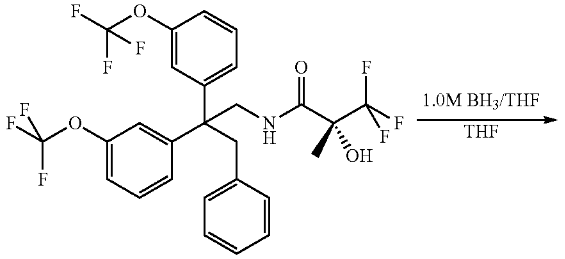

-continued

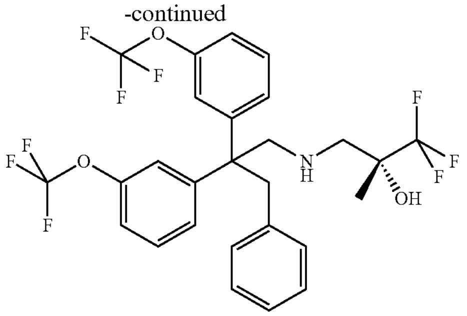

3-Phenyl-2,2-bis(3-(trifluoromethoxy)phenyl)propan-1-amine, prepared as described in Example 7 (Procedure 13, 14, 15, and 16), was converted to (R)-3,3,3-trifluoro-2-hydroxy-2-methyl-N-(3-phenyl-2,2-bis(3-(trifluoromethoxy)phenyl)propyl)propanamide (33 mg, 58% yield) as described in Procedure 8. (R)-3,3,3-trifluoro-2-hydroxy-2-methyl-N-(3-phenyl-2,2-bis(3-(trifluoromethoxy)phenyl)propyl)propanamide (24 mg, 0.04 mmol) was dissolved in anhydrous THF (2 mL), then 1.0 M $BH_3$ solution in THF (0.16 mL, 0.16 mmol) was added to the solution. The reaction mixture was heated at 70° C. for 4 h, cooled to rt and quenched with water. The aqueous portion was extracted with EtOAc (3x20 mL) and the combined organic portions were washed with sat. NaCl, dried over $Na_2SO_4$, filtered and concentrated under reduced pressure to yield the crude product. The crude product was purified by preparative HPLC (YMC Sunfire 5μ column, 30x100 mm eluting with 10-90% $MeOH/H_2O$ over 10 minutes containing 0.1% TFA; 40 mL/min, monitoring at 220 nm) to provide Example 46 as a white solid (12 mg, 52% yield). LCMS: [M+H] 582.2 (2 min Phenomenex Luna C18 column, 4.6x30 mm eluting with 10-90% $MeOH/H_2O$ over 2 minutes containing 0.1% TFA; 5 mL/min, monitoring at 220 nm); HPLC: RT=4.280 min (Phenomenex Luna C18 column, 4.6x50 mm eluting with 10-90% $MeOH/H_2O$ over 4 minutes containing 0.2% PPA; 4 mL/min, monitoring at 220 nm); NMR: 400 MHz $^1H(CDCl_3)$ ppm 1.40 (s, 3 H), 3.08 (d, J=13.18 Hz, 1 H), 3.29-3.40 (m, 3 H), 3.74 (d, J=12.30 Hz, 1 H), 3.83 (d, J=13.18 Hz, 1 H), 6.63 (d, J=7.47 Hz, 2 H), 6.70 (s, 1 H), 6.86 (d, J=7.91 Hz, 1 H), 7.03 (s, 1 H), 7.11 (t, J=7.47 Hz, 2 H), 7.16-7.25 (m, 4 H), 7.29 (d, J=8.35 Hz, 1 H), 7.36 (t, J=8.13 Hz, 2 H), 7.50 (t, J=7.91 Hz, 1 H).

TABLE 4

| Ex. No. | Structure | Name | Retention Time Min./ Molecular Mass | Prepared in the manner described in: |
|---|---|---|---|---|
| 47 | 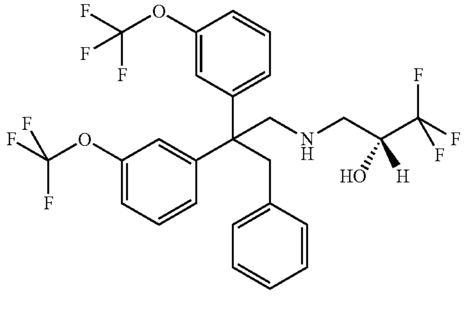 [SMILES: O[C@H](CNCC(Cc1ccccc1)(c1cccc(OC(F)(F)F)c1)c1cccc(OC(F)(F)F)c1)C(F)(F)F] | (R)-1,1,1-trifluoro-3-(3-phenyl-2,2-bis(3-(trifluoromethoxy) phenyl)propylamino)propan-2-ol | 3.896 LC (1) 568.11 $[M + H]^+$ | Procedure 13, 14, 15, 16, 6 |

TABLE 4-continued

| Ex. No. | Structure | Name | Retention Time Min./ Molecular Mass | Prepared in the manner described in: |
|---|---|---|---|---|
| 48 | 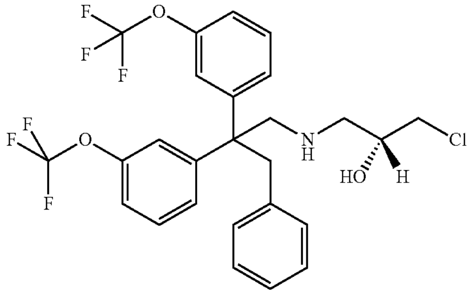 [SMILES: O[C@@H](CCl)CNCC(Cc1ccccc1)(c1cccc(OC(F)(F)F)c1)c1cccc(OC(F)(F)F)c1] | (R)-1-chloro-3-(3-phenyl-2,2-bis(3-(trifluoromethoxy) phenyl)propylamino)propan-2-ol | 1.90 LC (2) 548.08 $[M + H]^+$ | Procedure 13, 14, 15, 16, 6 |
| 49 | 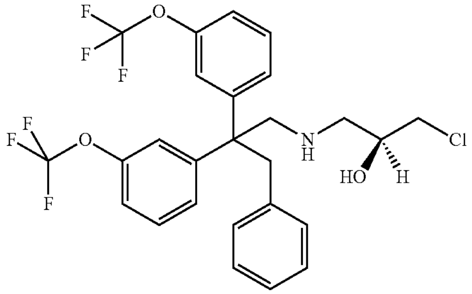 [SMILES: O[C@H](CCl)CNCC(Cc1ccccc1)(c1cccc(OC(F)(F)F)c1)c1cccc(OC(F)(F)F)c1] | (S)-1-chloro-3-(3-phenyl-2,2-bis(3-(trifluoromethoxy)phenyl) propylamino)propan-2-ol | 1.90 LC (2) 548.08 $[M + H]^+$ | Procedure 13, 14, 15,1 6, 6 |
| 50 | 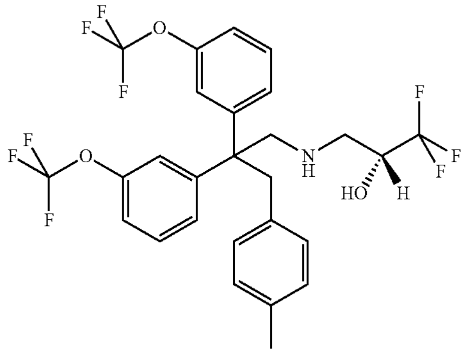 [SMILES: Cc1ccc(CC(CNC[C@@H](O)C(F)(F)F)(c2cccc(OC(F)(F)F)c2)c2cccc(OC(F)(F)F)c2)cc1] | (R)-1,1,1-trifluoro-3-(3-p-tolyl-2,2-bis(3-(trifluoromethoxy) phenyl)propylamino)propan-2-ol | 2.002 LC (2) 581.98 $[M + H]^+$ | Procedure 13, 14, 15, 16, 6 |
| 51 | 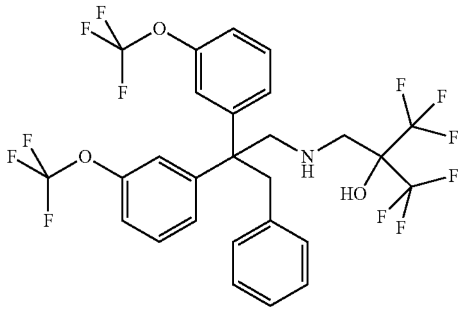 [SMILES: OC(CNCC(Cc1ccccc1)(c1cccc(OC(F)(F)F)c1)c1cccc(OC(F)(F)F)c1)(C(F)(F)F)C(F)(F)F] | 1,1,1,3,3,3 -hexafluoro-2-((3-phenyl-2,2-bis(3-(trifluoromethoxy)phenyl) propylamino)methyl)propan-2-ol | 4.768 LC (4) 636.1 $[M + H]^+$ | Procedure 13, 14, 15, 16, 8, 25 |

EXAMPLE 52

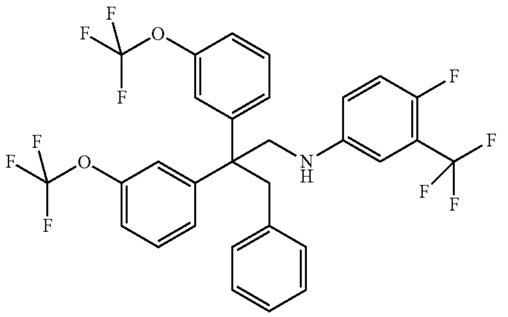 [SMILES: Fc1ccc(NCC(Cc2ccccc2)(c2cccc(OC(F)(F)F)c2)c2cccc(OC(F)(F)F)c2)cc1C(F)(F)F]

4-fluoro-N-(3-phenyl-2,2-bis(3-(trifluoromethoxy)phenyl)propyl)-3-(trifluoromethyl)benzenamine Procedure 26

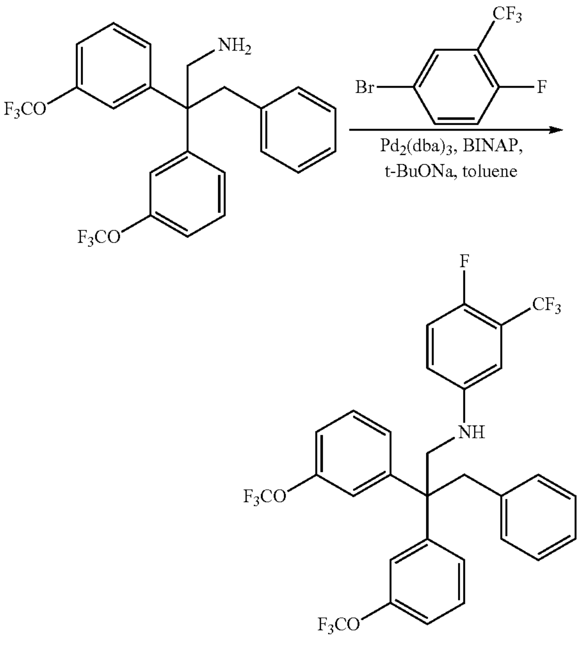

To a solution of 3-phenyl-2,2-bis(3-(trifluoromethoxy)phenyl)propan-1-amine (45 mg, 0.1 mmol), prepared as described in Example 7 (Procedure 13, 14, 15, and 16), in toluene (1 mL) was added 4-bromo-1-fluoro-2-(trifluoromethyl)benzene (29 mg, 0.1 mmol), sodium t-butoxide (29 mg, 0.3 mmol), BINAP (10 mg, 0.016 mmol), and tri(dibenzylideneacetone)dipalladium (10 mg, 0.011 mmol). The resulting reaction mixture was heated at 100° C. overnight, cooled to rt and diluted with EtOAc (approx 20 mL). The organic portion was washed with sat. $NaHCO_3$, sat. NaCl, dried over anhydrous $Na_2SO_4$, filtered and concentrated under reduced pressure to provide an oil. The oil was dissolved in $CH_2Cl_2$ and loaded directly onto a silica gel ISCO cartridge (12 g) with elution at 25 mL/min gradient 0 to 20% EtOAc in hexane over 22 min to provide Example 52 as a colorless oil (20 mg, 32% yield). LCMS: RT=2.52 min

[M+H] 618.11 (2 min Phenomenex Luna C18 column, 4.6×30 mm eluting with 10-90% $MeOH/H_2O$ over 2 minutes containing 0.1% TFA; 5 mL/min, monitoring at 220 nm); HPLC: RT=4.97 min (Phenomenex Luna C18 column, 4.6×50 mm eluting with 10-90% $MeOH/H_2O$ over 4 minutes containing 0.2% PPA; 4 mL/min, monitoring at 220 nm); NMR: 400 MHz $^1H(CDCl_3)$ ppm 3.48 (s, 2 H), 3.51 (s, 2 H), 6.47 (d, J=7.91 Hz, 2 H), 6.60-6.67 (m, 2 H), 6.94-7.00 (m, 3H), 7.03-7.08 (m, 4 H), 7.10-7.19 (m, 3 H), 7.35 (t, J=7.25 Hz, 2 H).

EXAMPLE 53

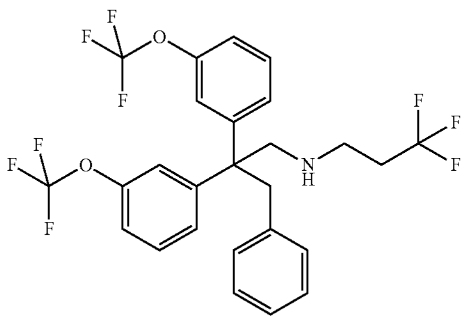 [SMILES: FC(F)(F)CCNCC(Cc1ccccc1)(c1cccc(OC(F)(F)F)c1)c1cccc(OC(F)(F)F)c1]

3,3,3-trifluoro-N-(3-phenyl-2,2-bis(3-(trifluoromethoxy)phenyl)propyl)propan-1-amine Procedure 27

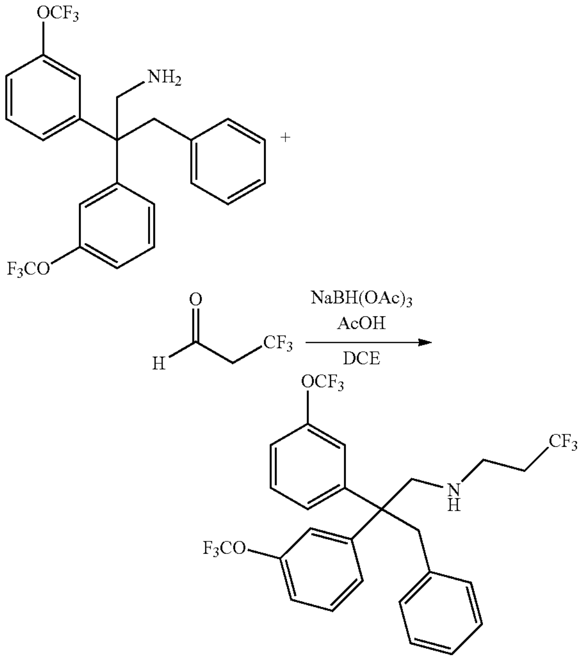

To a solution of 3-phenyl-2,2-bis(3-(trifluoromethoxy)phenyl)propan-1-amine (21 mg, 0.05 mmol), prepared as described in Example 10 (Procedure 13, 14, 15, and 16), in DCE (0.5 mL) was added 3,3,3-trifluoropropanal (8 mg, 0.07 mmol), $NaBH(OAc)_3$ (15 mg, 0.07 mmol) and acetic acid (3 uL, 0.05 mmol). The reaction mixture was stirred at rt for 4.5 h. The reaction mixture was quenched by addition of 1 N NaOH (1 mL) and extracted with $Et_2O$ (approx 20 mL). The organic portion was dried over anhydrous $Na_2SO_4$, filtered and concentrated under reduced pressure to yield a residue. The residue was first purified by a silica gel ISCO cartridge (12 g) with elution at 25 mL/min gradient 0 to 5% EtOAc in hexane, and then further purified by preparative HPLC (YMC Sunfire 5μ column, 30×100 mm eluting with 10-90% MeOH/$H_2O$ over 10 minutes containing 0.1% TFA; 40 mL/min, monitoring at 220 nm) to provide Example 53 as a colorless oil (5 mg, 18% yield). LCMS: RT=1.88 min [M+H] 552.11 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 2.22 (ddd, J=18.02, 10.77, 3.74 Hz, 2 H), 2.81 (t, J=7.03 Hz, 2 H), 3.01 (s, 2 H), 3.49 (s, 2 H), 6.58 (d, J=7.03 Hz, 2 H), 6.92 (s, 2 H), 7.01 (d, J=7.91 Hz, 2 H), 7.05-7.15 (m, 5 H), 7.31 (t, J=8.13 Hz, 2 H).

EXAMPLE 54

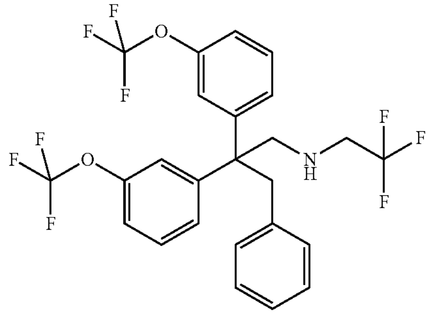 [SMILES: FC(F)(F)CNCC(Cc1ccccc1)(c1cccc(OC(F)(F)F)c1)c1cccc(OC(F)(F)F)c1]

3-phenyl-N-(2,2,2-trifluoroethyl)-2,2-bis(3-(trifluoromethoxy)phenyl)propan-1-amine Procedure 28

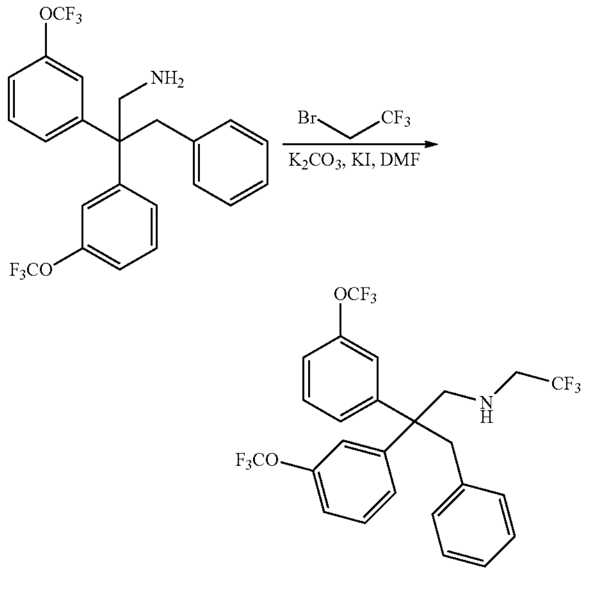

3-Phenyl-2,2-bis(3-(trifluoromethoxy)phenyl)propan-1-amine (45 mg, 0.1 mmol), prepared as described in Example 10 (Procedure 13, 14, 15, and 16), was dissolved in DMF (1 mL) in a microwave vial, followed by the addition of 2-bromo-1,1,1-trifluoroethane (24 mg, 0.2 mmol), $K_2CO_3$ (41 mg, 0.3 mmol) and KI (2 mg, 0.012 mmol). The sealed vial was heated to 230° C. for 1.5 h under microwave irradiation. The reaction mixture was first purified by preparative HPLC (YMC Sunfire 5μ column, 30×100 mm eluting with 10-90% MeOH/$H_2O$ over 10 minutes containing 0.1% TFA; 40 mL/min, monitoring at 220 nm), then further purified using a silica gel ISCO cartridge (4 g) with elution at 15 mL/min gradient 0 to 15% EtOAc in hexane to provide Example 54 as a colorless oil (6 mg, 11% yield). LCMS: RT=2.193 min [M+H] 538.08 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 3.01-3.09 (m, 4 H), 3.42 (s, 2 H), 6.51 (d, J=7.03 Hz, 2 H), 6.84 (s, 2 H), 6.95 (d, J=7.91 Hz, 2 H), 6.98-7.09 (m, 5 H), 7.25 (t, J=8.13 Hz, 2 H).

EXAMPLE 55

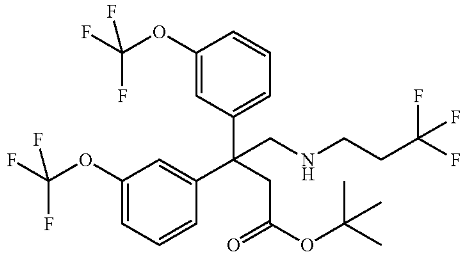 [SMILES: CC(C)(C)OC(=O)CC(CNCCC(F)(F)F)(c1cccc(OC(F)(F)F)c1)c1cccc(OC(F)(F)F)c1]

tert-Butyl 3,3-bis(3-(trifluoromethoxy)phenyl)-4-(3,3,3-trifluoropropylamino)butanoate Procedure 29

Step 1

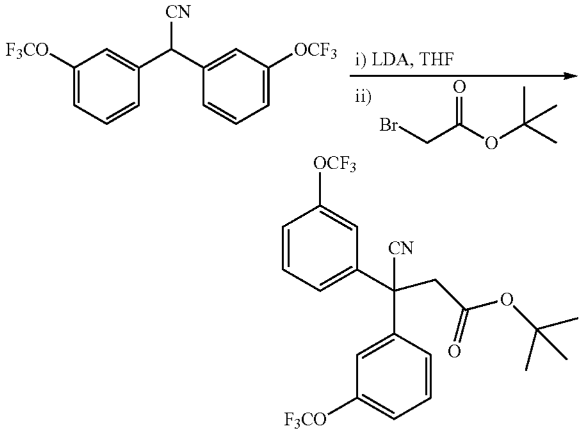

2,2-Bis(3-(trifluoromethoxy)phenyl)acetonitrile (100 mg, 0.3 mmol) was prepared as described in Example 10 (Procedure 13 and 14). To a solution of diisopropyl amine (0.146 mL, 1.04 mmol) in THF (3 mL) at −78° C. was added dropwise n-BuLi (1.6 M in hexane, 0.675 mL, 1.08 mmol) and the reaction mixture was stirred for 5 min. A solution of (2,2-bis (3-(trifluoromethoxy)phenyl)acetonitrile (300 mg, 0.83 mmol) in THF (0.5 mL) was added dropwise to the reaction mixture and stirred for 1 h. tert-Butyl 2-bromoacetate (0.159 mL, 1.08 mmol) was added dropwise, then the cooling bath was removed and the reaction mixture was stirred at rt for 45 min. The reaction mixture was poured into $H_2O$ (15 mL) and extracted with diethyl ether (2×15 mL). The combined organic portions were dried over $Na_2SO_4$, filtered and concentrated under reduced pressure to yield crude tert-butyl 3-cyano-3,3-bis(3-(trifluoromethoxy)phenyl)propanoate.

The crude tert-butyl 3-cyano-3,3-bis(3-(trifluoromethoxy) phenyl)propanoate was purified by a silica gel ISCO cartridge (12 g) with elution at 25 mL/min gradient 0 to 25% EtOAc in hexane to yield a white solid (84 mg, 63% yield). LCMS: RT=2.18 min [M+H] 476.02 (2 min Phenomenex Luna C18 column, 4.6×30 mm eluting with 75-90% MeOH/$H_2O$ over 2 minutes containing 0.1% TFA; 5 mL/min, monitoring at 220 nm); NMR: 400 MHz $^1H(CDCl_3)$ ppm 1.30 (s, 9 H), 3.33 (s, 2 H), 7.21-7.24 (m, 4 H), 7.36 (d, J=8.35 Hz, 2 H), 7.45 (t, J=8.35 Hz, 2 H).

Step 2

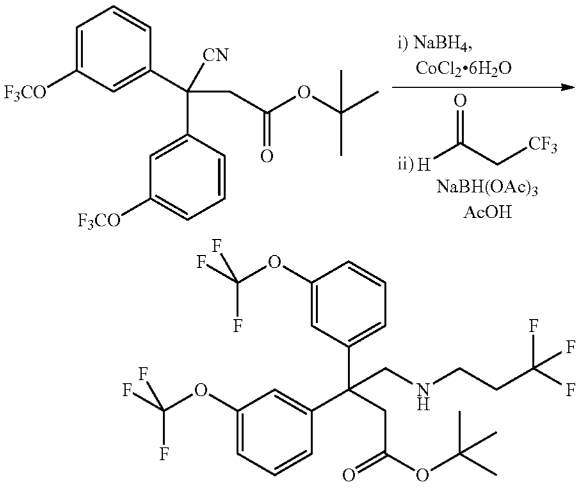

Purified tert-butyl 3-cyano-3,3-bis(3-(trifluoromethoxy) phenyl)propanoate (80 mg, 0.2 mmol) was converted to crude tert-butyl 4-amino-3,3-bis(3-(trifluoromethoxy)phenyl)butanoate (50 mg, 61% yield) as described in Procedure 5. The crude tert-butyl 4-amino-3,3-bis(3-(trifluoromethoxy)phenyl)butanoate was purified by a silica gel ISCO cartridge (12 g) with elution at 25 mL/min gradient 0 to 5% MeOH in $CH_2Cl_2$ to yield a clear oil. LCMS: RT=1.94 min [M+H] 479.98 (2 min Phenomenex Luna C18 column, 4.6×30 mm eluting with 10-90% MeOH/$H_2O$ over 2 minutes containing 0.1% TFA; 5 mL/min, monitoring at 220 nm). Purified tert-butyl 4-amino-3,3-bis(3-(trifluoromethoxy)phenyl)butanoate was converted to crude tert-butyl 3,3-bis(3-(trifluoromethoxy)phenyl)-4-(3,3,3-trifluoropropylamino) butanoate as described in Procedure 27. The crude reaction mixture was first purified by preparative HPLC (YMC Sunfire 5μ column, 30×100 mm eluting with 10-90% MeOH/$H_2O$ over 10 minutes containing 0.1% TFA; 40 mL/min, monitoring at 220 nm), then further purified using a silica gel ISCO cartridge (12 g) with elution at 25 mL/min gradient 0 to 20% EtOAc in hexane to give Example 55 as a colorless oil (12 mg, 21% yield). LCMS: RT=1.96 min [M+H] 576.0 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.85 min (Phenomenex Luna C18 column, 4.6×50 mm eluting with 10-90% MeOH/$H_2O$ over 4 minutes containing 0.2% PPA; 4 mL/min, monitoring at 220 nm); NMR: 400 MHz $^1H(CDCl_3)$ ppm 1.10-1.14 (s, 9 H), 2.16-2.24 (m, 2 H), 2.81 (t, J=7.03 Hz, 2 H), 3.17 (s, 2 H), 3.46 (s, 2 H), 6.97 (s, 2 H), 7.04 (d, J=7.91 Hz, 2 H), 7.09 (d, J=7.91 Hz, 2 H), 7.30 (t, J=8.13 Hz, 2 H).

EXAMPLE 56

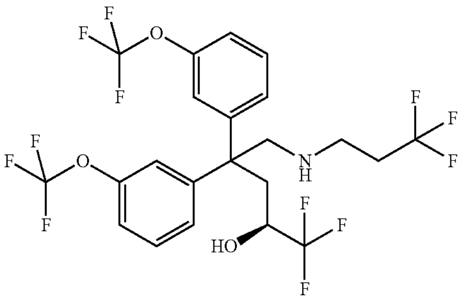 [SMILES: O[C@@H](CC(CNCCC(F)(F)F)(c1cccc(OC(F)(F)F)c1)c1cccc(OC(F)(F)F)c1)C(F)(F)F]

(S)-1,1,1-trifluoro-4,4-bis(3-(trifluoromethoxy)phenyl)-5-(3,3,3-trifluoropropylamino)pentan-2-ol Procedure 30

Step 1

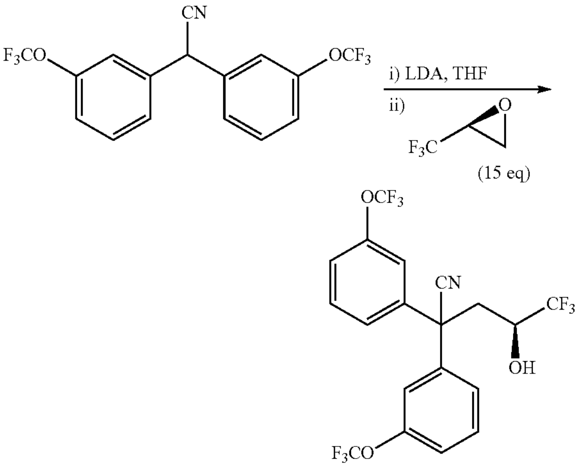

To a solution of diisopropyl amine (0.305 mL, 2.16 mmol) in THF (6 mL) at −78° C. was added dropwise a 1.6 M solution of n-BuLi in hexane (1.35 mL, 2.16 mmol) and the mixture was stirred for 5 min. To this mixture was added a solution of 2,2-bis(3-(trifluoromethoxy)phenyl)acetonitrile (600 mg, 1.7 mmol), prepared as described in Example 10 (Procedure 13 and 14). The reaction mixture was stirred at −78° C. for 1 h and then (S)-2-(trifluoromethyl)oxirane (2.8 g, 25.0 mmol, 70% ee, purchased from TCI America) was added dropwise to the mixture. The cooling bath was removed and the reaction mixture was stirred at rt for 1 h. Additional (S)-2-(trifluoromethyl)oxirane (0.12 g, 1.1 mmol, 70% ee, purchased from TCI America) was added and the reaction mixture was stirred for an additional 1 h then poured into $H_2O$ and extracted with EtOAc (50 mL). The combined organic portions were dried over $Na_2SO_4$, filtered and concentrated under reduced pressure to yield a residue. The residue was purified by preparative HPLC (RT=23.65 min, YMC Sunfire 5μ column, 30×100 mm eluting with 20-100% MeOH/$H_2O$ over 25 minutes containing 0.1% TFA; 30 mL/min, monitoring at 220 nm) to give (S)-5,5,5-trifluoro-4-hydroxy-2,2-bis(3-(trifluoromethoxy)phenyl)pentanenitrile (280 mg, 36% yield, 70% ee) as a clear colorless oil. LCMS: RT=3.898 min [M+H] 474.0 (4 min Phenomenex Luna C18 column, 4.6×50 mm eluting with 10-90% MeOH/$H_2O$ over 4 minutes containing 10 mM $NH_4OAc$; 4 mL/min, monitoring at 220 nm); NMR: 400 MHz $^1H(CDCl_3)$ ppm 2.55-2.64 (m, 1 H) 2.66-2.78 (m, 2 H) 3.87-3.95 (m, 1 H) 7.10-7.21 (m, 4 H) 7.23-7.27 (m, 1 H) 7.30-7.42 (m, 3 H).

Step 2

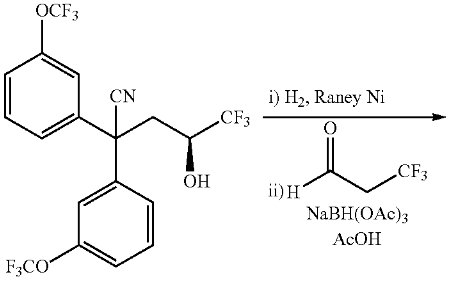

-continued

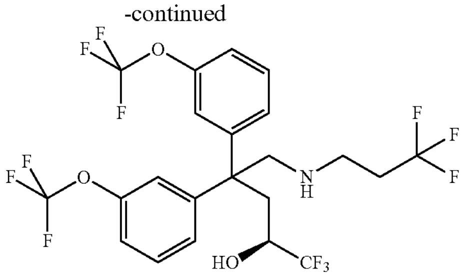

(S)-5,5,5-trifluoro-4-hydroxy-2,2-bis(3-(trifluoromethoxy)phenyl)-pentanenitrile (120 mg, 0.25 mmol, 70% ee), prepared as described in procedure 30, was converted to (S)-5-amino-1,1,1-trifluoro-4,4-bis(3-(trifluoromethoxy)phenyl)pentan-2-ol (60 mg, 50% yield, 70% ee) as described in Procedure 16. LCMS: RT=3.07 min [M+H] 478.1 (4 min Phenomenex Luna C18 column, 4.6×50 mm eluting with 10-90% MeOH/$H_2O$ over 4 minutes containing 0.1% TFA; 4 mL/min, monitoring at 220 nm). The (S)-5-amino-1,1,1-trifluoro-4,4-bis(3-(trifluoromethoxy)phenyl)pentan-2-ol (70% ee) was then converted to Example 56 (10 mg, 11% yield, 70% ee) as described in Procedure 27. LCMS: RT=1.89 min [M+H] 574.1 (2 min Phenomenex Luna C18 column, 4.6×30 mm eluting with 10-90% MeOH/$H_2O$ over 2 minutes containing 0.1% TFA; 5 mL/min, monitoring at 220 nm); HPLC: RT=3.61 min (Phenomenex Luna C18 column, 4.6×50 mm eluting with 10-90% MeOH/$H_2O$ over 4 minutes containing 0.2% PPA; 4 mL/min, monitoring at 220 nm). NMR: 400 MHz $^1H(CDCl_3)$ ppm 2.24-2.35 (m, J=10.58, 10.58, 10.58, 7.03, 6.92 Hz, 2 H), 2.54-2.60 (m, 1 H), 2.62-2.70 (m, 1 H), 2.86-2.96 (m, 2 H), 3.24 (d, J=11.42 Hz, 1 H), 3.63 (d, J=11.42 Hz, 1 H), 3.76-3.83 (m, 1H), 6.87 (s, 1 H), 7.00 (s, 1 H), 7.03 (d, J=7.91 Hz, 1 H), 7.12 (d, J=7.91 Hz, 2 H), 7.19 (d, J=7.47 Hz, 1 H), 7.35 (t, J=8.13 Hz, 1 H), 7.44 (t, J=7.91 Hz, 1 H).

TABLE 5

| Ex. No. | Structure | Name | Retention Time Min./ Molecular Mass | Prepared in the manner described in: |
|---|---|---|---|---|
| 57 | 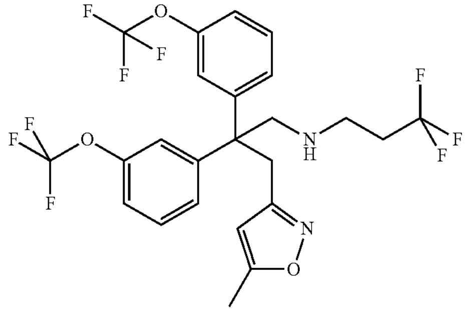 [SMILES: Cc1cc(CC(CNCCC(F)(F)F)(c2cccc(OC(F)(F)F)c2)c2cccc(OC(F)(F)F)c2)no1] | 3,3,3-trifluoro-N-(3-(5-methylisoxazol-3-yl)-2,2-bis(3-(trifluoromethoxy)phenyl)propyl)propan-1-amine | 3.62 LC (4) 557.2 $[M + H]^+$ | Procedure 13, 14, 15, 22, 27 |

TABLE 5-continued

| Ex. No. | Structure | Name | Retention Time Min./ Molecular Mass | Prepared in the manner described in: |
|---|---|---|---|---|
| 58 | 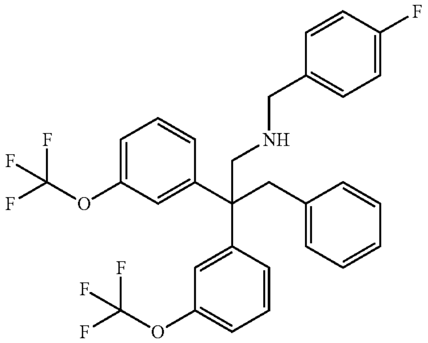 [SMILES: Fc1ccc(CNCC(Cc2ccccc2)(c2cccc(OC(F)(F)F)c2)c2cccc(OC(F)(F)F)c2)cc1] | N-(4-fluorobenzyl)-3-phenyl-2,2-bis(3-(trifluoromethoxy)phenyl)propan-1-amine | 3.70 LC (3) 564.21 $[M + H]^+$ | Procedure 13, 14, 15, 16, 27 |
| 59 | 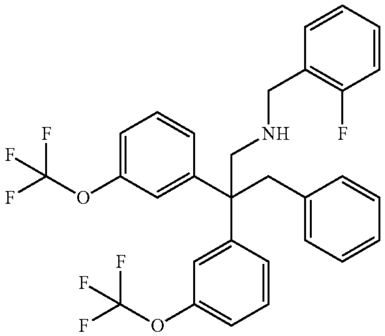 [SMILES: Fc1ccccc1CNCC(Cc1ccccc1)(c1cccc(OC(F)(F)F)c1)c1cccc(OC(F)(F)F)c1] | N-(2-fluorobenzyl)-3-phenyl-2,2-bis(3-(trifluoromethoxy)phenyl)propan-1-amine | 3.67 LC (3) 564.23 $[M + H]^+$ | Procedure 13, 14, 15, 16, 27 |
| 60 | 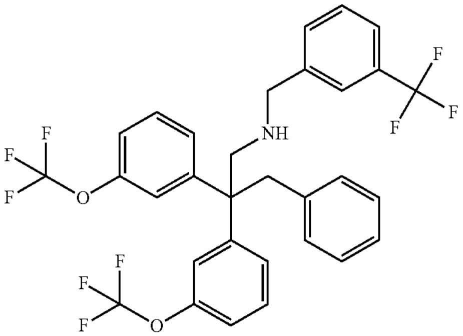 [SMILES: FC(F)(F)Oc1cccc(C(CNCc2cccc(C(F)(F)F)c2)(Cc2ccccc2)c2cccc(OC(F)(F)F)c2)c1] | 3-phenyl-2,2-bis(3-(trifluoromethoxy)phenyl)-N-(3-(trifluoromethyl)benzyl)propan-1-amine | 3.81 LC (3) 614.17 $[M + H]^+$ | Procedure 13, 14, 15, 16, 27 |
| 61 | 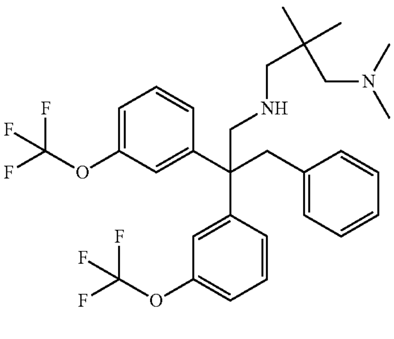 [SMILES: CN(C)CC(C)(C)CNCC(Cc1ccccc1)(c1cccc(OC(F)(F)F)c1)c1cccc(OC(F)(F)F)c1] | N1,N1,2,2-tetramethyl-N3-(3-phenyl-2,2-bis(3-(trifluoromethoxy)phenyl)propyl)propane-1,3-diamine | 3.64 LC (3) 569.3 $[M + H]^+$ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 62 | 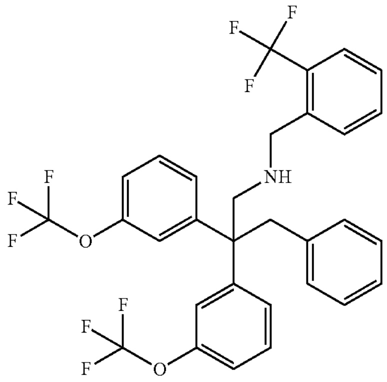 [SMILES: FC(F)(F)Oc1cccc(C(CNCc2ccccc2C(F)(F)F)(Cc2ccccc2)c2cccc(OC(F)(F)F)c2)c1] | 3-phenyl-2,2-bis(3-(trifluoromethoxy)phenyl)-N-(2-(trifluoromethyl)benzyl) propan-1-amine | 3.89 LC (3) 614.7 $[M + H]^+$ | Procedure 13, 14, 15, 16, 27 |
| 63 | 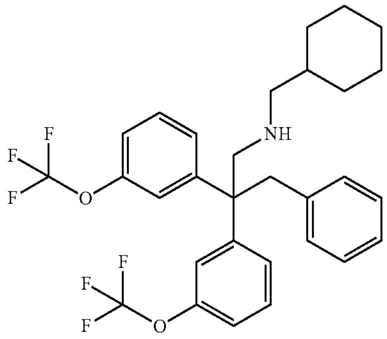 [SMILES: FC(F)(F)Oc1cccc(C(CNCC2CCCCC2)(Cc2ccccc2)c2cccc(OC(F)(F)F)c2)c1] | N-(cyclohexylmethyl)-3-phenyl-2,2-bis(3-(trifluoromethoxy)phenyl) propan-1-amine | 3.77 LC (3) 552.30 $[M + H]^+$ | Procedure 13, 14, 15, 16, 27 |
| 64 | 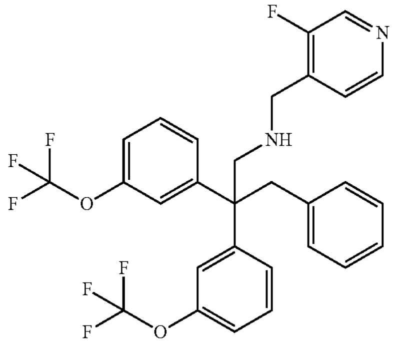 [SMILES: Fc1cnccc1CNCC(Cc1ccccc1)(c1cccc(OC(F)(F)F)c1)c1cccc(OC(F)(F)F)c1] | N-((3-fluoropyridin-4-yl) methyl)-3-phenyl-2,2-bis(3-(trifluoromethoxy)phenyl) propan-1-amine | 3.69 LC (3) 565.22 $[M + H]^+$ | Procedure 13, 14, 15, 16, 27 |
| 65 | 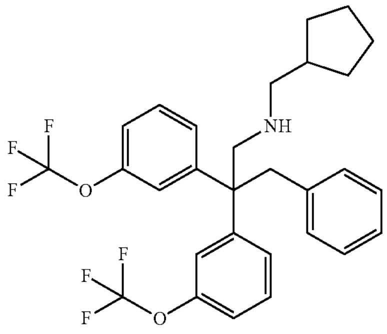 [SMILES: FC(F)(F)Oc1cccc(C(CNCC2CCCC2)(Cc2ccccc2)c2cccc(OC(F)(F)F)c2)c1] | N-(cyclopentylmethyl)-3-phenyl-2,2-bis(3-(trifluoromethoxy)phenyl) propan-1-amine | 3.71 LC (3) 538.29 $[M + H]^+$ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 66 | 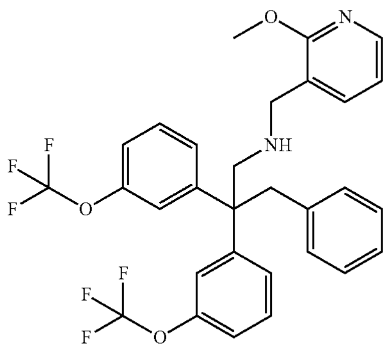 [SMILES: COc1ncccc1CNCC(Cc1ccccc1)(c1cccc(OC(F)(F)F)c1)c1cccc(OC(F)(F)F)c1] | N-((2-methoxypyridin-3-yl) methyl)-3-phenyl-2,2-bis(3-(trifluoromethoxy)phenyl) propan-1-amine | 3.64 LC (3) 577.22 $[M + H]^+$ | Procedure 13, 14, 15, 16, 27 |
| 67 | 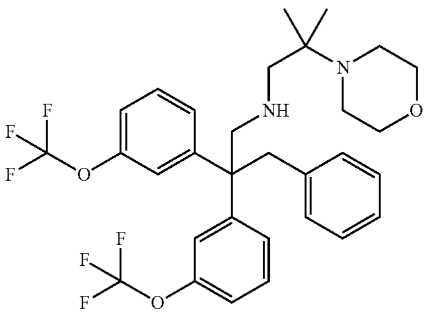 [SMILES: CC(C)(CNCC(Cc1ccccc1)(c1cccc(OC(F)(F)F)c1)c1cccc(OC(F)(F)F)c1)N1CCOCC1] | N-(2-methyl-2-morpholinopropyl)-3-phenyl-2,2-bis(3-(trifluoromethoxy) phenyl)propan-1-amine | 3.73 LC (3) 597.25 $[M + H]^+$ | Procedure 13, 14, 15, 16, 27 |
| 68 | 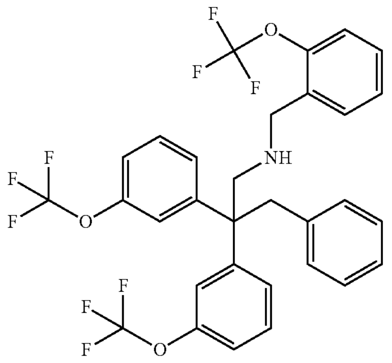 [SMILES: FC(F)(F)Oc1cccc(C(CNCc2ccccc2OC(F)(F)F)(Cc2ccccc2)c2cccc(OC(F)(F)F)c2)c1] | 3-phenyl-N-(2-(trifluoromethoxy)benzyl)-2,2-bis(3-(trifluoromethoxy) phenyl)propan-1-amine | 3.82 LC (3) 630.17 $[M + H]^+$ | Procedure 13, 14,15, 16, 27 |
| 69 | 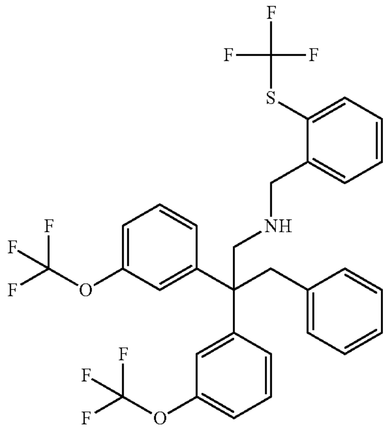 [SMILES: FC(F)(F)Oc1cccc(C(CNCc2ccccc2SC(F)(F)F)(Cc2ccccc2)c2cccc(OC(F)(F)F)c2)c1] | 3-phenyl-2,2-bis(3-(trifluoromethoxy)phenyl)-N-(2-(trifluoromethylthio)benzyl) propan-1-amine | 3.90 LC (3) 646.13 $[M + H]^+$ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 70 | 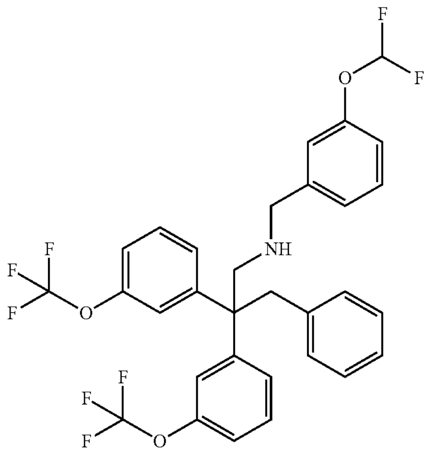 [SMILES: FC(F)Oc1cccc(CNCC(Cc2ccccc2)(c2cccc(OC(F)(F)F)c2)c2cccc(OC(F)(F)F)c2)c1] | N-(3-(difluoromethoxy)benzyl)-3-phenyl-2,2-bis(3-(trifluoromethoxy)phenyl) propan-1-amine | 3.73 LC (3) 612.18 [M + H]+ | Procedure 13, 14,15, 16, 27 |
| 71 | 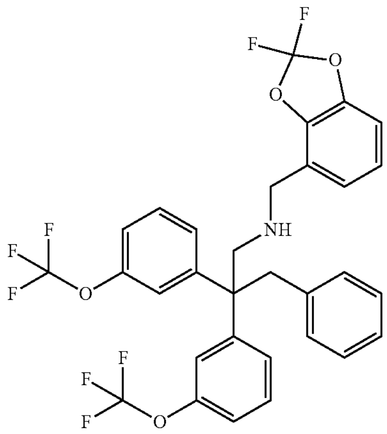 [SMILES: FC(F)(F)Oc1cccc(C(CNCc2cccc3c2OC(F)(F)O3)(Cc2ccccc2)c2cccc(OC(F)(F)F)c2)c1] | N-((2,2-difluorobenzo[d][1,3] dioxol-4-yl)methyl)-3-phenyl-2,2-bis(3-(trifluoromethoxy) phenyl)propan-1-amine | 3.82 LC (3) 626.15 [M + H]+ | Procedure 13, 14, 15, 16, 27 |
| 72 | 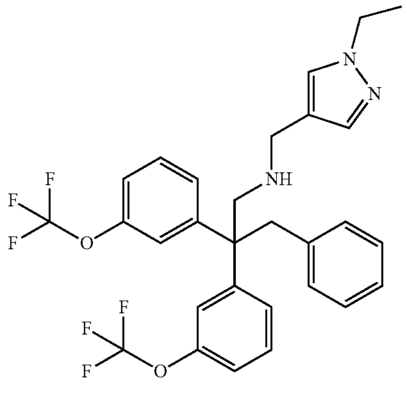 [SMILES: CCn1cc(CNCC(Cc2ccccc2)(c2cccc(OC(F)(F)F)c2)c2cccc(OC(F)(F)F)c2)cn1] | N-((1-ethyl-1H-pyrazol-4-yl)methyl)-3-phenyl-2,2-bis(3-(trifluoromethoxy)phenyl) propan-1-amine | 3.59 LC (3) 564.25 [M + H]+ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 73 | 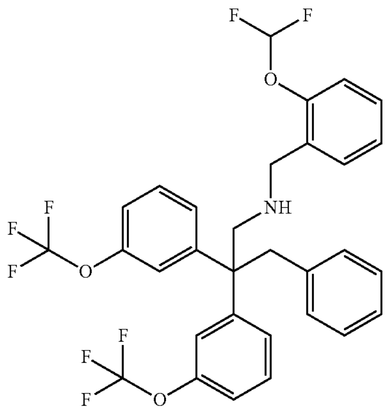 [SMILES: FC(F)Oc1ccccc1CNCC(Cc1ccccc1)(c1cccc(OC(F)(F)F)c1)c1cccc(OC(F)(F)F)c1] | N-(2-(difluoromethoxy)benzyl)-3-phenyl-2,2-bis(3-(trifluoromethoxy)phenyl) propan-1-amine | 3.71 LC (3) 612.17 [M + H]+ | Procedure 13, 14, 15, 16, 27 |
| 74 | 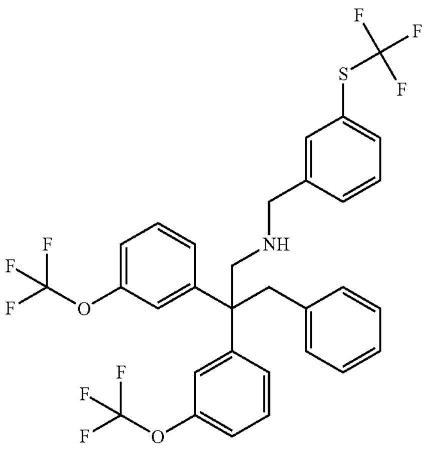 [SMILES: FC(F)(F)Oc1cccc(C(CNCc2cccc(SC(F)(F)F)c2)(Cc2ccccc2)c2cccc(OC(F)(F)F)c2)c1] | 3-phenyl-2,2-bis(3-(trifluoromethoxy)phenyl)-N-(3 -(trifluoromethylthio)benzyl) propan-1-amine | 3.91 LC (3) 646.13 [M + H]+ | Procedure 13, 14, 15, 16, 27 |
| 75 | 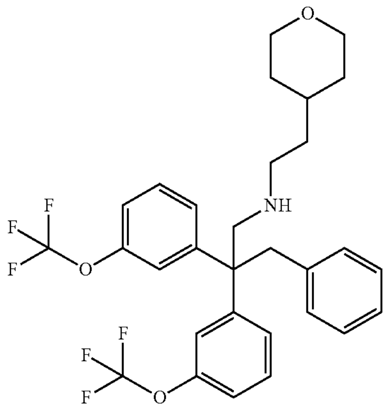 [SMILES: FC(F)(F)Oc1cccc(C(CNCCC2CCOCC2)(Cc2ccccc2)c2cccc(OC(F)(F)F)c2)c1] | 3-phenyl-N-(2-(tetrahydro-2H-pyran-4-yl)ethyl)-2,2-bis(3-(trifluoromethoxy)phenyl) propan-1-amine | 3.62 LC (3) 568.26 [M + H]+ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 76 | 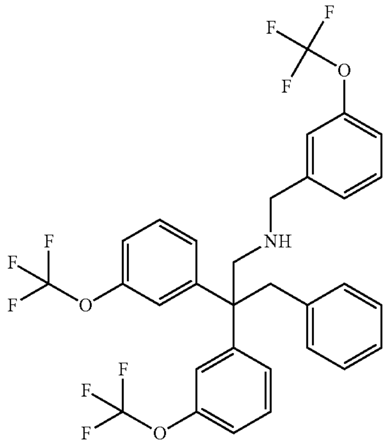 [SMILES: FC(F)(F)Oc1cccc(CNCC(Cc2ccccc2)(c2cccc(OC(F)(F)F)c2)c2cccc(OC(F)(F)F)c2)c1] | 3-phenyl-N-(3-(trifluoromethoxy)benzyl)-2,2-bis(3-(trifluoromethoxy)phenyl) propan-1-amine | 3.83 LC (3) 630.16 [M + H]+ | Procedure 13, 14, 15, 16, 27 |
| 77 | 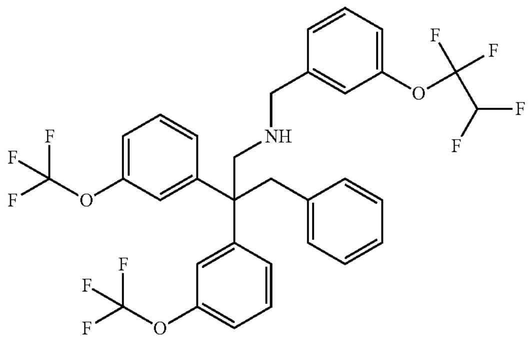 [SMILES: FC(F)C(F)(F)Oc1cccc(CNCC(Cc2ccccc2)(c2cccc(OC(F)(F)F)c2)c2cccc(OC(F)(F)F)c2)c1] | 3-phenyl-N-(3-(1,1,2,2-tetrafluoroethoxy)benzyl)-2,2-bis(3-(trifluoromethoxy)phenyl) propan-1-amine | 3.77 LC (3) 662.17 [M + H]+ | Procedure 13, 14,15, 16, 27 |
| 78 | 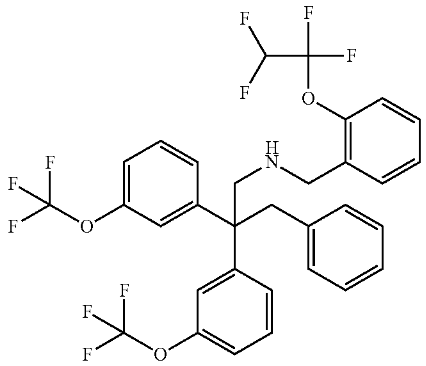 [SMILES: FC(F)C(F)(F)Oc1ccccc1CNCC(Cc1ccccc1)(c1cccc(OC(F)(F)F)c1)c1cccc(OC(F)(F)F)c1] | 3-phenyl-N-(2-(1,1,2,2-tetrafluoroethoxy)benzyl)-2,2-bis(3-(trifluoromethoxy)phenyl) propan-1-amine | 3.80 LC (3) 662.16 [M + H]+ | Procedure 13, 14, 15, 16, 27 |
| 79 | 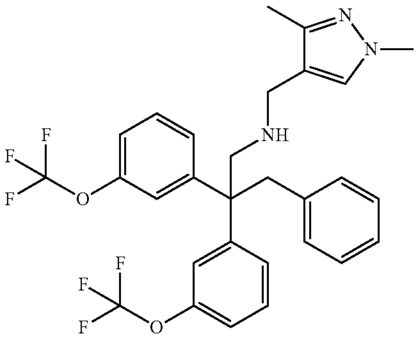 [SMILES: Cc1nn(C)cc1CNCC(Cc1ccccc1)(c1cccc(OC(F)(F)F)c1)c1cccc(OC(F)(F)F)c1] | N-((1,3-dimethyl-1H-pyrazol-4-yl)methyl)-3-phenyl-2,2-bis(3-(trifluoromethoxy)phenyl) propan-1-amine | 3.55 LC (3) 564.25 [M + H]+ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 80 | 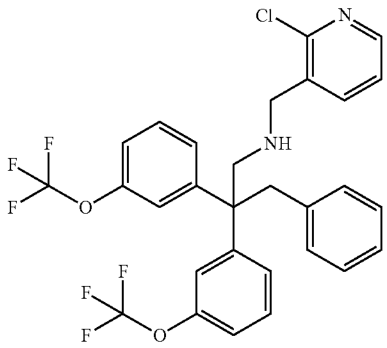 [SMILES: FC(F)(F)Oc1cccc(C(CNCc2cccnc2Cl)(Cc2ccccc2)c2cccc(OC(F)(F)F)c2)c1] | N-((2-chloropyridin-3-yl) methyl)-3-phenyl-2,2-bis(3-(trifluoromethoxy)phenyl) propan-1-amine | 3.70 LC (3) 581.17 $[M + H]^+$ | Procedure 13, 14, 15, 16, 27 |
| 81 | 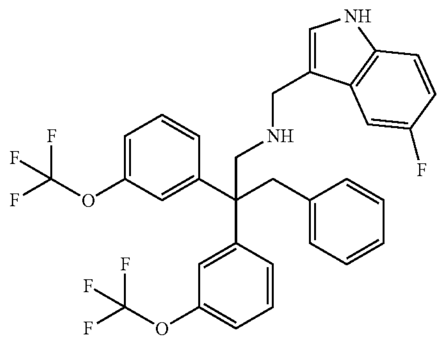 [SMILES: Fc1ccc2[nH]cc(CNCC(Cc3ccccc3)(c3cccc(OC(F)(F)F)c3)c3cccc(OC(F)(F)F)c3)c2c1] | N-((5-fluoro-1H-indol-3-yl) methyl)-3-phenyl-2,2-bis(3-(trifluoromethoxy)phenyl) propan-1-amine | 3.72 LC (3) 603.18 $[M + H]^+$ | Procedure 13, 14, 15, 16, 27 |
| 82 | 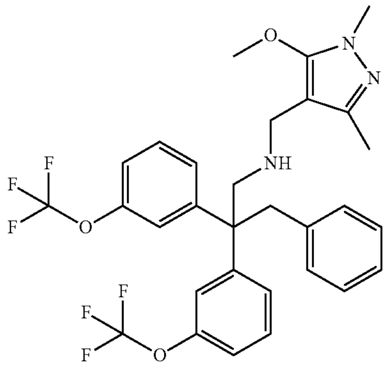 [SMILES: COc1c(CNCC(Cc2ccccc2)(c2cccc(OC(F)(F)F)c2)c2cccc(OC(F)(F)F)c2)c(C)nn1C] | N-((5-methoxy-1,3-dimethyl-1H-pyrazol-4-yl)methyl)-3-phenyl-2,2-bis(3-(trifluoromethoxy) phenyl)propan-1-amine | 3.56 LC (3) 594.23 $[M + H]^+$ | Procedure 13, 14,15, 16, 27 |
| 83 | 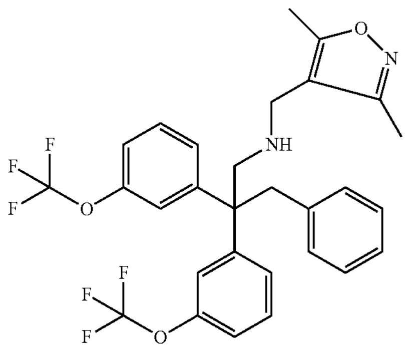 [SMILES: Cc1noc(C)c1CNCC(Cc1ccccc1)(c1cccc(OC(F)(F)F)c1)c1cccc(OC(F)(F)F)c1] | N-((3,5-dimethylisoxazol-4-yl) methyl)-3-phenyl-2,2-bis(3-(trifluoromethoxy)phenyl) propan-1-amine | 3.62 LC (3) 565.24 $[M + H]^+$ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 84 | 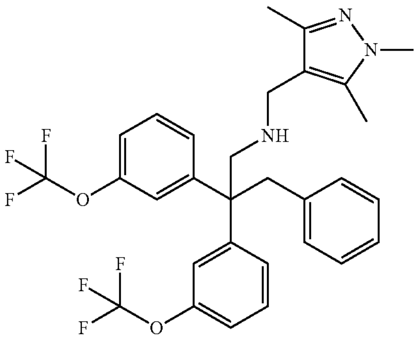 [SMILES: Cc1nn(C)c(C)c1CNCC(Cc1ccccc1)(c1cccc(OC(F)(F)F)c1)c1cccc(OC(F)(F)F)c1] | 3-phenyl-2,2-bis(3-(trifluoromethoxy)phenyl)-N-((1,3,5-trimethyl-1H-pyrazol-4-yl)methyl)propan-1-amine | 3.56 LC (3) 578.24 $[M + H]^+$ | Procedure 13, 14, 15, 16, 27 |
| 85 | 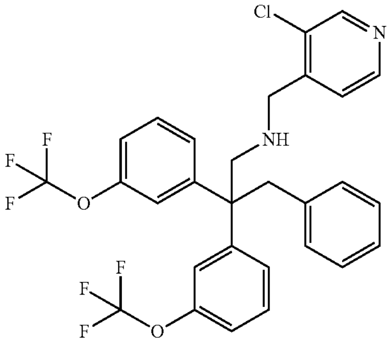 | N-((3-chloropyridin-4-yl) methyl)-3-phenyl-2,2-bis(3-(trifluoromethoxy)phenyl) propan-1-amine | 3.87 LC (3) 581.18 $[M + H]^+$ | Procedure 13, 14, 15, 16, 27 |
| 86 | 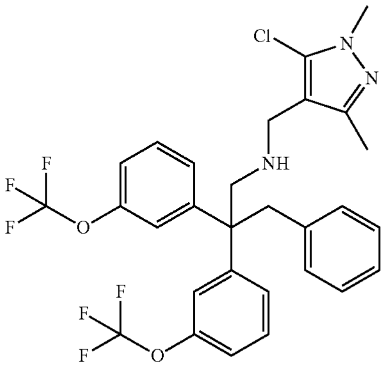 [SMILES: Cc1nn(C)c(Cl)c1CNCC(Cc1ccccc1)(c1cccc(OC(F)(F)F)c1)c1cccc(OC(F)(F)F)c1] | N-((5-chloro-1,3-dimethyl-1H-pyrazol-4-yl)methyl)-3-phenyl-2,2-bis(3-(trifluoromethoxy) phenyl)propan-1-amine | 3.59 LC (3) 598.20 $[M + H]^+$ | Procedure 13, 14, 15, 16, 27 |
| 87 | 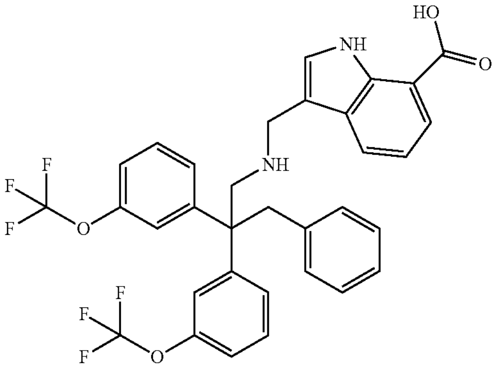 [SMILES: O=C(O)c1cccc2c(CNCC(Cc3ccccc3)(c3cccc(OC(F)(F)F)c3)c3cccc(OC(F)(F)F)c3)c[nH]c12] | 3-((3-phenyl-2,2-bis(3-(trifluoromethoxy)phenyl) propylamino)methyl)-1H-indole-7-carboxylic acid | 3.63 LC (3) 629.17 $[M + H]^+$ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 88 | 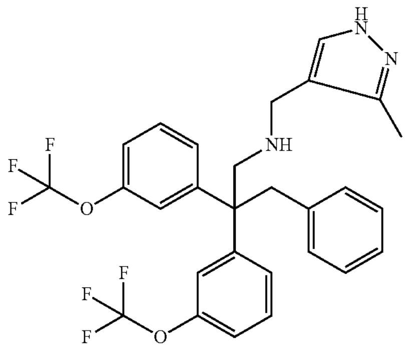 [SMILES: Cc1n[nH]cc1CNCC(Cc1ccccc1)(c1cccc(OC(F)(F)F)c1)c1cccc(OC(F)(F)F)c1] | N-((3-methyl-1H-pyrazol-4-yl) methyl)-3-phenyl-2,2-bis(3-(trifluoromethoxy)phenyl) propan-1-amine | 3.52 LC (3) 552.26 [M + H]+ | Procedure 13, 14, 15, 16, 27 |
| 89 | 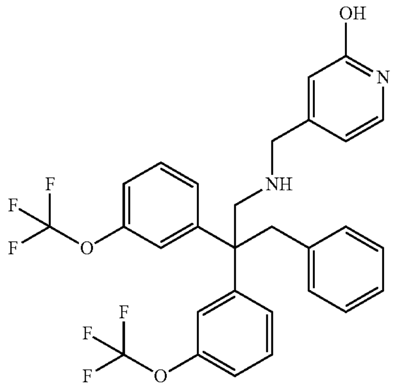 [SMILES: Oc1cc(CNCC(Cc2ccccc2)(c2cccc(OC(F)(F)F)c2)c2cccc(OC(F)(F)F)c2)ccn1] | 4-((3-phenyl-2,2-bis(3-(trifluoromethoxy)phenyl) propylamino)methyl)pyridin-2-ol | 3.53 LC (3) 563.19 [M + H]+ | Procedure 13, 14, 15, 16, 27 |
| 90 | 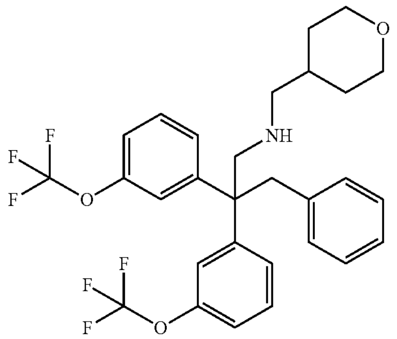 | 3-phenyl-N-((tetrahydro-2H-pyran-4-yl)methyl)-2,2-bis(3-(trifluoromethoxy)phenyl) propan- -amine | 3.62 LC (3) 554.26 [M + H]+ | Procedure 13, 14, 15, 16, 27 |
| 91 | 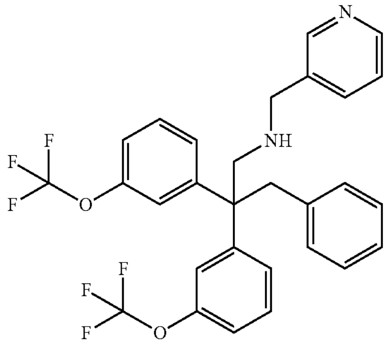 [SMILES: FC(F)(F)Oc1cccc(C(CNCc2cccnc2)(Cc2ccccc2)c2cccc(OC(F)(F)F)c2)c1] | 3-phenyl-N-(pyridin-3-ylmethyl)-2,2-bis(3-(trifluoromethoxy)phenyl) propan-1-amine | 3.54 LC (3) 547.26 [M + H]+ | Procedure 13, 14, 15, 16, 27 |

TABLE 5-continued

| Ex. No. | Structure | Name | Retention Time Min./ Molecular Mass | Prepared in the manner described in: |
|---|---|---|---|---|
| 92 | 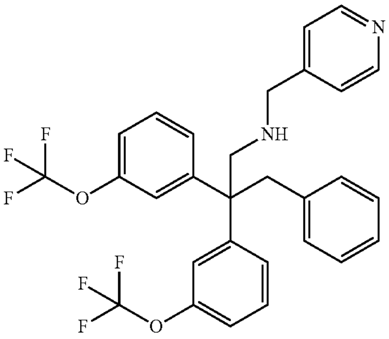 [SMILES: FC(F)(F)Oc1cccc(C(CNCc2ccncc2)(Cc2ccccc2)c2cccc(OC(F)(F)F)c2)c1] | 3-phenyl-N-(pyridin-4-ylmethyl)-2,2-bis(3-(trifluoromethoxy)phenyl) propan-1-amine | 3.60 LC (3) 547.26 [M + H]+ | Procedure 13, 14, 15, 16, 27 |
| 93 | 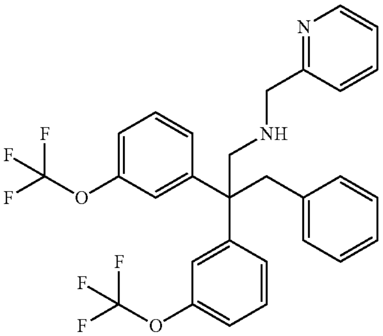 [SMILES: FC(F)(F)Oc1cccc(C(CNCc2ccccn2)(Cc2ccccc2)c2cccc(OC(F)(F)F)c2)c1] | 3-phenyl-N-(pyridin-2-ylmethyl)-2,2-bis(3-(trifluoromethoxy)phenyl) propan-1-amine | 3.62 LC (3) 547.25 [M + H]+ | Procedure 13, 14, 15, 16, 27 |
| 94 | 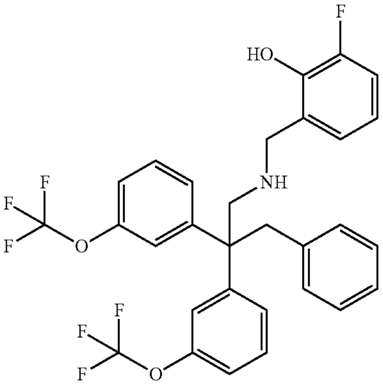 [SMILES: Oc1c(F)cccc1CNCC(Cc1ccccc1)(c1cccc(OC(F)(F)F)c1)c1cccc(OC(F)(F)F)c1] | 2-fluoro-6-((3-phenyl-2,2-bis(3-(trifluoromethoxy)phenyl) propylamino)methyl)phenol | 3.63 LC (3) 580.21 [M + H]+ | Procedure 13, 14, 15, 16, 27 |
| 95 | 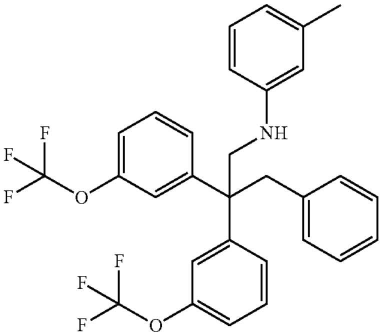 [SMILES: Cc1cccc(NCC(Cc2ccccc2)(c2cccc(OC(F)(F)F)c2)c2cccc(OC(F)(F)F)c2)c1] | 3-methyl-N-(3-phenyl-2,2-bis (3-(trifluoromethoxy)phenyl) propyl)aniline | 5.04 LC (3) 546.22 [M + H]+ | Procedure 13, 14, 15, 16, 26 |

TABLE 5-continued

| Ex. No. | Structure | Name | Retention Time Min./ Molecular Mass | Prepared in the manner described in: |
|---|---|---|---|---|
| 96 | 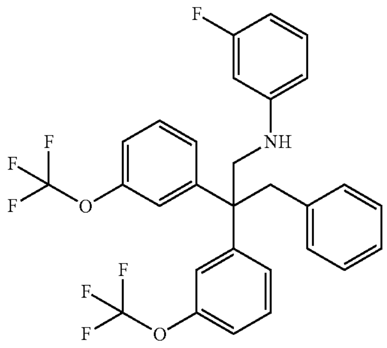 [SMILES: Fc1cccc(NCC(Cc2ccccc2)(c2cccc(OC(F)(F)F)c2)c2cccc(OC(F)(F)F)c2)c1] | 3-fluoro-N-(3-phenyl-2,2-bis(3-(trifluoromethoxy)phenyl) propyl)aniline | 4.72 LC (3) 550.28 $[M + H]^+$ | Procedure 13, 14, 15, 16, 26 |
| 97 | 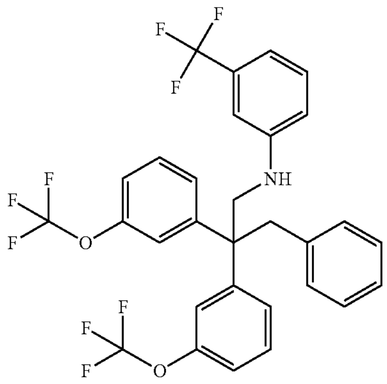 [SMILES: FC(F)(F)Oc1cccc(C(CNc2cccc(C(F)(F)F)c2)(Cc2ccccc2)c2cccc(OC(F)(F)F)c2)c1] | 3-fluoro-N-(3-phenyl-2,2-bis(3-(trifluoromethoxy)phenyl) propyl)aniline | 4.86 LC (3) 600.28 $[M + H]^+$ | Procedure 13, 14, 15, 16, 26 |
| 98 | 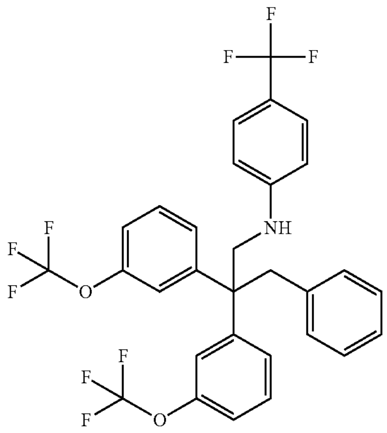 [SMILES: FC(F)(F)Oc1cccc(C(CNc2ccc(C(F)(F)F)cc2)(Cc2ccccc2)c2cccc(OC(F)(F)F)c2)c1] | N-(3-phenyl-2,2-bis(3-(trifluoromethoxy)phenyl) propyl)-4-(trifluoromethyl) aniline | 4.80 LC (3) 600.28 $[M + H]^+$ | Procedure 13, 14, 15, 16, 26 |

TABLE 5-continued

| Ex. No. | Structure | Name | Retention Time Min./ Molecular Mass | Prepared in the manner described in: |
|---|---|---|---|---|
| 99 | 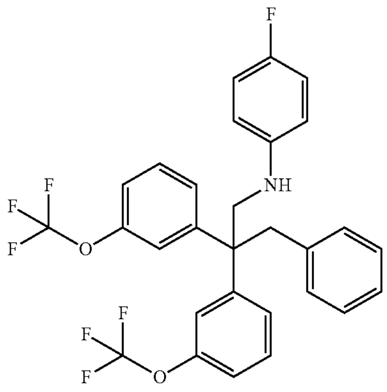 [SMILES: Fc1ccc(NCC(Cc2ccccc2)(c2cccc(OC(F)(F)F)c2)c2cccc(OC(F)(F)F)c2)cc1] | 4-fluoro-N-(3-phenyl-2,2-bis(3-(trifluoromethoxy)phenyl) propyl)aniline | 4.73 LC (3) 550.29 $[M + H]^+$ | Procedure 13, 14, 15, 16, 26 |
| 100 | 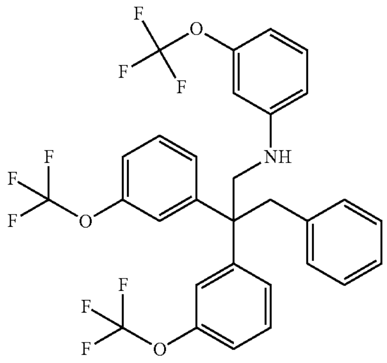 [SMILES: FC(F)(F)Oc1cccc(NCC(Cc2ccccc2)(c2cccc(OC(F)(F)F)c2)c2cccc(OC(F)(F)F)c2)c1] | N-(3-phenyl-2,2-bis(3-(trifluoromethoxy)phenyl) propyl)-3-(trifluoromethoxy) aniline | 4.95 LC (3) 616.26 $[M + H]^+$ | Procedure 13, 14, 15, 16, 26 |
| 101 | 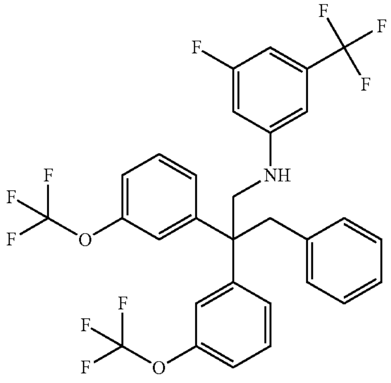 [SMILES: Fc1cc(NCC(Cc2ccccc2)(c2cccc(OC(F)(F)F)c2)c2cccc(OC(F)(F)F)c2)cc(C(F)(F)F)c1] | 3-fluoro-N-(3-phenyl-2,2-bis(3-(trifluoromethoxy)phenyl) propyl)-5-(trifluoromethyl) aniline | 4.92 LC (3) 618.24 $[M + H]^+$ | Procedure 13, 14, 15, 16, 26 |
| 102 | 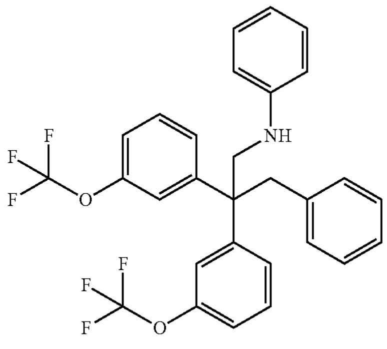 [SMILES: FC(F)(F)Oc1cccc(C(CNc2ccccc2)(Cc2ccccc2)c2cccc(OC(F)(F)F)c2)c1] | N-(3-phenyl-2,2-bis(3-(trifluoromethoxy)phenyl) propyl)aniline | 4.79 LC (3) 532.29 $[M + H]^+$ | Procedure 13, 14, 15, 16, 26 |

TABLE 5-continued

| Ex. No. | Structure | Name | Retention Time Min./ Molecular Mass | Prepared in the manner described in: |
|---|---|---|---|---|
| 103 | 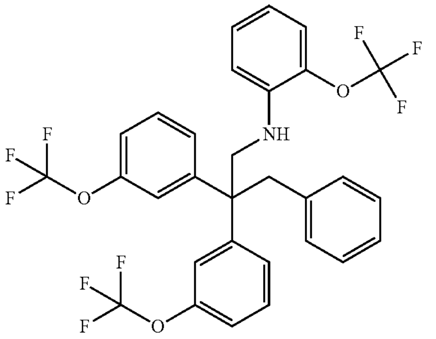 [SMILES: FC(F)(F)Oc1cccc(C(CNc2ccccc2OC(F)(F)F)(Cc2ccccc2)c2cccc(OC(F)(F)F)c2)c1] | N-(3-phenyl-2,2-bis(3-(trifluoromethoxy)phenyl) propyl)-2-(trifluoromethoxy) aniline | 5.12 LC (3) 616.10 [M + H]+ | Procedure 13, 14, 15, 16, 26 |
| 104 | 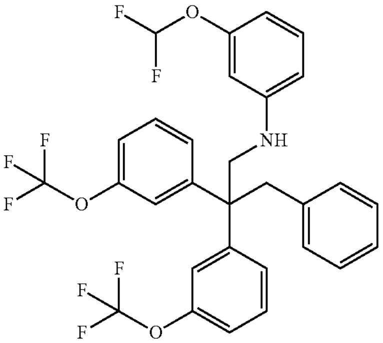 [SMILES: FC(F)Oc1cccc(NCC(Cc2ccccc2)(c2cccc(OC(F)(F)F)c2)c2cccc(OC(F)(F)F)c2)c1] | 3-(difluoromethoxy)-N-(3-phenyl-2,2-bis(3-(trifluoromethoxy) phenyl)propyl)aniline | 4.62 LC (3) 598.25 [M + H]+ | Procedure 13, 14, 15, 16, 26 |
| 105 | 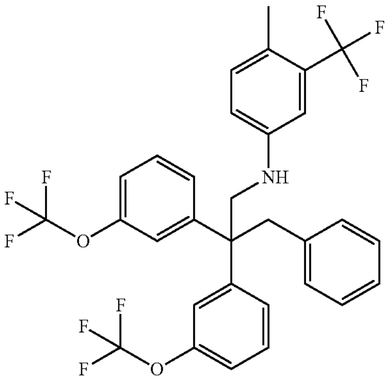 [SMILES: Cc1ccc(NCC(Cc2ccccc2)(c2cccc(OC(F)(F)F)c2)c2cccc(OC(F)(F)F)c2)cc1C(F)(F)F] | 4-methyl-N-(3-phenyl-2,2-bis(3-(trifluoromethoxy)phenyl) propyl)-3-(trifluoromethyl) aniline | 5.16 LC (3) 614.28 [M + H]+ | Procedure 13, 14, 15, 16, 26 |
| 106 | 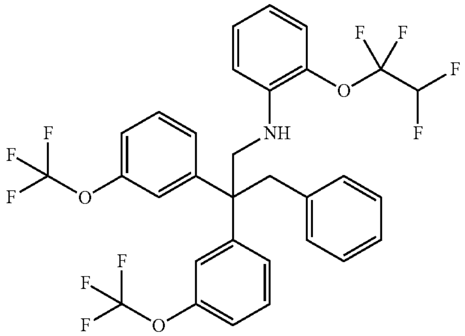 [SMILES: FC(F)C(F)(F)Oc1ccccc1NCC(Cc1ccccc1)(c1cccc(OC(F)(F)F)c1)c1cccc(OC(F)(F)F)c1] | N-(3-phenyl-2,2-bis(3-(trifluoromethoxy)phenyl) propyl)-2-(1,1,2,2-tetrafluoroethoxy)aniline | 4.79 LC (3) 648.26 [M + H]+ | Procedure 13, 14, 15, 16, 26 |

TABLE 5-continued

| Ex. No. | Structure | Name | Retention Time Min./ Molecular Mass | Prepared in the manner described in: |
|---|---|---|---|---|
| 107 | 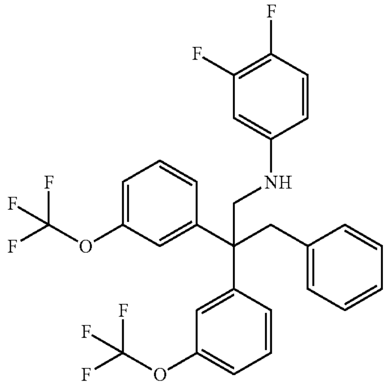 [SMILES: Fc1ccc(NCC(Cc2ccccc2)(c2cccc(OC(F)(F)F)c2)c2cccc(OC(F)(F)F)c2)cc1F] | 3,4-difluoro-N-(3-phenyl-2,2-bis(3-(trifluoromethoxy)phenyl)propyl)aniline | 4.73 LC (3) 568.27 $[M + H]^+$ | Procedure 13, 14, 15, 16, 26 |
| 108 | 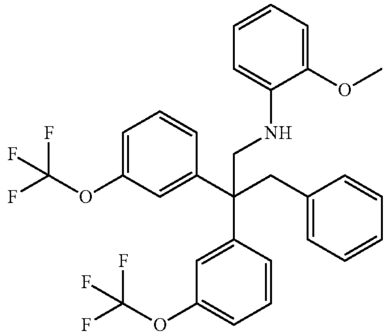 [SMILES: COc1ccccc1NCC(Cc1ccccc1)(c1cccc(OC(F)(F)F)c1)c1cccc(OC(F)(F)F)c1] | 2-methoxy-N-(3-phenyl-2,2-bis(3-(trifluoromethoxy)phenyl)propyl)aniline | 4.91 LC (3) 562.3 $[M + H]^+$ | Procedure 13, 14, 15, 16, 26 |

EXAMPLE 109

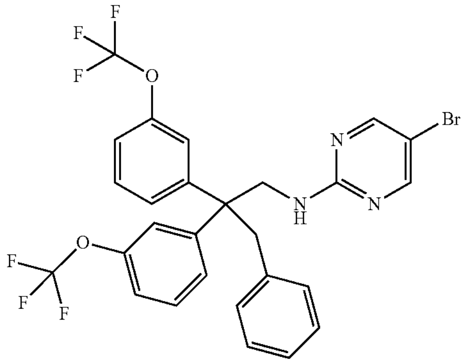 [SMILES: FC(F)(F)Oc1cccc(C(CNc2ncc(Br)cn2)(Cc2ccccc2)c2cccc(OC(F)(F)F)c2)c1]

5-bromo-N-(3-phenyl-2,2-bis(3-(trifluoromethoxy)phenyl)propyl)pyrimidin-2-amine

Procedure 31

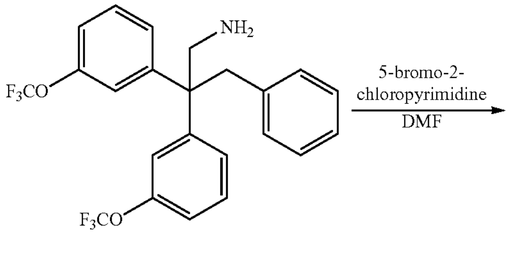

-continued

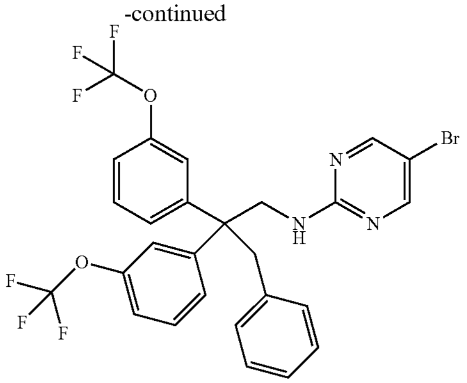

To a solution of 3-phenyl-2,2-bis(3-(trifluoromethoxy)phenyl)propan-1-amine (118 mg, 0.3 mmol), prepared as described in Example 10 (Procedure 13, 14, 15, and 16), in DMF (1 mL) was added 5-bromo-2-chloropyrimidine (100 mg, 0.5 mmol) and the reaction was heated at 150° C. for 1.5 h. The reaction mixture was cooled, poured into sat. $NaHCO_3$ (5 mL) and extracted with EtOAc (2×5 mL). The combined organic extracts were dried over $Na_2SO_4$, filtered and concentrated under reduced pressure to yield a residue. The residue was purified on a silica gel ISCO cartridge with elution at gradient 0 to 20% EtOAc in hexane to provide Example 109 as a clear colorless oil (94 mg, 59% yield). LCMS: RT=2.49 min [M+H] 613.81 (2 min Phenomenex Luna C18 column, 4.6×30 mm eluting with 10-90% MeOH/$H_2O$ over 2 minutes containing 0.1% TFA; 5 mL/min, monitoring at 220 nm);

NMR: 400 MHz [1] $H(CDCl_3)$ ppm 3.43 (s, 2 H), 4.00 (d, J=5.71 Hz, 2 H), 4.76 (t, J=5.49 Hz, 1 H), 6.51 (d, J=7.03 Hz, 2 H), 6.98 (s, 2 H) 7.03-7.15 (m, 7 H), 7.32 (t, J=8.13 Hz, 2H), 8.25 (s, 2 H).

EXAMPLE 110

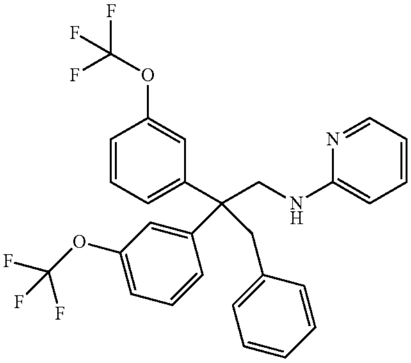 [SMILES: FC(F)(F)Oc1cccc(C(CNc2ccccn2)(Cc2ccccc2)c2cccc(OC(F)(F)F)c2)c1]

N-(3-phenyl-2,2-bis(3-(trifluoromethoxy)phenyl) propyl)pyridin-2-amine

Procedure 32

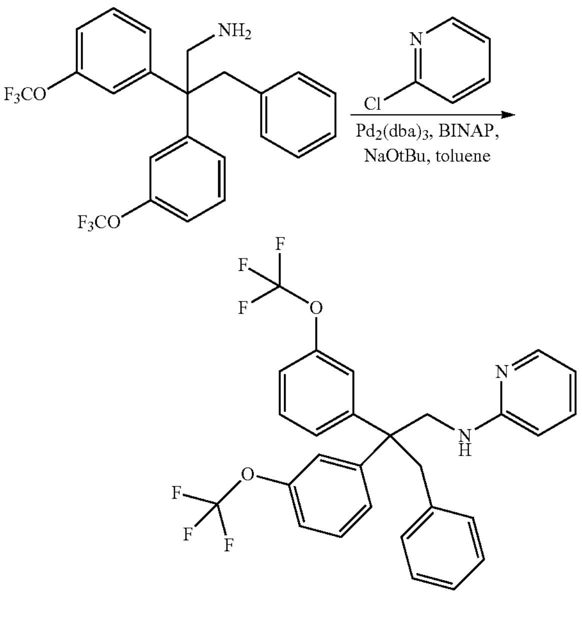

To a solution of 3-phenyl-2,2-bis(3-(trifluoromethoxy) phenyl)propan-1-amine (34 mg, 0.08 mmol), prepared as described in Example 10 (Procedure 13, 14, 15, and 16), in toluene (1 mL) was added 2-chloropyridine (0.007 mL, 0.08 mmol), $Pd_2(dba)_3$ (4 mg, 0.004 mmol), BINAP (5 mg, 0.006 mmol) and sodium t-butoxide (13.5 mg, 0.14 mmol). The reaction mixture was heated at 80° C. for 16 h to yield crude product. The crude product was purified on a silica gel ISCO cartridge with elution at gradient 0 to 30% EtOAc in hexane to provide Example 110 as a white foam (34 mg, 85% yield). LCMS: RT=1.92 min [M+H] 533.07 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H$ $(CDCl_3)$ ppm 3.48 (s, 2 H), 3.83 (d, J=5.71 Hz, 2 H), 6.29 (d, J=8.35 Hz, 1 H), 6.53 (d, J=7.47 Hz, 2 H), 6.58-6.62 (m, 1 H), 6.99-7.06 (m, 4 H), 7.09-7.16 (m, 5 H), 7.33 (t, J=7.91 Hz, 2 H), 7.37-7.43 (m, 1 H), 8.08 (d, J=3.95 Hz, 1 H).

EXAMPLES 111 and 112

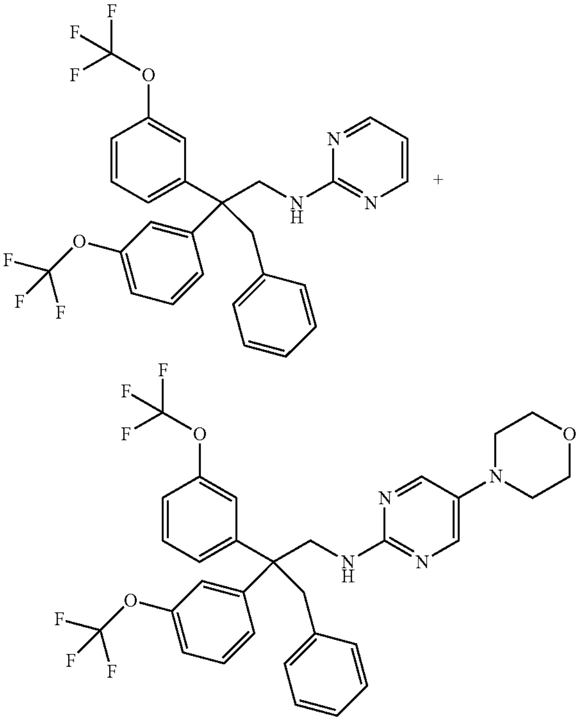

N-(3-phenyl-2,2-bis(3-(trifluoromethoxy)phenyl) propyl)pyrimidin-2-amine and 5-morpholino-N-(3-phenyl-2,2-bis(3-(trifluoromethoxy)phenyl)propyl) pyrimidin-2-amine, respectively Procedure 33

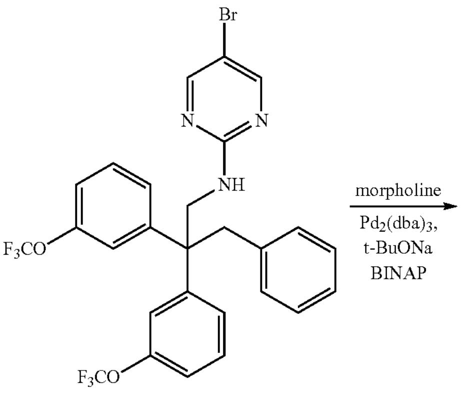

-continued

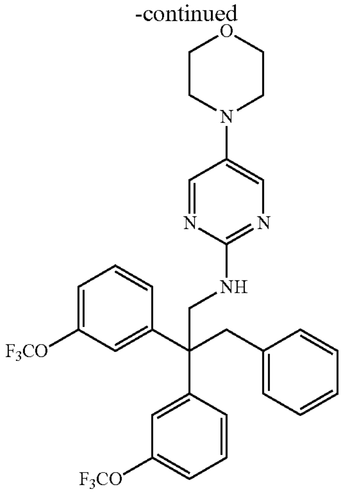

+

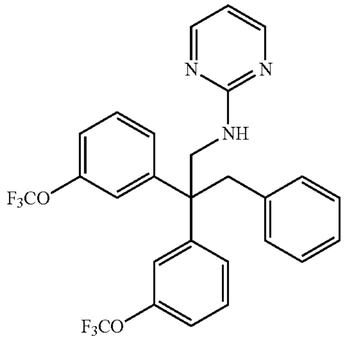

To a solution of Example 109 (41 mg, 0.068 mmol) in toluene (0.5 mL) was added morpholine (0.006 mL, 0.068 mmol), $Pd_2(dba)_3$ (4 mg, 0.004 mmol), BINAP (5 mg, 0.008 mmol) and sodium t-butoxide (14 mg, 0.14 mmol). The reaction mixture was heated at 80° C. for 16 h to yield the crude products. The crude products were purified on a silica gel ISCO cartridge with elution at gradient 0 to 100% EtOAc in hexane to provide Example 112 as a pale yellow oil (10 mg, 24% yield): LCMS: RT=2.16 min [M+H] 619.10 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 2.98-3.02 (m, 4 H) 3.45 (s, 2 H) 3.83-3.88 (m, 4 H) 4.00 (d, J=5.71 Hz, 2 H) 4.50 (t, J=5.71 Hz, 1 H) 6.55 (d, J=7.03 Hz, 2 H) 6.99-7.06 (m, 4 H) 7.08-7.14 (m, 5 H) 7.31 (t, J=8.13 Hz, 2 H) 8.02 (s, 2 H); and Example 111 as a pale yellow oil (8 mg, 22% yield): LCMS: RT=2.10 min [M+H] 534.00 (2 min Phenomenex Luna C18 column, 4.6×30 mm eluting with 10-90% MeOH/$H_2O$ over 2 minutes containing 0.1% TFA; 5 mL/min, monitoring at 220 nm); NMR: 400 MHz $^1H(CDCl_3)$ ppm 3.45 (s, 2 H) 4.05 (d, J=5.71 Hz, 2 H) 4.73 (t, J=5.71 Hz, 1 H) 6.54-6.59 (m, 3 H) 6.98-7.07 (m, 4H) 7.08-7.15 (m, 5 H) 7.31 (t, J=8.13 Hz, 2 H) 8.25 (d, J=4.83 Hz, 2 H).

TABLE 6

| Ex. No. | Structure | Name | Retention Time Min./ Molecular Mass | Prepared in the manner described in: |
|---|---|---|---|---|
| 113 | 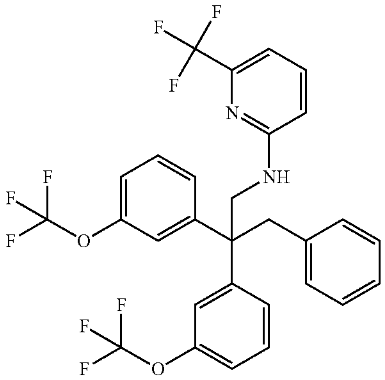 [SMILES: FC(F)(F)Oc1cccc(C(CNc2cccc(C(F)(F)F)n2)(Cc2ccccc2)c2cccc(OC(F)(F)F)c2)c1] | N-(3-phenyl-2,2-bis(3-(trifluoromethoxy)phenyl)-propyl)-6-(trifluoromethyl)-pyridin-2-amine | 4.64 LC (3) 601.24 $[M + H]^+$ | Procedure 13, 14, 15, 16, 32 |

TABLE 6-continued

| Ex. No. | Structure | Name | Retention Time Min./ Molecular Mass | Prepared in the manner described in: |
|---|---|---|---|---|
| 114 | 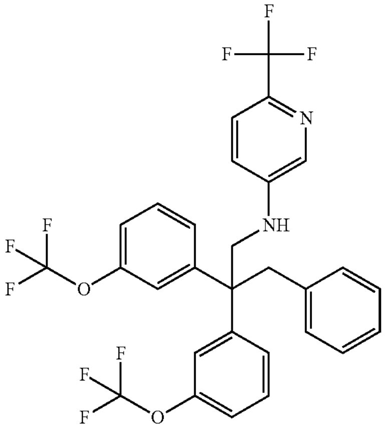 [SMILES: FC(F)(F)Oc1cccc(C(CNc2ccc(C(F)(F)F)nc2)(Cc2ccccc2)c2cccc(OC(F)(F)F)c2)c1] | N-(3-phenyl-2,2-bis(3-(trifluoromethoxy)phenyl)-propyl)-6-(trifluoromethyl)-pyridin-3-amine | 4.41 LC (3) 601.24 $[M + H]^+$ | Procedure 13, 14, 15, 16, 32 |
| 115 | 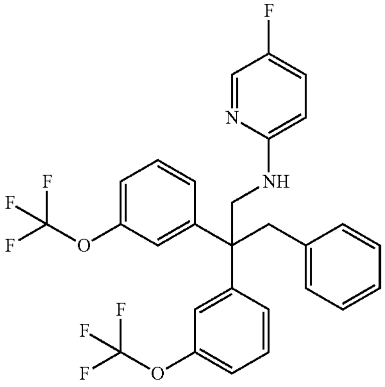 [SMILES: Fc1ccc(NCC(Cc2ccccc2)(c2cccc(OC(F)(F)F)c2)c2cccc(OC(F)(F)F)c2)nc1] | 5-fluoro-N-(3-phenyl-2,2-bis(3-(trifluoromethoxy)phenyl)-propyl)pyridin-2-amine | 3.91 LC (3) 551.24 $[M + H]^+$ | Procedure 13, 14, 15, 16, 32 |
| 116 | 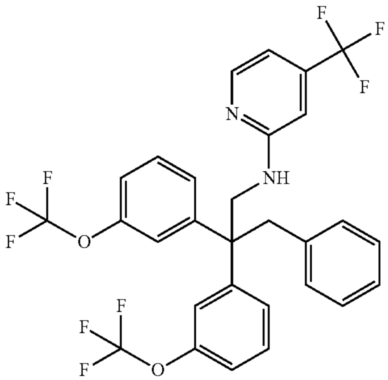 [SMILES: FC(F)(F)Oc1cccc(C(CNc2cc(C(F)(F)F)ccn2)(Cc2ccccc2)c2cccc(OC(F)(F)F)c2)c1] | N-(3-phenyl-2,2-bis(3-(trifluoromethoxy)phenyl)-propyl)-4-(trifluoromethyl)-pyridin-2-amine | 4.20 LC (3) 601.23 $[M + H]^+$ | Procedure 13, 14, 15, 16, 32 |

EXAMPLE 117

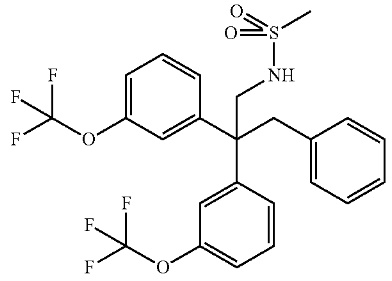 [SMILES: CS(=O)(=O)NCC(Cc1ccccc1)(c1cccc(OC(F)(F)F)c1)c1cccc(OC(F)(F)F)c1]

N-(3-phenyl-2,2-bis(3-(trifluoromethoxy)phenyl)propyl)methanesulfonamide

Procedure 34

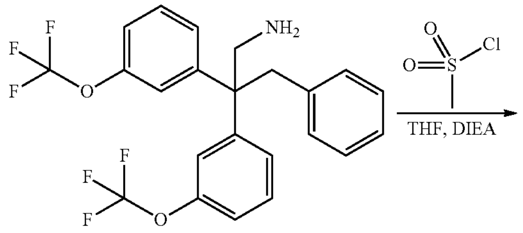

-continued

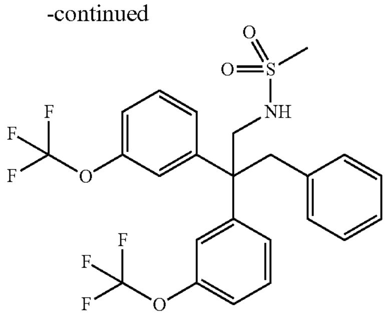

3-Phenyl-2,2-bis(3-(trifluoromethoxy)phenyl)propan-1-amine (18 mg, 0.04 mmol), prepared as described in Example 10 (Procedure 13, 14, 15, and 16), was dissolved in anhydrous THF (1.4 mL), then N,N-diisopropylethylamine (0.021 mL, 0.12 mmol) and methanesulfonyl chloride (6.8 mg, 0.06 mmol) were added to the solution. The reaction mixture was stirred at rt overnight. The reaction mixture was concentrated under reduced pressure and dissolved in DMF followed by purification by preparative HPLC (Waters SunFire C18 OBD column, 19×100 mm×5 μm eluting with 10-90% MeOH/$H_2O$ over 10 minutes containing 0.1% TFA; 20 mL/min, monitoring at 220 nm) to provide Example 117 (13 mg, 62% yield). LCMS: [M+H] 534.13 (4 min Waters Sunfire C18 column, 4.6×50 mm×5 μm eluting with 10-90% MeOH/$H_2O$ over 4 minutes containing 0.1% TFA; 4 mL/min, monitoring at 220 nm); HPLC: RT=4.14 min (4 min Waters Sunfire C18 column, 4.6×50 mm×5 μm eluting with 10-90% MeOH/$H_2O$ over 4 minutes containing 0.1% TFA; 4 mL/min, monitoring at 220 nm.

TABLE 7

| Ex. No. | Structure | Name | Retention Time Min./ Molecular Mass | Prepared in the manner described in: |
|---|---|---|---|---|
| 118 | 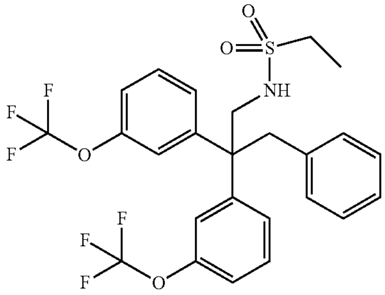 [SMILES: CCS(=O)(=O)NCC(Cc1ccccc1)(c1cccc(OC(F)(F)F)c1)c1cccc(OC(F)(F)F)c1] | N-(3-phenyl-2,2-bis(3-(trifluoromethoxy)phenyl)propyl)-ethanesulfonamide | 4.17 LC (3) 548.14 [M + H]+ | Procedure 13, 14, 15, 16, 34 |
| 119 | 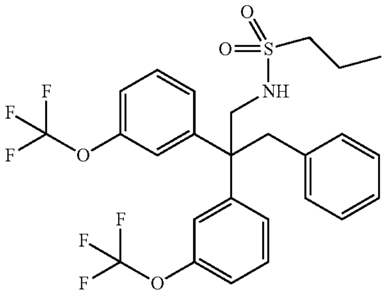 [SMILES: CCCS(=O)(=O)NCC(Cc1ccccc1)(c1cccc(OC(F)(F)F)c1)c1cccc(OC(F)(F)F)c1] | N-(3-phenyl-2,2-bis(3-(trifluoromethoxy)phenyl)propyl)-propane-1-sulfonamide | 4.23 LC (3) 562.14 [M + H]+ | Procedure 13, 14, 15, 16, 34 |

TABLE 7-continued

| Ex. No. | Structure | Name | Retention Time Min./ Molecular Mass | Prepared in the manner described in: |
| --- | --- | --- | --- | --- |
| 120 | 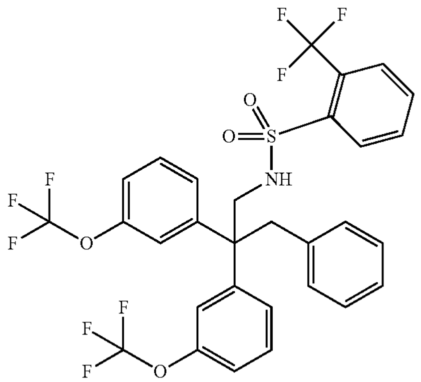 [SMILES: O=S(=O)(NCC(Cc1ccccc1)(c1cccc(OC(F)(F)F)c1)c1cccc(OC(F)(F)F)c1)c1ccccc1C(F)(F)F] | N-(3-phenyl-2,2-bis(3-(trifluoromethoxy)phenyl)propyl)-2-(trifluoromethyl)-benzenesulfonamide | 4.32 LC (3) 664.13 [M + H]+ | Procedure 13, 14, 15, 16, 34 |
| 121 | 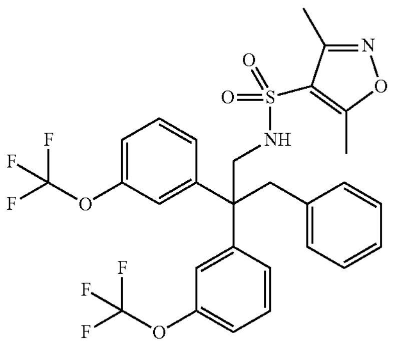 [SMILES: Cc1noc(C)c1S(=O)(=O)NCC(Cc1ccccc1)(c1cccc(OC(F)(F)F)c1)c1cccc(OC(F)(F)F)c1] | 3,5-dimethyl-N-(3-phenyl-2,2-bis(3-(trifluoromethoxy)phenyl)-propyl)isoxazole-4-sulfonamide | 4.25 LC (3) 615.14 [M + H]+ | Procedure 13, 14, 15, 16, 34 |
| 122 | 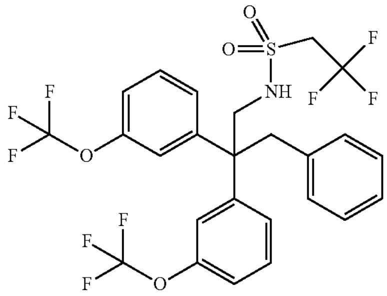 [SMILES: O=S(=O)(CC(F)(F)F)NCC(Cc1ccccc1)(c1cccc(OC(F)(F)F)c1)c1cccc(OC(F)(F)F)c1] | 2,2,2-trifluoro-N-(3-phenyl-2,2-bis(3-(trifluoromethoxy)phenyl)-propyl)ethanesulfonamide | 4.21 LC (3) 602.10 [M + H]+ | Procedure 13, 14, 15, 16, 34 |
| 123 | 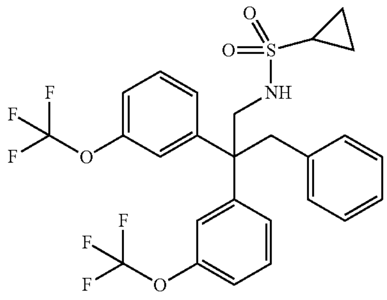 [SMILES: O=S(=O)(NCC(Cc1ccccc1)(c1cccc(OC(F)(F)F)c1)c1cccc(OC(F)(F)F)c1)C1CC1] | N-(3-phenyl-2,2-bis-(trifluoromethoxy)phenyl)propyl)-cyclopropanesulfonamide | 4.19 LC (3) 560.14 [M + H]+ | Procedure 13, 14, 15, 16, 34 |

TABLE 7-continued

| Ex. No. | Structure | Name | Retention Time Min./ Molecular Mass | Prepared in the manner described in: |
|---|---|---|---|---|
| 124 | 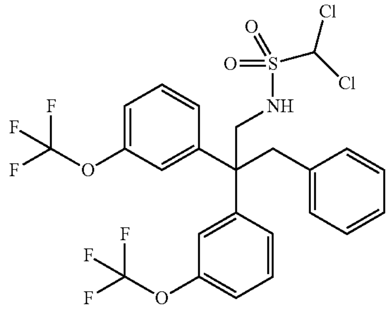 [SMILES: O=S(=O)(NCC(Cc1ccccc1)(c1cccc(OC(F)(F)F)c1)c1cccc(OC(F)(F)F)c1)C(Cl)Cl] | dichloro-N-(3-phenyl-2,2-bis(3-(trifluoromethoxy)phenyl)propyl)-methanesulfonamide | 4.26 LC (3) 602.00 $[M + H]^+$ | Procedure 13, 14, 15, 16, 34 |
| 125 | 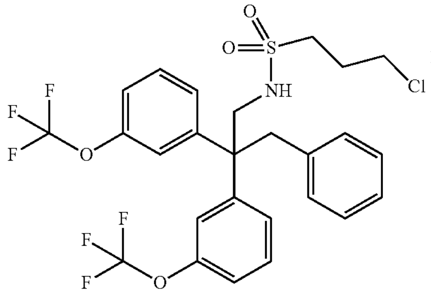 [SMILES: O=S(=O)(CCCCl)NCC(Cc1ccccc1)(c1cccc(OC(F)(F)F)c1)c1cccc(OC(F)(F)F)c1] | 3-chloro-N-(3-phenyl-2,2-bis(3-(trifluoromethoxy)phenyl)propyl)-propane-1-sulfonamide | 4.25 LC (3) 596.12 $[M + H]^+$ | Procedure 13, 14, 15, 16, 34 |

EXAMPLE 126

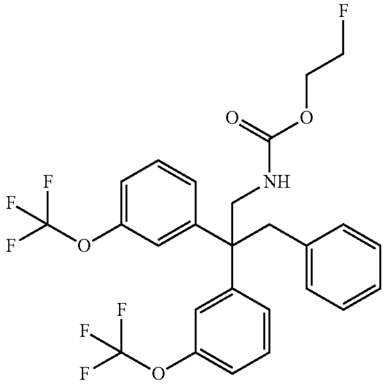 [SMILES: O=C(NCC(Cc1ccccc1)(c1cccc(OC(F)(F)F)c1)c1cccc(OC(F)(F)F)c1)OCCF]

2-fluoroethyl 3-phenyl-2,2-bis(3-(trifluoromethoxy) phenyl)propylcarbamate

Procedure 35

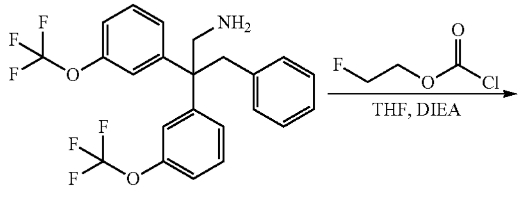

-continued

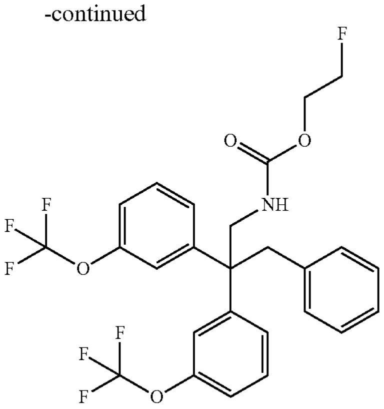

3-Phenyl-2,2-bis(3-(trifluoromethoxy)phenyl)propan-1-amine (18 mg, 0.04 mmol), prepared as described in Example 10 (Procedure 13, 14, 15, and 16), was dissolved in anhydrous THF (1.4 mL), then N,N-diisopropylethylamine (0.035 mL, 0.20 mmol) and 2-fluoroethyl carbonochloridate (7.6 mg, 0.06 mmol) were added to the solution. The reaction mixture was stirred at rt overnight. The reaction mixture was concentrated under reduced pressure and dissolved in DMF followed by purification by preparative HPLC (Waters SunFire C18 OBD column, 19×100 mm×4 μm eluting with 10-90% MeOH/$H_2O$ over 10 minutes containing 0.1% TFA; 20 mL/min, monitoring at 220 nm) to provide Example 126 (14 mg, 64% yield). LCMS: [M+H] 546.14 (4 min Waters Sunfire C18 column, 4.6×50 mm×4 μm eluting with 10-90% MeOH/$H_2O$ over 4 minutes containing 0.1% TFA; 4 mL/min, monitoring at 220 nm); HPLC: RT=4.20 min (4 min Waters Sunfire C18 column, 4.6×50 mm×5 μm eluting with 10-90% MeOH/$H_2O$ over 4 minutes containing 0.1% TFA; 4 mL/min, monitoring at 220 nm).

TABLE 8
| Ex. No. | Structure | Name | Retention Time Min./ Molecular Mass | Prepared in the manner described in: |
|---|---|---|---|---|
| 127 | 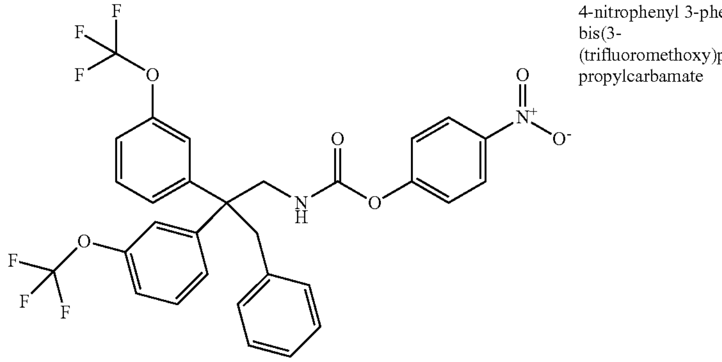 | 4-nitrophenyl 3-phenyl-2,2-bis(3-(trifluoromethoxy)phenyl)-propylcarbamate | 2.30 LC (3) 620.9 $[M + H]^+$ | Procedure 13, 14, 15, 16, 35 |
| 128 | 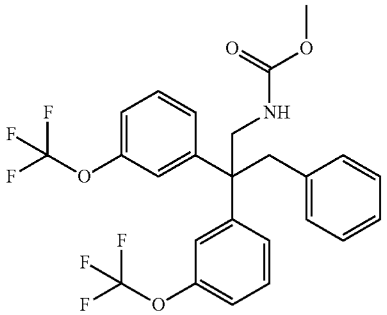 [SMILES: COC(=O)NCC(Cc1ccccc1)(c1cccc(OC(F)(F)F)c1)c1cccc(OC(F)(F)F)c1] | methyl 3-phenyl-2,2-bis(3-(trifluoromethoxy)phenyl)-propylcarbamate | 4.21 LC (3) 514.13 $[M + H]^+$ | Procedure 13, 14, 15, 16, 35 |
| 129 | 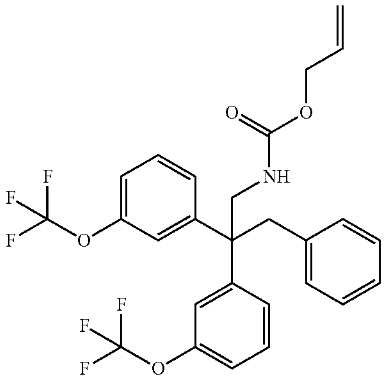 [SMILES: C=CCOC(=O)NCC(Cc1ccccc1)(c1cccc(OC(F)(F)F)c1)c1cccc(OC(F)(F)F)c1] | allyl 3-phenyl-2,2-bis(3-(trifluoromethoxy)phenyl)-propylcarbamate | 4.29 LC (3) 540.14 $[M + H]^+$ | Procedure 13, 14, 15, 16, 35 |

TABLE 8-continued

| Ex. No. | Structure | Name | Retention Time Min./ Molecular Mass | Prepared in the manner described in: |
|---|---|---|---|---|
| 130 | 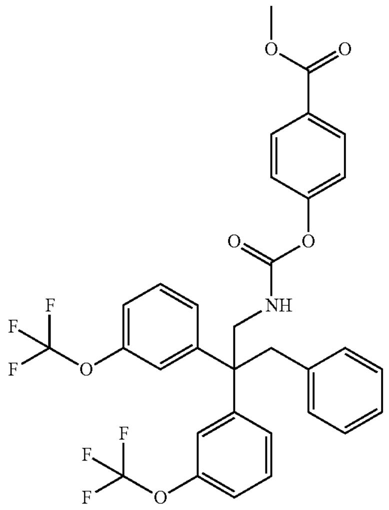 [SMILES: COC(=O)c1ccc(OC(=O)NCC(Cc2ccccc2)(c2cccc(OC(F)(F)F)c2)c2cccc(OC(F)(F)F)c2)cc1] | methyl 4-(3-phenyl-2,2-bis(3-(trifluoromethoxy)phenyl)-propylcarbamoyloxy)benzoate | 4.32 LC (3) 634.11 $[M + H]^+$ | Procedure 13, 14, 15, 16, 35 |
| 131 | 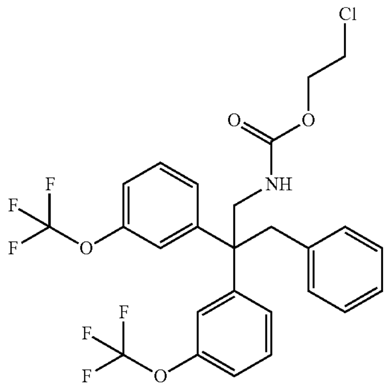 [SMILES: O=C(NCC(Cc1ccccc1)(c1cccc(OC(F)(F)F)c1)c1cccc(OC(F)(F)F)c1)OCCCl] | 2-chloroethyl 3-phenyl-2,2-bis(3-(trifluoromethoxy)phenyl)-propylcarbamate | 4.28 LC (3) 562.08 $[M + H]^+$ | Procedure 13, 14, 15, 16, 35 |
| 132 | 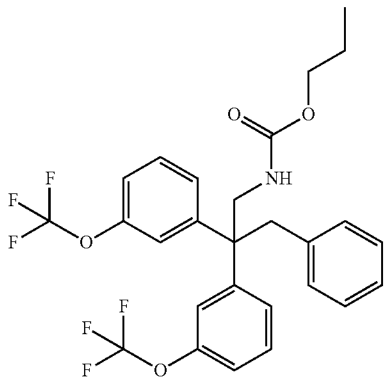 [SMILES: CCCOC(=O)NCC(Cc1ccccc1)(c1cccc(OC(F)(F)F)c1)c1cccc(OC(F)(F)F)c1] | propyl 3-phenyl-2,2-bis(3-(trifluoromethoxy)phenyl)-propylcarbamate | 4.34 LC (3) 542.14 $[M + H]^+$ | Procedure 13, 14, 15, 16, 35 |

TABLE 8-continued

| Ex. No. | Structure | Name | Retention Time Min./ Molecular Mass | Prepared in the manner described in: |
|---|---|---|---|---|
| 133 | 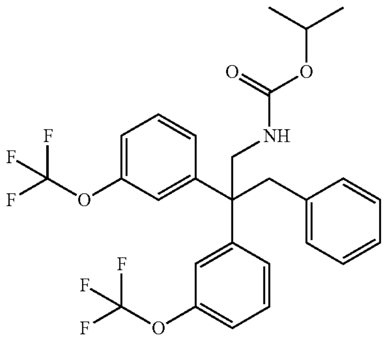 [SMILES: CC(C)OC(=O)NCC(Cc1ccccc1)(c1cccc(OC(F)(F)F)c1)c1cccc(OC(F)(F)F)c1] | isopropyl 3-phenyl-2,2-bis(3-(trifluoromethoxy)phenyl)-propylcarbamate | 4.34 LC (3) 542.14 [M + H]+ | Procedure 13, 14, 15, 16, 35 |

EXAMPLE 134

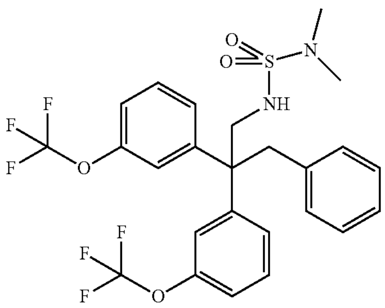 [SMILES: CN(C)S(=O)(=O)NCC(Cc1ccccc1)(c1cccc(OC(F)(F)F)c1)c1cccc(OC(F)(F)F)c1]

N,N-dimethyl-N'-(3-phenyl-2,2-bis(3-(trifluoromethoxy)phenyl)propyl)sulfamide

Procedure 36

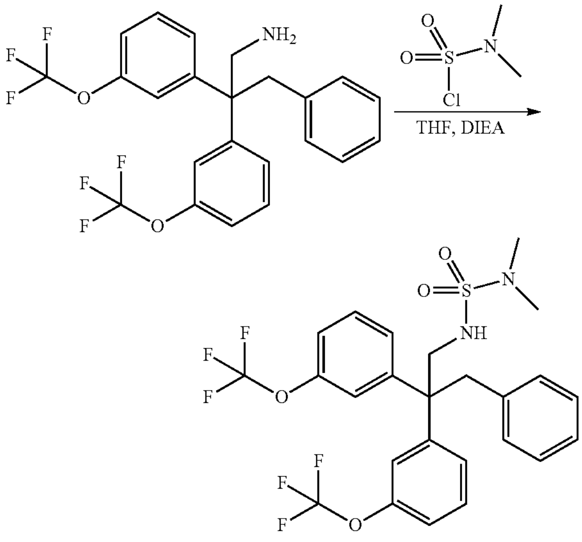

3-Phenyl-2,2-bis(3-(trifluoromethoxy)phenyl)propan-1-amine (18 mg, 0.04 mmol), prepared as described in Example 10 (Procedure 13, 14, 15, and 16), was dissolved in anhydrous THF (1.4 mL), then N,N-diisopropylethylamine (0.021 mL, 0.12 mmol) and dimethylsulfamoyl chloride (8.6 mg, 0.06 mmol) were added to the solution. The reaction mixture was stirred at rt overnight. The reaction mixture was concentrated under reduced pressure and dissolved in DMF followed by purification by preparative HPLC (Waters SunFire C18 OBD column, 19×100 mm×5 μm eluting with 10-90% MeOH/$H_2O$ over 10 minutes containing 0.1% TFA; 20 mL/min, monitoring at 220 nm) to provide Example 134 (18 mg, 78% yield). LCMS: [M+H] 563.15 (4 min Waters Sunfire C18 column, 4.6×50 mm×5 μm eluting with 10-90% MeOH/$H_2O$ over 4 minutes containing 0.1% TFA; 4 mL/min, monitoring at 220 nm); HPLC: RT=4.21 min (4 min Waters Sunfire C18 column, 4.6×50 mm×5 μm eluting with 10-90% MeOH/$H_2O$ over 4 minutes containing 0.1% TFA; 4 mL/min, monitoring at 220 nm).

EXAMPLE 135

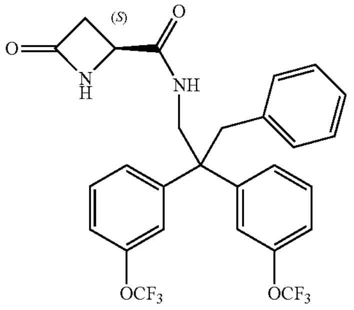

(S)-4-oxo-N-(3-phenyl-2,2-bis(3-(trifluoromethoxy)phenyl)propyl)azetidine-2-carboxamide Procedure 37

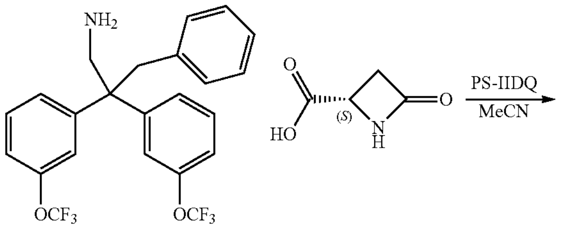

-continued

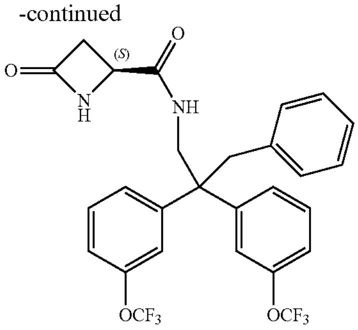

Reference: Valeur, E. and M. Bradley, "PS-IIDQ: an efficient polymer-supported amide coupling reagent", *Chemical Communications* (Cambridge, United Kingdom), 9:1164-1166 (2005).

Polymer supported IIDQ 1.6 mmol/g (250 mg, 0.400 mmol, NovaBioChem) was swollen in acetonitrile (1333 μL) and 3-phenyl-2,2-bis(3-(trifluoromethoxy)phenyl)propan-1-amine (91 mg, 0.2 mmol) and (S)-4-oxoazetidine-2-carboxylic acid (34.5 mg, 0.300 mmol) were added in a 2 dram vial and the mixture was stirred for 3h. HPLC (Phenominex, Onyx C18, 4.6×100 mm, 2 min gradient from 10% MeCN, 90% water, 0.1% TFA to 90% MeCN, 10% water, 0.1% TFA) showed complete conversion of the starting amine (1.59 min) and formation of a new major peak 1.86 min (75% pure). The sample was filtered, washed with DCM (3×8 mL), washed with 2 N $K_2CO_3$ (8 ml), dried over $MgSO_4$, filtered and concentrated to give 100.4 mg of colorless oil. The oil was purified by flash (Analogix 12 g, hex toe EA). The desired product was obtained as a glassy solid (55 mg). LCMS (Phenominex, Luna C18, 4.6x50 mm, 4 min gradient from 10% MeOH, 90% water, 0.1% TFA to 90% MeOH, 10% water, 0.1% TFA) and $^1H$ NMR indicated that the product was not pure but was the desired product (4.05 min, MH+553.1). The sample was purified by flash (ISCO, 4.2 g, hexane to ethyl acetate gradient) to give the desired product (50 mg, 0.085 mmol, 42.5% yield)) HPLC (8 min gradient, 4.77 min, 94%); $^1H$ NMR (500 MHz, CDCl3) δ ppm 2.71 (dd, J=15.1, 3.0 Hz, 1 H), 3.26 (ddd, J=14.8, 6.0, 3.3 Hz, 1 H), 3.36 (s, 2 H), 3.85-3.97 (m, 2 H), 3.99 (dd, J=6.0, 2.7 Hz, 1 H), 5.86 (t, J=5.8 Hz, 1 H), 6.06 (d, J=2.2 Hz, 1 H), 6.58 (d, J=7.1 Hz, 2 H), 6.93 (s, 1 H), 6.98 (s, 1 H), 7.02-7.10 (m, 4 H), 7.15 (dd, J=14.8, 7.1 Hz, 3 H), 7.35 (td, J=8.0, 3.8 Hz, 2 H); $^{19}F$ NMR (471 MHz, CDCl3) δ ppm −57.68 (s, 6 F). HRMS $C_{22}H_{22}F_6N_2O_4$—H+ calcd 553.15565 measured 553.1544.

Utility

Compounds of the present invention have been shown to inhibit cholesterol ester transfer protein (CETP). Accordingly, compounds within the scope of the present invention inhibit the CETP protein, and as such are expected to be useful in the treatment, prevention, and/or slowing of the progression of various disorders.

For example, the compounds of the present invention, their prodrugs and the salts of such compounds and prodrugs can be adapted to therapeutic use as agents that inhibit cholesterol ester transfer protein activity in mammals, particularly humans. Thus, the compounds of the present invention are expected to be useful in elevating plasma HDL cholesterol, its associated components, and the functions performed by them in mammals, particularly humans. By virtue of their expected activity, these agents are also expected to reduce VLDL cholesterol, LDL cholesterol and their associated components in mammals, particularly humans. Hence, these compounds are expected to be useful for the treatment and correction of the various dyslipidemias observed to be associated with the development and incidence of atherosclerosis and cardiovascular disease, including hypoalphalipoproteinemia, hyperbetalipoproteinemia, hypertriglyceridemia, and familial-hypercholesterolemia (see U.S. Pat. No. 6,489,478, incorporated herein by reference).

Further, introduction of a functional CETP gene into an animal lacking CETP (mouse) results in reduced HDL levels (Agellon, L. B. et al., *J. Biol. Chem.,* 266:10796-10801 (1991) and, increased susceptibility to atherosclerosis. (Marotti, K. R. et al., *Nature,* 364:73-75 (1993)). Also, inhibition of CETP activity with an inhibitory antibody raises HDL-cholesterol in hamster (Evans, G. F. et al., *J. Lipid Res.,* 35:1634-1645 (1994)) and rabbit (Whitlock, M. E. et al., *J. Clin. Invest.,* 84:129-137 (1989)). Suppression of increased plasma CETP by intravenous injection with antisense oligodeoxynucleotides against CETP mRNA reduced atherosclerosis in cholesterol-fed rabbits (Sugano, M. et al., *J. Biol. Chem.,* 273:5033-5036 (1998)). Importantly, human subjects deficient in plasma CETP, due to a genetic mutation possess markedly elevated plasma HDL-cholesterol levels and apolipoprotein A-I, the major apoprotein component of HDL. In addition, most demonstrate markedly decreased plasma LDL cholesterol and apolipoprotein B (the major apolipoprotein component of LDL. (Inazu, A. et al., *N. Engl. J. Med.,* 323:1234-1238 (1990).)

Given the negative correlation between the levels of HDL cholesterol and HDL associated lipoproteins, and the positive correlation between triglycerides, LDL cholesterol, and their associated apolipoproteins in blood with the development of cardiovascular, cerebral vascular and peripheral vascular diseases, the compounds of the present invention, their prodrugs and the salts of such compounds and prodrugs, by virtue of their pharmacologic action, are expected to be useful for the treatment, prevention, the arrestment and/or regression of atherosclerosis and its associated disease states. These include cardiovascular disorders (e.g., angina, cardiac ischemia and myocardial infarction), complications due to cardiovascular disease therapies (e.g., reperfusion injury and angioplastic restenosis), hypertension, stroke, and atherosclerosis associated with organ transplantation.

Because of the beneficial effects widely associated with elevated HDL levels, an agent which inhibits CETP activity in humans, by virtue of its HDL increasing ability, also provides valuable avenues for therapy in a number of other disease areas as well.

Accordingly, given the ability of the compounds of the present invention, their prodrugs and the salts of such compounds and prodrugs to alter lipoprotein composition via inhibition of cholesterol ester transfer, they are expected to be useful in the treatment, prevention and/or slowing of the progression of vascular complications associated with diabetes. Hyperlipidemia is present in most subjects with diabetes mellitus (Howard, B. V., *J. Lipid Res.,* 28:613 (1987)). Even in the presence of normal lipid levels, diabetic subjects experience a greater risk of cardiovascular disease (Kannel, W. B. et al., *Diabetes Care,* 2:120 (1979)). CETP-mediated cholesteryl ester transfer is known to be abnormally increased in both insulin-dependent (Bagdade, J. D. et al., *Eur. J. Clin. Invest.,* 21:161 (1991)) and non-insulin dependent diabetes (Bagdade, J. D. et al., *Atherosclerosis,* 104:69 (1993)). It has been suggested that the abnormal increase in cholesterol transfer results in changes in lipoprotein composition, particularly for VLDL and LDL, that are more atherogenic (Bagdade, J. D. et al., *J. Lipid Res.,* 36:759 (1995)). These changes would not necessarily be observed during routine lipid screening. Thus, it is expected that the present invention will be useful in reducing the risk of vascular complications as a result of the diabetic condition.

In addition, the compounds of the present invention are expected to be useful in the treatment of obesity. In both humans (Radeau, T. et al., *J. Lipid Res.,* 36(12):2552-2561 (1995)) and nonhuman primates (Quinet, E. et al., *J. Clin. Invest.,* 87(5):1559-1566 (1991)) mRNA for CETP is expressed at high levels in adipose tissue. The adipose message increases with fat feeding (Martin, L. J. et al., *J. Lipid Res.,* 34(3):437-446 (1993)), and is translated into functional transfer protein and through secretion contributes significantly to plasma CETP levels. In human adipocytes the bulk of cholesterol is provided by plasma LDL and HDL (Fong, B. S. et al., *Biochim. Biophys. Acta,* 1004(1):53-60 (1989)). The uptake of HDL cholesteryl ester is dependent in large part on CETP (Benoist, F. et al., *J. Biol. Chem.,* 272(38):23572-23577 (1997)). This ability of CETP to stimulate HDL cholesteryl uptake, coupled with the enhanced binding of HDL to adipocytes in obese subjects (Jimenez, J. G. et al., *Int. J. Obesity,* 13(5):699-709 (1989)), suggests a role for CETP, not only in generating the low HDL phenotype for these subjects, but in the development of obesity itself by promoting cholesterol accumulation Inhibitors of CETP activity that block this process therefore serve as useful adjuvants to dietary therapy in causing weight reduction.

CETP inhibitors are useful in the treatment of inflammation due to Gram-negative sepsis and septic shock. For example, the systemic toxicity of Gram-negative sepsis is in large part due to endotoxin, a lipopolysaccharide (LPS) released from the outer surface of the bacteria, which causes an extensive inflammatory response. Lipopolysaccharide can form complexes with lipoproteins (Ulevitch, R. J. et al., *J. Clin. Invest.,* 67:827-837 (1981)). In vitro studies have demonstrated that binding of LPS to HDL substantially reduces the production and release of mediators of inflammation (Ulevitch, R. J. et al., *J. Clin. Invest.,* 62:1313-1324 (1978)). In vivo studies show that transgenic mice expressing human apo-Al and elevated HDL levels are protected from septic shock (Levine, D. M. et al., *Proc. Natl. Acad. Sci.,* 90:12040-12044 (1993)). Importantly, administration of reconstituted HDL to humans challenged with endotoxin resulted in a decreased inflammatory response (Pajkrt, D. et al., *J. Exp. Med.,* 184:1601-1608 (1996)). The CETP inhibitors, by virtue of the fact that they raise HDL levels, attenuate the development of inflammation and septic shock.

Thus, the present invention provides methods for the prevention or treatment of one or more of the aforementioned disorders, comprising the step of administering to a subject in need thereof an effective amount of at least one compound of the present invention, its prodrug and the salt of such compound and prodrugs. Other therapeutic agents such as those described below may be employed with the inventive compounds in the present methods. In the methods of the present invention, such other therapeutic agent(s) may be administered prior to, simultaneously with or following the administration of the compound(s) of the present invention.

In addition, the compounds of the present invention are expected to be useful in the inhibition of remnant lipoprotein production (Okamoto et al., WO 2005/030185).

CETP Assay

CETP inhibition can be determined at a specific concentration of test compound in any of the assays described herein. Potencies are more generally calculated by determining $IC_{50}$ values using these assays.

CETP Scintillation Proximity Assay

Compounds of the present invention inhibit CETP-dependent cholesterol ester transfer from HDL to LDL as described here. Dilutions of compounds in DMSO (1 μl) are added to BD plates (#353232). To this is added 20 μl of a mixture containing $^{3}H$-CE/HDL (0.15 μl), biotinylated LDL (~5 μg protein/ml final concentration) and unlabeled HDL (16 μg/ml final concentration) in a buffer containing 50 mM HEPES, pH 7.4, 150 mM NaCl and 0.05% sodium azide. Reactions are initiated by the addition of 10 μl of buffer containing purified human recombinant CETP, and incubated at 37° C. At the end of the reaction, 60 μl of LEADseeker beads (#RPNQ0261, 2 mg/ml in buffer containing 1 mg/ml BSA and 0.05 mg protein/ml HDL) are added, the plates are covered and subsequently read. Background activity is determined in a set of wells that receive buffer but no CETP. The level of inhibition is determined by comparing the readings in wells that contain compound to the readings in control wells containing DMSO.

Compounds of the present invention were tested in the assay described immediately above and the results shown in the Table 9 below were obtained.

TABLE 9

| Example No. | Structure | CETP SPA $IC_{50}$ (μM) |
|---|---|---|
| 2 | 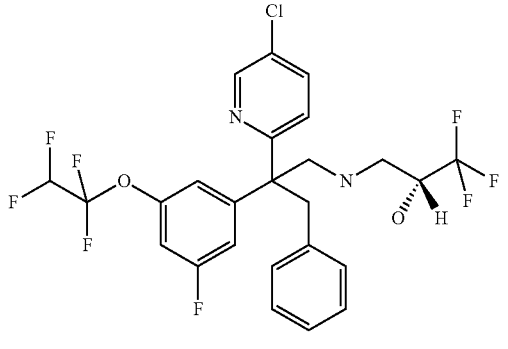 Chiral | 0.009 |

TABLE 9-continued
| Example No. | Structure | | CETP SPA $IC_{50}$ (μM) |
|---|---|---|---|
| 5 | 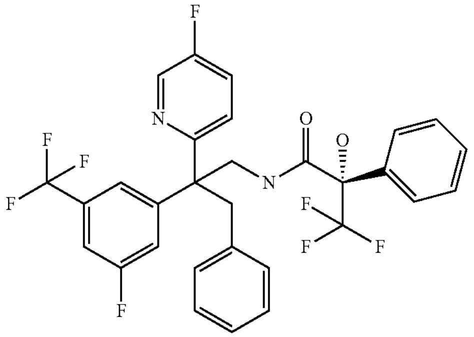 | Chiral | 4.356 |
| 6 | 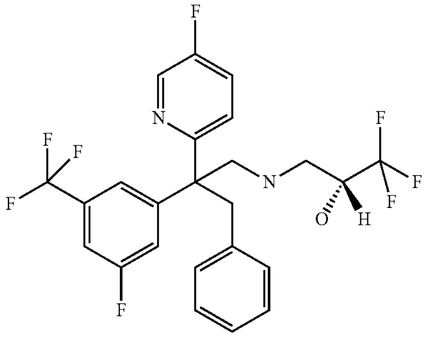 | Chiral | 0.030 |
| 11 | 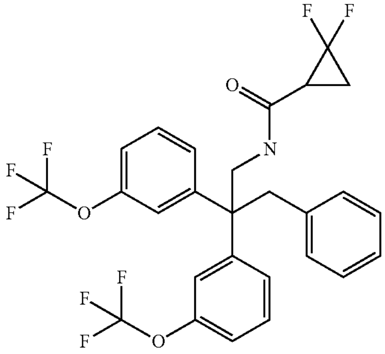 [SMILES: O=C(NCC(Cc1ccccc1)(c1cccc(OC(F)(F)F)c1)c1cccc(OC(F)(F)F)c1)C1CC1(F)F] | | 1.432 |
| 27 | 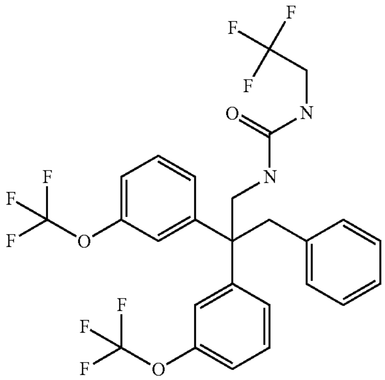 [SMILES: O=C(NCC(F)(F)F)NCC(Cc1ccccc1)(c1cccc(OC(F)(F)F)c1)c1cccc(OC(F)(F)F)c1] | | 0.132 |

TABLE 9-continued
| Example No. | Structure | | CETP SPA $IC_{50}$ (μM) |
|---|---|---|---|
| 43 | 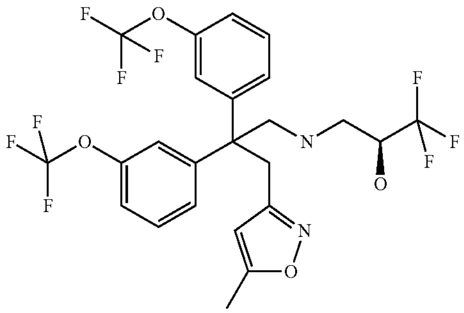 | Chiral | 0.134 |
| 44 | 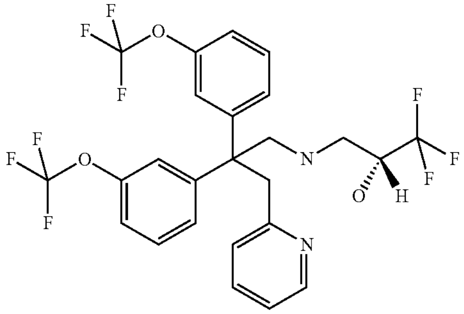 | Chiral | 0.019 |
| 45 | 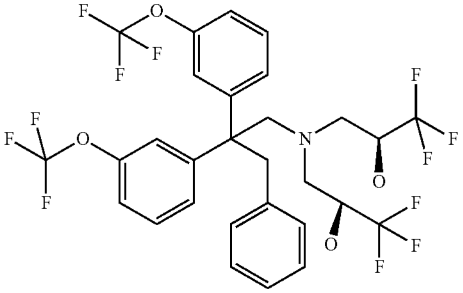 [SMILES: O[C@H](CN(C[C@H](O)C(F)(F)F)CC(Cc1ccccc1)(c1cccc(OC(F)(F)F)c1)c1cccc(OC(F)(F)F)c1)C(F)(F)F] | | 2.811 |
| 47 | 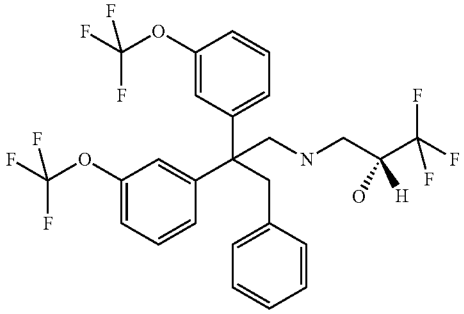 | Chiral | 0.014 |

TABLE 9-continued
| Example No. | Structure | CETP SPA $IC_{50}$ (μM) |
|---|---|---|
| 50 | 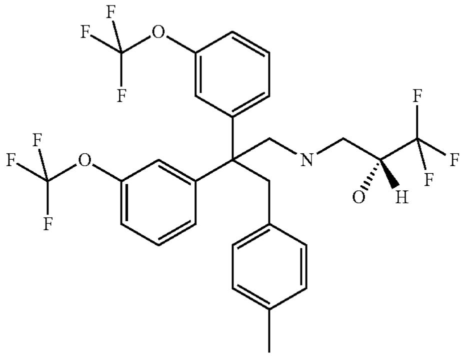 Chiral | 0.009 |
| 53 | 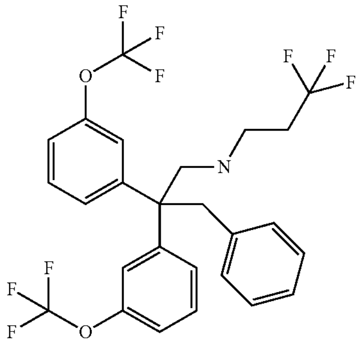 [SMILES: FC(F)(F)CCNCC(Cc1ccccc1)(c1cccc(OC(F)(F)F)c1)c1cccc(OC(F)(F)F)c1] | 0.025 |
| 94 | 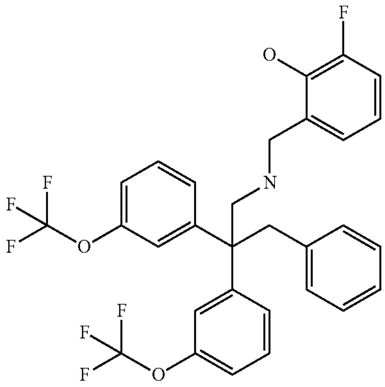 [SMILES: Oc1c(F)cccc1CNCC(Cc1ccccc1)(c1cccc(OC(F)(F)F)c1)c1cccc(OC(F)(F)F)c1] | 0.184 |
| 112 | 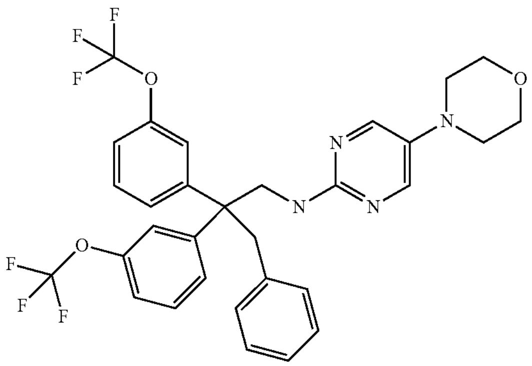 [SMILES: FC(F)(F)Oc1cccc(C(CNc2ncc(N3CCOCC3)cn2)(Cc2ccccc2)c2cccc(OC(F)(F)F)c2)c1] | 0.2476 |

TABLE 9-continued

| Example No. | Structure | CETP SPA $IC_{50}$ (μM) |
|---|---|---|
| 122 | 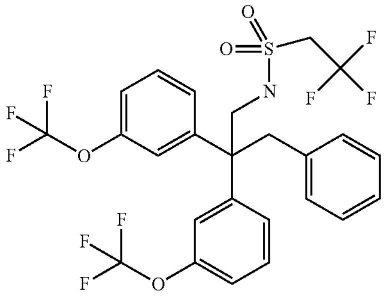 [SMILES: O=S(=O)(CC(F)(F)F)NCC(Cc1ccccc1)(c1cccc(OC(F)(F)F)c1)c1cccc(OC(F)(F)F)c1] | 0.129 |
| 133 | 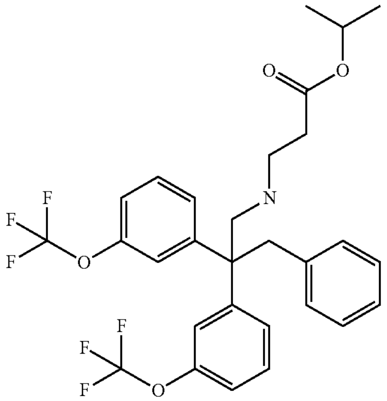 [SMILES: CC(C)OC(=O)CCNCC(Cc1ccccc1)(c1cccc(OC(F)(F)F)c1)c1cccc(OC(F)(F)F)c1] | 1.089 |

Plasma Cholesterol Ester Transfer Assay

Compounds of the present invention can also be tested for the ability to inhibit cholesterol ester transfer activity in plasma as described here. Dilutions of compounds in DMSO (1 μl) are added to 384-well polypropylene plates. To each well is added 29 ul of human plasma containing 0.15 ul $^3$H-CE/HDL. The reaction is incubated at 37° C. and terminated by the addition of 6 ul of precipitation reagent (2:1:1 of water:1M $MgCl_2$:2% Dextralip 50), to precipitate LDL and VLDL. After 10 minutes at room temperature, 15 μl of the reaction is transferred to filter plates (Millipore, #MHVBN45) pre-wetted with 100 ul phosphate buffered saline. The plates are centrifuged (1800 rpm) at room temperature for 10 minutes, and 50 ul Microscint-20 is added. The plates are then sealed and read. Background activity is determined with plasma samples incubated at 4° C. The level of inhibition is determined by comparing the readings in wells that contain compound to the readings in control wells containing DMSO.

In Vivo Cholesterol Ester Transfer Activity

Compounds of the present invention may further be shown to inhibit plasma cholesterol ester transfer activity in mice that are dually transgenic for human CETP and apoB-100 (hCETP/apoB-100) as described here.

Mice (commercially available from Taconic) are fasted for two hours and plasma obtained before dosing. The animals are then dosed with vehicle or compound (p.o.). The vehicle may vary as needed to dissolve the compound, while at the same time having no, or minimal, activity on plasma cholesterol ester transfer activity. Plasma samples are collected again at various times after dosing and assayed for cholesterol ester transfer activity.

To measure CETP activity in plasma samples obtained from animals treated with compounds, the following methodology can be employed. To a sample of plasma (typically between 9 and 30 ul), 1 μl of diluted $^3$H-CE/HDL is added (0.15 μl $^3$H-CE/HDL and 0.85 ul assay buffer) to label endogenous HDL. Assay buffer contains 50 mM HEPES, pH 7.4, and 150 mM NaCl. The reaction is incubated at 37° C., and LDL/VLDL precipitated with 3 μl of precipitation reagent (4:1:1 of water:0.5M $MgCl_2$:1% Dextralip 50). The tubes are centrifuged for 15-30 minutes at 10,000×g (10° C.), the supernatants discarded, and the pellets dissolved in 140 μl of 2% SDS. Half of the SDS solution (70 μl) is transferred to scintillation tubes, scintillation fluid is added, and radioactivity measured in a scintillation counter. Background activity is determined for each sample with an aliquot incubated at 4° C. Plasma cholesterol ester transfer inhibition is calculated by comparing the transfer activity in a plasma sample obtained after dosing to the transfer activity in the plasma sample obtained from the same animal before dosing. All data are background subtracted.

The in vivo assay described above (with appropriate modifications within the skill in the art) may be used to determine the activity of other lipid or triglyceride controlling agents as well as the compounds of this invention. The assays set forth above also provide a means whereby the activities of the compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of the above described disease/conditions.

HDL Cholesterol Protocol

The ability of CETP inhibitors to increase HDL cholesterol (HDL-C) can be shown in mammalian subjects via methods known to one of ordinary skill in the art (see Evans, G. F. et al.,

*J. Lipid Res.*, 35:1634-1645 (1994)). For example, compounds of the present invention have been shown to be efficacious in the elevation of HDL-C in golden syrian hamsters. The hamsters are fed a moderate fat diet containing variable amounts of coconut oil and cholesterol to alter their HDL-C and LDL-C levels. The moderately fat-fed hamsters are fasted and bled to determine baseline HDL-C levels, then dosed orally with compound for three days in an appropriate vehicle. The animals are fasted and bled again on the third day of dosing, and the results are compared to the baseline HDL-C levels. The compounds increase HDL-C in this model in a dose-dependent manner, demonstrating their usefulness to alter plasma lipids.

Antiobesity Protocol

The ability of CETP inhibitors to cause weight loss can be assessed in obese human subjects with body mass index (BMI) ≥30 kg/$m^2$. Doses of inhibitor are administered sufficient to result in an increase of ≥25% in HDL cholesterol levels. BMI and body fat distribution, defined as waist (W) to hip (H) ratio (WHR), are monitored during the course of the 3-6 month studies, and the results for treatment groups compared to those receiving placebo.

The above assays can of course be varied by those skilled in the art.

The present invention also provides pharmaceutical compositions comprising at least one of the compounds of the present invention, their prodrugs and the salts of such compounds and prodrugs capable of preventing, treating, and/or slowing the progression of one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release Immediate release or extended release may be achieved by the use of suitable pharmaceutical compositions comprising the present compounds, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of present invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders.

For example, they may be used in combination with a HMG-CoA reductase inhibitor, a cholesterol synthesis inhibitor, a cholesterol absorption inhibitor, another CETP inhibitor, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), aspirin (acetylsalicylic acid) and niacin and combinations thereof.

Any HMG-CoA reductase inhibitor may be used in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., *Meth. Enzymol.,* 71:455-509 (1981) and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as Iovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP 491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin and any pharmaceutically acceptable form thereof (i.e., LIPITOR®). Additional HMG-CoA reductase inhibitors include rosuvastatin and pitavastatin. Statins also include such compounds as rosuvastatin disclosed in U.S. RE 37,314 E, pitavastatin disclosed in EP 304063 B1 and U.S. Pat. No. 5,011,930; mevastatin, disclosed in U.S. Pat. No. 3,983,140; velostatin, disclosed in U.S. Pat. No. 4,448,784 and U.S. Pat. No. 4,450,171; compactin, disclosed in U.S. Pat. No. 4,804,770; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171.

Any PPAR modulator may be used In the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein AI gene transcription), accordingly reducing whole body fat and increasing HDL cholesterol. By virtue of their activity, these compounds also reduce plasma levels of triglycerides, VLDL cholesterol, LDL cholesterol and their associated components such as apolipoprotein B in mammals, particularly humans, as welt as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 02/064549 and WO 02/064130, U.S. patent application Ser. No. 10/720,942, and U.S. patent application 60/552,114 disclose certain compounds which are PPARα activators.

Any other PPAR modulator may be used in the combination aspect of this invention. In particular, modulators of PPARβ and/or PPARγ may be useful in combination with compounds of the present invention. An example PPAR inhibitor is described in US 2003/0225158 as {5-methoxy-2-methyl-4-[4-(4-trifluoromethyl-benzy]oxy)-benzylsulfany]-phenoxy}-acetic acid.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R., *Science,* 258:999 (1992)). A variety of these compounds are described and referenced below however other MTP/Apo B secretion inhibitors will be known to those skilled in the art, including implitapride (Bayer) and additional compounds such as those disclosed in WO 96/40640 and WO 98/23593, (two exemplary publications). For example, the following MTP/Apo B secretion inhibitors are particularly useful: 4'-trifluoromethyl-biphenyl-2-carboxylic acid [2-(1H-[1,2,4,]triazol-3-ylmethyl)-1,2,3,4-tetrahydro-isoquinolin-6-yl]-amide; 4'-trifluoromethyl-biphenyl-2-carboxylic acid [2-(2-acetylamino-ethyl)-1,2,3,4-tetrahydro-isoquinolin-6-yl]-amide; (2-{6-[(4'-trifiuoromethyl-biphenyl-2-carbonyl)-amino]-3,4-dihydro-1H-isoquinolin-2-yl}-ethyl)-carbamic acid methyl ester; 4'-trifluoromethyl-biphenyl-2-carboxylic acid [2-(1H-imidazol-2-ylmethyl)-1,2,3,4-tetrahydro-isoquinolin-6-yl]-amide; 4'-trifluoromethyl-biphenyl-2-carboxylic acid [2-(2,2-diphenyl-ethyl)-1,2,3,4-tetrahydro-isoquinolin-6-yl]-amide; 4'-trifluoromethyl-biphenyl-2-carboxylic acid [2-(2-ethoxy-ethyl)-1,2,3,4-tetrahydro-isoquinolin-6-yl]-amide; (S)—N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide; (S)-2-[(4'-trifluoromethyl-biphenyl-2-carbonyl)-amino]-quinoline-6-carboxy; ic acid (pentylcarbamoyl-phenyl-methyl)-amide; 1H-indole-2-carboxamide, 1-methyl-N-[(1S)-2-[methyl (phenylmethyl)amino]-2-oxo-1-phenylethyl]-5-[[[4'-(trifluoromethyl)[1,1'-biphenyl]-2-yl]carbonyl]amino]; and N-[(1S)-2-(benzylmethylamino)-2-oxo-1-phenylethyl]-1-methyl-5-[[[4'-(trifluoromethyl)[1,1'-biphenyl]-2-yl]carbonyl]amino]-1H-indole-2-carboxamide.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (*Meth. Enzymol.,* 35:155-160 (1975); *Meth. Enzymol.,* 110:19-26 (1985) and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undecadienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (SIP) or agonizing the oxysterol receptor or SCAP. Such regulation is readily determined by those skilled in the art according to standard assays (*Meth. Enzymol.,* 110:9-19 (1985)). Several compounds are described and referenced below, however other inhibitors of HMG-CoA reductase gene expression will be known to those skilled in the art. U.S. Pat. No. 5,041,432 discloses certain 15-substituted lanosterol derivatives. Other oxygenated sterols that suppress synthesis of HMG-CoA reductase are discussed by E. I. Mercer (*Prog. Lip. Res.,* 32:357-416 (1993)).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in U.S. Pat. Nos. 6,140,343 and 6,197,786. CETP inhibitors disclosed in these patents include compounds, such as [2R,4S]-4-[(3,5-bis-trifluoromethylbenzyl)methoxycarbonylamino]-2-ethyl-6-trifluoromethyl-3,4-dihydro-2H-quinoline-1-carboxylic acid ethyl ester (torcetrapib). CETP inhibitors are also described in U.S. Pat. No. 6,723,752, which includes a number of CETP inhibitors including (2R)-3-{[3-(4-chloro-3-ethyl-phenoxy)-phenyl]-[[3-(1,1,2,2-tetrafluoroethoxy) phenyl]methyl]amino}-1,1,1-trifluoro-2-propanol. Moreover, CETP inhibitors included herein are also described in U.S. patent application Ser. No. 10/807,838 and PCT Publication No. WO 2006/090250. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in *J. Antibiot.,* 49(8):815-816 (1996), and *Bioorg. Med. Chem. Lett.,* 6:1951-1954 (1996), respectively.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (*Meth. Enzymol.,* 15:393-454 (1969) and *Meth. Enzymol.,* 110:359-373 (1985) and references contained therein). A variety of these compounds are described in and referenced below however other squalene synthetase inhibitors will be known to those skilled in the art. U.S. Pat. No. 5,026,554 discloses fermentation products of the microorganism MF5465 (ATCC 74011) including zaragozic acid. A summary of other patented squalene synthetase inhibitors has been compiled (*Curr. Op. Ther. Patents,* 861-864 (1993)).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (*Biochim. Biophys. Acta,* 794:466-471 (1984)). A variety of these compounds are described and referenced below, however other squalene epoxidase inhibitors will be known to those skilled in the art. U.S. Pat. Nos. 5,011,859 and 5,064,864 disclose certain fluoro analogs of squalene. EP publication 395,768 A discloses certain substituted allylamine derivatives. PCT publication WO 93/12069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibiter refers to compounds which inhibit the bioconversion of squalene-2,3-epoxide to lanosterol, catalyzed by the enzyme squalene cyclase. Such inhibition is readily determined by those skilled in the art according to standard assays (*FEBS Lett.,* 244:347-350 (1989)). In addition, the compounds described and referenced below are squalene cyclase inhibitors, however other squalene cyclase inhibitors will also be known to those skilled in the art. PCT publication WO 94/10150 discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine French patent publication 2697250 discloses certain beta, beta-dimethyl-4-piperidine ethanol derivatives such as 1-(1,5,9-trimethyldecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 disclose certain azadecalin derivatives. EP publication 468,434 discloses certain piperidyl ether and thio-ether derivatives such as 2-(1-piperidyl)pentyl isopentyl sulfoxide and 2-(1-piperidyl)ethyl ethyl sulfide. PCT publication WO 94/01404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

The compounds of the present invention may also be administered in combination with naturally occurring compounds that act to lower plasma LDL cholesterol levels or raise plasma HDL levels via a pathway distinct from CETP inhibitors. These naturally occurring compounds are commonly called nutraceuticals and include, for example, garlic extract and niacin. Niacin is a particularly attractive secondary agent for combination with a CETP inhibitor as it also raises HDL cholesterol levels. Furthermore, niacin lowers LDL cholesterol and triglycerides. Therefore, a combination of niacin and a CETP inhibitor would not only provide the potential for enhanced HDL-raising efficacy, it would yield a very favorable shift in the overall cardiovascular risk profile by decreasing LDL cholesterol and triglycerides. Niacin is commercially available in various dosage forms Immediate release niacin may be purchase over-the-counter in pharmacies or health-food stores. A slow-release form of niacin is available and is known as Niaspan. Niacin may also be combined with other therapeutic agents such as iovastatin, an HMG-CoA reductase inhibitor. This combination therapy with iovastatin is known as ADVICOR™ (Kos Pharmaceuticals Inc.). In long term clinical trials, niacin either as monotherapy or in combination with HMG-CoA reductase inhibitors has been shown to reduce cardiovascular events, cardiovascular deaths and all cause mortality.

Any cholesterol absorption inhibitor can be used as an additional component in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., *J. Lipid Res.,* 34:377-395 (1993)). Cholesterol absorption inhibitors are known to those skilled in the art and are described, for example, in PCT WO 94/00480. An example of a recently approved cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in *J. Lipid Res.,* 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (E11 Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g., EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., *Meth. Enzymol.,* 286:190-231). Pancreatic lipase mediates the metabolic cleavage of fatty acids from triglycerides at the 1- and 3-carbon positions. The primary site of the metabolism of ingested fats is in the duodenum and proximal jejunum by pancreatic tipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., *Meth. Enzymol.,* 286:190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams et al., *Gastroenterology,* 92:125 (1987). Such gastric lipase inhibition activity is readily determined by those skilled in the art according to standard assays (e.g., *Meth. Enzymol.,* 286:190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis (iminocarbonyl)dioximes related thereto may be prepared as described in Petersen et al., *Liebig's Annalen,* 562:205-229 (1949).

A variety of pancreatic lipase inhibitors are described herein below. The pancreatic lipase inhibitors lipstatin, (2S, 3S,5S,7Z,10Z)-5-[(S)-2-formamido-4-methyl-valeryloxy]-2-hexyl-3-hydroxy-7,10-hexadecanoic acid lactone, and tetrahydrolipstatin (orlistat), (2S,3S,5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed In U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571 and 5,602,151. The pancreatic lipase inhibitor, valilactone, and a process for the preparation thereof by the microbial cultivation of Actinomycetes strain MG147-$CF_2$, are disclosed in Kitahara et al., *J. Antibiotics,* 40(11): 1647-1650 (1987). The pancreatic lipase inhibitors, ebelactone A and ebelactone B, and a process for the preparation thereof by the microbial cultivation of Actinomycetes strain MG7-G1, are disclosed in Umezawa et al., *J. Antibiotics,*

33:1594-1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fabric acid derivatives, such as Atromid®, Lopid® and Tricot®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., *J. Med. Chem.,* 41:2934-2938 (1998)). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., J. Malone, "Red Cell Sorbitol, an Indicator of Diabetic Control", *Diabetes,* 29:861-864 (1980)). A variety of aldose reductase inhibitors are known to those skilled in the art, such as those described in U.S. Pat. No. 6,579,879, which includes 6-(5-chloro-3-methylbenzofuran-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., *Analyt. Biochem.,* 280:329-331 (2000)). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., *Biochemistry,* 8:4214 (1969)). A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., *Meth. Enzymol.,* 1:149 (1955)). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5S)-3,4,5-trihydroxy-2-(hydroxymethyl)piperidino]-(α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed In U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products).

Other examples would include PKC-13 inhibitors and AGE breakers.

The compounds of the present invention can be used in combination with anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, $\beta_3$ adrenergic receptor agonists, apolipoprotein-B secretion/microsomal triglyceride transfer protein (apo-B/MTP) inhibitors, MCR-4-agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant described in U.S. Pat. No. 5,624,941 (SR-141,716A), purine compounds, such as those described in US Patent Publication No. 2004/0092520; pyrazolo[1,5-a][1,3,5]triazine compounds, such as those described in US Non-Provisional patent application Ser. No. 10/763,105; and bicyclic pyrazolyl and imidazolyl compounds, such as those described in U.S. Provisional Application No. 60/518,280, dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e., orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like. Rimonabant (SR-141,716A also known under the trade name Acomplia™ available from Sanofi-Aventis) can be prepared as described in U.S. Pat. No. 5,624,941. Other suitable CB-1 antagonists include those described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971,599; and PCT Patent Publication Nos. WO 02/076949, WO 03/1075660, WO 04/048317, WO 04/013120, and WO 04/012671.

Preferred apolipoprotein-B secretion/microsomal triglyceride transfer protein (apo-B/MTP) inhibitors for use as anti-obesity agents are gut-selective MTP inhibitors, such as dirlotapide described in U.S. Pat. No. 6,720,351; 4-(4-(4-(4-((2-((4-methyl-4H-1,2,4-triazol-3-ylthio)methyl)-2-(4-chlorophenyl)-1,3-dioxolan-4-yl)methoxy)phenyl) piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,431. As used herein, the term "gut-selective" means that the MTP Inhibitor has a higher exposure to the gastro-intestinal tissues versus systemic exposure.

Any thyromimetic can be used as the second agent in combination with a compound of the present Invention. Such thyromimetic activity is readily determined by those skilled in the art according to standard assays (e.g., Atherosclerosis, 126: 53-63 (1996)). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629 and bromocriptine which can be prepared as described in U.S. Pat. Nos. 3,752,814 and 3,752,888.

The compounds of the present invention can also be used in combination with other antihypertensive agents. Any antihypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL°, Sular®, Tiazac®, Vascor®, Verelan®, Isoptin®, Nimotop®, Norvasc®, and Plendile; angiotensin converting enzyme (ACE) inhibitors, such as Accupril®, Altace®, Captopril®, Lotensin®, Malik®, Monopril®, Prinivil®, Univasc®, Vasotec® and Zestril Amlodipine and related dihydropyridine compounds are disclosed in U.S. Pat. No. 4,572,909, as potent anti-ischemic and antihypertensive agents. U.S. Pat. No. 4,879,303 discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®.

Calcium channel blockers which are within the scope of this invention include, but are not limited to: bepridil, which may be prepared as disclosed in U.S. Pat. No. 3,962,238 or U.S. Reissue No. 30,577; clentiazem, which may be prepared as disclosed in U.S. Pat. No. 4,567,175; diltiazem, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572,909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485, 847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267, 104; Iomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265, 758; and perhexyline, which may be prepared as disclosed in British Patent No. 1,025,578.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046, 889 and 4,105,776; ceronapril, which may be prepared as disclosed in U.S. Pat. No. 4,462,790; delapril, which may be prepared as disclosed in U.S. Pat. No. 4,385,051; enalapril, which may be prepared as disclosed in U.S. Pat. No. 4,374, 829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470, 972; temocapril, which may be prepared as disclosed in U.S. Pat. No. 4,699,905; and trandolapril, which may be prepared as disclosed in U.S. Pat. No. 4,933,361.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270, 317; Iosartan, which may be prepared as disclosed in U.S. Pat. No. 5,138,069; and valsartan, which may be prepared as disclosed in U.S. Pat. No. 5,399,578.

Beta-adrenergic receptor blockers (beta- or (3-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836, 671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252, 825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., *J. Med. Chem.,* 25:670 (1982); epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176;

mepindolol, which may be prepared as disclosed in Seeman et al., *Heir. Chim. Acta,* 54:241 (1971); metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501, 7691; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394, 382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337, 628 and 3,520,919; sotalol, which may be prepared as disclosed in Uloth et al., *J. Med. Chem.,* 9:88 (1966); sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

Alpha-adrenergic receptor blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252, 721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol; naftopidil, which may be prepared as disclosed in U.S. Pat.

No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, which may be isolated from natural sources as disclosed in Kennedy et al., *J. Am. Chem. Soc.,* 77:250 (1955) or synthesized as disclosed in Kennedy, *J. Biol. Chem.,* 222:185 (1956); cyclandelate, which may be prepared as disclosed in U.S. Pat. No. 3,663,597; ciclonicate, which may be prepared as disclosed in German Patent No, 1,910,481; diisopropylamine dichloroacetate, which may be prepared as disclosed in British Patent No. 862,248; eburnamonine, which may be prepared as disclosed in Hermann et al., *J. Am. Chem. Soc.,* 101:1540 (1979);

fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; Iomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., *J. Am. Chem. Soc.,* 64:1722 (1942); nicergoline, which may be prepared as disclosed above; nimodipine, which may be prepared as disclosed in U.S. Pat. No. 3,799,934; papaverine, which may be prepared as reviewed in Goldberg, *Chem. Prod. Chem. News,* 17:371 (1954); pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444.

Coronary vasodilators within the scope of this invention include, but are not limited to: amotriphene, which may be prepared as disclosed in U.S. Pat. No. 3,010,965; bendazol, which may be prepared as disclosed in *J. Chem. Soc.,* 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., *J. Chem. Soc.,* 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638, 422-3; perhexylline, which may be prepared as disclosed above; pimethylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., *J. Am. Chem. Soc.,* 67:1894 (1945); bencyclane, which may be prepared as disclosed above; betahistine, which may be prepared as disclosed in Walter et al., *J. Am. Chem. Soc.,* 63:2771 (1941); bradykinin, which may be prepared as disclosed in Hamburg et al., *Arch. Biochem. Biophys.,* 76:252 (1958); brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent No. 1,460,571; ciclonicate, which may be prepared as disclosed in German Patent No, 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; hepronicate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., *J. Am. Chem. Soc.,* 69:2907 (1947); isoxsuprine, which may be prepared as disclosed in U.S. Pat. No. 3,056,836; kallidin, which may be prepared as disclosed in *Biochem. Biophys. Res. Commun.,* 6:210 (1961); kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the *Merck Index*, Twelfth Edition, Budaveri, ed., New Jersey, p. 1353 (1996); suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750.

The term “diuretic,” within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., *Ber.,* 90:957 (1957); muzolimine, which may be prepared as disclosed in U.S. Pat. No. 4,018,890; perhexyline, which may be prepared as disclosed above; ticrynafen, which may be prepared as disclosed in U.S. Pat. No. 3,758,506; triamterene which may be prepared as disclosed in U.S. Pat. No. 3,051,230; and urea.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136*th Am. Soc. Meeting* (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which maybe prepared as disclosed in Belgian Patent No. 587,225; cyclothiazide, which may be prepared as disclosed in Whitehead et al., *J. Org. Chem.,* 26:2814 (1961); epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al., *J. Am. Chem. Soc.,* 82:1132 (1960); meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., *J. Am. Chem. Soc.,* 82:1132 (1960); and trichlormethiazide, which may be prepared as disclosed in deStevens et al., *Experientia,* 16:113 (1960).

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, *Rec. Tray. Chim.,* 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777.

Osteoporosis is a systemic skeletal disease, characterized by low bone mass and deterioration of bone tissue, with a consequent increase in bone fragility and susceptibility to fracture, in the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly within the aging of the population. Worldwide fracture incidence is forecasted to increase three-fold over the next 60 years, and one study has estimated that there will be 4.5 million hip fractures worldwide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenproprionate, progesterone, quingestanol acetate, quingestrone, and tigestol. Preferred progestins are medroxyprogestrone, norethindrone and norethynedrel.

Exemplary bone resorption inhibiting polyphosphonates include polyphosphenates of the type disclosed in U.S. Pat.

No. 3,683,080. Preferred polyphosphonates are geminal diphosphonates (also referred to as bis-phosphonates). Tiludronate disodium is an especially preferred polyphosphonate. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N-(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods (Eriksen, E. F. et al., *Bone Histomorphometry*, Raven Press, New York, pp. 1-74 (1994); Grier S. J. et al., "The Use of Dual-Energy X-Ray Absorptiometry In Animals", *Inv. Radiol.*, 31(1):50-62 (1996); Wahner H. W. et al., *The Evaluation of Osteoporosis: Dual Energy X-Ray Absorptiometry in Clinical Practice*, Martin Dunitz Ltd., London, pp. 1-296 (1994)). A variety of these compounds are described and referenced below. Another preferred estrogen agonist/antagonist is 3-(4-{1,2-diphenyl-but-1-enyl)-phenyl)-acrylic acid, which is disclosed in Willson et al., *Endocrinology,* 138:3901-3911 (1997). Another preferred estrogen agonist/antagonist is tamoxifen: (ethanamine,2-(−4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen, which is disclosed in U.S. Pat. No. 4,623,660. A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)—, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2, dimethyl-3-phenyl-chroman-4-yl)-phenoxy)-ethyl)-pyrrolidine, which is disclosed in U.S. Pat. No. 3,822,287. Also preferred is levormeloxifene.

Another preferred estrogen agonist/antagonist is idoxifene: (E)-1-(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another preferred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxyphenyl)-benzo[b]thiophen-3-yl)-methanone which is disclosed, along with methods of preparation, in PCT Publication No. WO 95/10513. Other preferred estrogen agonist/antagonists include the compounds, TSE-424 (Wyeth-Ayerst Laboratories) and arazoxifene.

Other preferred estrogen agonist/antagonists include compounds as described in U.S. Pat. No. 5,552,412. Especially preferred compounds described therein are: cis-6-('4-fluorophenyl)-5-(4-(2-piperidin-1-yl-ethoxy)-phenyl)-5,6,7,8-tetrahydronaphthalene-2-ol; (−)-cis-6-phenyl-5-(4-(2-pyrrolidin-1-yl-ethoxy)-phenyl)-5,6,7,8-tetrahydronaphthalene-2-ol (also known as lasofoxifene); cis-6-phenyl-5-(4-(2-pyrrolidin-1-yl-ethoxy)-phenyl)-5,6,7,8-tetrahydronaphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,44etrahydroisoquinoline; cis-6-(4-hydroxyphenyl)-5-(4-(2-piperidin-1-yl-ethoxy)-phenyl)-5,6,7,8-tetrahydronaphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814, which discloses derivatives of 2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132,774), particularly calcium receptor antagonists; calcitonin; vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone, 4-(trifluoromethyl)-2(1H)-pyrrolidino[3,2-g]quinoline derivatives, 1,2-dihydropyridino[5,6-g]quinoline derivatives and piperidino[3,2-g]quinolinone derivatives.

Cypterone, also known as (1b,2b)-6-chloro-1,2-dihydro-17-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4-,6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl)phenyl]-2,4-imidazolidinedione and by the trade name Nilandron® is disclosed in U.S. Pat. No. 4,097,578. Flutamide, also known as 2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy- 2-methylpropiono-m-toluidide and the trade name Casodex® is disclosed in EP-100172. The enantiomers of biclutamide are discussed by Tucker et al., *J. Med. Chem.*, 31:885-887 (1988). Hydroxyflutamide, a known androgen receptor antagonist in most tissues, has been suggested to function as a SARM for effects on IL-6 production by osteoblasts as disclosed in Hofbauer et al., *J. Bone Miner. Res.*, 14:1330-1337 (1999). Additional SARMs have been disclosed in U.S. Pat. No. 6,017,924; WO 01/16108, WO 01/16133, WO 01/16139, WO 02/00617, WO 02/16310, U.S. Patent Application Publication No, US 2002/0099096, U.S. Patent Application Publication No. US 2003/0022868, WO 03/011302 and WO 03/011824.

Any compound having activity as an LXR modulator can serve as the second compound in the combination therapy aspect of the present invention. The term LXR modulator refers to compounds that modulate the liver X receptor (LXR), which has been identified as a regulator of cellular and whole body cholesterol metabolism. Such LXR modulation activity is readily determined by those skilled in the art according to standard assays (e.g., U.S. Pat. No. 6,140,343). A variety of LXR modulators will be known to those skilled in the art, for example, those disclosed in U.S. Patent Application Publication Nos. 2003/01814206, 2005/0080111, and 2005/0245515.

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

What is claimed is:

1. A compound selected from the group consisting of:

| Structure | Name |
|---|---|
| 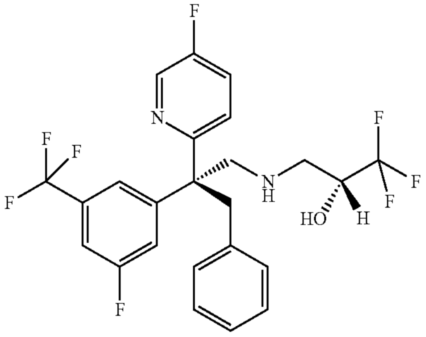 [SMILES: O[C@H](CNC[C@](Cc1ccccc1)(c1cc(F)cc(C(F)(F)F)c1)c1ccc(F)cn1)C(F)(F)F] | (R)-1,1,1-trifluoro-3-((S)-2-(3-fluoro-5-(trifluoromethyl)-phenyl)-2-(5-fluoropyridin-2-yl)-3-phenyl-propylamino)-propan-2-ol |
| 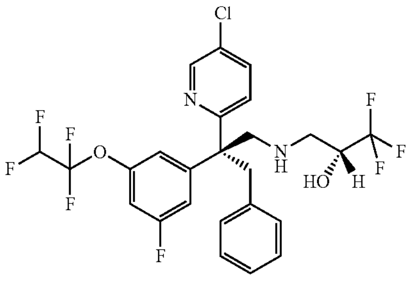 [SMILES: O[C@H](CNC[C@@](Cc1ccccc1)(c1cc(F)cc(OC(F)(F)C(F)F)c1)c1ccc(Cl)cn1)C(F)(F)F] | (R)-3-((R)-2-(5-chloro-pyridin-2-yl)-2-(3-fluoro-5-(1,1,2,2-tetrafluoro-ethoxy)phenyl)-3-phenylpropyl-amino)-1,1,1-trifluoropropan-2-ol |

-continued

| Structure | Name |
|---|---|
| 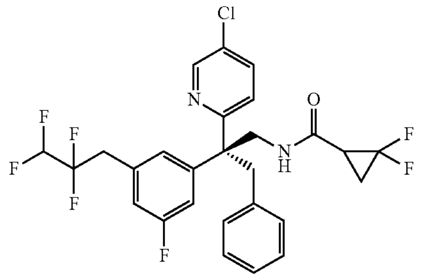 [SMILES: O=C(NC[C@@](Cc1ccccc1)(c1cc(F)cc(CC(F)(F)C(F)F)c1)c1ccc(Cl)cn1)C1CC1(F)F] | N-((R)-2-(5-chloropyridin-2-yl)-2-(3-fluoro-5-(2,2,3,3-tetrafluoro-propyl)phenyl)-3-phenyl-propyl)-2,2-difluorocyclo-propanecarbox-amide |
| 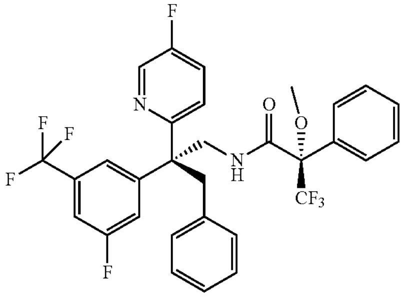 | (S)-3,3,3-trifluoro-N-((S)-2-(3-fluoro-5-(trifluoro-methyl)phenyl)-2-(5-fluoro-pyridin-2-yl)-3-phenylpropyl)-2-methoxy-2-phenylpropan-amide |
| 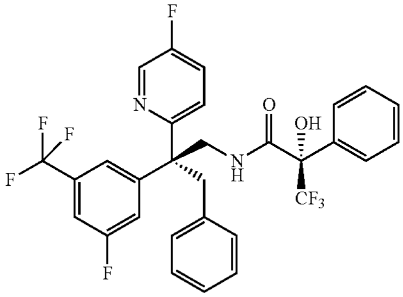 | (S)-3,3,3-trifluoro-N-((R)-2-(3-fluoro-5-(trifluoro-methyl)phenyl)-2-(5-fluoro-pyridin-2-yl)-3-phenylpropyl)-2-hydroxy-2-phenylpropan-amide |
| 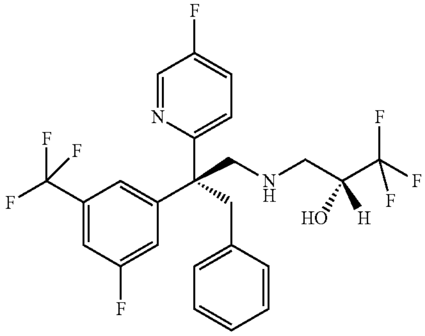 [SMILES: O[C@H](CNC[C@@](Cc1ccccc1)(c1cc(F)cc(C(F)(F)F)c1)c1ccc(F)cn1)C(F)(F)F] | (R)-1,1,1-trifluoro-3-((R)-2-(3-fluoro-5-(trifluoro-methyl)-phenyl)-2-(5-fluoro-pyridin-2-yl)-3-phenyl-propylamino)-propan-2-ol |
| 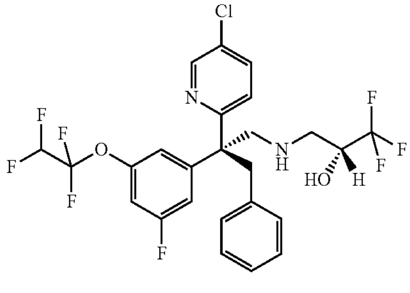 [SMILES: O[C@H](CNC[C@](Cc1ccccc1)(c1cc(F)cc(OC(F)(F)C(F)F)c1)c1ccc(Cl)cn1)C(F)(F)F] | (R)-3-((S)-2-(5-chloro-pyridin-2-yl)-2-(3-fluoro-5-(1,1,2,2-tetrafluoro-ethoxy)-phenyl)-3-phenylpropyl-amino)-1,1,1-trifluoropro-pan-2-ol |

| Structure | Name |
|---|---|
| 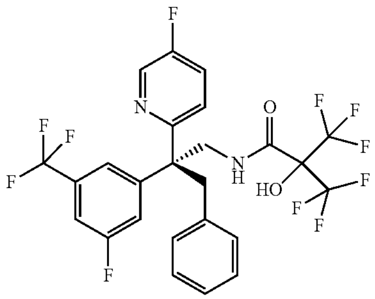 [SMILES: O=C(NC[C@](Cc1ccccc1)(c1cc(F)cc(C(F)(F)F)c1)c1ccc(F)cn1)C(O)(C(F)(F)F)C(F)(F)F] | (R)-3,3,3-trifluoro-N-(2-(3-fluoro-5-(trifluoro-methyl)-phenyl)-2-(5-fluoropyridin-2-yl)-3-phenyl-propyl)-2-hydroxy-2-(trifluoro-methyl)-propanamide |
| 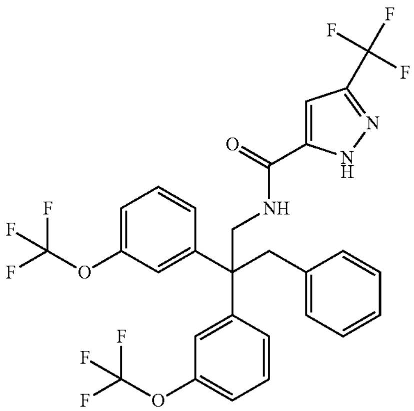 [SMILES: O=C(NCC(Cc1ccccc1)(c1cccc(OC(F)(F)F)c1)c1cccc(OC(F)(F)F)c1)c1cc(C(F)(F)F)n[nH]1] | N-(3-phenyl-2,2-bis(3-(tri-fluorometh-oxy)phenyl)-propyl)-3-(tri-fluoromethyl)-1H-pyrazole-5-carboxamide |
| 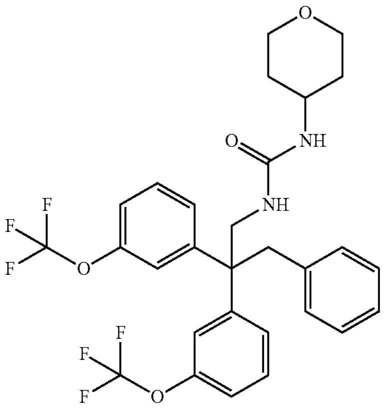 [SMILES: O=C(NCC(Cc1ccccc1)(c1cccc(OC(F)(F)F)c1)c1cccc(OC(F)(F)F)c1)NC1CCOCC1] | 1-(3-phenyl-2,2-bis(3-(tri-fluorometh-oxy)phenyl)-propyl)-3-(tetrahydro-2H-pyran-4-yl)urea |
| 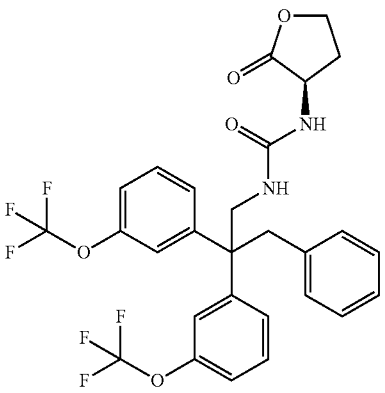 [SMILES: O=C(NCC(Cc1ccccc1)(c1cccc(OC(F)(F)F)c1)c1cccc(OC(F)(F)F)c1)N[C@@H]1CCOC1=O] | (R)-1-(2-oxo-tetrahydro-furan-3-yl)-3-(3-phenyl-2,2-bis(3-(tri-fluorometh-oxy)phenyl)-propyl)-urea |

| Structure | Name |
|---|---|
| 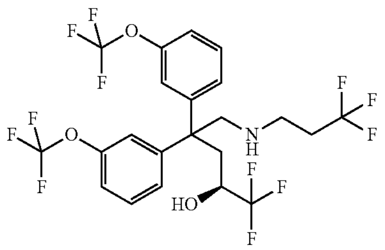 [SMILES: O[C@@H](CC(CNCCC(F)(F)F)(c1cccc(OC(F)(F)F)c1)c1cccc(OC(F)(F)F)c1)C(F)(F)F] | (S)-1,1,1-trifluoro-4,4-bis(3-(tri-fluorometh-oxy)phenyl)-5-(3,3,3-tri-fluoropropyl-amino)pentan-2-ol |
| 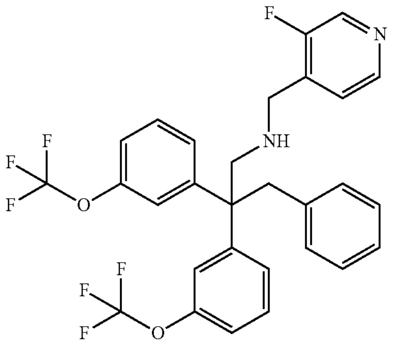 [SMILES: Fc1cnccc1CNCC(Cc1ccccc1)(c1cccc(OC(F)(F)F)c1)c1cccc(OC(F)(F)F)c1] | N-((3-fluoro-pyridin-4-yl)-methyl)-3-phenyl-2,2-bis(3-(tri-fluorometh-oxy)phenyl)-propan-1-amine |
| 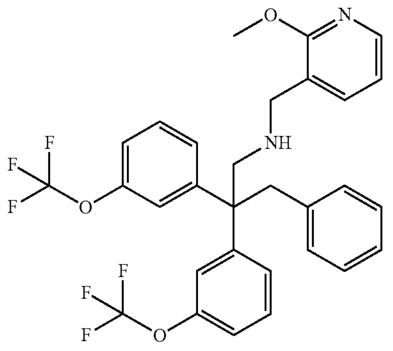 [SMILES: COc1ncccc1CNCC(Cc1ccccc1)(c1cccc(OC(F)(F)F)c1)c1cccc(OC(F)(F)F)c1] | N-((2-meth-oxypyridin-3-yl)-methyl)-3-phenyl-2,2-bis(3-(tri-fluorometh-oxy)phenyl)-propan-1-amine |
| 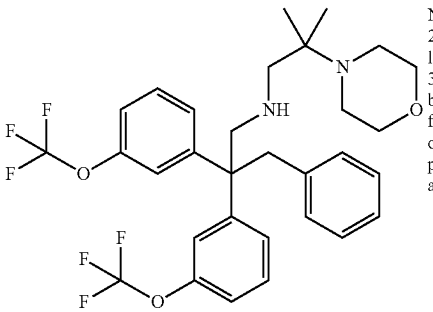 | N-(2-methyl-2-morpho-linopropyl)-3-phenyl-2,2-bis(3-(tri-fluorometh-oxy)-phenyl)-propan-1-amine |

-continued

| Structure | Name |
| --- | --- |
| 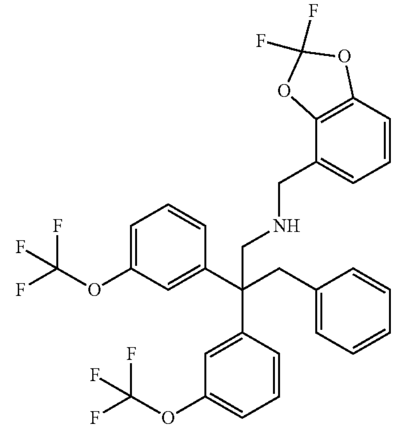 [SMILES: FC(F)(F)Oc1cccc(C(CNCc2cccc3c2OC(F)(F)O3)(Cc2ccccc2)c2cccc(OC(F)(F)F)c2)c1] | N-((2,2-di-fluorobenzo-[d][1,3]-dioxol-4-yl)methyl)-3-phenyl-2,2-bis(3-(trifluoro-methoxy)-phenyl)propan-1-amine |
| 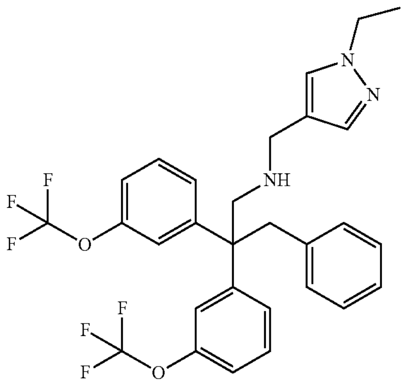 [SMILES: CCn1cc(CNCC(Cc2ccccc2)(c2cccc(OC(F)(F)F)c2)c2cccc(OC(F)(F)F)c2)cn1] | N-((1-ethyl-1H-pyrazol-4-yl)methyl)-3-phenyl-2,2-bis(3-(tri-fluorometh-oxy)phenyl)-propan-1-amine |
| 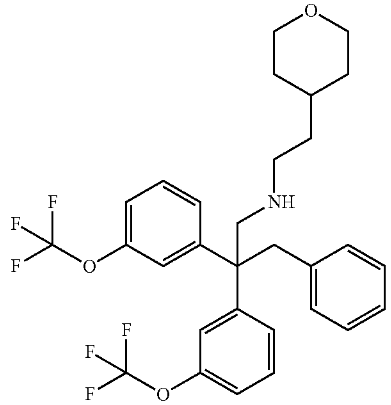 [SMILES: FC(F)(F)Oc1cccc(C(CNCCC2CCOCC2)(Cc2ccccc2)c2cccc(OC(F)(F)F)c2)c1] | 3-phenyl-N-(2-(tetra-hydro-2H-pyran-4-yl)-ethyl)-2,2-bis(3-(tri-fluorometh-oxy)phenyl)-propan-1-amine |
| 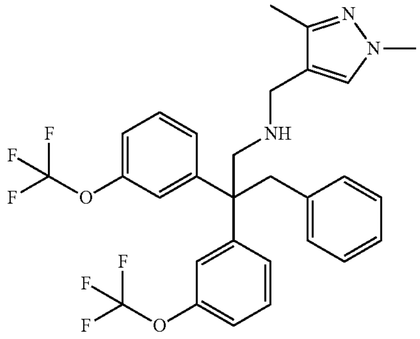 [SMILES: Cc1nn(C)cc1CNCC(Cc1ccccc1)(c1cccc(OC(F)(F)F)c1)c1cccc(OC(F)(F)F)c1] | N-((1,3-di-methyl-1H-pyrazol-4-yl)methyl)-3-phenyl-2,2-bis(3-(tri-fluorometh-oxy)phenyl)-propan-1-amine |

-continued

| Structure | Name |
| --- | --- |
| 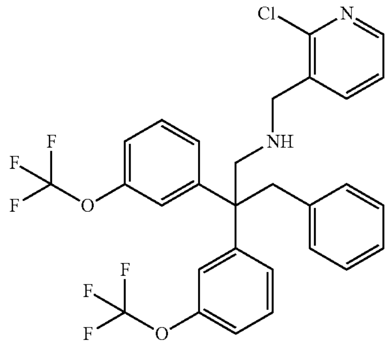 [SMILES: FC(F)(F)Oc1cccc(C(CNCc2cccnc2Cl)(Cc2ccccc2)c2cccc(OC(F)(F)F)c2)c1] | N-((2-chloro-pyridin-3-yl)-methyl)-3-phenyl-2,2-bis(3-(tri-fluorometh-oxy)phenyl)-propan-1-amine |
| 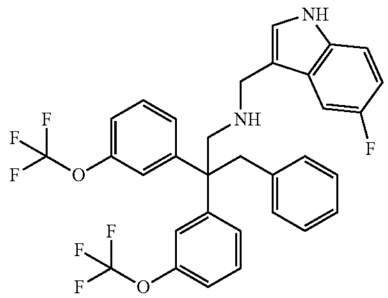 [SMILES: Fc1ccc2[nH]cc(CNCC(Cc3ccccc3)(c3cccc(OC(F)(F)F)c3)c3cccc(OC(F)(F)F)c3)c2c1] | N-((5-fluoro-1H-indol-3-yl)-methyl)-3-phenyl-2,2-bis(3-(tri-fluorometh-oxy)phenyl)-propan-1-amine |
| 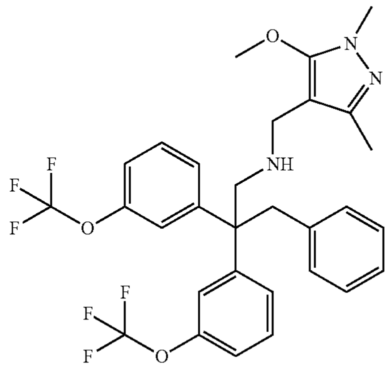 [SMILES: COc1c(CNCC(Cc2ccccc2)(c2cccc(OC(F)(F)F)c2)c2cccc(OC(F)(F)F)c2)c(C)nn1C] | N-((5-meth-oxy-1,3-di-methyl-1H-pyrazol-4-yl)methyl)-3-phenyl-2,2-bis(3-(trifluoro-methoxy)-phenyl)propan-1-amine |
| 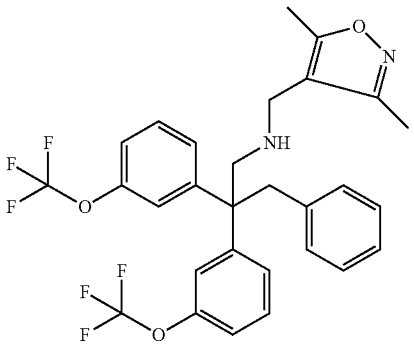 [SMILES: Cc1noc(C)c1CNCC(Cc1ccccc1)(c1cccc(OC(F)(F)F)c1)c1cccc(OC(F)(F)F)c1] | N-((3,5-di-methylisox-azol-4-yl)-methyl)-3-phenyl-2,2-bis(3-(tri-fluorometh-oxy)phenyl)-propan-1-amine |

-continued

| Structure | Name |
|---|---|
| 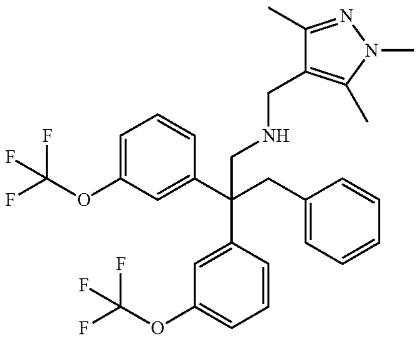 [SMILES: Cc1nn(C)c(C)c1CNCC(Cc1ccccc1)(c1cccc(OC(F)(F)F)c1)c1cccc(OC(F)(F)F)c1] | 3-phenyl-2,2-bis(3-(trifluoromethoxy)phenyl)-N-((1,3,5-trimethyl-1H-pyrazol-4-yl)methyl)-propan-1-amine |
| 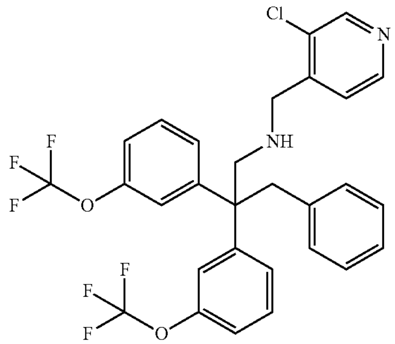 | N-((3-chloropyridin-4-yl)-methyl)-3-phenyl-2,2-bis(3-(trifluoromethoxy)phenyl)-propan-1-amine |
| 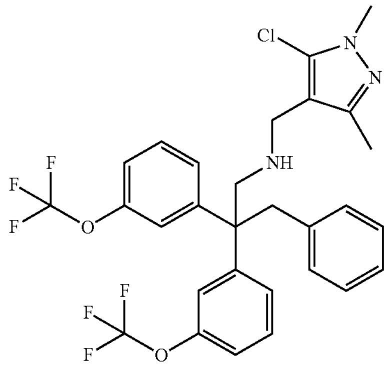 [SMILES: Cc1nn(C)c(Cl)c1CNCC(Cc1ccccc1)(c1cccc(OC(F)(F)F)c1)c1cccc(OC(F)(F)F)c1] | N-((5-chloro-1,3-dimethyl-1H-pyrazol-4-yl)methyl)-3-phenyl-2,2-bis(3-(trifluoromethoxy)-phenyl)propan-1-amine |
| 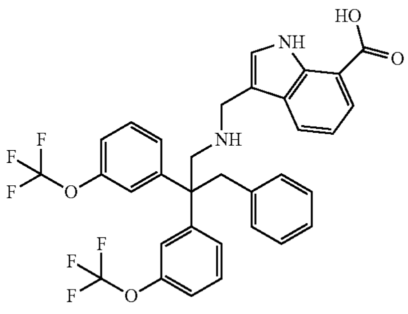 [SMILES: O=C(O)c1cccc2c(CNCC(Cc3ccccc3)(c3cccc(OC(F)(F)F)c3)c3cccc(OC(F)(F)F)c3)c[nH]c12] | 3-((3-phenyl-2,2-bis(3-(trifluoromethoxy)phenyl)-propylamino)-methyl)-1H-indole-7-carboxylic acid |

-continued

| Structure | Name |
|---|---|
| 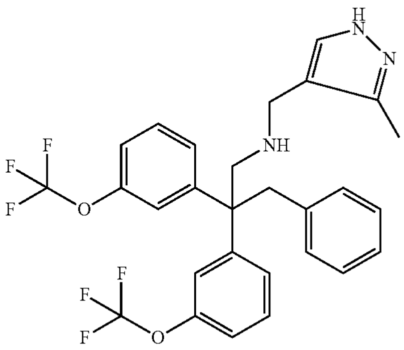 [SMILES: Cc1n[nH]cc1CNCC(Cc1ccccc1)(c1cccc(OC(F)(F)F)c1)c1cccc(OC(F)(F)F)c1] | N-((3-methyl-1H-pyrazol-4-yl)-methyl)-3-phenyl-2,2-bis(3-(trifluoromethoxy)phenyl)-propan-1-amine |
| 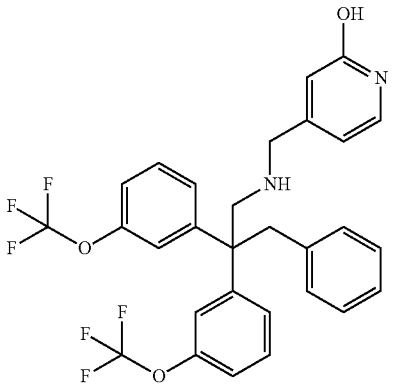 [SMILES: Oc1cc(CNCC(Cc2ccccc2)(c2cccc(OC(F)(F)F)c2)c2cccc(OC(F)(F)F)c2)ccn1] | 4-((3-phenyl-2,2-bis(3-(trifluoromethoxy)phenyl)-propylamino)-methyl)pyridin-2-ol |
| 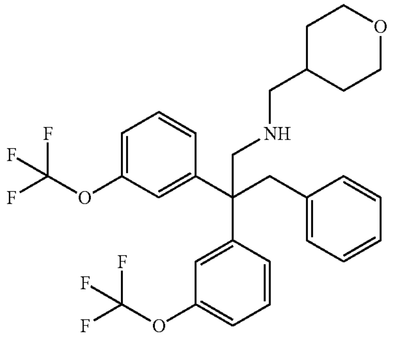 [SMILES: FC(F)(F)Oc1cccc(C(CNCC2CCOCC2)(Cc2ccccc2)c2cccc(OC(F)(F)F)c2)c1] | 3-phenyl-N-((tetrahydro-2H-pyran-4-yl)methyl)-2,2-bis(3-(trifluoromethoxy)phenyl)-propan-1-amine |
| 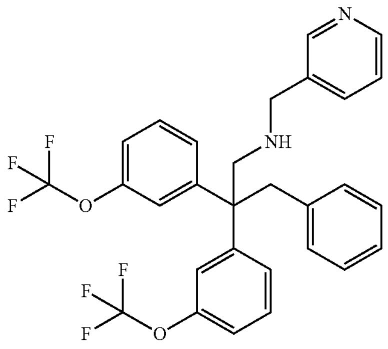 [SMILES: FC(F)(F)Oc1cccc(C(CNCc2cccnc2)(Cc2ccccc2)c2cccc(OC(F)(F)F)c2)c1] | 3-phenyl-N-(pyridin-3-ylmethyl)-2,2-bis(3-(trifluoromethoxy)-phenyl)-propan-1-amine |

-continued

| Structure | Name |
|---|---|
| 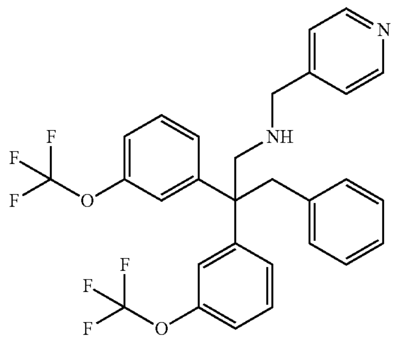 [SMILES: FC(F)(F)Oc1cccc(C(CNCc2ccncc2)(Cc2ccccc2)c2cccc(OC(F)(F)F)c2)c1] | 3-phenyl-N-(pyridin-4-ylmethyl)-2,2-bis(3-(trifluorometh-oxy)phenyl)-propan-1-amine |
| 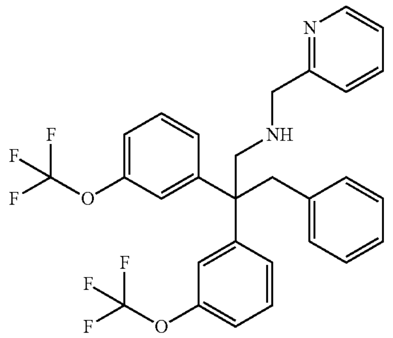 [SMILES: FC(F)(F)Oc1cccc(C(CNCc2ccccn2)(Cc2ccccc2)c2cccc(OC(F)(F)F)c2)c1] | 3-phenyl-N-(pyridin-2-ylmethyl)-2,2-bis(3-(trifluorometh-oxy)phenyl)-propan-1-amine |
| 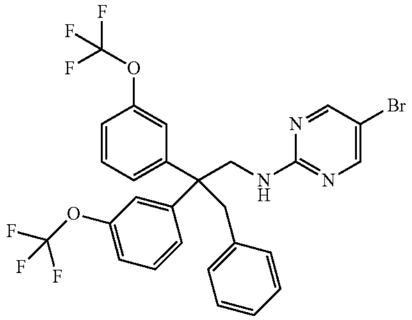 [SMILES: FC(F)(F)Oc1cccc(C(CNc2ncc(Br)cn2)(Cc2ccccc2)c2cccc(OC(F)(F)F)c2)c1] | 5-bromo-N-(3-phenyl-2,2-bis(3-(trifluorometh-oxy)phenyl)-propyl)-pyrimidin-2-amine |
| 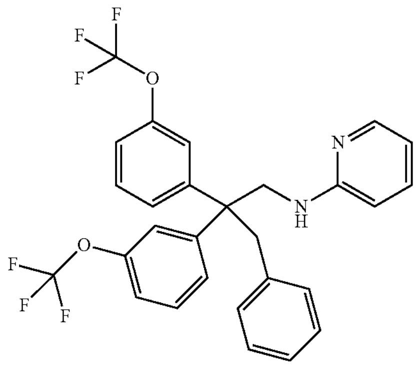 [SMILES: FC(F)(F)Oc1cccc(C(CNc2ccccn2)(Cc2ccccc2)c2cccc(OC(F)(F)F)c2)c1] | N-(3-phenyl-2,2-bis(3-(tri-fluorometh-oxy)phenyl)-propyl)-pyridin-2-amine |

-continued

| Structure | Name |
|---|---|
| 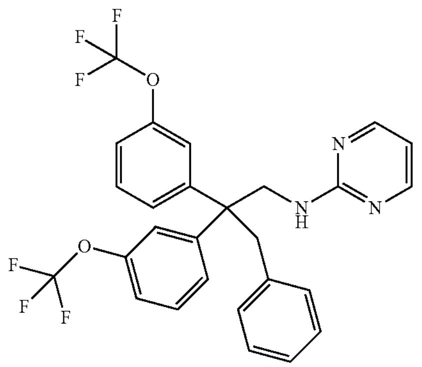 [SMILES: FC(F)(F)Oc1cccc(C(CNc2ncccn2)(Cc2ccccc2)c2cccc(OC(F)(F)F)c2)c1] | N-(3-phenyl-2,2-bis(3-(tri-fluorometh-oxy)phenyl)-propyl)-pyrimidin-2-amine |
| 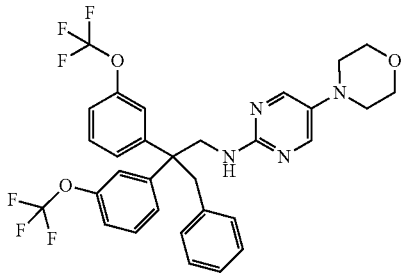 [SMILES: FC(F)(F)Oc1cccc(C(CNc2ncc(N3CCOCC3)cn2)(Cc2ccccc2)c2cccc(OC(F)(F)F)c2)c1] | 5-morpholino-N-(3-phenyl-2,2-bis(3-(tri-fluorometh-oxy)phenyl)-propyl)-pyrimidin-2-amine |
| 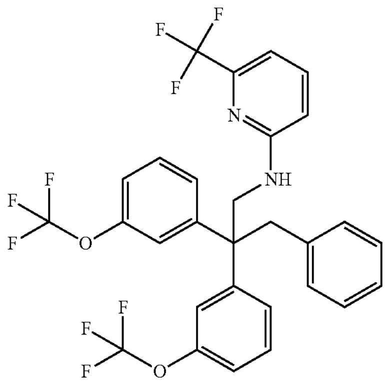 [SMILES: FC(F)(F)Oc1cccc(C(CNc2cccc(C(F)(F)F)n2)(Cc2ccccc2)c2cccc(OC(F)(F)F)c2)c1] | N-(3-phenyl-2,2-bis(3-(trifluoro-methoxy)phenyl)-propyl)-6-(tri-fluoromethyl)-pyridin-2-amine |
| 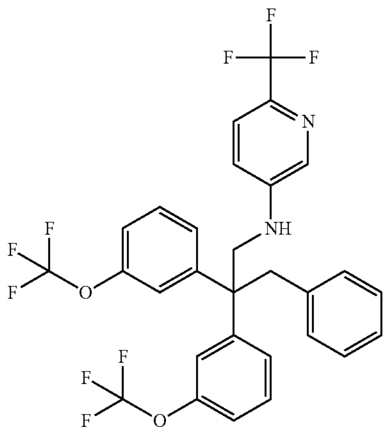 [SMILES: FC(F)(F)Oc1cccc(C(CNc2ccc(C(F)(F)F)nc2)(Cc2ccccc2)c2cccc(OC(F)(F)F)c2)c1] | N-(3-phenyl-2,2-bis(3-(trifluoro-methoxy)phenyl)-propyl)-6-(tri-fluoromethyl)-pyridin-3-amine |

-continued

| Structure | Name |
|---|---|
| 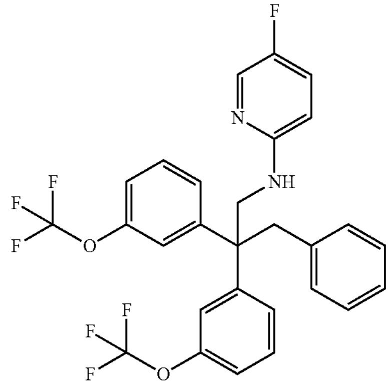 [SMILES: Fc1ccc(NCC(Cc2ccccc2)(c2cccc(OC(F)(F)F)c2)c2cccc(OC(F)(F)F)c2)nc1] | 5-fluoro-N-(3-phenyl-2,2-bis(3-(trifluorometh-oxy)phenyl)-propyl)pyridin-2-amine |
| 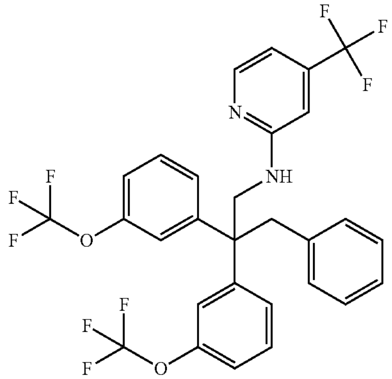 [SMILES: FC(F)(F)Oc1cccc(C(CNc2cc(C(F)(F)F)ccn2)(Cc2ccccc2)c2cccc(OC(F)(F)F)c2)c1] | N-(3-phenyl-2,2-bis(3-(trifluoro-methoxy)phenyl)-propyl)-4-(tri-fluoromethyl)-pyridin-2-amine |

-continued

| Structure | Name |
|---|---|
| 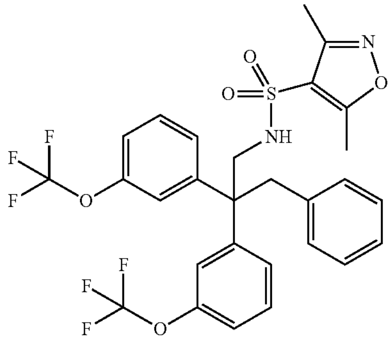 [SMILES: Cc1noc(C)c1S(=O)(=O)NCC(Cc1ccccc1)(c1cccc(OC(F)(F)F)c1)c1cccc(OC(F)(F)F)c1] | 3,5-dimethyl-N-(3-phenyl-2,2-bis(3-(trifluoro-methoxy)phenyl)-propyl)isoxazole-4-sulfonamide |
| 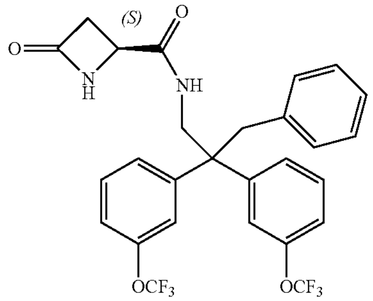 | (S)-4-oxo-N-(3-phenyl-2,2-bis(3-(trifluorometh-oxy)phenyl)-propyl)-azetidine-2-carboxamide. |

2. A pharmaceutical composition comprising at least one compound of claim 1.

* * * * *